United States Patent
Fujiwara et al.

(10) Patent No.: US 11,215,926 B2
(45) Date of Patent: *Jan. 4, 2022

(54) SULFONIUM COMPOUND, RESIST COMPOSITION, AND PATTERNING PROCESS

(71) Applicant: Shin-Etsu Chemical Co., Ltd., Tokyo (JP)

(72) Inventors: Takayuki Fujiwara, Joetsu (JP); Ryo Mitsui, Joetsu (JP); Masaki Ohashi, Joetsu (JP); Ryosuke Taniguchi, Joetsu (JP); Koji Hasegawa, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 232 days.

This patent is subject to a terminal disclaimer.

(21) Appl. No.: 16/108,645

(22) Filed: Aug. 22, 2018

(65) Prior Publication Data

US 2019/0064665 A1    Feb. 28, 2019

(30) Foreign Application Priority Data

Aug. 24, 2017 (JP) .............. JP2017-161031

(51) Int. Cl.
| | | |
|---|---|---|
| G03F 7/06 | (2006.01) | |
| G03F 7/004 | (2006.01) | |
| G03F 7/033 | (2006.01) | |
| C07D 333/76 | (2006.01) | |
| C07D 327/08 | (2006.01) | |
| G03F 7/32 | (2006.01) | |
| C07D 339/08 | (2006.01) | |
| G03F 7/039 | (2006.01) | |
| C07C 381/12 | (2006.01) | |
| C07C 323/64 | (2006.01) | |

(52) U.S. Cl.
CPC ............ *G03F 7/066* (2013.01); *C07C 381/12* (2013.01); *C07D 327/08* (2013.01); *C07D 333/76* (2013.01); *C07D 339/08* (2013.01); *G03F 7/0045* (2013.01); *G03F 7/0046* (2013.01); *G03F 7/0048* (2013.01); *G03F 7/033* (2013.01); *G03F 7/0397* (2013.01); *G03F 7/322* (2013.01); *G03F 7/325* (2013.01); *C07C 323/64* (2013.01); *C07C 2601/14* (2017.05); *C07C 2603/74* (2017.05)

(58) Field of Classification Search
CPC ........ G03F 7/066; G03F 7/0045; G03F 7/033; G03F 7/029
See application file for complete search history.

(56) References Cited

U.S. PATENT DOCUMENTS

| | | |
|---|---|---|
| 7,511,169 B2 | 3/2009 | Ohsawa et al. |
| 7,919,226 B2 | 4/2011 | Ohsawa et al. |
| 8,034,547 B2 | 10/2011 | Tsubaki et al. |
| 8,173,354 B2 | 5/2012 | Ohsawa et al. |
| 8,227,183 B2 | 7/2012 | Tsubaki et al. |
| 8,241,840 B2 | 8/2012 | Tsubaki et al. |
| 9,069,246 B2 | 6/2015 | Takizawa et al. |
| 10,025,180 B2 * | 7/2018 | Mitsui .................. G03F 7/0397 |
| 2014/0120471 A1 | 5/2014 | Aqad et al. |
| 2016/0152755 A1 | 6/2016 | Fujiwara et al. |
| 2017/0052450 A1 * | 2/2017 | Nakagawa ............... G03F 7/38 |
| 2020/0133122 A1 * | 4/2020 | Fukushima ............. C08L 33/14 |
| 2020/0209747 A1 * | 7/2020 | Hatakeyama ......... G03F 7/0045 |
| 2020/0223796 A1 * | 7/2020 | Fukushima ........... G03F 7/2041 |
| 2020/0249571 A1 * | 8/2020 | Fujiwara ............... G03F 7/0048 |
| 2020/0319550 A1 * | 10/2020 | Fukushima .......... C07D 317/18 |
| 2020/0369605 A1 * | 11/2020 | Sagehashi ............. G03F 7/0382 |
| 2020/0379345 A1 * | 12/2020 | Fukushima ............. G03F 7/039 |

FOREIGN PATENT DOCUMENTS

| | | |
|---|---|---|
| CN | 103787923 A | 5/2014 |
| JP | 2007-145797 A | 6/2007 |
| JP | 2008-281974 A | 11/2008 |
| JP | 2008-281975 A | 11/2008 |
| JP | 4554665 A | 7/2010 |
| JP | 2011-16746 A | 1/2011 |
| JP | 2013-167826 A | 8/2013 |
| TW | 201616222 A | 5/2016 |

OTHER PUBLICATIONS

Tsuda et al., "Journal of Photopolymer Science and Technology", (2004), vol. 17, No. 4, pp. 587. Cited in Specification. (18 pages).
Office Action dated Apr. 1, 2020, issued in counterpart CN application No. 201810970031.8, with English translation (16 pages).

* cited by examiner

*Primary Examiner* — Daborah Chacko-Davis
(74) *Attorney, Agent, or Firm* — Westerman, Hattori, Daniels & Adrian, LLP

(57) ABSTRACT

A resist composition comprising a sulfonium compound of specific structure as PAG has excellent lithography performance factors such as minimal defects, high sensitivity, improved LWR and CDU, and is a quite effective resist material for precise micropatterning.

19 Claims, 32 Drawing Sheets

SULFONIUM COMPOUND, RESIST COMPOSITION, AND PATTERNING PROCESS

CROSS-REFERENCE TO RELATED APPLICATION

This non-provisional application claims priority under 35 U.S.C. § 119(a) on Patent Application No. 2017-161031 filed in Japan on Aug. 24, 2017, the entire contents of which are hereby incorporated by reference.

TECHNICAL FIELD

This invention relates to a sulfonium compound, a resist composition comprising the same, and a pattern forming process using the resist composition.

BACKGROUND ART

While a number of recent efforts are being made to achieve a finer pattern rule in the drive for higher integration and operating speeds in LSI devices, DUV and EUV lithography processes are thought to hold particular promise as the next generation in microfabrication technology. In particular, photolithography using an ArF excimer laser is requisite to the micropatterning technique capable of achieving a feature size of 0.13 μm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Non-Patent Document 1. The ArF immersion lithography is now implemented on the commercial stage. The immersion lithography requires a resist material which is substantially insoluble in water.

In the photolithography using an ArF excimer laser (wavelength 193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polymers of acrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in that the transparency of a resin alone is increased.

Recently a highlight is put on the negative tone resist adapted for organic solvent development as well as the positive tone resist adapted for alkaline development. It would be desirable if a very fine hole pattern, which is not achievable with the positive tone, is resolvable through negative tone exposure. To this end, a positive resist material featuring a high resolution is subjected to organic solvent development to form a negative pattern. An attempt to double a resolution by combining two developments, alkaline development and organic solvent development is under study.

As the ArF resist material for negative tone development with organic solvent, positive ArF resist compositions of the prior art design may be used. Such pattern forming processes are described in Patent Documents 1 to 3.

To meet the current rapid progress of microfabrication technology, development efforts are put on not only the process, but also the resist material. Studies have also been made on photoacid generators (PAGs). Commonly used are sulfonium salts of triphenylsulfonium cation with perfluoroalkanesulfonic acid anion. These salts generate perfluoroalkanesulfonic acids, especially perfluorooctanesulfonic acid (PFOS), which are considered problematic with respect to their non-degradability, biological concentration and toxicity. It is rather restricted to apply these salts to the resist material. Instead, PAGs capable of generating perfluorobutanesulfonic acid are currently used, but are awkward to achieve a high resolution because of substantial diffusion of the generated acid in the resist material. To address the problem, partially fluorinated alkane sulfonic acids and salts thereof are developed. For instance, Patent Document 1 refers to the prior art PAGs capable of generating α,α-difluoroalkanesulfonic acid, such as di(4-t-butylphenyl)iodonium 1,1-difluoro-2-(1-naphthyl)ethanesulfonate and PAGs capable of generating α,α,β,β-tetrafluoroalkanesulfonic acid. Despite a reduced degree of fluorine substitution, these PAGs still have the following problems. Since they do not have a decomposable substituent group such as ester structure, they are unsatisfactory from the aspect of environmental safety due to ease of decomposition. The molecular design to change the size of alkanesulfonic acid is limited. Fluorine-containing starting reactants are expensive.

Incorporating a bulky substituent or polar group into PAG is effective for suppressing acid diffusion. Patent Document 4 describes a PAG capable of generating 2-acyloxy-1,1,3,3,3-pentafluoropropane-1-sulfonic acid, which is fully soluble and stable in resist solvents and allows for a wide span of molecular design. In particular, a PAG having incorporated therein a bulky substituent, 2-(1-adamantyloxy)-1,1,3,3,3-pentafluoropropane-1-sulfonic acid is characterized by slow acid diffusion. A resist composition comprising this PAG, however, is still insufficient in precise control of acid diffusion, and its lithography performance is unsatisfactory when evaluated totally in terms of LWR (as an index of pattern roughness) and resolution.

As the PAG which is effective for controlling acid diffusion, for example, Patent Document 5 describes a sulfonium compound of betaine structure. The betaine type sulfonium compound, however, has a giant molecular structure and can form a dimer in the resist film. It thus has a high acid diffusion controlling ability, but a low solvent solubility, which can cause coating defects and defects after development. Since the betaine type sulfonium compound has a low solubility in resist solvent and a dimer-formable structure, partial agglomeration can occur in the resist film, whereby its uniform dispersion within the resist film is reduced, inviting degradation of LWR and CDU.

CITATION LIST

Patent Document 1: JP-A 2008-281974
Patent Document 2: JP-A 2008-281975
Patent Document 3: JP 4554665 (U.S. Pat. No. 8,227,183)
Patent Document 4: JP-A 2007-145797

Patent Document 5: JP-A 2013-167826
Patent Document 6: JP-A 2011-016746
Non-Patent Document 1: Journal of Photopolymer Science and Technology, Vol. 17, No. 4, p 587 (2004)

DISCLOSURE OF THE INVENTION

An object of the invention is to provide a resist composition which forms a pattern with advantages including sensitivity, LWR, CDU, and minimal defects, when processed by photolithography using high-energy radiation such as KrF excimer laser, ArF excimer laser, EB or EUV as the light source; and a patterning process using the resist composition.

The inventors have found that a resist composition comprising a sulfonium compound of specific structure has excellent lithography performance factors such as minimal defects, sensitivity, CDU and LWR, and is a quite effective resist material for precise micropatterning.

In one aspect, the invention provides a sulfonium compound having the formula (1).

Herein $L^1$ is a straight, branched or cyclic $C_1$-$C_{20}$ divalent hydrocarbon group which may contain a heteroatom-containing moiety, X is a divalent linking group, and Z is a group of sulfonium cation structure having the formula (1A), (1B) or (1C).

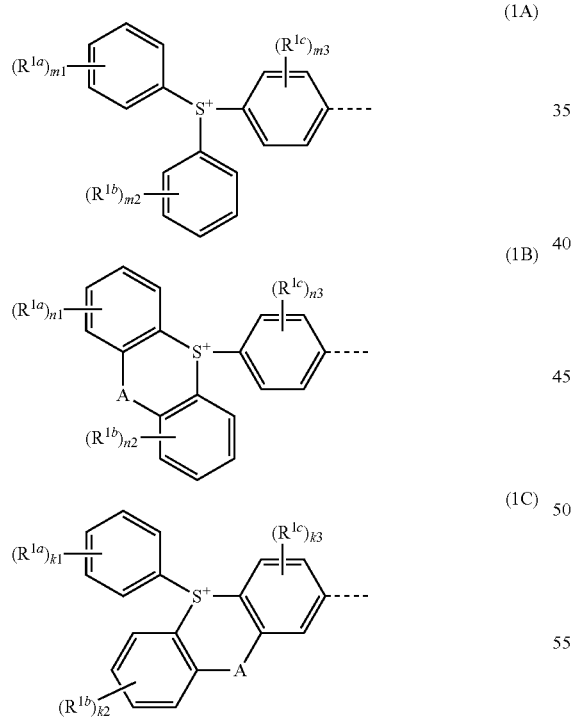

Herein the broken line denotes a valence bond to X; A is a single bond, methylene, carbonyl, sulfinyl, sulfonyl, amino, ether bond, thioether bond, ester bond, carbonate bond, carbamate bond or sulfonic acid ester bond; $R^{1a}$ to $R^{1c}$ are each independently a straight, branched or cyclic $C_1$-$C_{20}$ monovalent hydrocarbon group which may contain a heteroatom-containing moiety, at least one of $R^{1a}$ to $R^{1c}$ being a group of the formula (1-1) shown below, with the proviso that where at least two $R^{1a}$ are included, two of them may bond together to form a ring with carbon atoms on the benzene ring to which they are attached, where at least two $R^{1b}$ are included, two of them may bond together to form a ring with carbon atoms on the benzene ring to which they are attached, and where at least two $R^{1c}$ are included, two of them may bond together to form a ring with carbon atoms on the benzene ring to which they are attached; m1, m2 and m3 are integers in the range: $0 \le m1 \le 5$, $0 \le m2 \le 5$, $0 \le m3 \le 4$, and $m1+m2+m3 \ge 1$; n1, n2 and n3 are integers in the range: $0 \le n1 \le 4$, $0 \le n2 \le 4$, $0 \le n3 \le 4$, and $n1+n2+n3 \ge 1$; k1, k2 and k3 are integers in the range: $0 \le k1 \le 5$, $0 \le k2 \le 4$, $0 \le k3 \le 3$, and $k1+k2+k3 \ge 1$.

Herein $L^2$ is a straight, branched or cyclic $C_1$-$C_{20}$ divalent hydrocarbon group which may contain a heteroatom-containing moiety, $R^{f1}$ and $R^{f2}$ are each independently hydrogen, a straight, branched or cyclic $C_1$-$C_{20}$ alkyl, fluorine, or straight, branched or cyclic $C_1$-$C_{20}$ fluoroalkyl having at least one fluorine atom, at least one of $R^{f1}$ and $R^{f2}$ being fluorine or fluoroalkyl, the broken line denotes a valence bond.

In a preferred embodiment, $R^{f1}$ and $R^{f2}$ are trifluoromethyl.

In a preferred embodiment, the sulfonium compound has the formula (2):

wherein X and Z are as defined above, $R^{f3}$, $R^{f4}$, $R^{f5}$ and $R^{f6}$ are each independently hydrogen, fluorine or trifluoromethyl.

In a preferred embodiment, both $R^{f5}$ and $R^{f6}$ are fluorine.

In a second aspect, the invention provides a photoacid generator comprising the sulfonium compound defined above.

In a third aspect, the invention provides a resist composition comprising the photoacid generator.

In a preferred embodiment, the resist composition may further comprise a base resin containing a polymer comprising recurring units having the formula (a) and recurring units having the formula (b).

-continued

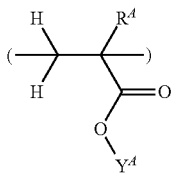
(b)

Herein $R^A$ is hydrogen, fluorine, methyl or trifluoromethyl, $Z^A$ is a single bond, phenylene group, naphthylene group or (backbone)-C(=O)—O—Z'—, Z' is a straight, branched or cyclic $C_1$-$C_{10}$ alkylene group which may contain a hydroxyl moiety, ether bond, ester bond or lactone ring, or phenylene group or naphthylene group, $X^A$ is an acid labile group, and $Y^A$ is hydrogen or a polar group having at least one structure selected from the group consisting of hydroxyl, cyano, carbonyl, carboxyl, ether bond, ester bond, sulfonic acid ester bond, carbonate bond, lactone ring, sultone ring and carboxylic anhydride.

The resist composition may further comprise an organic solvent.

The resist composition may further comprise a photoacid generator other than the photoacid generator defined above.

Preferably, the other photoacid generator has the formula (4) or (5).

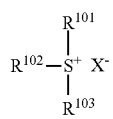
(4)

Herein $R^{101}$, $R^{102}$ and $R^{103}$ are each independently a straight, branched or cyclic $C_1$-$C_{20}$ monovalent hydrocarbon group which may contain a heteroatom, any two of $R^{101}$, $R^{102}$ and $R^{103}$ may bond together to form a ring with the sulfur atom to which they are attached, and $X^-$ is an anion selected from the formulae (4A) to (4D):

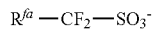
(4A)

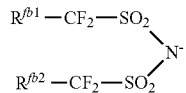
(4B)

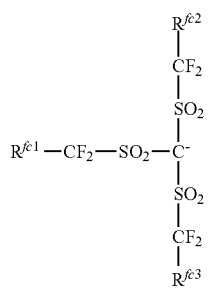
(4C)

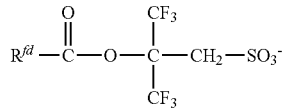
(4D)

wherein $R^{fa}$, $R^{fb1}$, $R^{fb2}$, $R^{fc1}$, $R^{fc2}$ and $R^{fc3}$ are each independently fluorine or a straight, branched or cyclic $C_1$-$C_{40}$ monovalent hydrocarbon group which may contain a heteroatom, or a pair of $R^{fb1}$ and $R^{fb2}$, or $R^{fc1}$ and $R^{fc2}$ may bond together to form a ring with the carbon atom to which they are attached and any intervening atoms, $R^{fd}$ is a straight, branched or cyclic $C_1$-$C_{40}$ monovalent hydrocarbon group which may contain a heteroatom,

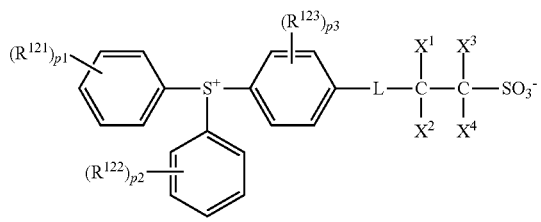
(5)

wherein $R^{121}$, $R^{122}$ and $R^{123}$ are each independently a straight, branched or cyclic $C_1$-$C_{20}$ alkyl group, L is a single bond, ether bond, or a straight, branched or cyclic $C_1$-$C_{20}$ divalent hydrocarbon group which may contain a heteroatom, $X^1$, $X^2$, $X^3$ and $X^4$ are each independently hydrogen, fluorine or trifluoromethyl, at least one of $X^1$, $X^2$, $X^3$ and $X^4$ is fluorine or trifluoromethyl, p1 and p2 are each independently an integer of 0 to 5, and p3 is an integer of 0 to 4.

In a preferred embodiment, the resist composition may further comprise an onium salt having the formula (6) or (7).

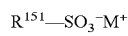
(6)

(7)

Herein $R^{151}$ and $R^{152}$ are each independently hydrogen or a straight, branched or cyclic $C_1$-$C_{40}$ monovalent hydrocarbon group which may contain a heteroatom, exclusive of hydrocarbon groups in which the hydrogen atom in bond with the carbon atom at α-position relative to the sulfo group is replaced by a fluorine atom or fluoroalkyl moiety, and $M^+$ is an onium cation.

In a preferred embodiment, the resist composition may further comprise an amine compound.

In a preferred embodiment, the resist composition may further comprise a surfactant which is insoluble or substantially insoluble in water and soluble in alkaline developer, and/or a surfactant which is insoluble or substantially insoluble in water and alkaline developer.

In a fourth aspect, the invention provides a pattern forming process comprising the steps of applying the resist composition defined above onto a substrate, prebaking to form a resist film, exposing a selected region of the resist film to KrF excimer laser, ArF excimer laser, EB or EUV, baking, and developing the exposed resist film in a developer.

In a preferred embodiment, the developing step uses an alkaline aqueous solution as the developer, thereby forming a positive pattern in which an exposed region of the resist film is dissolved away and an unexposed region of the resist film is not dissolved.

In another preferred embodiment, the developing step uses an organic solvent as the developer, thereby forming a negative pattern in which an unexposed region of the resist film is dissolved away and an exposed region of the resist film is not dissolved.

Typically, the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

In a preferred embodiment, the exposure step is carried out by immersion lithography while a liquid having a refractive index of at least 1.0 is held between the resist film and a projection lens. In a more preferred embodiment, the process may further comprise the step of coating a protective film on the resist film prior to the exposure step, wherein immersion lithography is carried out while the liquid is held between the protective film and the projection lens.

Advantageous Effects of Invention

Since the inventive sulfonium compound is fully compatible with a resist solvent and developer, it causes minimal coating defects and minimal defects resulting from any residues after development. Owing to a uniform dispersion ability, a pattern profile with improved CDU and reduced LWR can be constructed.

DESCRIPTION OF THE PREFERRED EMBODIMENTS

Figure 1:
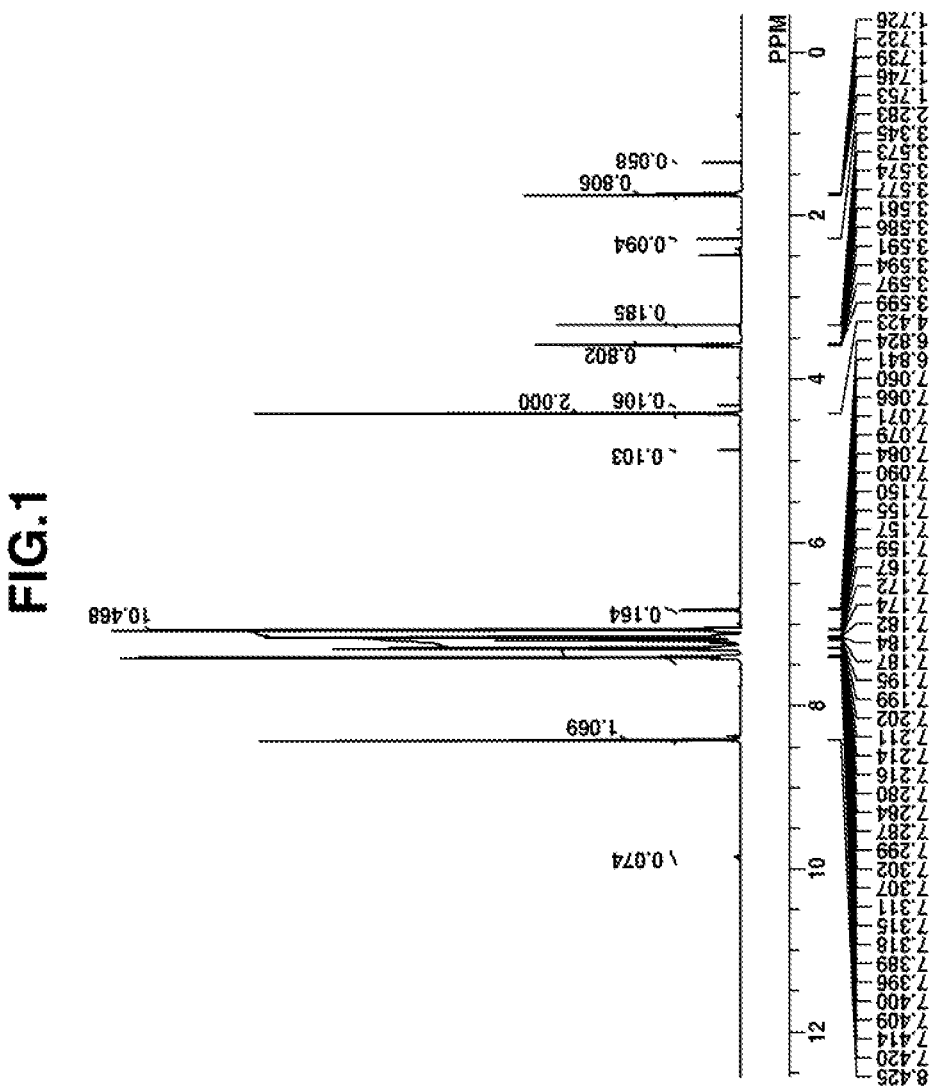
FIGS. 1 and 2 are diagrams showing $^1$H- and $^{19}$F-NMR spectra of Intermediate A in Example 1-1-1, respectively.

The singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, the broken line denotes a valence bond; Me stands for methyl, Ac for acetyl, and Ph for phenyl. It is understood that for some structures represented by chemical formulae, there can exist enantiomers and diastereomers because of the presence of asymmetric carbon atoms. In such a case, a single formula collectively represents all such isomers. The isomers may be used alone or in admixture.

The abbreviations have the following meaning.
EB: electron beam
UV: ultraviolet
EUV: extreme ultraviolet
PAG: photoacid generator
PEB: post-exposure bake
LER: line edge roughness
LWR: line width roughness
CDU: critical dimension uniformity Sulfonium Compound The invention provides a sulfonium compound having the formula (1).

In formula (1), $L^1$ is a straight, branched or cyclic $C_1$-$C_{20}$ divalent hydrocarbon group which may contain a heteroatom-containing moiety. X is a divalent linking group.

In formula (1), Z is a group of sulfonium cation structure having the formula (1A), (1B) or (1C).

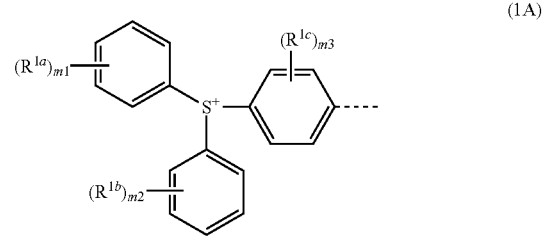

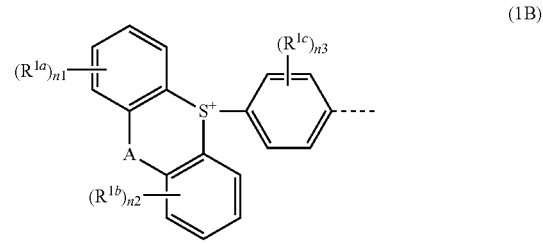

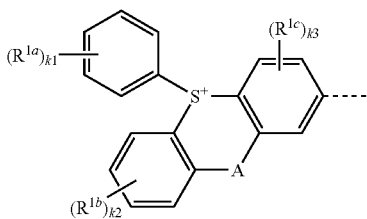

(1C)

In formulae (1A) to (1C), the broken line denotes a valence bond to X. "A" is a single bond, methylene, carbonyl, sulfinyl, sulfonyl, amino, ether bond, thioether bond, ester bond, carbonate bond, carbamate bond or sulfonic acid ester bond.

In formulae (1A) to (1C), $R^{1a}$ to $R^{1c}$ are each independently a straight, branched or cyclic $C_1$-$C_{20}$ monovalent hydrocarbon group which may contain a heteroatom-containing moiety. Where at least two $R^{1a}$ are included, two of them may bond together to form a ring with carbon atoms on the benzene ring to which they are attached. Where at least two $R^{1b}$ are included, two of them may bond together to form a ring with carbon atoms on the benzene ring to which they are attached. Where at least two $R^{1c}$ are included, two of them may bond together to form a ring with carbon atoms on the benzene ring to which they are attached. The subscripts m1, m2 and m3 are integers in the range: $0 \leq m1 \leq 5$, $0 \leq m2 \leq 5$, $0 \leq m3 \leq 4$, and $m1+m2+m3 \geq 1$; n1, n2 and n3 are integers in the range: $0 \leq n1 \leq 4$, $0 \leq n2 \leq 4$, $0 \leq n3 \leq 4$, and $n1+n2+n3 \geq 1$; k1, k2 and k3 are integers in the range: $0 \leq k1 \leq 5$, $0 \leq k2 \leq 4$, $0 \leq k3 \leq 3$, and $k1+k2+k3 \geq 1$.

At least one of $R^{1a}$ to $R^{1c}$ is a group of the formula (1-1).

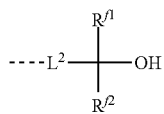

(1-1)

Herein $L^2$ is a straight, branched or cyclic $C_1$-$C_{20}$ divalent hydrocarbon group which may contain a heteroatom-containing moiety. $R^{f1}$ and $R^{f2}$ are each independently hydrogen, a straight, branched or cyclic $C_1$-$C_{20}$ alkyl, fluorine, or straight, branched or cyclic $C_1$-$C_{20}$ fluoroalkyl having at least one fluorine atom, at least one of $R^{f1}$ and $R^{f2}$ being fluorine or fluoroalkyl.

Suitable divalent hydrocarbon groups $L^1$ and $L^2$ include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic hydrocarbon groups such as cyclopentanediyl, cyclohexanediyl, norbornanediyl, and adamantanediyl; and unsaturated cyclic hydrocarbon groups such as phenylene and naphthylene. Also included are the foregoing groups in which at least one hydrogen atom is replaced by an alkyl group such as methyl, ethyl, propyl, n-butyl or t-butyl, or in which at least one hydrogen atom is replaced by a moiety containing a heteroatom such as oxygen, sulfur, nitrogen or halogen, or in which at least one carbon atom is replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic acid anhydride or haloalkyl moiety.

Suitable divalent linking groups X include an ether bond, thioether bond, ester bond, sulfonic acid ester bond, amide bond, carbonate bond, and carbamate bond. Inter alia, ether, thioether and ester bonds are preferred.

Suitable $C_1$-$C_{20}$ alkyl groups, as represented by $R^{f1}$ and $R^{f2}$ in formula (1-1), include methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl. Suitable $C_1$-$C_{20}$ fluoroalkyl groups include substituted forms of the foregoing alkyl groups in which some hydrogen is substituted by fluorine, with trifluoromethyl being preferred.

Of the groups having formula (1-1), groups having the formula (1-2) are especially preferred.

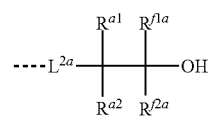

(1-2)

In formula (1-2), $L^{2a}$ is an ester, ether or thioether bond, with the ether bond being preferred. $R^{a1}$ and $R^{a2}$ are each independently hydrogen or methyl, preferably hydrogen. $R^{f1a}$ and $R^{f2a}$ are each independently fluorine or a straight, branched or cyclic $C_1$-$C_{20}$ fluoroalkyl group (having at least one fluorine atom), preferably fluorine or trifluoromethyl, with trifluoromethyl being most preferred.

In formulae (1A) to (1C), $R^{1a}$ to $R^{1c}$ are monovalent hydrocarbon groups. Suitable monovalent hydrocarbon groups include alkyl groups such as methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl and adamantylmethyl; and aryl groups such as phenyl, naphthyl and anthracenyl. Also included are substituted forms of the foregoing in which at least one (one or more) hydrogen is replaced by a moiety containing a heteroatom such as oxygen, sulfur, nitrogen or halogen, or in which at least one carbon atom is replaced by a moiety containing a heteroatom such as oxygen, sulfur, or nitrogen; so that the group may contain a halogen atom, hydroxyl, cyano, carbonyl, ether bond, ester bond, sulfonic acid ester bond, carbonate bond, lactone ring, sultone ring, carboxylic acid anhydride, or haloalkyl moiety.

Of the sulfonium compounds having formula (1), compounds having the formula (2) are preferred.

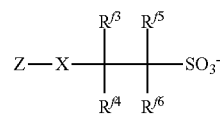

(2)

Herein X and Z are as defined above, $R^{f3}$, $R^{f4}$, $R^{f5}$ and $R^{f6}$ are each independently hydrogen, fluorine or trifluoromethyl.

Preferably at least one of $R^{f3}$, $R^{f4}$, $R^{f5}$ and $R^{f6}$ is fluorine or trifluoromethyl because the acid generated by the corresponding sulfonium compound has a higher acidity sufficient for effective cleavage of acid labile groups on the base resin. More preferably both $R^{f5}$ and $R^{f6}$ are fluorine. That is, a structure having fluorine at α-position of the sulfo group as represented by the following formula (3) is preferred because the acid generated therefrom has a higher acidity.

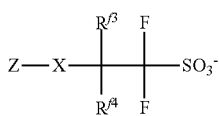
(3)

Herein X, Z, $R^{f3}$ and $R^{f4}$ are as defined above.

Examples of the sulfonium compound having formula (1) wherein Z is a group of formula (1A) are shown below, but not limited thereto.

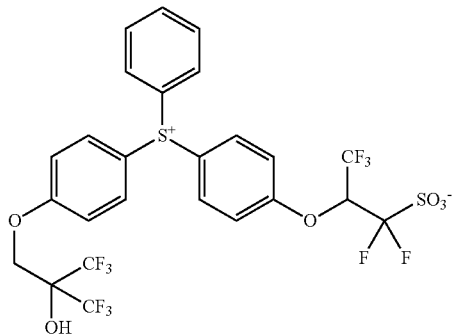

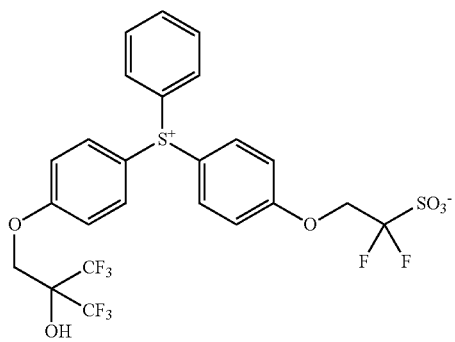

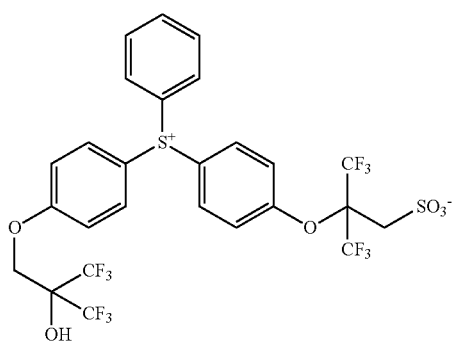

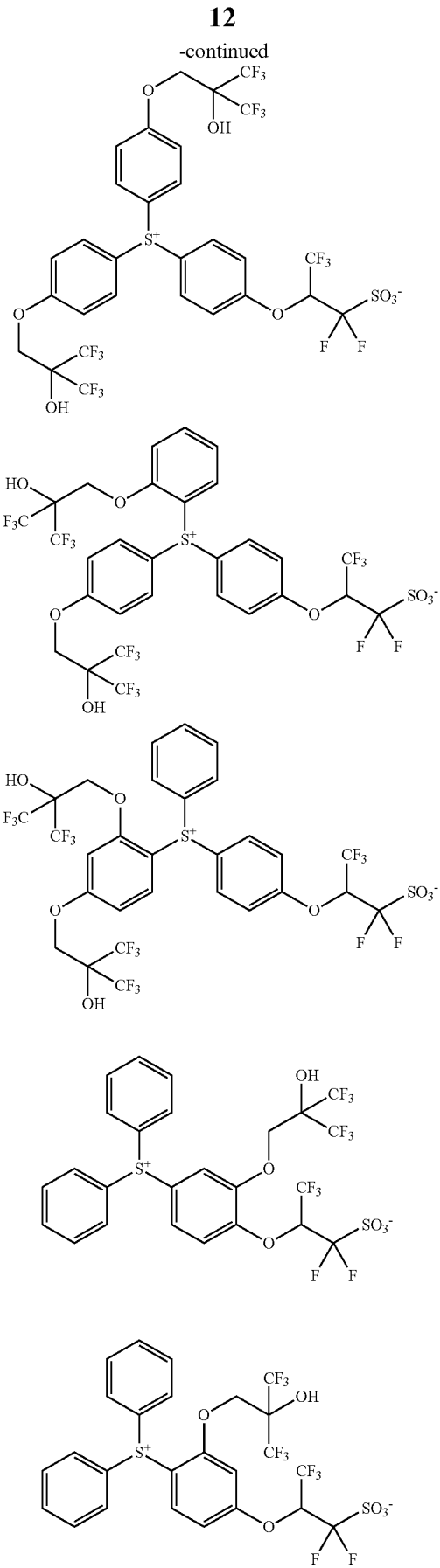

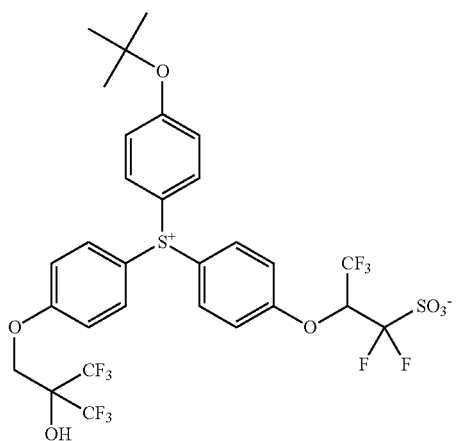
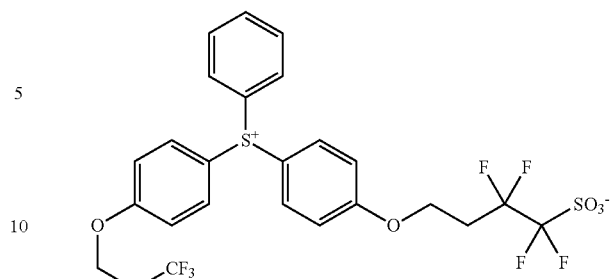
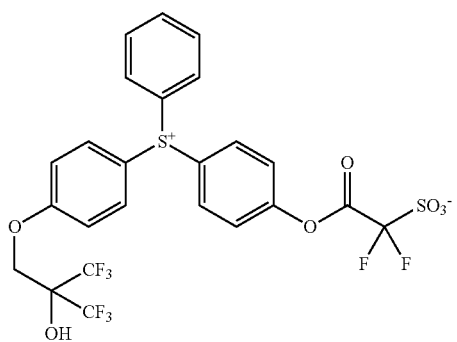
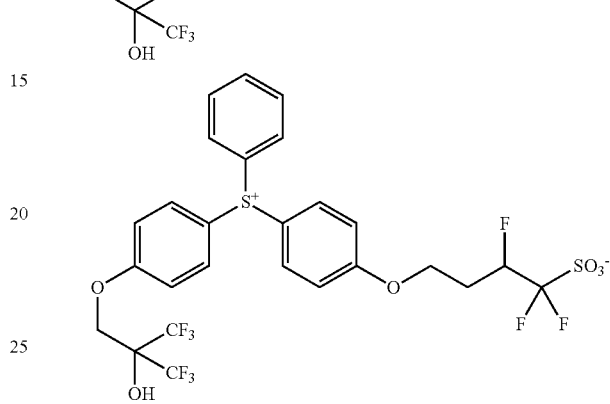
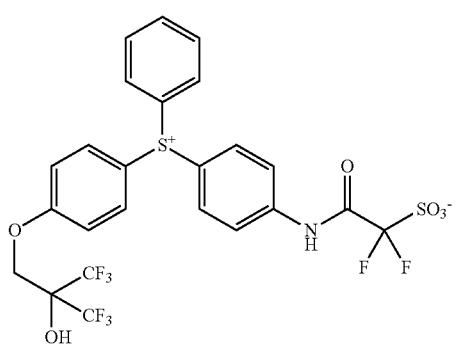
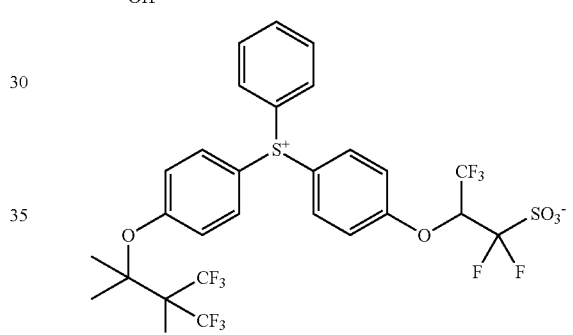
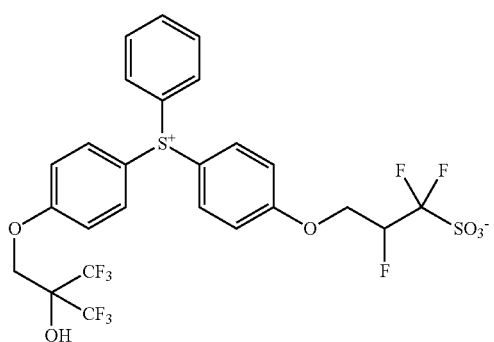
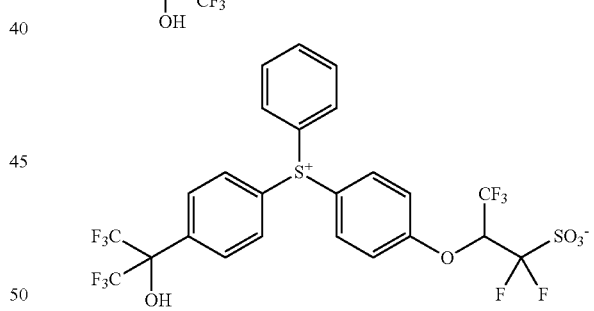
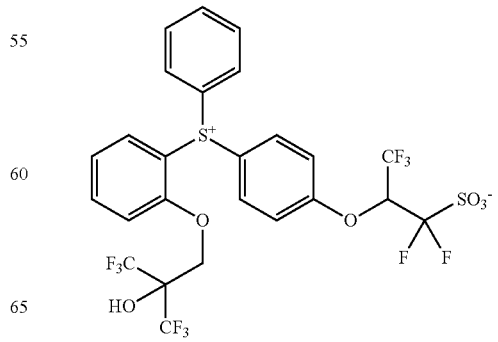

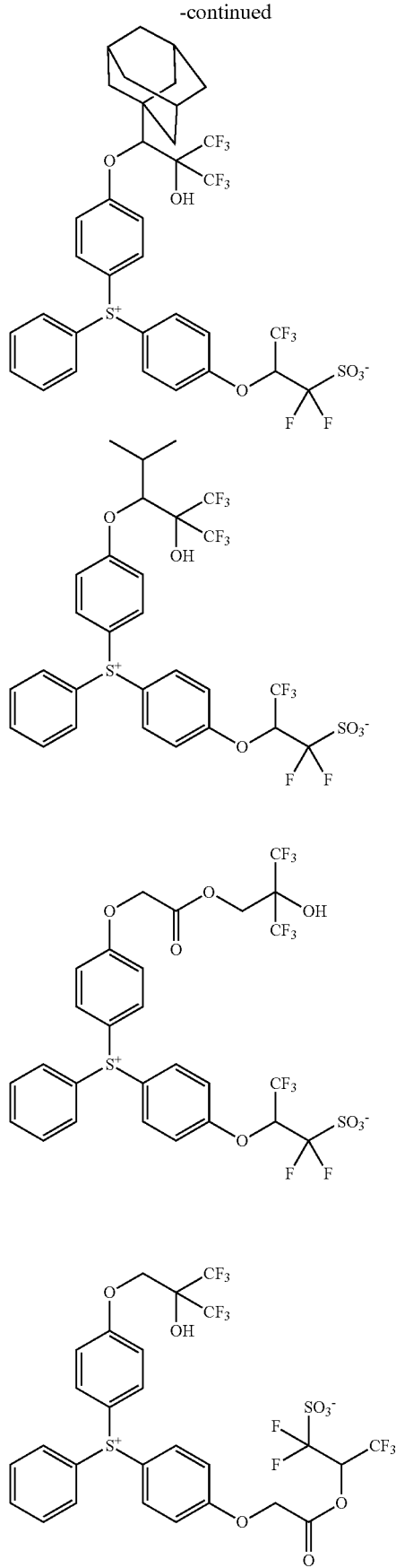
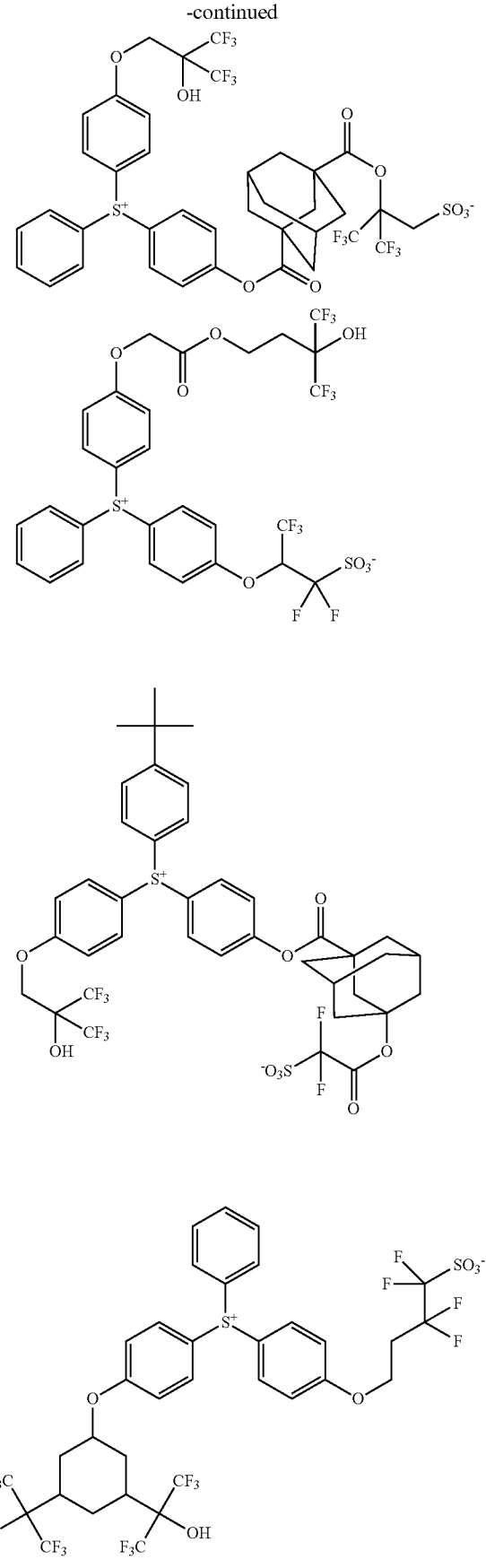

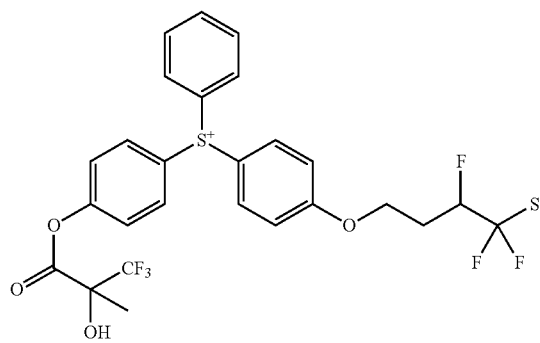

Examples of the sulfonium compound having formula (1) wherein Z is a group of formula (1B) are shown below, but not limited thereto.

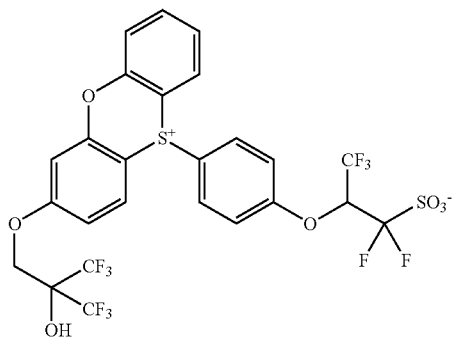

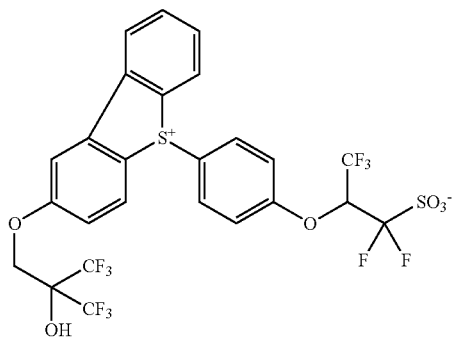

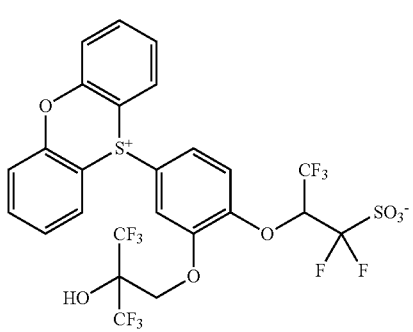

Examples of the sulfonium compound having formula (1) wherein Z is a group of formula (1C) are shown below, but not limited thereto.

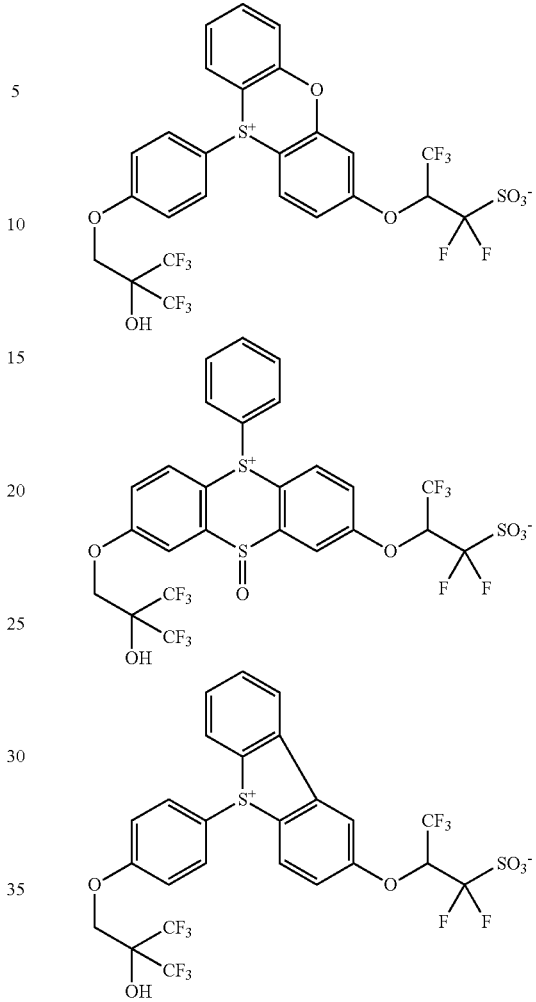

The sulfonium compound of the invention is characterized by having a betaine structure and a fluoroalcohol unit. Because of the betaine structure, a bulky structure is retained even after acid generation, indicating that acid diffusion is controllable at a high level. In general, when the generated acid is of bulky structure, acid diffusion is reduced. In addition, owing to the fluoroalcohol unit which is highly compatible, the sulfonium compound has a higher solubility in resist solvent and developer, leading to fewer defects.

The resist composition comprising the betaine structure sulfonium compound of the invention is superior in sensitivity, CDU and LWR to prior art resist compositions comprising an acid generator of betaine structure, as described in Patent Documents 5 and 6, for example. A reduction in coating defects and post-development defects is another advantage. Although the reason is not well understood, the following two reasons are probable.

The sulfonium compound of the invention has a fluorinated alcohol unit, i.e., partial structure having formula (1-1), which exerts an effect of improving solvent solubility. In general, because of their high polarity, betaine compounds have poor solubility in solvents, for example, in propylene glycol monomethyl ether acetate (PGMEA) commonly used as the casting solvent for resist compositions. In contrast, the inventive sulfonium compound has a fluorinated alcohol unit which contributes to an improvement in solvent solubility. As a result, the sulfonium compound is uniformly dispersed in the resist composition, probably leading to improvements in CDU and LWR. The improved compatibility leads to a reduction of defects originating from the PAG.

Another reason which can be contemplated herein is that the sulfonium compound of the invention has a fluorinated alcohol unit having formula (1-1) whereby the hydroxyl group in that structure forms a hydrogen bond with the acid generated upon exposure, leading to acid diffusion suppression. As a result, various lithography performance factors are improved.

Further, when the compound has a partial structure of formula (1-2), which is preferred among the structures of formula (1-1), some protons generated upon exposure are trapped to form a 5-membered ring, as shown by the following formula with the oxygen or sulfur atom in $L^{2a}$ moiety and the oxygen atom in the terminal hydroxyl group, leading to suppression of acid diffusion and improvements in various lithography performance factors.

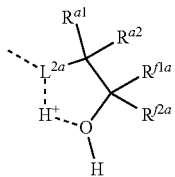

Herein $L^{2a}$, $R^{a1}$, $R^{a2}$, $R^{f1a}$ and $R^{f2a}$ are as defined above.

Described below is the synthesis of the inventive sulfonium compound. Reference is made to the synthesis of the compound of formula (1) wherein Z is a group of formula (1A) and X is an ether bond as a typical example. While there are several synthesis routes, one typical route is by reacting a sulfoalkyloxybenzene or sulfoaryloxybenzene with a diaryl sulfoxide in the presence of an acid catalyst. The reaction is outlined below as Scheme A.

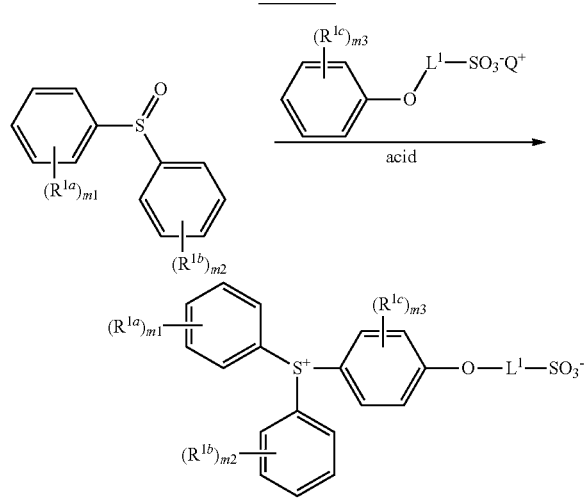

Herein $R^{1a}$, $R^{1b}$, $R^{1c}$, m1, m2, m3 and $L^1$ are as defined above. $Q^+$ is an alkali metal ion such as sodium or potassium ion, ammonium ion or hydrogen ion. In this reaction, diphosphorus pentoxide-methanesulfonic acid or the like may be used as the acid catalyst.

Another route is by nucleophilic displacement reaction of a 4-fluorophenyldiphenylsulfonium compound with a sulfoalcohol. The reaction is outlined below as Scheme B.

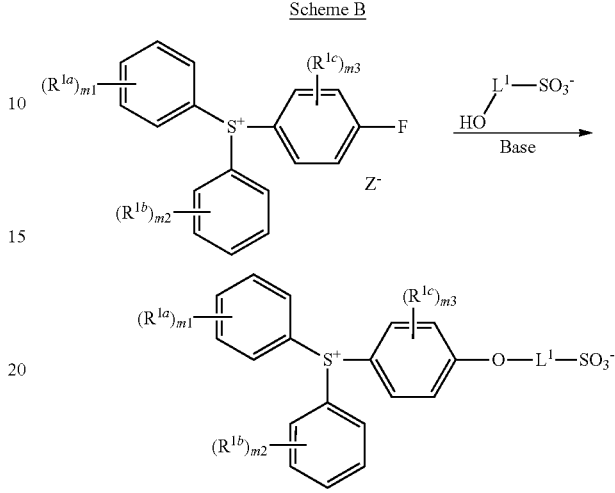

Herein $R^{1a}$, $R^{1b}$, $R^{1c}$, m1, m2, m3, and $L^1$ are as defined above. $Z^-$ is a chloride, bromide, iodide, methylsulfate or p-toluenesulfonate ion. Although Scheme B refers to the 4-fluorophenyldiphenylsulfonium compound, similar reaction is possible with any 4-halophenyldiphenylsulfonium compounds.

Further, the sulfonium compound may be synthesized by intramolecular reaction according to the following Scheme C.

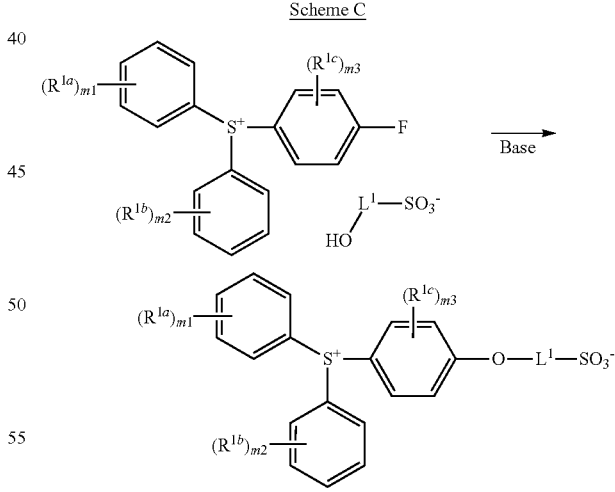

Herein $R^{1a}$, $R^{1b}$, $R^{1c}$ m1, m2, m3, and $L^1$ are as defined above.

As still further synthesis routes, the sulfonium compound may be synthesized by utilizing addition reaction of a sulfite or hydrogensulfite ion to a sulfonium salt having terminal olefin, or reaction of a corresponding halide with a sulfur compound. For example, the addition reaction is outlined below as Scheme D.

Scheme D

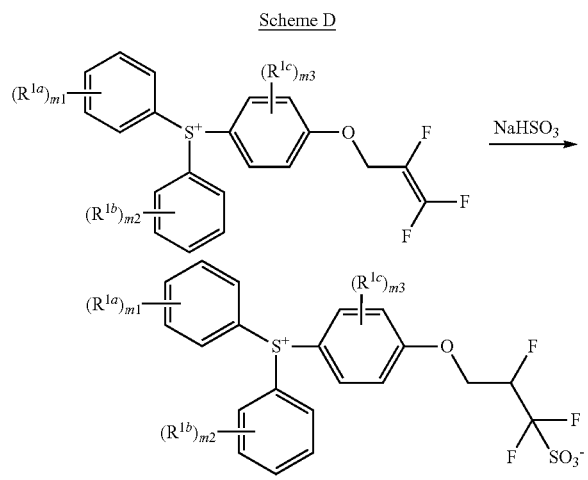

Herein $R^{1a}$, $R^{1b}$, $R^{1c}$, m1, m2, and m3 are as defined above.

The synthesis routes described above are merely exemplary, and the method of preparing the sulfonium compound of the invention is not limited thereto.

Resist Composition

Another embodiment of the invention is a resist composition comprising (A) a photoacid generator in the form of a sulfonium compound having formula (1) as an essential component. The resist composition may further comprise:

(B) a base resin, (C) an organic solvent, (D) a photoacid generator other than the sulfonium compound having formula (1) (also referred to as second photoacid generator), (E) a quencher, and (F) a surfactant which is insoluble or substantially insoluble in water and soluble in alkaline developer, and/or a surfactant which is insoluble or substantially insoluble in water and alkaline developer. Components (D), (E), and (F) are optional, that is, may be added if necessary.

In the resist composition, an appropriate amount of the PAG as component (A) is 0.1 to 40 parts by weight, more preferably 1 to 20 parts by weight per 100 parts by weight of the base resin (B). As long as the amount is within the range, component (A) exerts a full function of photoacid generator, eliminating any performance degradations including a drop of sensitivity, solubility shortage, and foreign particles. The PAG may be used alone or in admixture of two or more.

(B) Base Resin

The base resin used herein as component (B) preferably contains a polymer comprising recurring units having the formula (a) and recurring units having the formula (b).

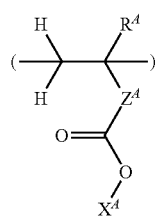

(a)

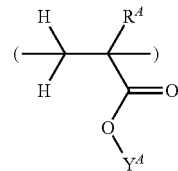

(b)

In formulae (a) and (b), $R^A$ is hydrogen, fluorine, methyl or trifluoromethyl. $Z^A$ is a single bond, phenylene group, naphthylene group or (backbone)-C(=O)—O—Z'—, wherein Z' is a straight, branched or cyclic $C_1$-$C_{10}$ alkylene group which may contain a hydroxyl moiety, ether bond, ester bond or lactone ring, or phenylene group or naphthylene group. $X^A$ is an acid labile group. $Y^A$ is hydrogen or a polar group having at least one structure selected from among hydroxyl, cyano, carbonyl, carboxyl, ether bond, ester bond, sulfonic acid ester bond, carbonate bond, lactone ring, sultone ring and carboxylic anhydride.

Examples of the structure having formula (a) wherein $Z^A$ is a variant are shown below, but not limited thereto. Notably, $R^A$ and $X^A$ are as defined above.

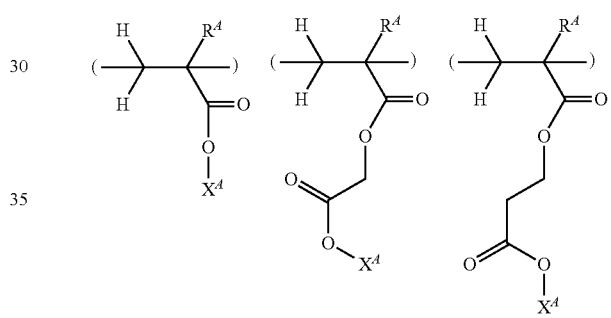

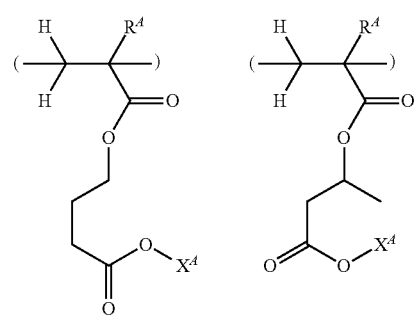

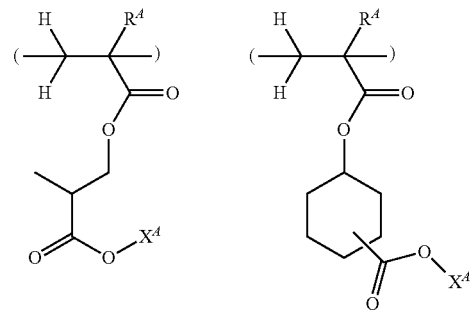

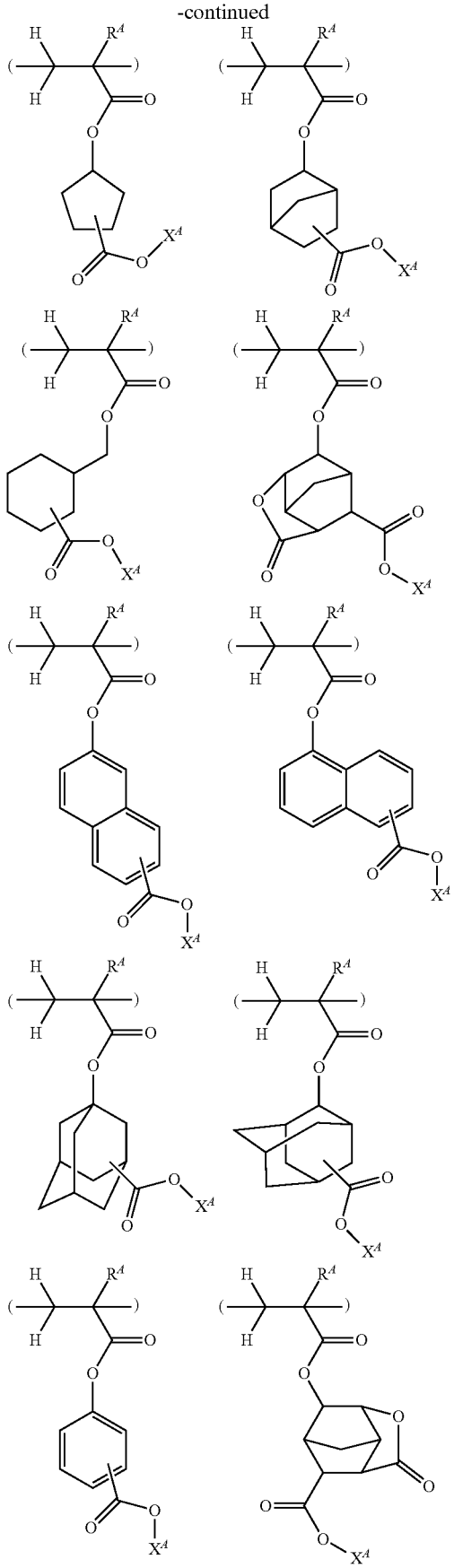
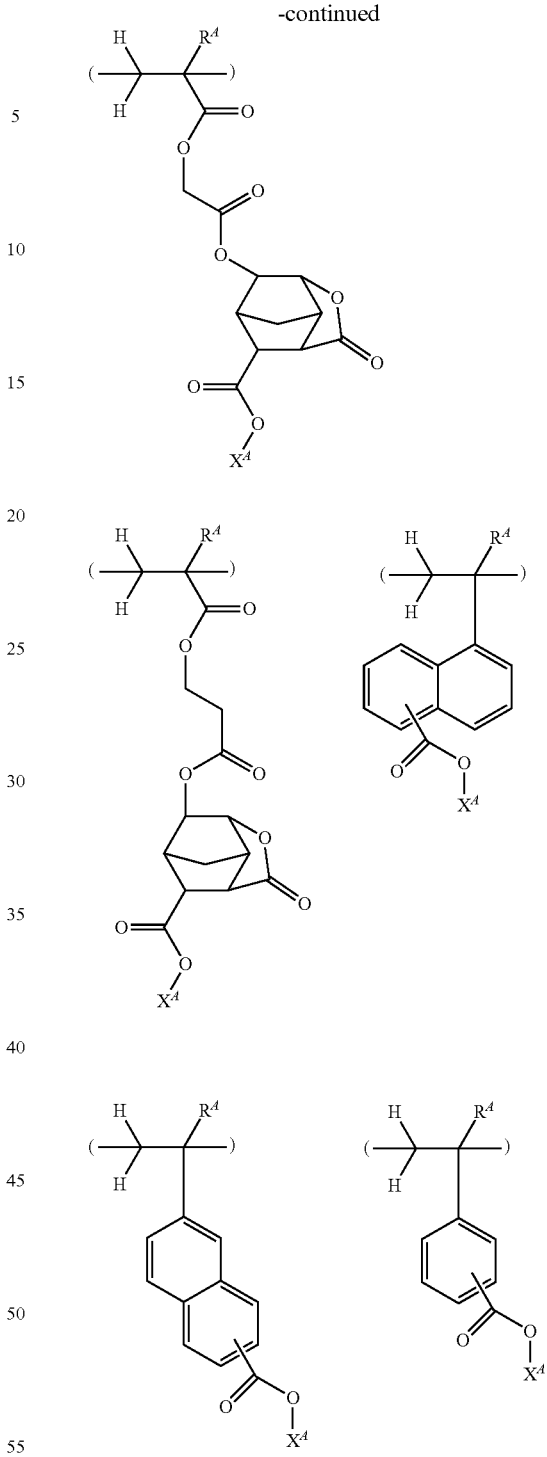

Under the action of acid, a polymer comprising recurring units of formula (a) is decomposed to generate carboxylic acid, turning to be alkali soluble.

The acid labile group $X^A$ may be selected from a variety of such groups. Examples of the acid labile group include groups of the following formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

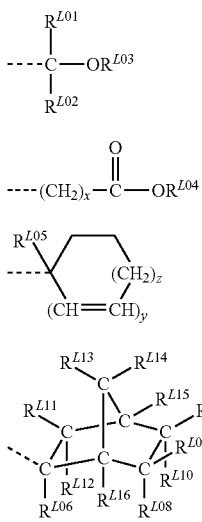

(L1)

(L2)

(L3)

(L4)

In formula (L1), $R^{L01}$ and $R^{L02}$ each are hydrogen or a straight, branched or cyclic alkyl group of 1 to 18 carbon atoms, preferably 1 to 10 carbon atoms. Exemplary alkyl groups include methyl, ethyl, propyl, isopropyl, n-butyl, s-butyl, t-butyl, cyclopentyl, cyclohexyl, 2-ethylhexyl, n-octyl, norbornyl, tricyclodecanyl, tetracyclododecanyl, and adamantyl.

$R^{L03}$ is a monovalent hydrocarbon group of 1 to 18 carbon atoms, preferably 1 to 10 carbon atoms, which may contain a heteroatom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like, or in which at least one carbon atom is replaced by a heteroatom such as oxygen. Suitable alkyl groups are as exemplified above for $R^{L01}$ and $R^{L02}$. Illustrative examples of the substituted alkyl groups are shown below.

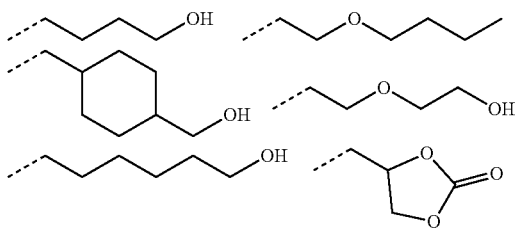

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Ring-forming participants of $R^{L01}$, $R^{L02}$ and $R^{L03}$ represent a straight or branched alkylene group of 1 to 18 carbon atoms, preferably 1 to 10 carbon atoms.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are t-butyl, t-pentyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-t-butylsilyl. Exemplary oxoalkyl groups are 3-oxocyclohexyl, 4-methyl-2-oxooxan-4-yl, and 5-methyl-2-oxooxolan-5-yl. Letter x is an integer of 0 to 6.

In formula (L3), $R^{L05}$ is a substituted or unsubstituted, straight, branched or cyclic $C_1$-$C_8$ alkyl group or a substituted or unsubstituted $C_6$-$C_{20}$ aryl group. Examples of the optionally substituted alkyl group include straight, branched or cyclic alkyl groups such as methyl, ethyl, propyl, isopropyl, n-butyl, s-butyl, t-butyl, t-pentyl, n-pentyl, n-hexyl, cyclopentyl, and cyclohexyl, and substituted forms of such groups in which some hydrogen atoms are substituted by hydroxyl, alkoxy, carboxyl, alkoxycarbonyl, oxo, amino, alkylamino, cyano, mercapto, alkylthio, sulfo or the like. Examples of the optionally substituted aryl groups include phenyl, methylphenyl, naphthyl, anthryl, phenanthryl, and pyrenyl, and substituted forms of such groups in which some hydrogen atoms are substituted by hydroxyl, alkoxy, carboxyl, alkoxycarbonyl, oxo, amino, alkylamino, cyano, mercapto, alkylthio, sulfo or the like. Letter y is equal to 0 or 1, z is an integer of 0 to 3, and 2y+z is equal to 2 or 3.

In formula (L4), $R^{L06}$ is an optionally substituted straight, branched or cyclic $C_1$-$C_8$ alkyl group or optionally substituted $C_6$-$C_{20}$ aryl group. Examples of these groups are the same as exemplified for $R^{L05}$.

$R^{L07}$ to $R^{L16}$ independently represent hydrogen or optionally substituted $C_1$-$C_{15}$ monovalent hydrocarbon groups. Exemplary hydrocarbon groups are straight, branched or cyclic alkyl groups such as methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxyl, alkoxycarbonyl, oxo, amino, alkylamino, cyano, mercapto, alkylthio, sulfo or the like. Alternatively, two of $R^{L07}$ to $R^{L16}$, taken together, form a ring with the carbon atom to which they are attached (for example, a pair of $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, or $R^{L13}$ and $R^{L14}$ form a ring). Ring-forming participants of $R^{L07}$ to $R^{L16}$ represent a $C_1$-$C_{15}$ divalent hydrocarbon group, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or $R^{L14}$ and $R^{L15}$).

Of the acid labile groups of formula (L1), the straight and branched ones are exemplified by the following groups.

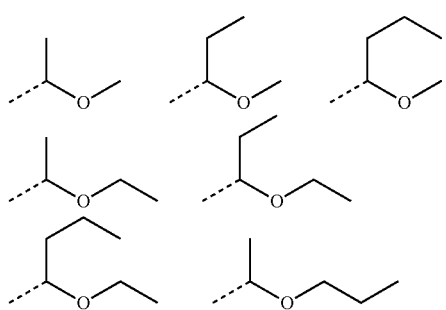

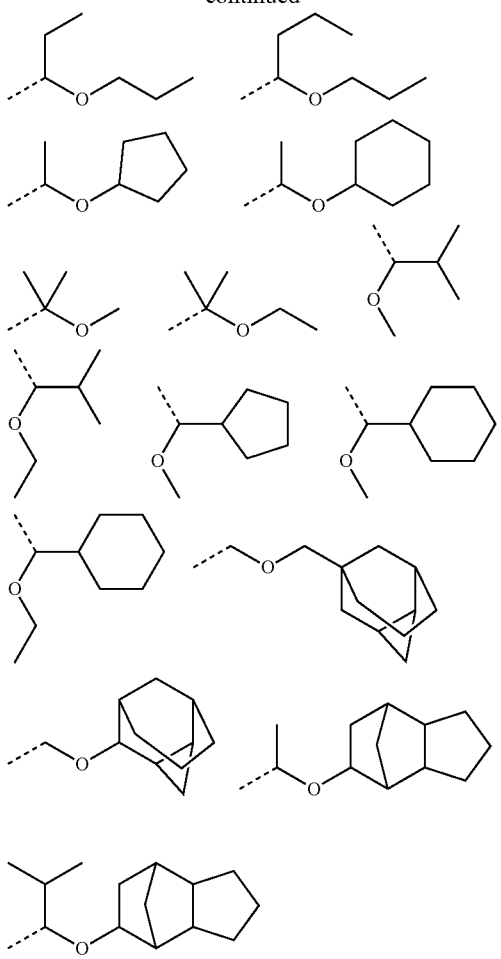

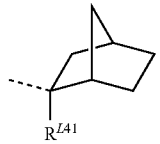

(L4-1)

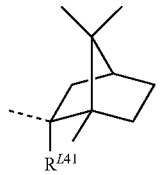

(L4-2)

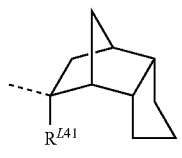

(L4-3)

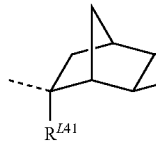

(L4-4)

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile group of formula (L2) include t-butoxycarbonyl, t-butoxycarbonylmethyl, t-pentyloxycarbonyl, t-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile group of formula (L3) include 1-methylcyclopentyl, 1-ethylcyclopentyl, 1-n-propylcyclopentyl, 1-isopropylcyclopentyl, 1-n-butylcyclopentyl, 1-s-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups having formula (L4), groups having the following formulae (L4-1) to (L4-4) are preferred.

In formulae (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, s-butyl, t-butyl, t-pentyl, n-pentyl, n-hexyl, cyclopentyl and cyclohexyl.

For formulae (L4-1) to (L4-4), there can exist enantiomers and diastereomers. Each of formulae (L4-1) to (L4-4) collectively represents all such stereoisomers. When $X^A$ is an acid labile group of formula (L4), a plurality of stereoisomers may be contained.

For example, the formula (L4-3) represents one or a mixture of two selected from groups having the following formulae (L4-3-1) and (L4-3-2).

Similarly, the formula (L4-4) represents one or a mixture of two or more selected from groups having the following formulae (L4-4-1) to (L4-4-4).

(L4-4-1)
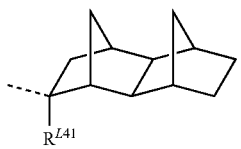

(L4-4-2)
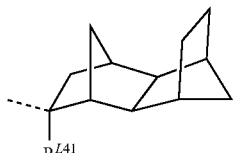

(L4-4-3)
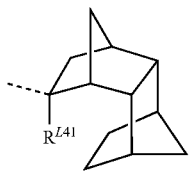

(L4-4-4)
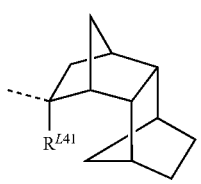

Herein $R^{L41}$ is as defined above.

Each of formulae (L4-1) to (L4-4), (L4-3-1) and (L4-3-2), and (L4-4-1) to (L4-4-4) collectively represents an enantiomer thereof and a mixture of enantiomers.

It is noted that in the above formulae (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulae (L4-1-endo) to (L4-4-endo). For good reactivity, an exo proportion of at least 50 mol % is preferred, with an exo proportion of at least 80 mol % being more preferred.

(L4-1-endo)
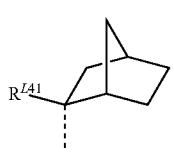

(L4-2-endo)
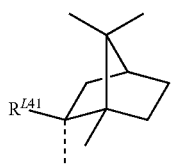

(L4-3-endo)
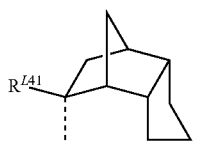

(L4-4-endo)
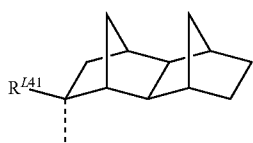

Herein $R^{L41}$ is as defined above.

Illustrative, non-limiting examples of the acid labile group of formula (L4) are given below.

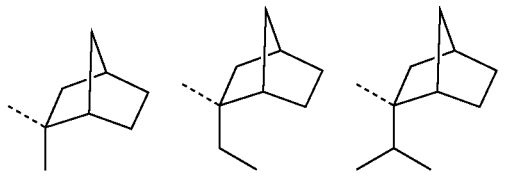

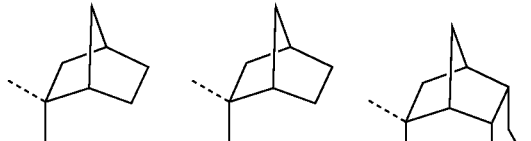

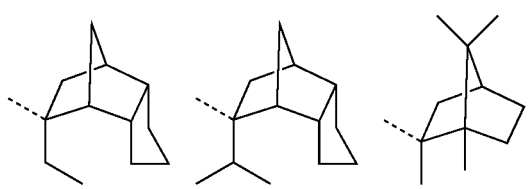

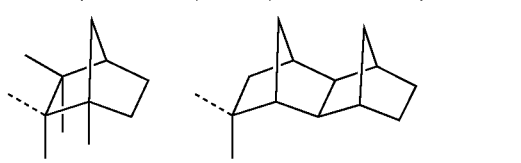

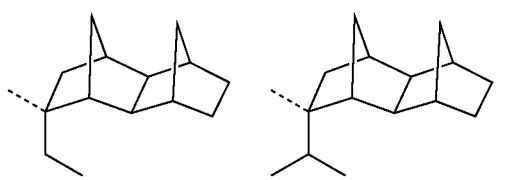

Examples of the $C_4$-$C_{20}$ tertiary alkyl groups, trialkylsilyl groups in which each alkyl moiety has 1 to 6 carbon atoms, and $C_4$-$C_{20}$ oxoalkyl groups, represented by $X^A$, are as exemplified above for $R^{LO4}$.

Illustrative examples of the recurring units of formula (a) are given below, but not limited thereto. Herein $R^A$ is as defined above.

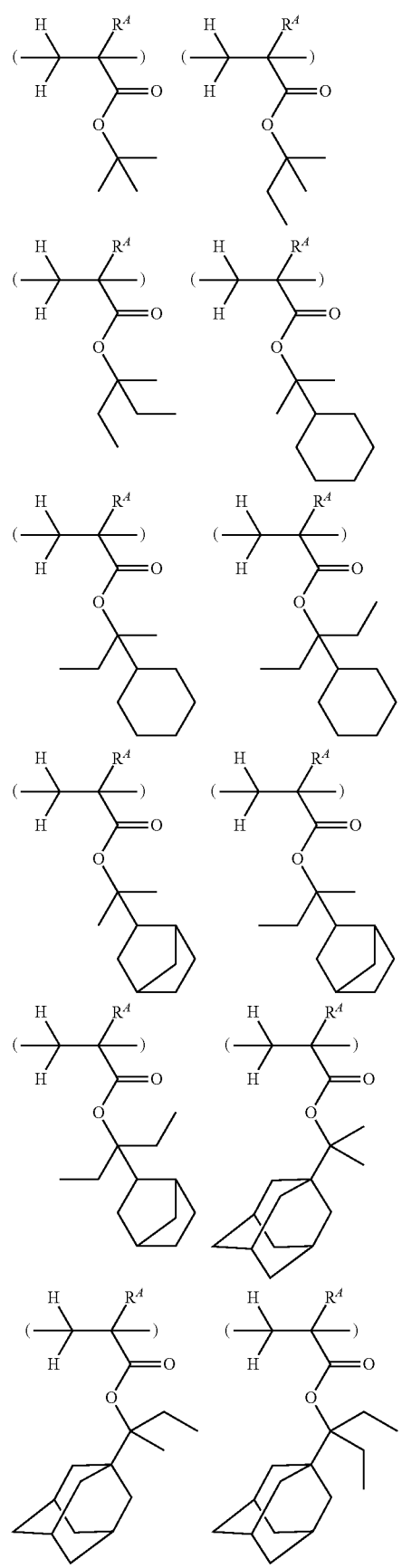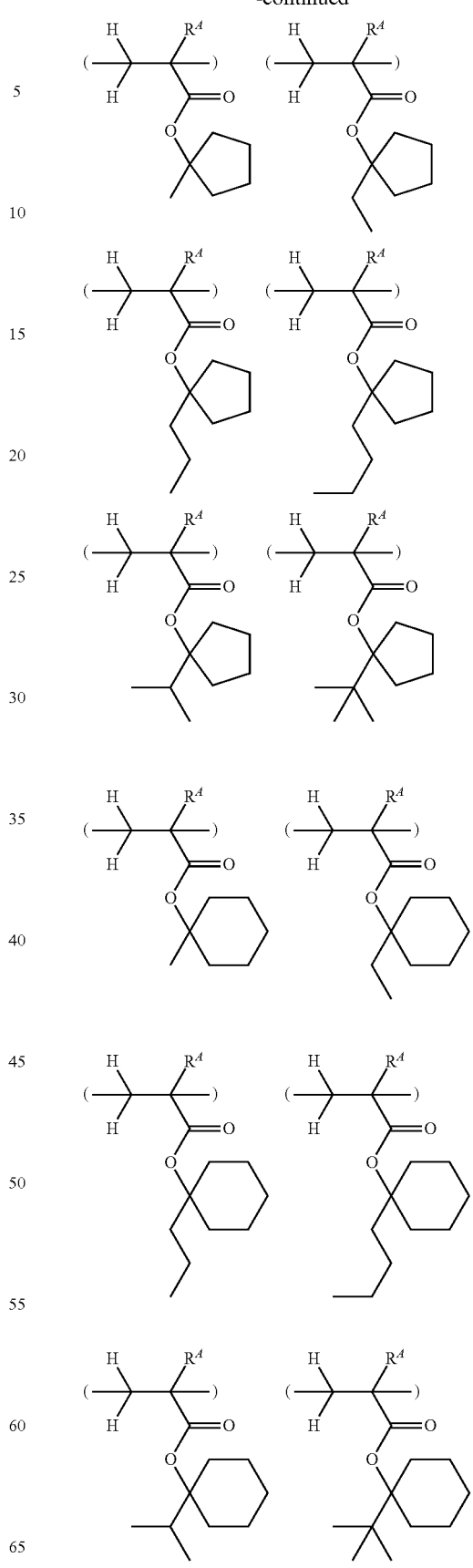

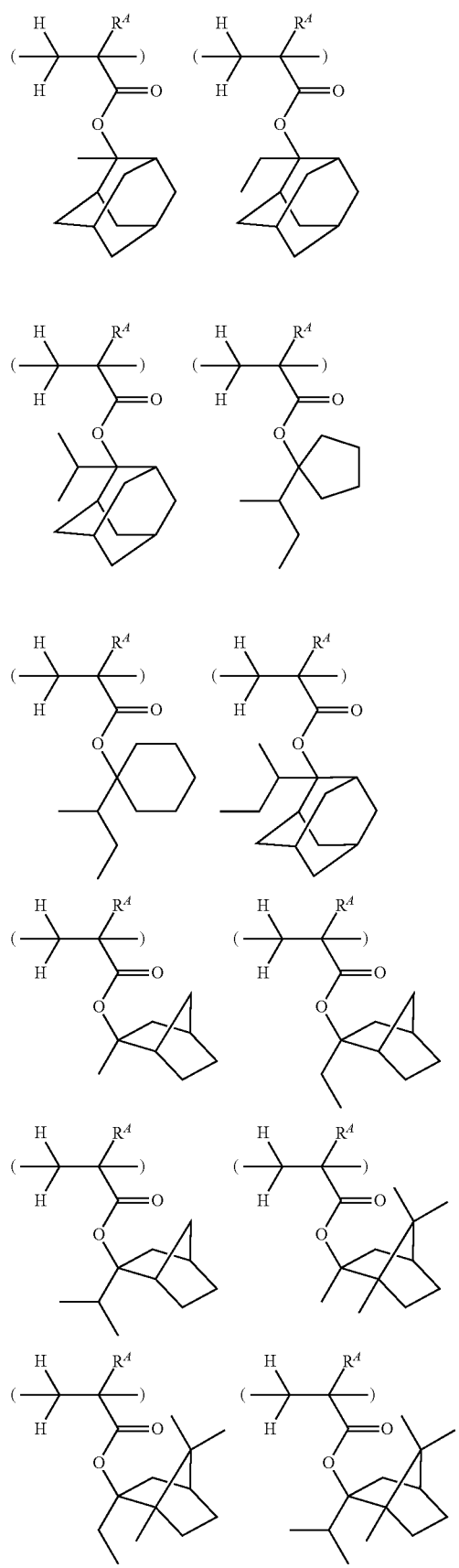
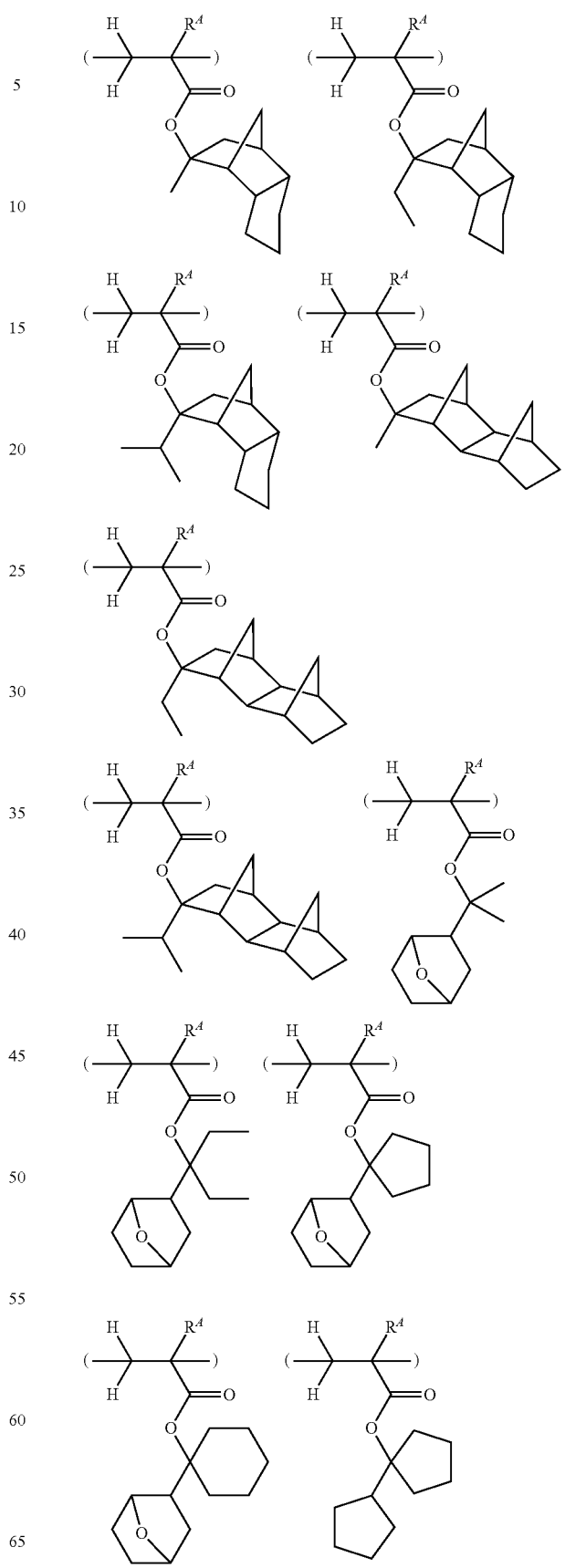

-continued
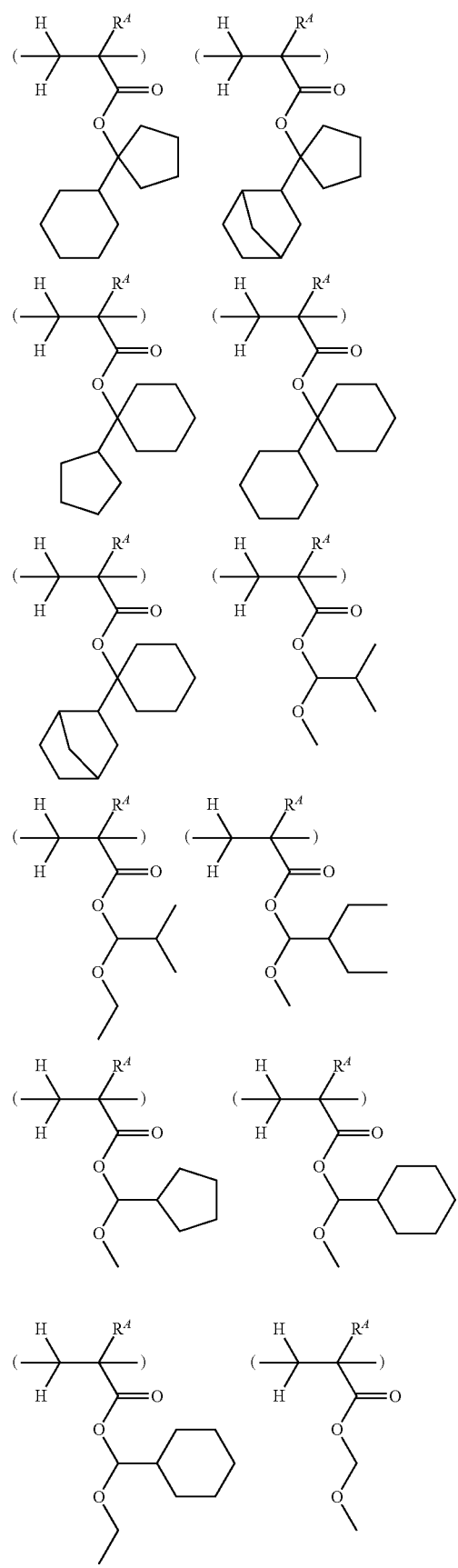
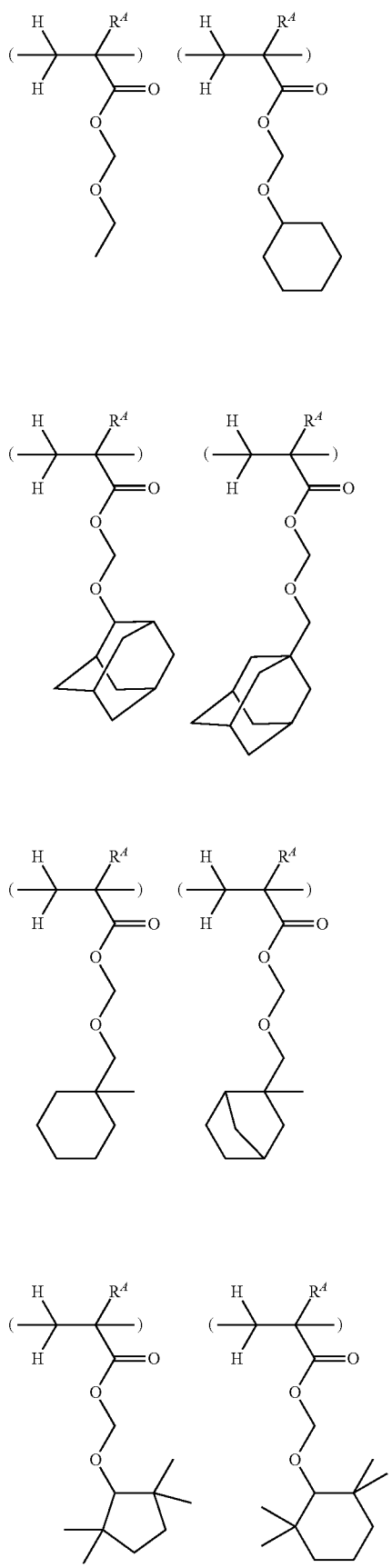

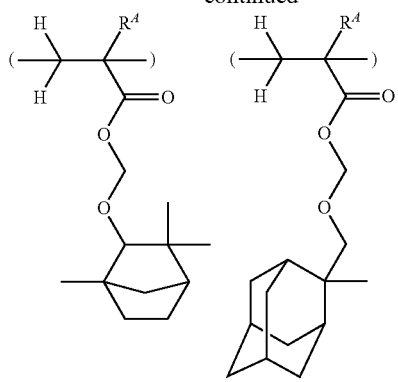
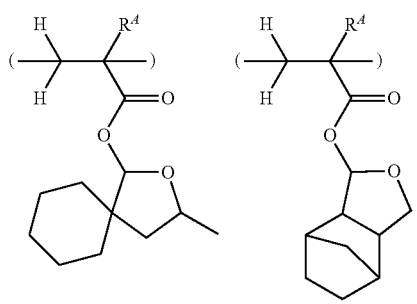
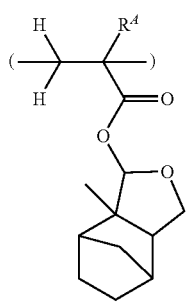
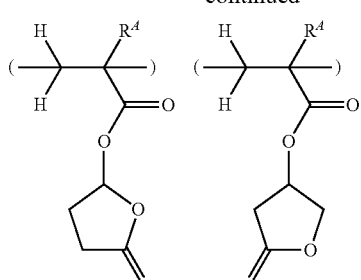
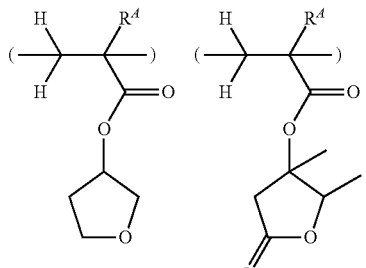
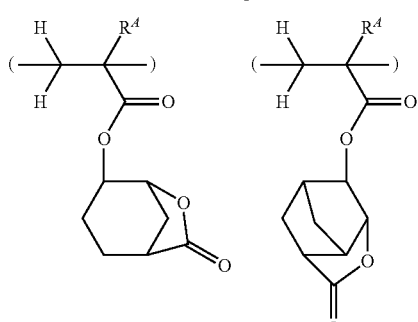

While the foregoing examples correspond to those units wherein $Z^A$ is a single bond, $Z^A$ which is other than a single bond may be combined with similar acid labile groups. Examples of units wherein $Z^A$ is other than a single bond are substantially the same as illustrated above.

Illustrative, non-limiting examples of the recurring units having formula (b) are shown below. Herein $R^A$ is as defined above.

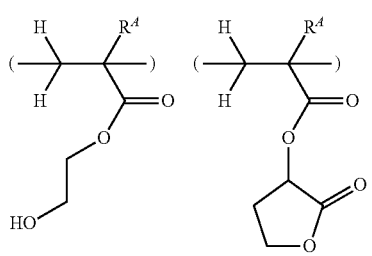
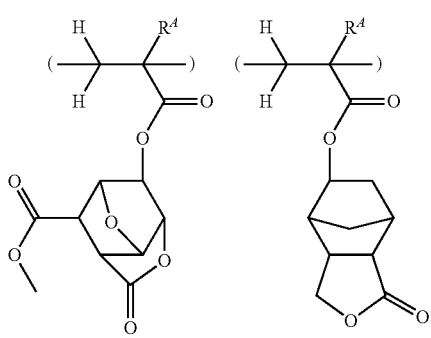
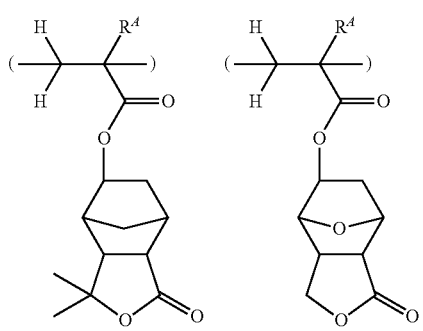

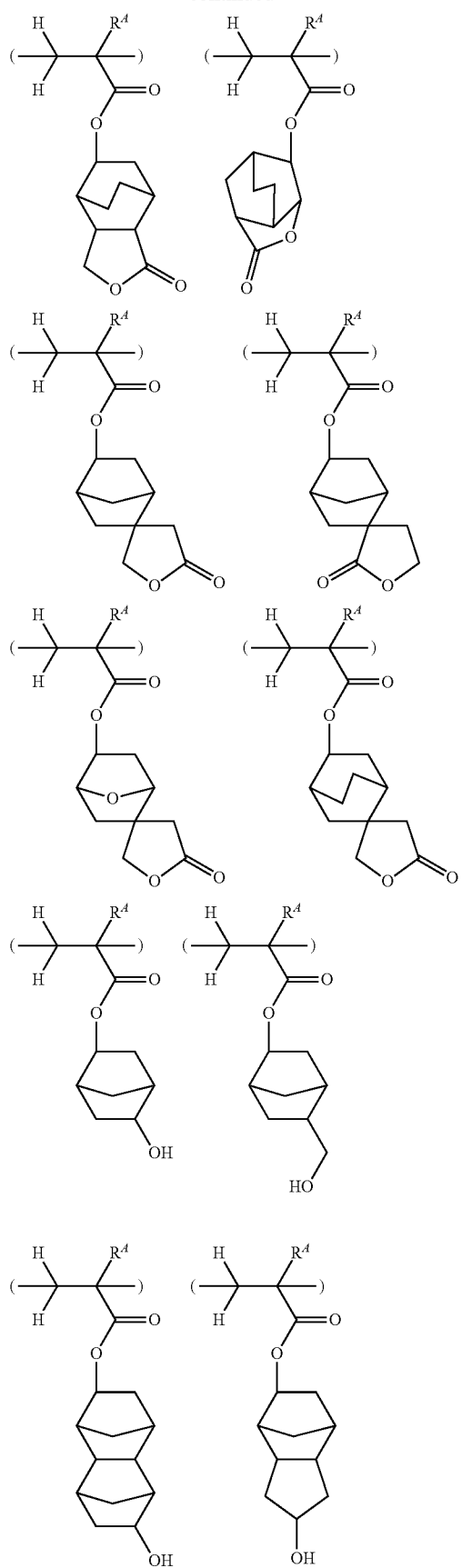
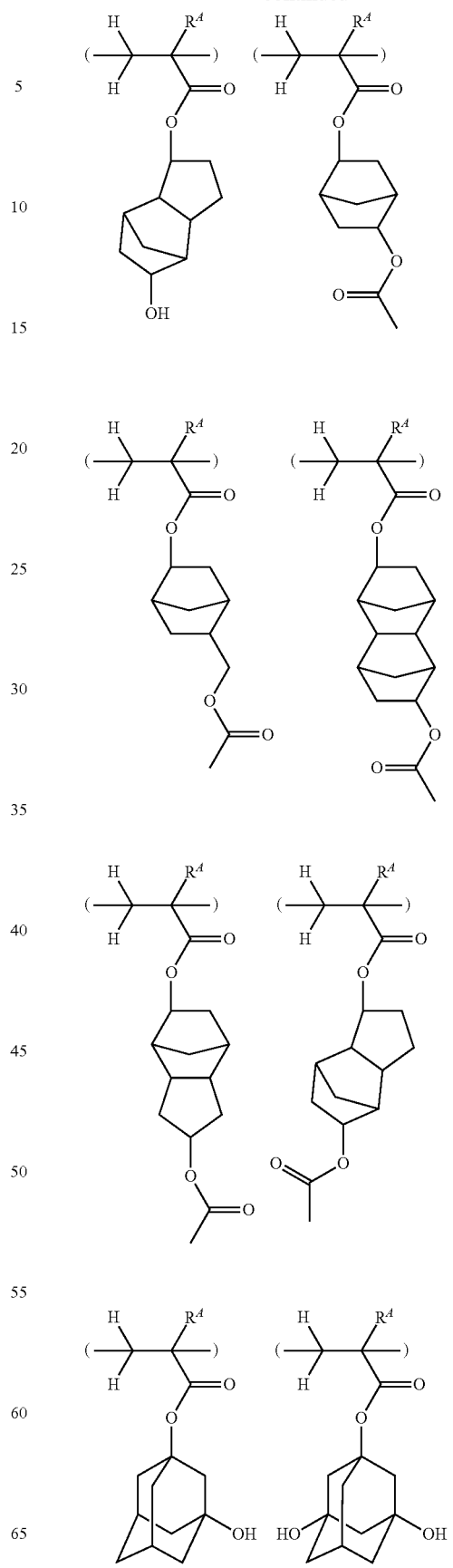

-continued
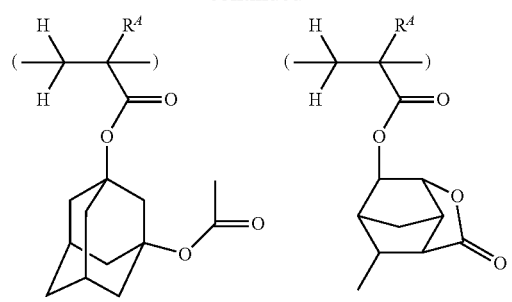
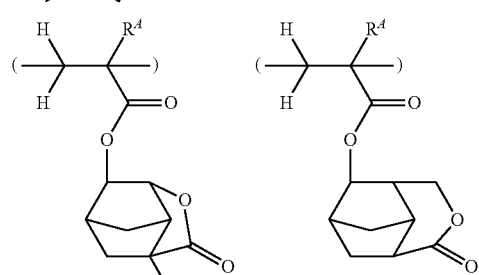
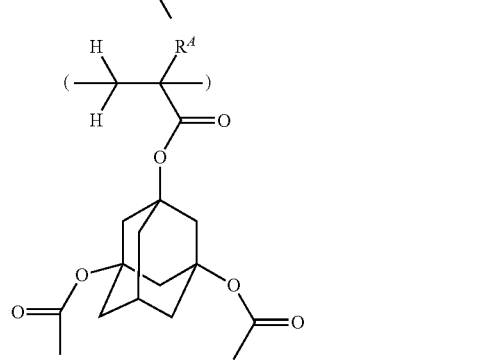
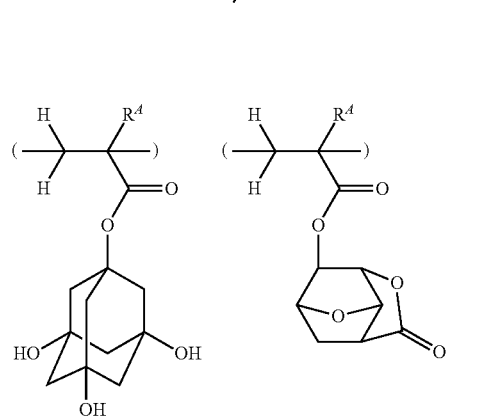
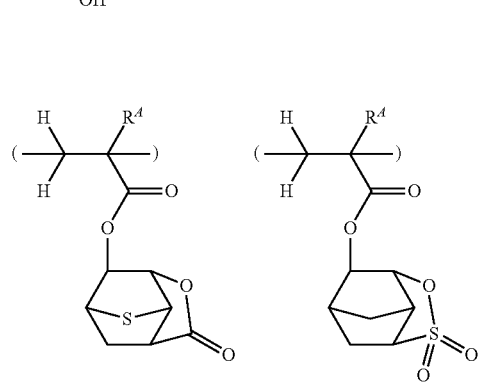
-continued
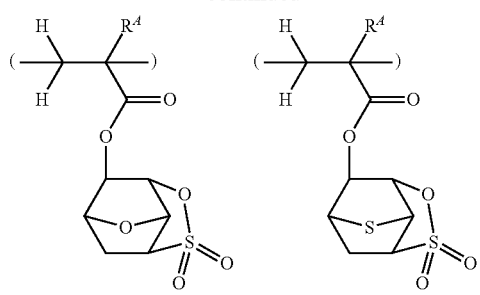
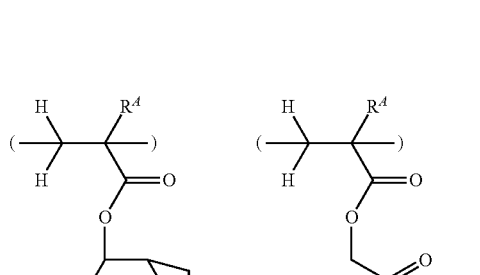
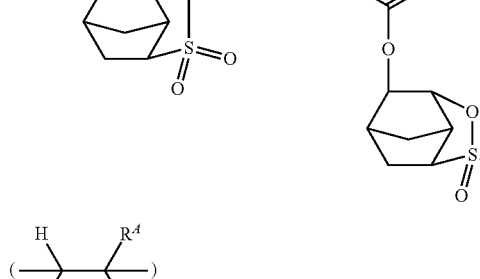
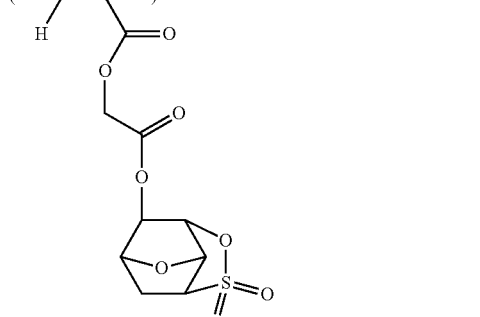
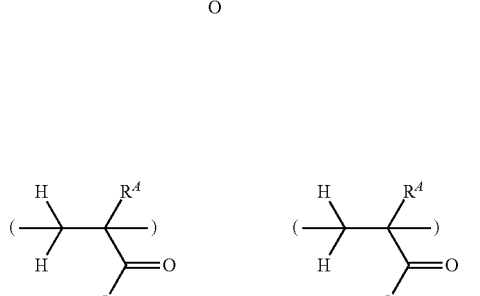
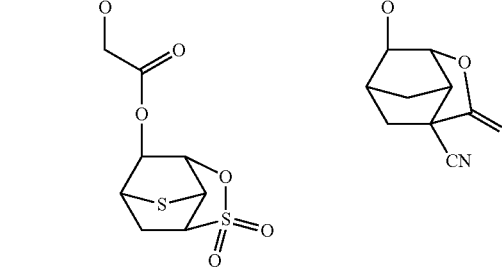

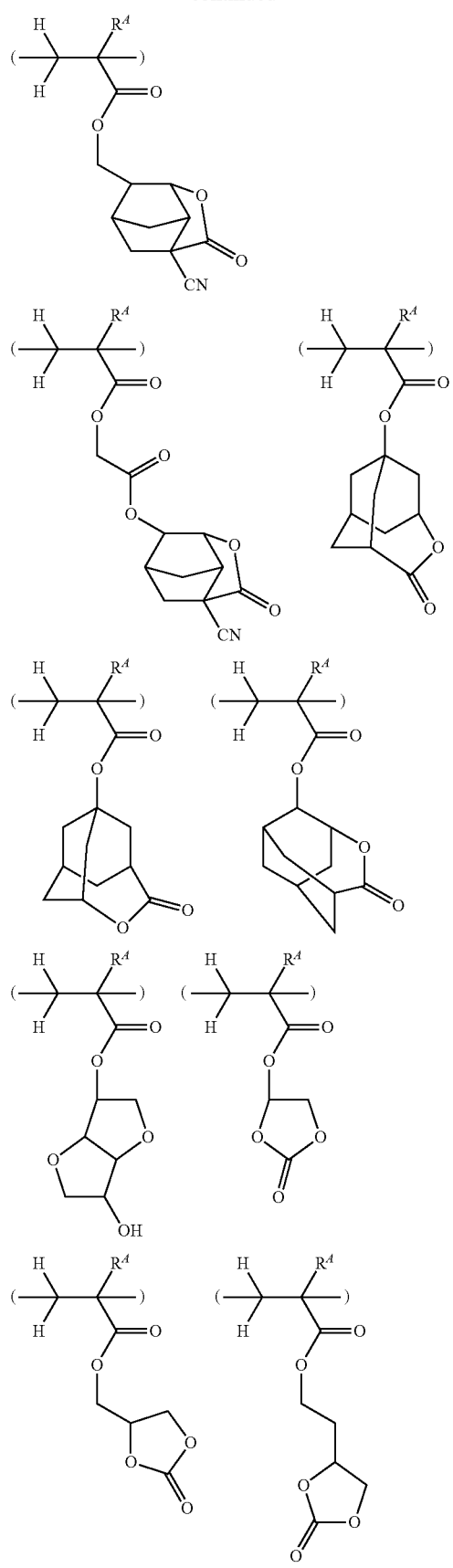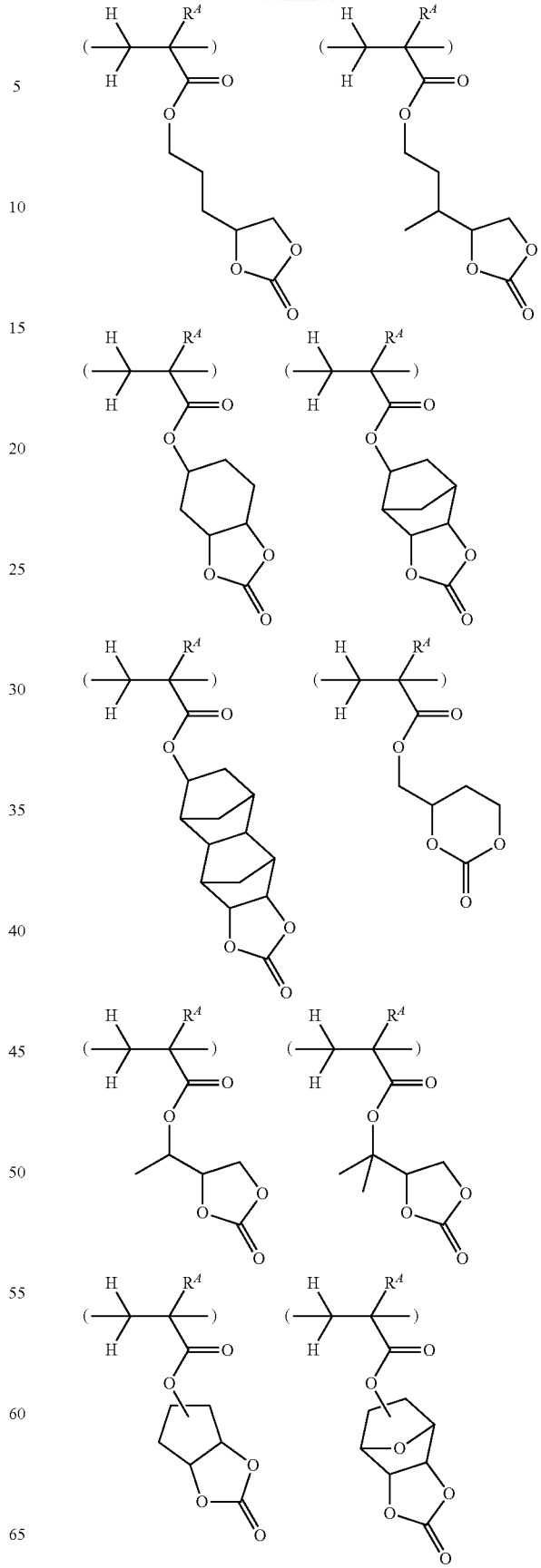

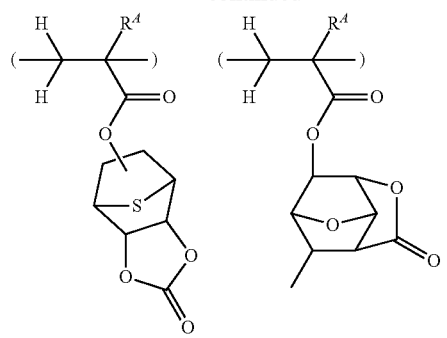
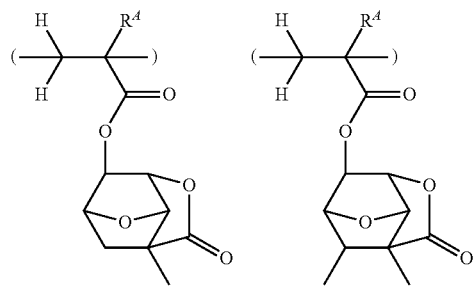
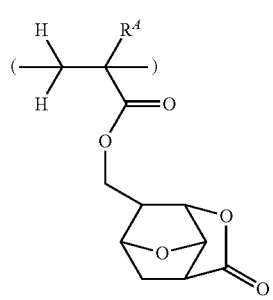
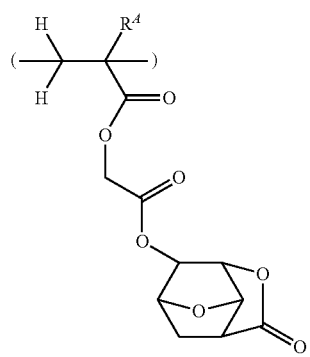
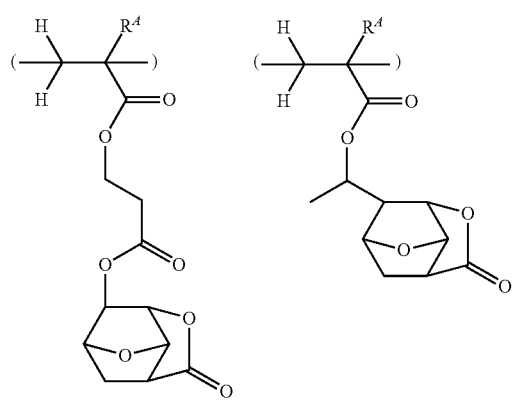
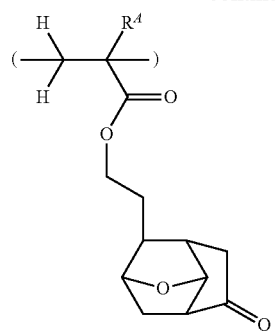
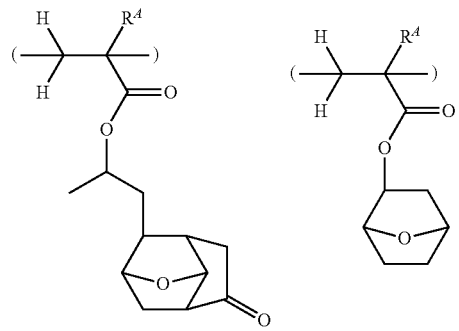
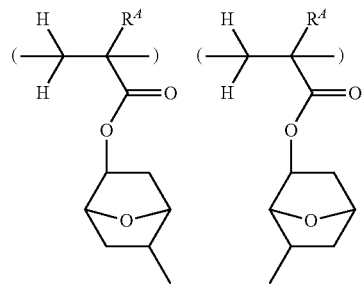
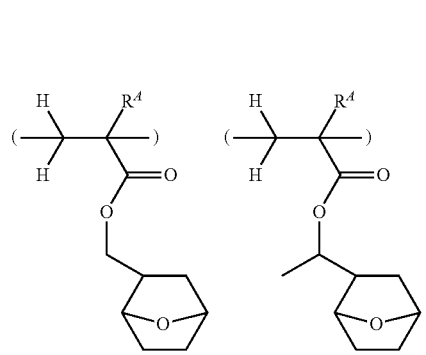
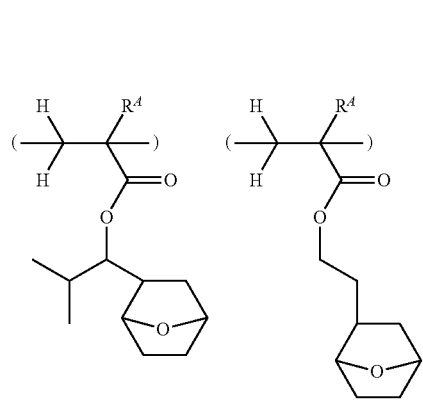

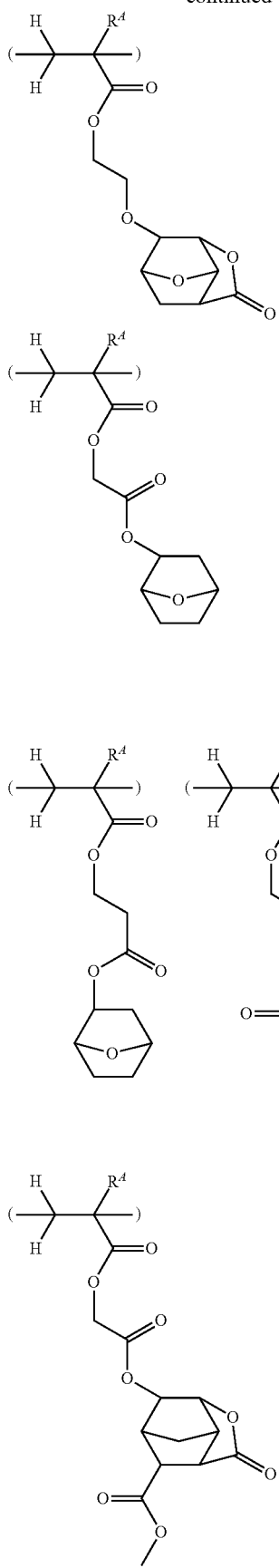
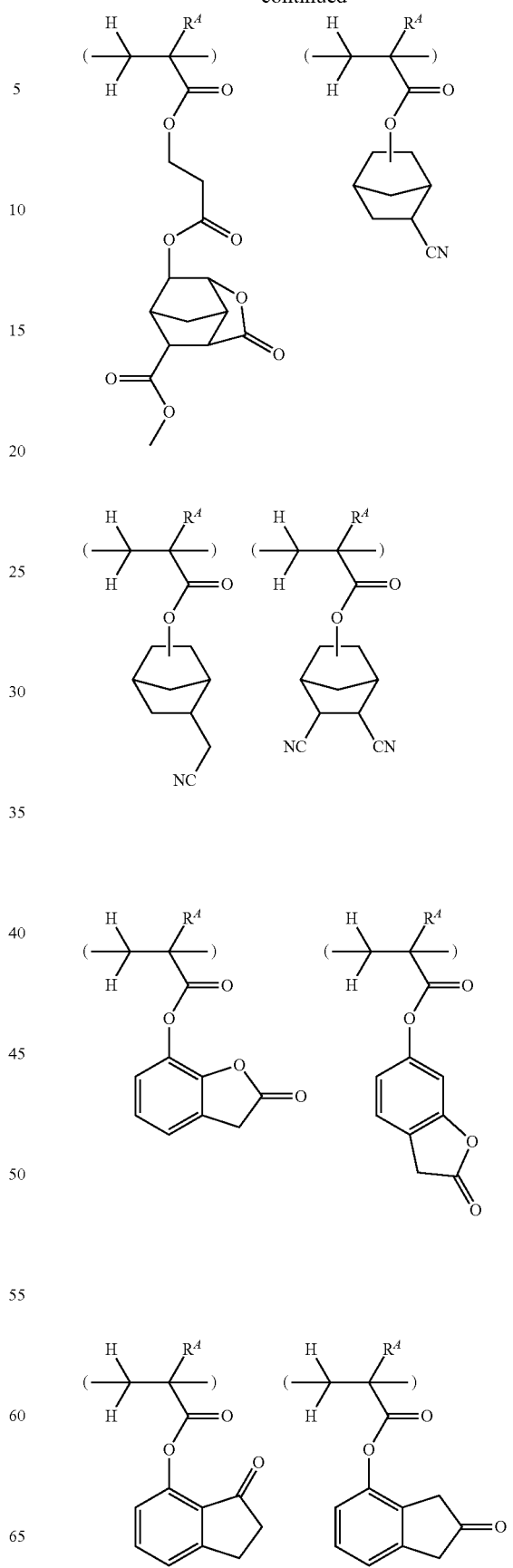

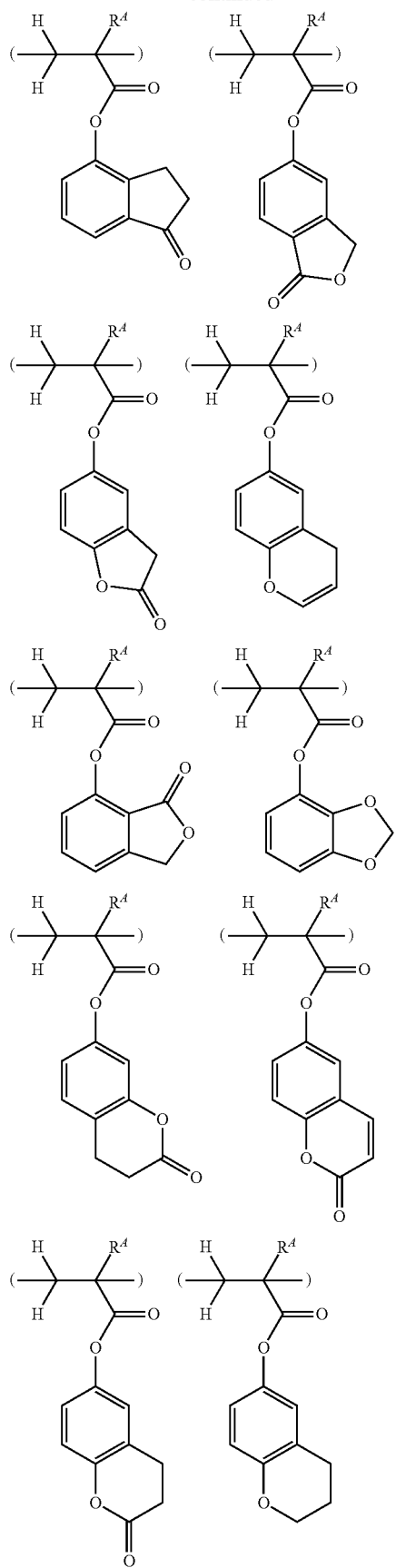
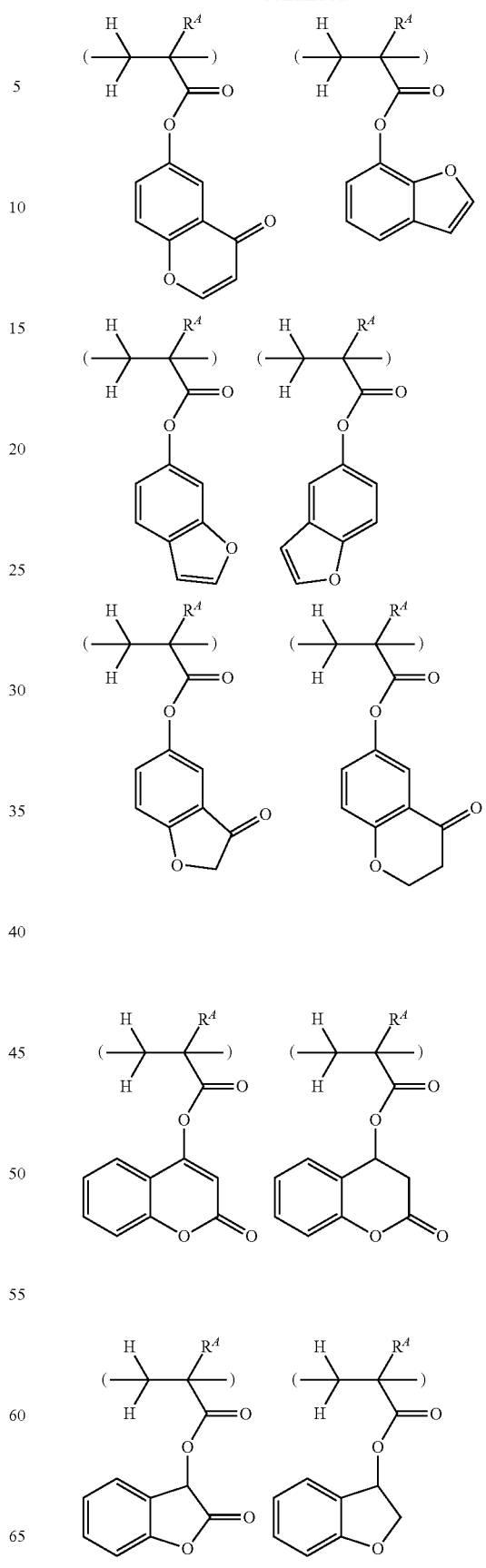

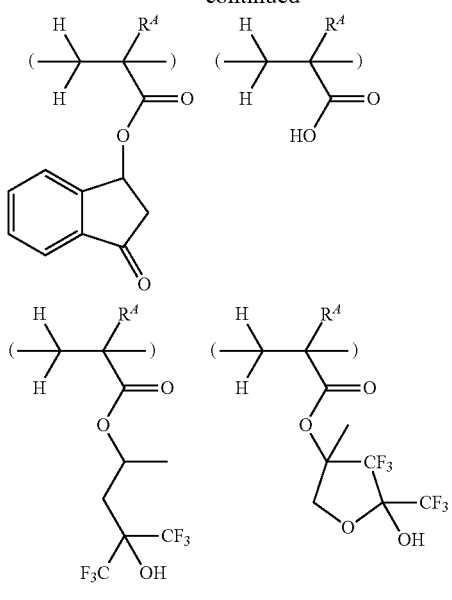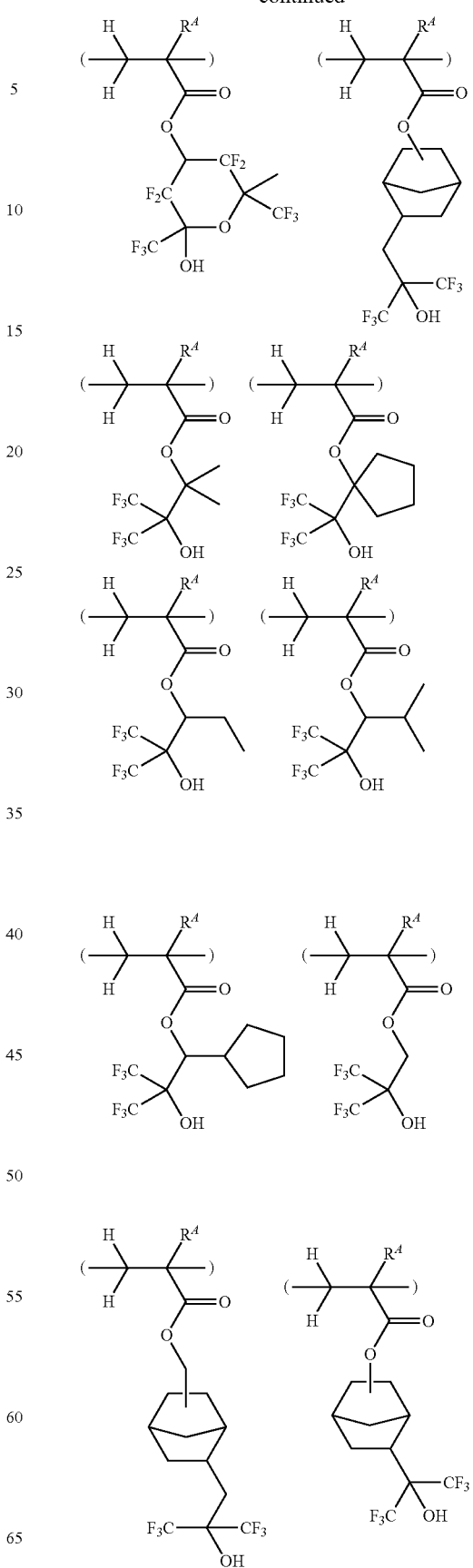

-continued
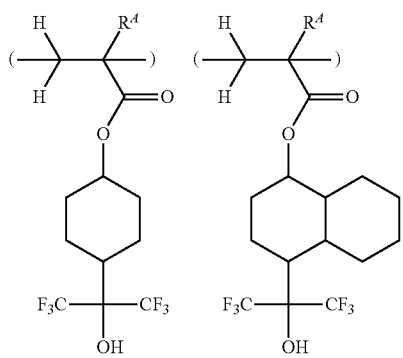
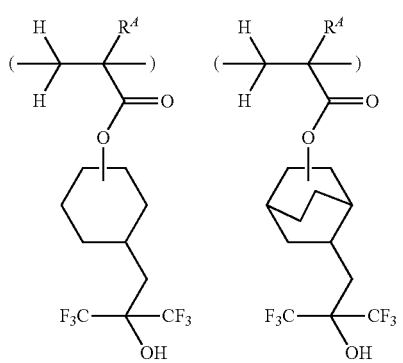
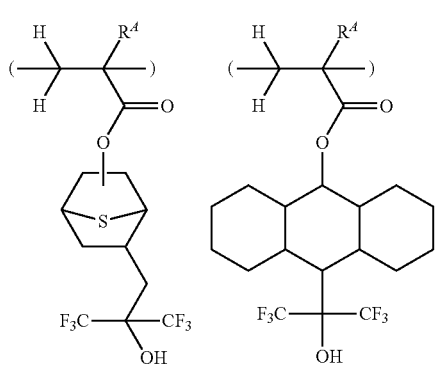
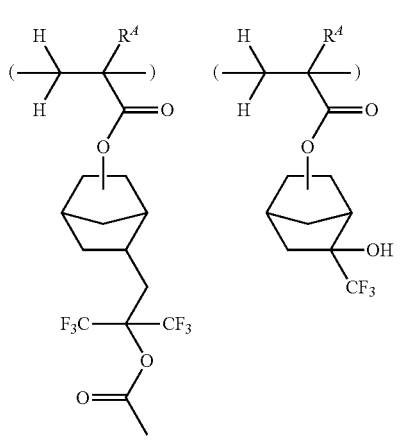
-continued
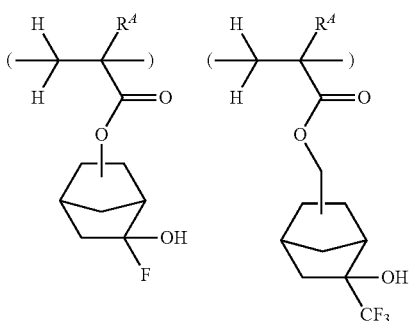
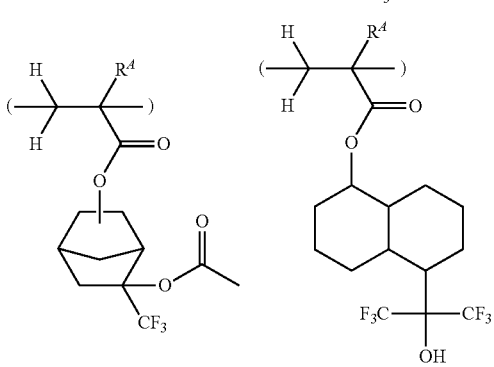
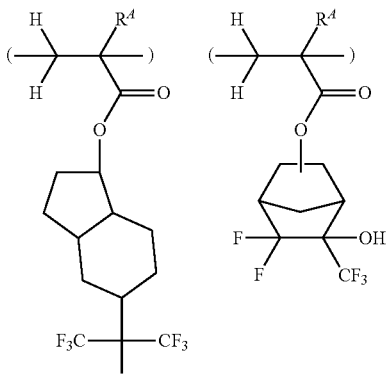
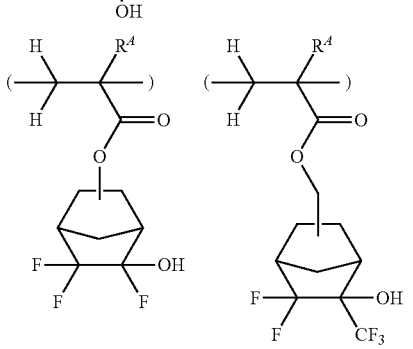
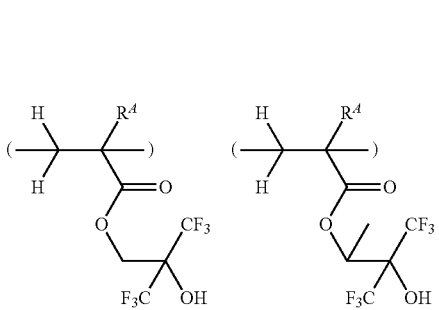

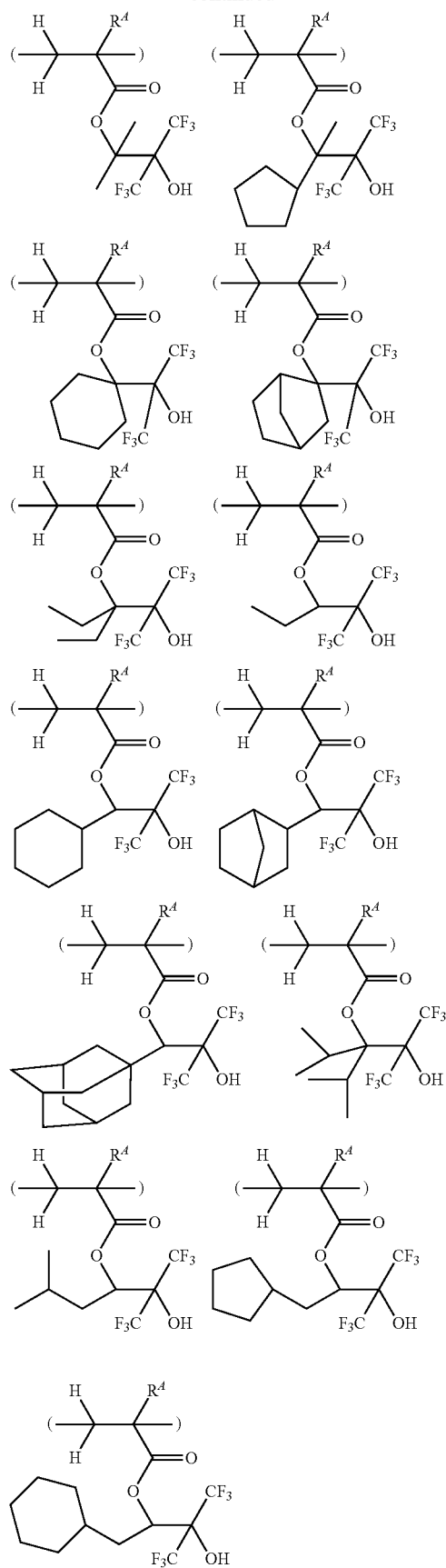
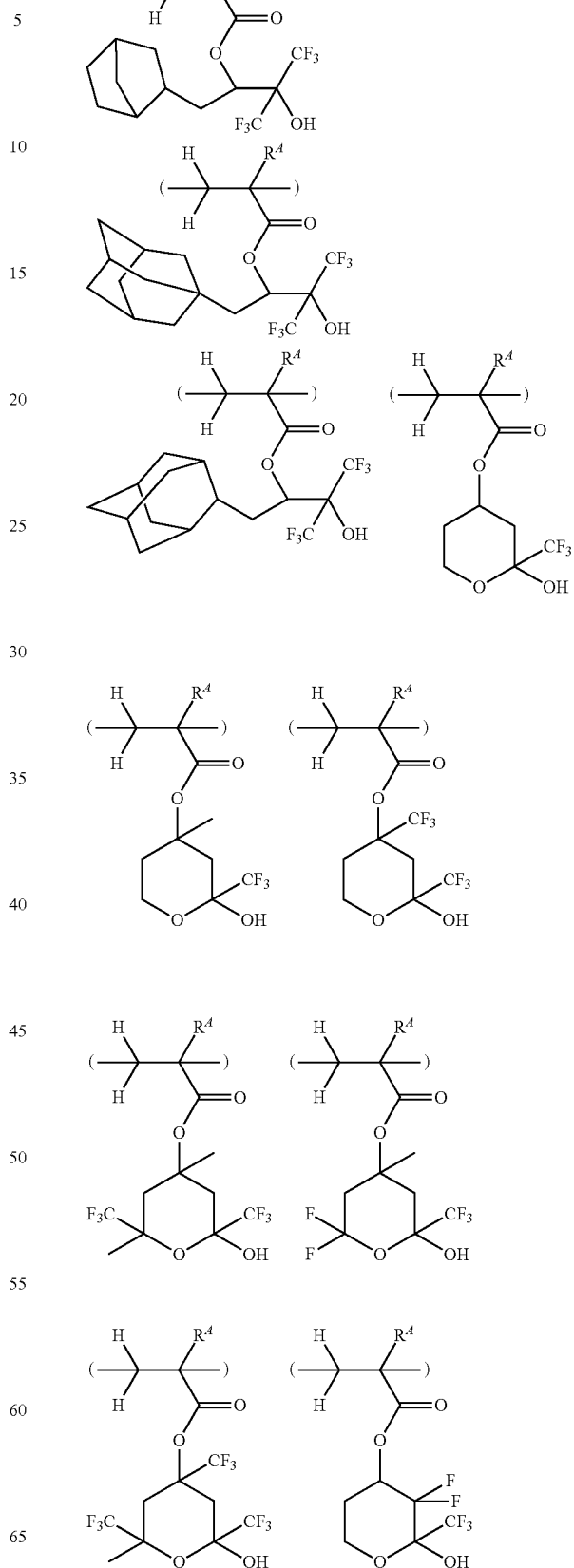

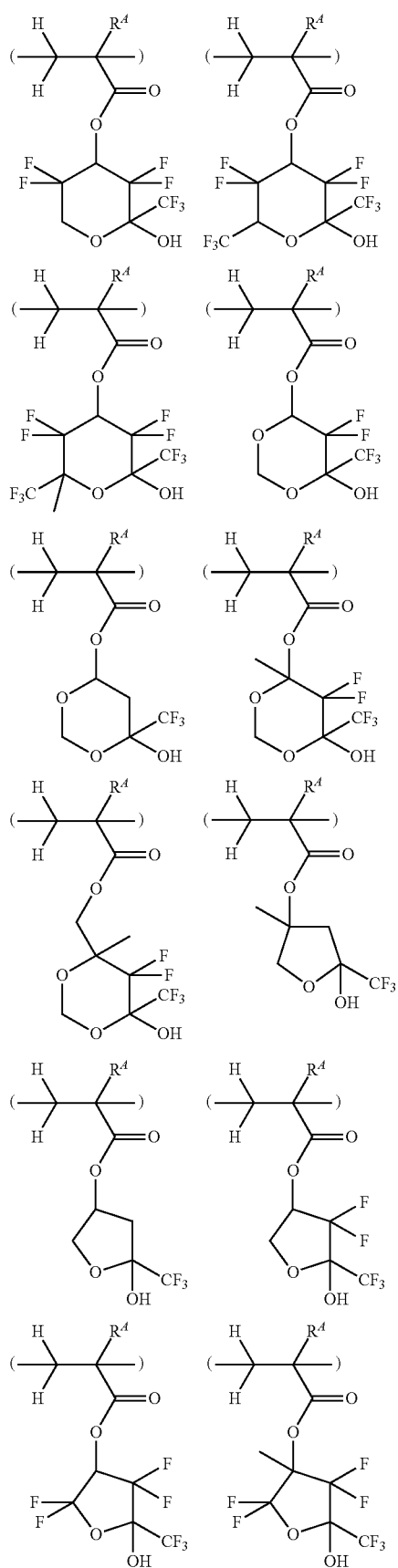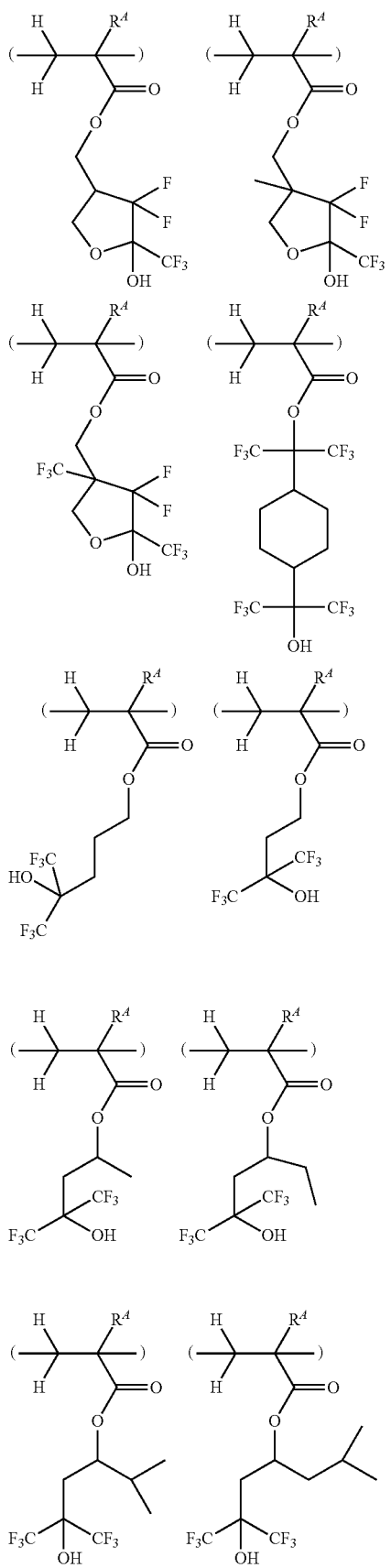

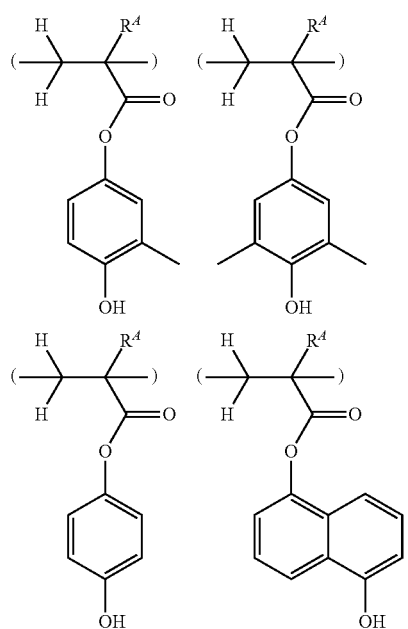
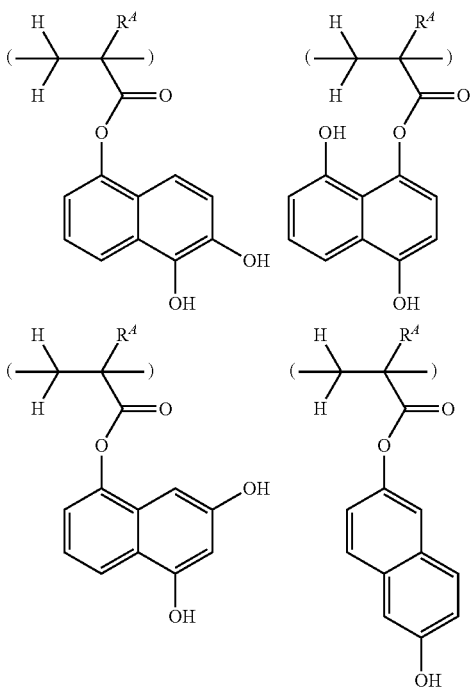
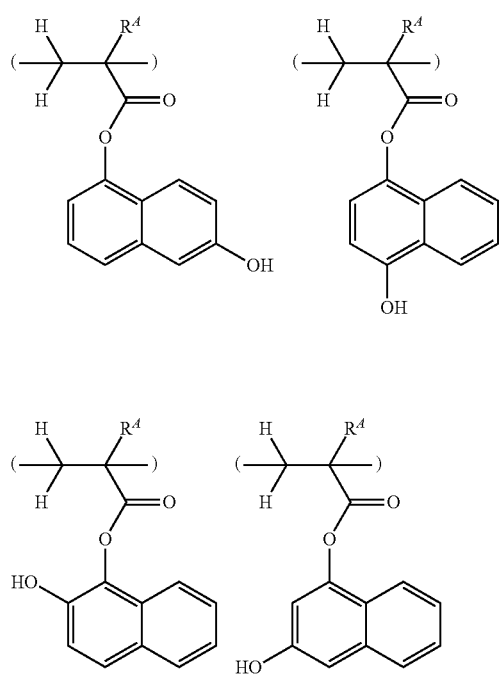
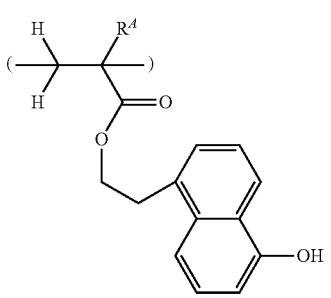

-continued

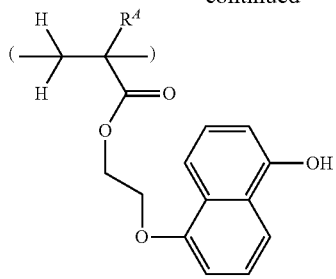

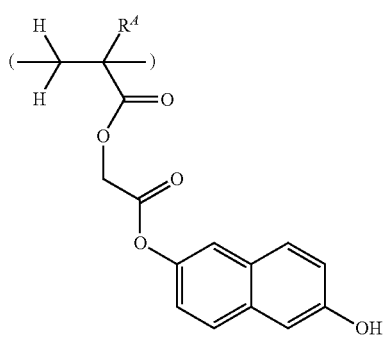

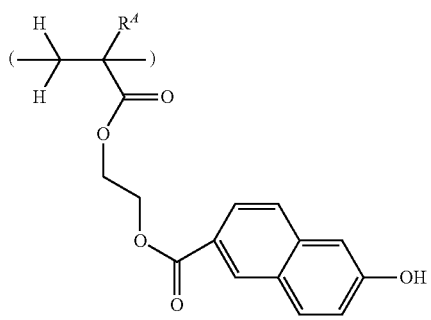

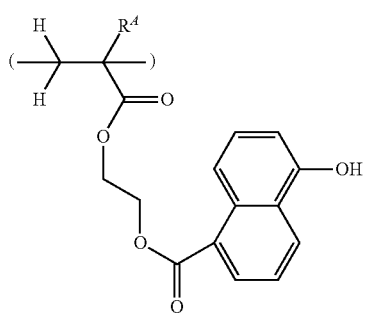

Of the recurring units having formula (b), those units having a lactone ring as the polar group are most preferred.

In addition to the recurring units having formulae (a) and (b), the polymer may further comprise recurring units having the formula (c1) or (c2).

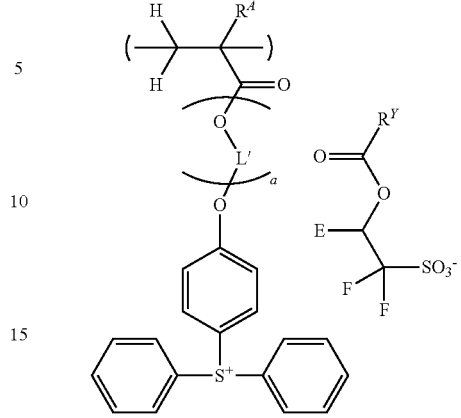
(c1)

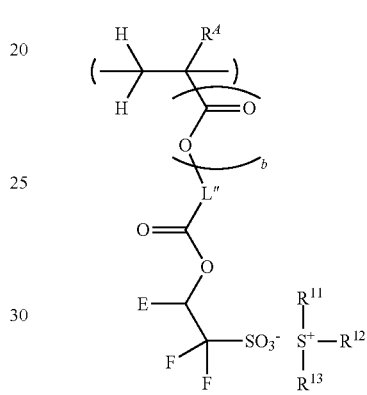
(c2)

In formulae (c1) and (c2), $R^A$ is as defined and exemplified above. $R^{11}$, $R^{12}$ and $R^{13}$ are each independently a straight, branched or cyclic $C_1$-$C_{20}$ monovalent hydrocarbon group which may contain a heteroatom. L' is $C_2$-$C_5$ alkylene. $R^Y$ is a straight, branched or cyclic $C_1$-$C_{20}$ monovalent hydrocarbon group which may contain a heteroatom. E is hydrogen or trifluoromethyl. L" is a single bond or a straight, branched or cyclic $C_1$-$C_{20}$ divalent hydrocarbon group which may contain a heteroatom. The subscript a is 0 or 1, b is 0 or 1, with the proviso that b is 0 when L" is a single bond.

Exemplary of L' are ethylene, propylene and butylene. E is preferably trifluoromethyl. Examples of the monovalent hydrocarbon groups represented by $R^Y$, $R^{11}$, $R^{12}$ and $R^{13}$ are the same as will be exemplified for $R^{101}$, $R^{102}$ and $R^{103}$ in formula (4) below.

Examples of the divalent hydrocarbon group L" include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; saturated cyclic hydrocarbon groups such as cyclopentanediyl, cyclohexanediyl, norbornanediyl, and adamantanediyl; and unsaturated cyclic hydrocarbon groups such as phenylene and naphthylene. Also included are the foregoing groups in which at least one hydrogen atom is replaced by an alkyl moiety such as methyl, ethyl, propyl, n-butyl or t-butyl, or in which at least one hydrogen atom is replaced by a moiety containing a heteroatom such as oxygen, sulfur, nitrogen or halogen, or in which at least one carbon atom is replaced by a moiety containing a heteroatom such as oxygen, sulfur or nitrogen, so that the group may contain a hydroxyl, cyano, carbonyl, ether bond, thioether bond, ester bond, sulfonic acid ester bond, carbonate bond, carbamate bond, lactone ring, sultone ring, carboxylic acid anhydride or haloalkyl moiety.

Exemplary structures of the anion moiety in formula (c1) include those described in JP-A 2010-113209 and JP-A 2007-145797. Exemplary structures of the unit having formula (c2) wherein E is hydrogen include those described in JP-A 2010-116550, and exemplary structures of the unit having formula (c2) wherein E is trifluoromethyl include those described in JP-A 2010-077404.

The polymer may have further copolymerized therein recurring units of the structure having a hydroxyl group protected with an acid labile group. The recurring unit of the structure having a hydroxyl group protected with an acid labile group is not particularly limited as long as it has one or more protected hydroxyl-bearing structure such that the protective group may be decomposed to generate a hydroxyl group under the action of acid. Inter alia, recurring units having the formula (d1) are preferred.

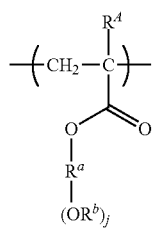
(d1)

In formula (d1), $R^A$ is as defined above, $R^a$ is a straight, branched or cyclic $C_1$-$C_{30}$ (j+1)-valent hydrocarbon group which may contain a heteroatom, $R^b$ is an acid labile group, and j is an integer of 1 to 4.

Examples of the recurring unit of formula (d1) are shown below, but not limited thereto. Herein $R^A$ and $R^b$ are as defined above.

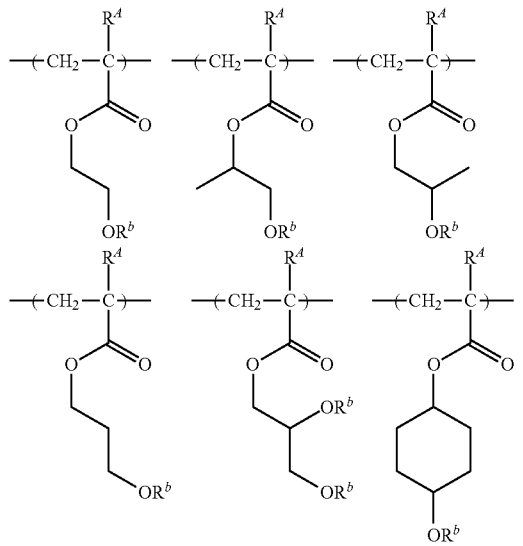

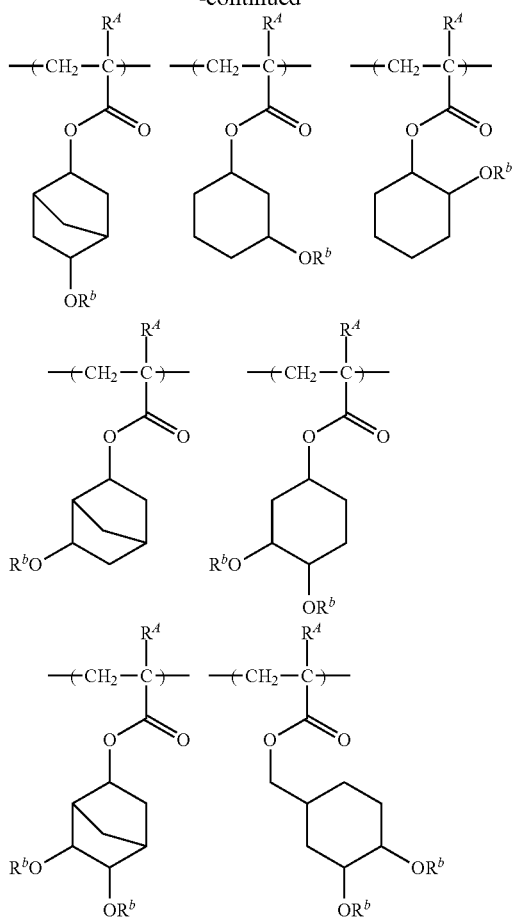

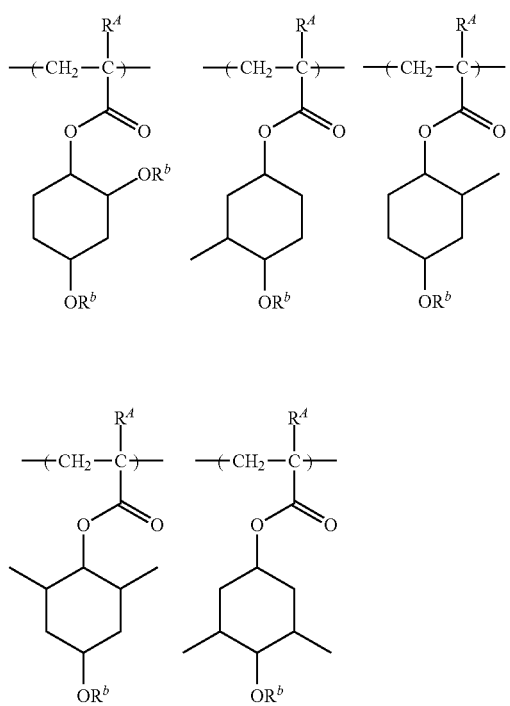

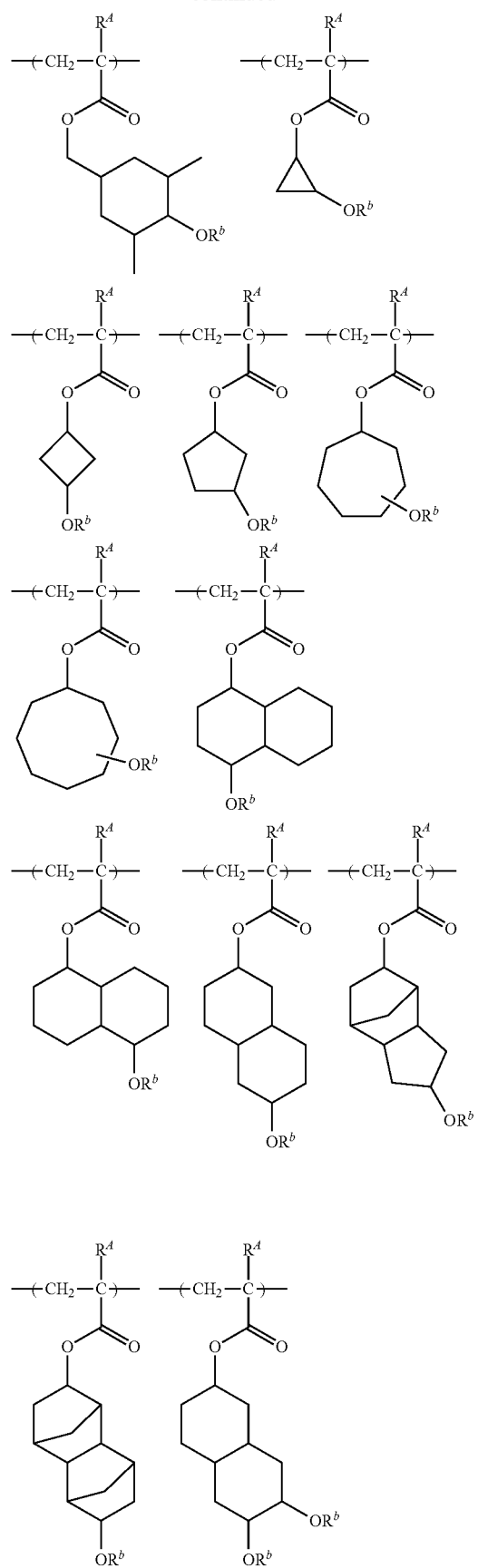
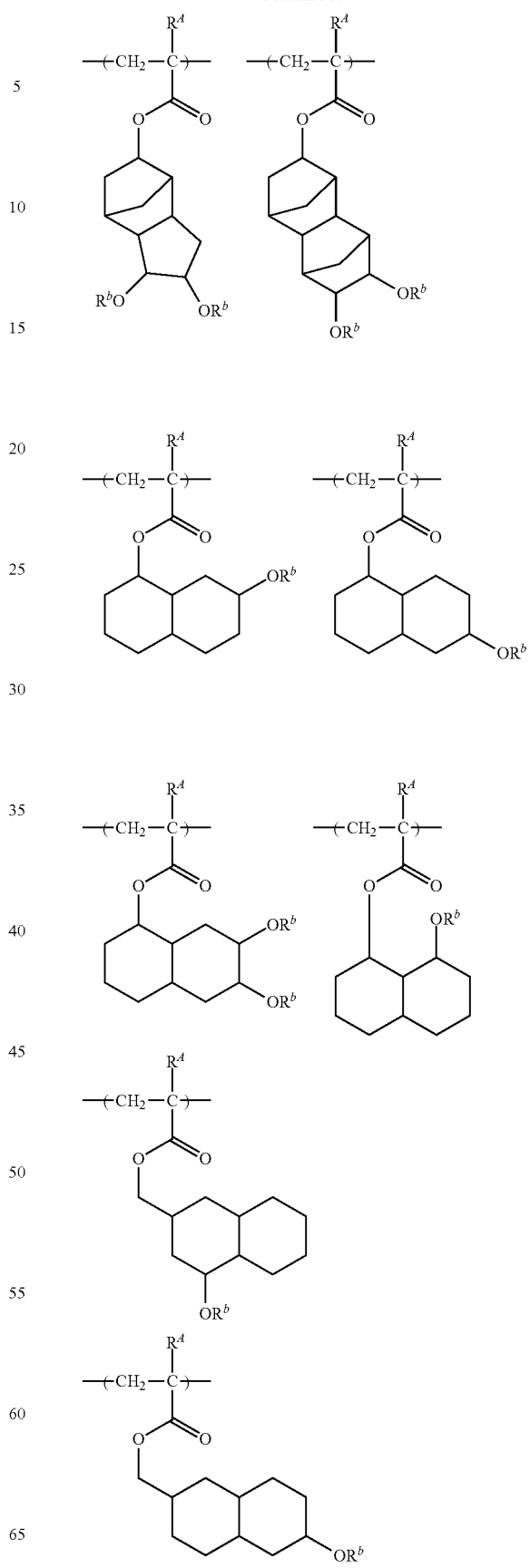

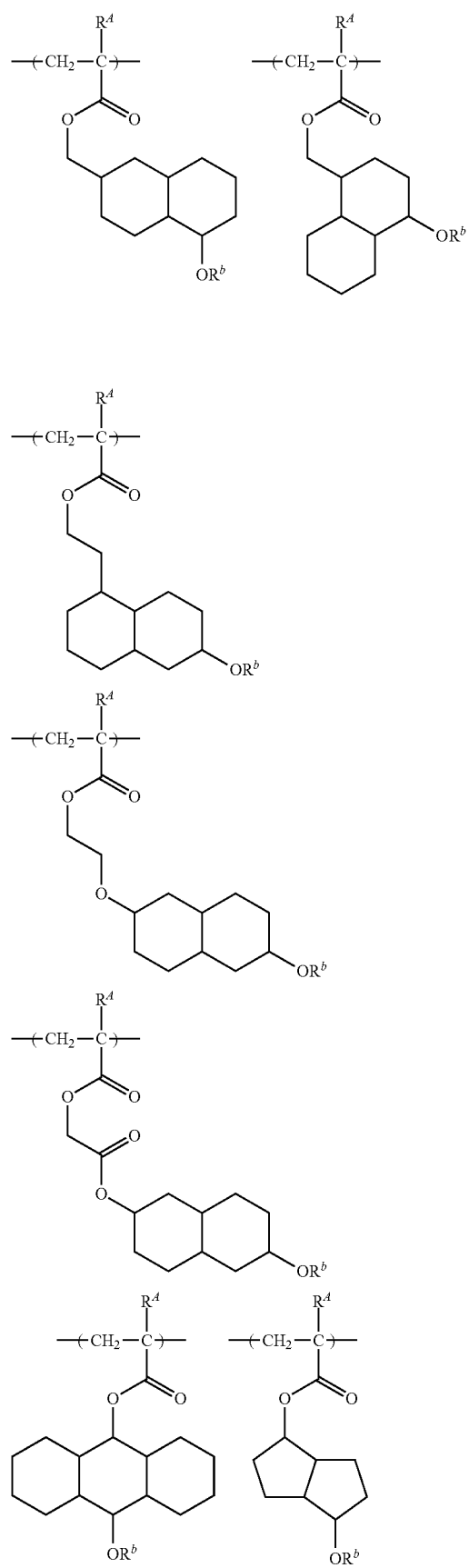
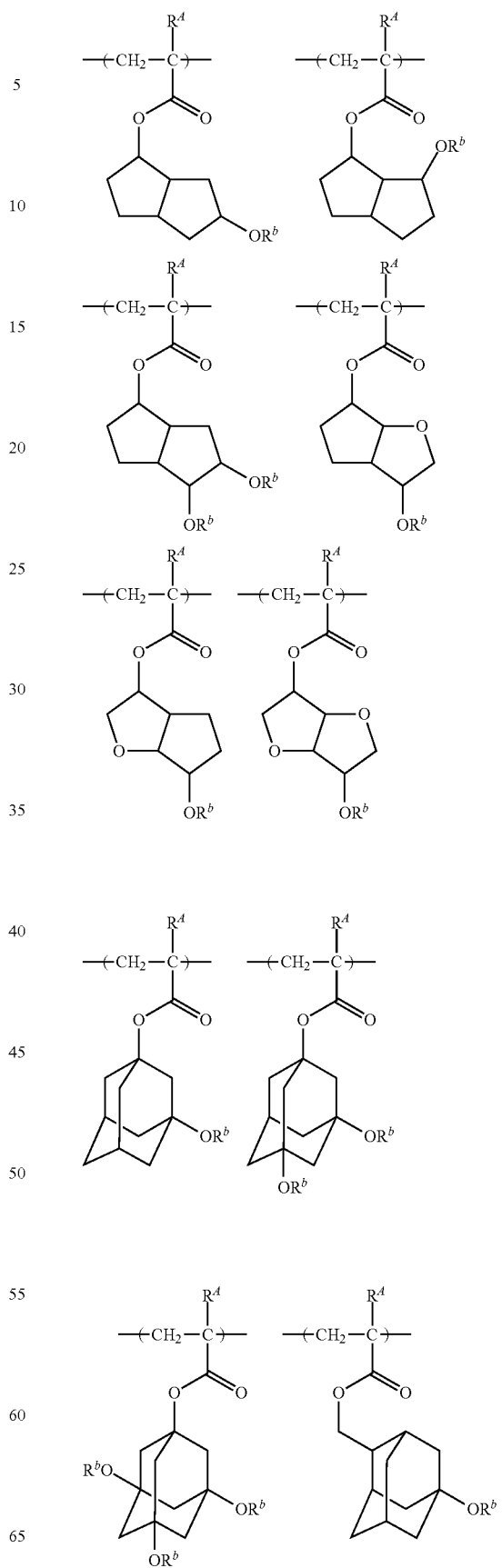

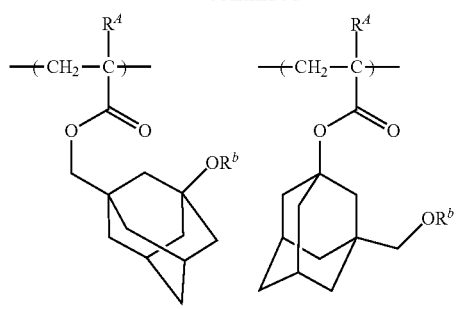
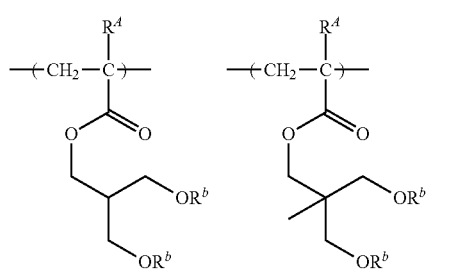
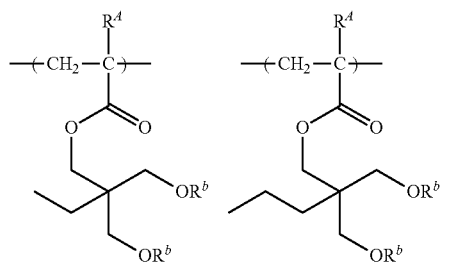
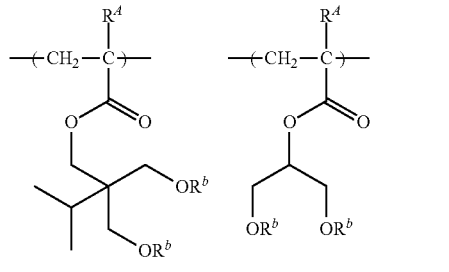
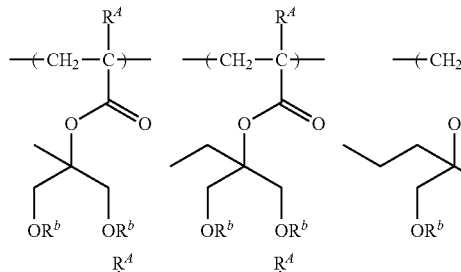
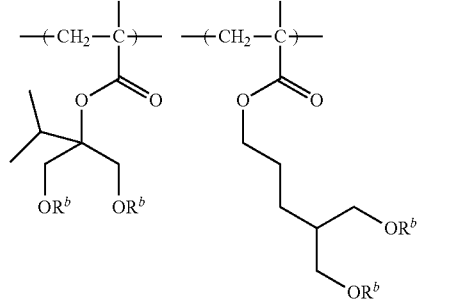
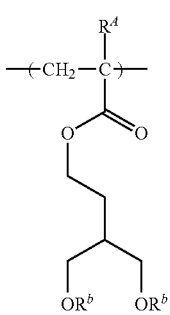
The structure of the acid labile group $R^b$ in formula (d1) is not particularly limited as long as it is deprotected to generate a hydroxyl group under the action of acid. Typical acid labile groups are groups of acetal or ketal structure and alkoxycarbonyl groups, with their examples being shown below.
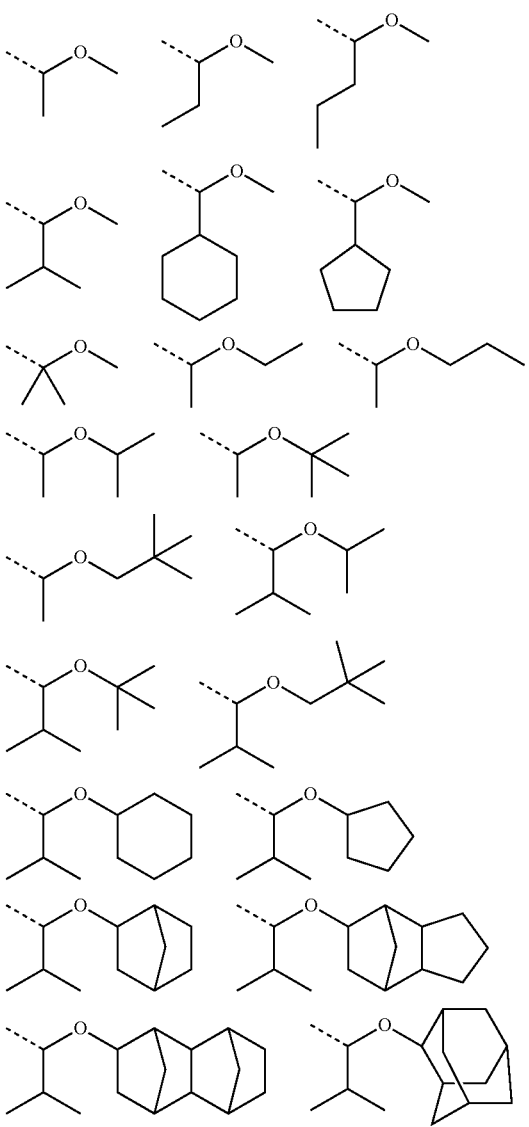

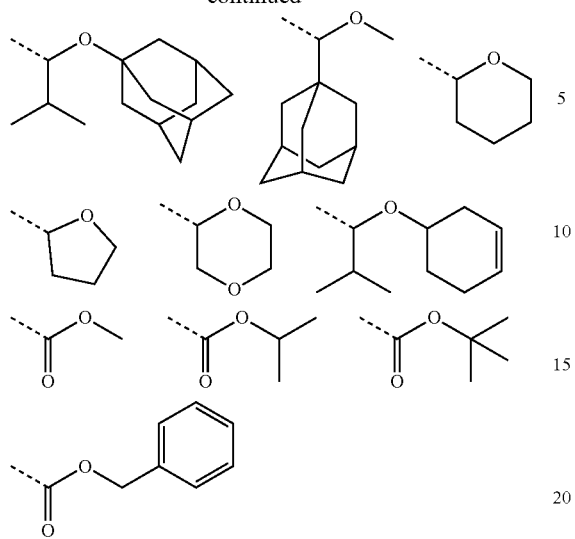
Of the acid labile group $R^b$, preferred are alkoxymethyl groups having the formula (d2):
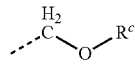 (d2)
wherein $R^c$ is a straight, branched or cyclic $C_1$-$C_{15}$ monovalent hydrocarbon group.
Examples of the acid labile group of formula (d2) are shown below, but not limited thereto.
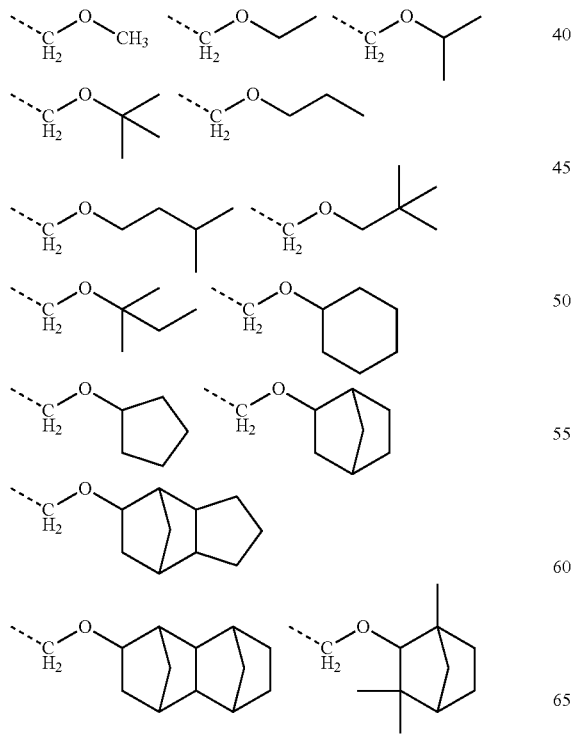
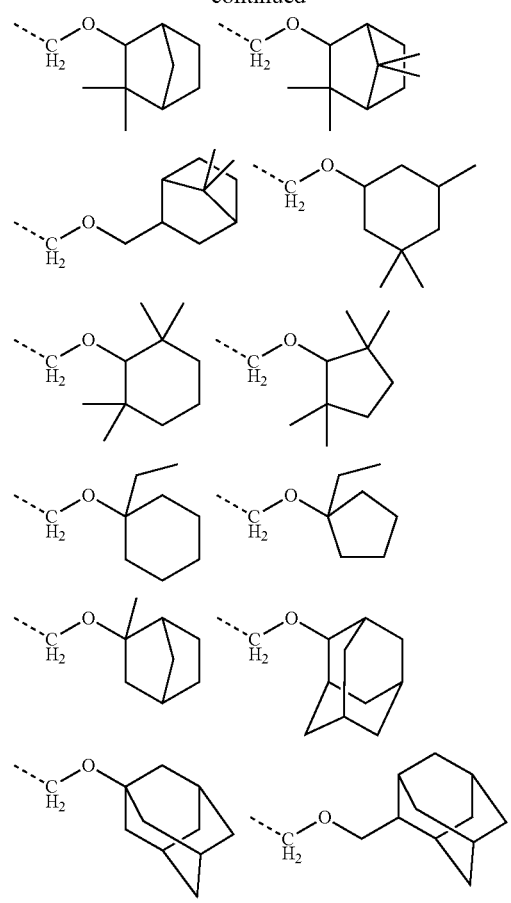
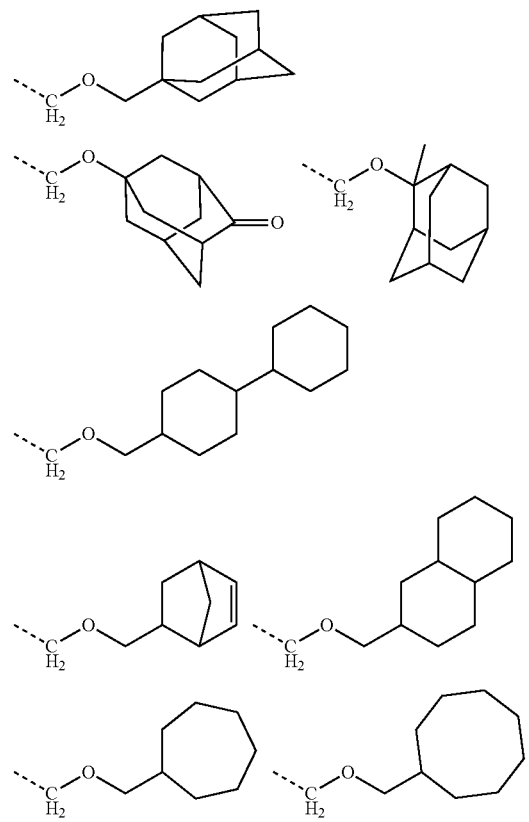

-continued

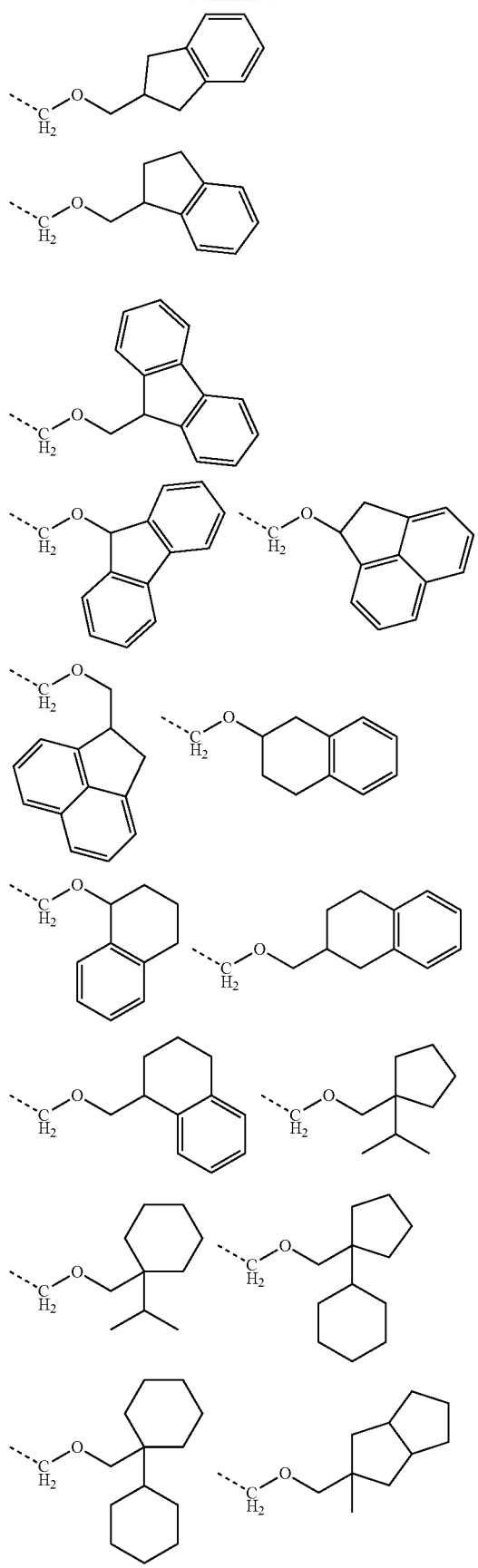

-continued

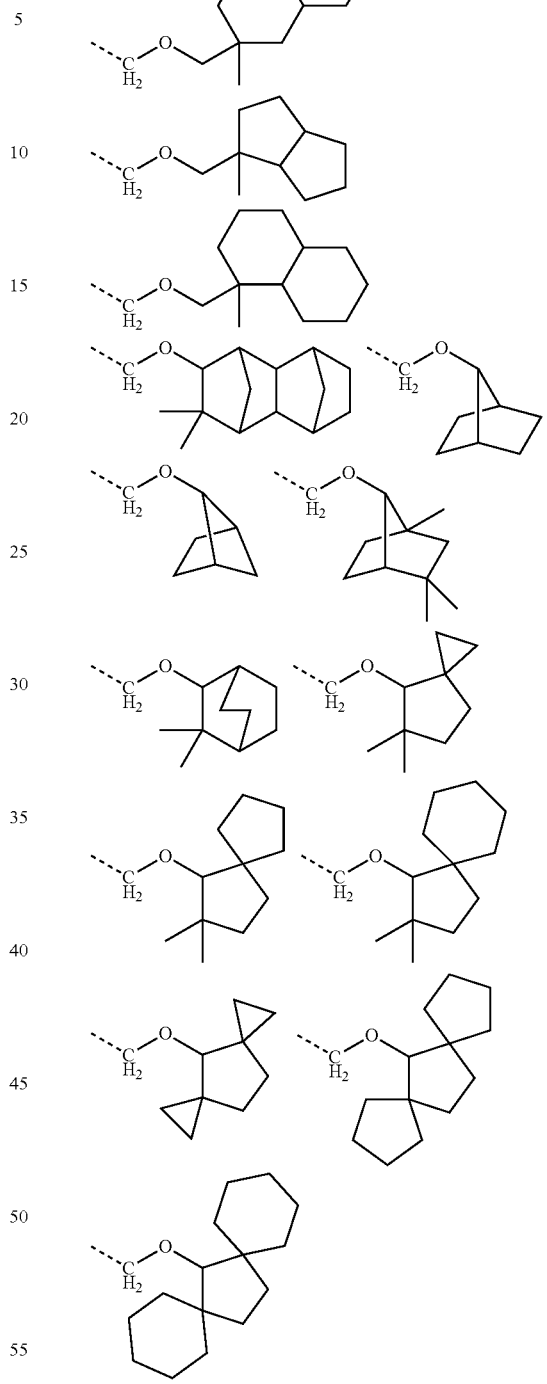

In addition to the foregoing units, the polymer may further comprise recurring units derived from other monomers, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[6.2.1.1$^{3,6}$.0$^{2,7}$]dodecene derivatives, unsaturated acid anhydrides such as itaconic anhydride, and other monomers.

The polymer has a weight average molecular weight (Mw) of preferably 1,000 to 500,000, more preferably 3,000 to 100,000, as measured by gel permeation chromatography (GPC) versus polystyrene standards using tetrahydrofuran (THF) solvent. As long as Mw is within the range, sufficient etching resistance is obtainable, and any drop of resolution due to a failure to establish a dissolution rate difference before and after exposure is avoided.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the polymer should preferably have a narrow dispersity (Mw/Mn) of 1.0 to 2.0 in order to formulate a resist composition suited for fine size pattern formation.

The method of synthesizing the polymer is, for example, by dissolving one or more unsaturated bond-bearing monomers in an organic solvent, adding a moiety initiator, and heating for polymerization. Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the reaction temperature is in a range of 50 to 80° C. and the reaction time is 2 to 100 hours, more preferably 5 to 20 hours. The acid labile group that has been incorporated in the monomer may be kept as such, or polymerization may be followed by protection or partial protection.

While the polymer comprises recurring units derived from monomers, the molar fractions of respective units preferably fall in the following range (mol %), but are not limited thereto:

(I) 1 to 60 mol %, more preferably 5 to 50 mol %, even more preferably 10 to 50 mol % of recurring units of at least one type having formula (a),
(II) 40 to 99 mol %, more preferably 50 to 95 mol %, even more preferably 50 to 90 mol % of recurring units of at least one type having formula (b), and optionally,
(III) 0 to 30 mol %, more preferably 0 to 20 mol %, and even more preferably 0 to 10 mol % of recurring units of at least one type having formula (c1) or (c2), and optionally,
(IV) 0 to 80 mol %, more preferably 0 to 70 mol %, and even more preferably 0 to 50 mol % of recurring units of at least one type derived from another monomer(s).

It is acceptable to use a blend of two or more polymers which differ in compositional ratio, molecular weight or dispersity as the base resin (B).

(C) Organic Solvent

The resist composition may comprise (C) an organic solvent. The organic solvent used herein is not particularly limited as long as the above and other components are soluble therein. Examples of the organic solvent are described in JP-A 2008-111103, paragraphs [0144] to [0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, cyclohexanone, γ-butyrolactone, and mixtures thereof because the PAG is most soluble therein.

An appropriate amount of the organic solvent (C) used is 200 to 5,000 parts, more preferably 400 to 3,000 parts by weight per 100 parts by weight of the base resin (B).

(D) Second PAG

The resist composition may further comprise (D) a photoacid generator other than the sulfonium compound defined herein, which is referred to as second photoacid generator. The second PAG may be any compound capable of generating an acid upon exposure to high-energy radiation such as UV, DUV, EB, EUV, x-ray, excimer laser, γ-ray or synchrotron radiation. Suitable PAGs include sulfonium salts, iodonium salts, sulfonyldiazomethane, N-sulfonyloxydicarboxyimide, O-arylsulfonyloxime, and O-alkylsulfonyloxime compounds. These PAGs may be used alone or in admixture of two or more. Suitable PAGs are described, for example, in JP-A 2007-145797, paragraphs [0102]-[0113]. In the iodonium salts, diphenyliodonium and di-tert-butylphenyliodonium cations are preferred.

As the second PAG, those having the formula (4) are preferred.

(4)

In formula (4), $R^{101}$, $R^{102}$ and $R^{103}$ are each independently a straight, branched or cyclic $C_1$-$C_{20}$ monovalent hydrocarbon group which may contain a heteroatom. Suitable monovalent hydrocarbon groups include alkyl groups such as methyl, ethyl, propyl, isopropyl, n-butyl, s-butyl, t-butyl, t-pentyl, n-pentyl, n-hexyl, n-octyl, cyclopentyl, cyclohexyl, 2-ethylhexyl, cyclopentylmethyl, cyclopentylethyl, cyclohexylmethyl, cyclohexylethyl, norbornyl, oxanorbornyl, tricyclo[5.2.1.0$^{2,6}$]decanyl, and adamantyl; and aryl groups such as phenyl and naphthyl. Also included are the foregoing groups in which at least one hydrogen atom is replaced by a moiety containing a heteroatom such as oxygen, sulfur, nitrogen or halogen, or in which at least one carbon atom is replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic acid anhydride or haloalkyl moiety. Preferably, $R^{101}$, $R^{102}$ and $R^{103}$ are optionally substituted aryl groups.

Any two of $R^{101}$, $R^{102}$ and $R^{103}$ may bond together to form a ring with the sulfur atom to which they are attached. Examples of the cation in this embodiment are shown below, but not limited thereto.

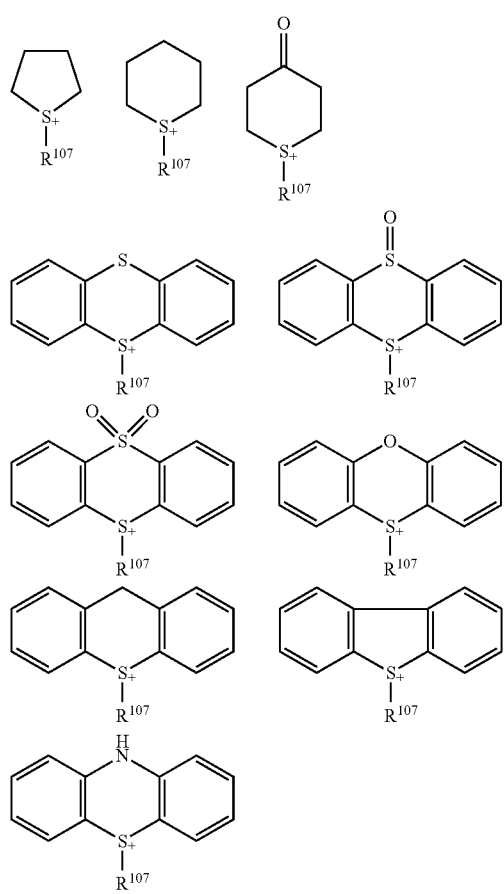
Herein $R^{107}$ is a straight, branched or cyclic $C_1$-$C_{20}$ monovalent hydrocarbon group which may contain a heteroatom, examples of which are as exemplified above for $R^{101}$ to $R^{103}$.
Exemplary structures of the sulfonium cation in formula (4) are shown below, but not limited thereto.
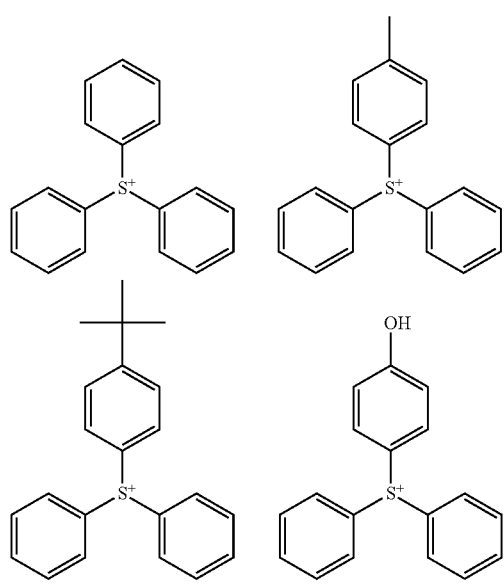
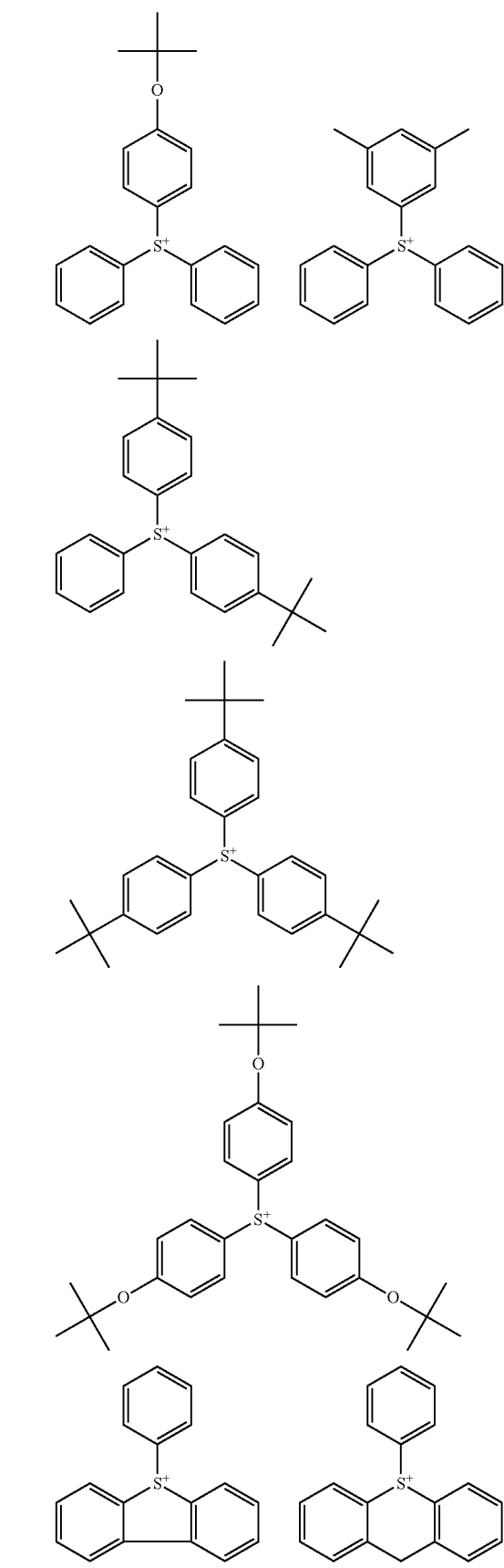

-continued

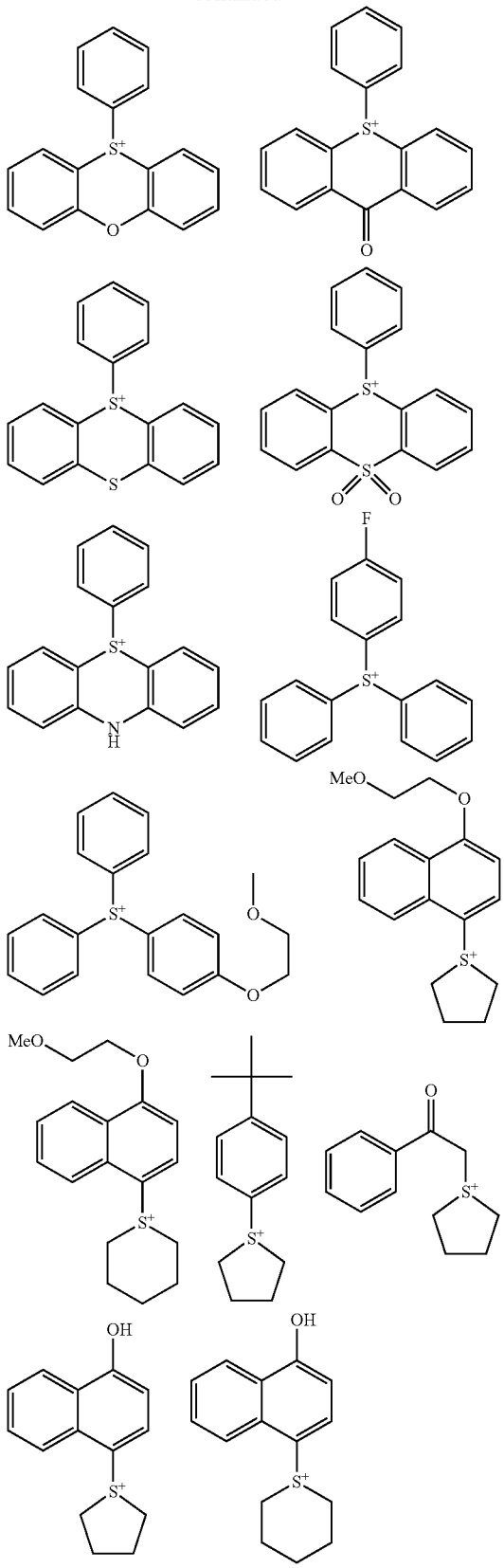

In formula (4), X⁻ is an anion selected from the formulae (4A) to (4D).

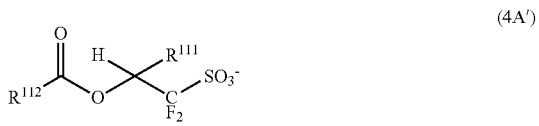

$$R^{fa}-CF_2-SO_3^- \quad (4A)$$

$$\begin{array}{c} R^{fb1}-CF_2-SO_2 \\ \phantom{R^{fb1}-CF_2-SO_2}\diagdown \\ \phantom{R^{fb1}-CF_2-SO_2}N^- \\ \phantom{R^{fb1}-CF_2-SO_2}\diagup \\ R^{fb2}-CF_2-SO_2 \end{array} \quad (4B)$$

$$R^{fc1}-CF_2-SO_2-\underset{\underset{\underset{R^{fc3}}{|}}{\underset{CF_2}{|}}}{\overset{\overset{\overset{R^{fc2}}{|}}{\overset{CF_2}{|}}}{\overset{|}{SO_2}}}C^- \quad (4C)$$

$$R^{fd}-\overset{O}{\underset{}{C}}-O-\underset{CF_3}{\overset{CF_3}{\underset{|}{C}}}-CH_2-SO_3^- \quad (4D)$$

In formula (4A), $R^{fa}$ is fluorine or a straight, branched or cyclic $C_1$-$C_{40}$ monovalent hydrocarbon group which may contain a heteroatom. Suitable structures include nonafluorobutane sulfonate, partially fluorinated sulfonates described in JP-A 2012-189977, paragraphs [0247]-[0251], partially fluorinated sulfonates described in JP-A 2013-101271, paragraphs [0261]-[0265], and partially fluorinated sulfonates described in JP-A 2013-101271, paragraphs [0261]-[0265].

Of the anions of formula (4A), a structure having formula (4A') is preferred.

$$R^{112}\overset{O}{\underset{}{\overset{\|}{C}}}-O-\underset{F_2}{\overset{H \quad R^{111}}{\underset{|}{C}}}SO_3^- \quad (4A')$$

In formula (4A'), $R^{111}$ is hydrogen or trifluoromethyl. $R^{112}$ is a straight, branched or cyclic $C_1$-$C_{30}$ monovalent hydrocarbon group which may contain a heteroatom. Suitable heteroatoms include oxygen, nitrogen, sulfur and halogen, with oxygen being preferred. Of the monovalent hydrocarbon groups, those of 6 to 30 carbon atoms are preferred because a high resolution is available in fine pattern formation. Suitable monovalent hydrocarbon groups include methyl, ethyl, propyl, isopropyl, butyl, isobutyl, s-butyl, t-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, icosanyl, allyl, benzyl, diphenylmethyl, tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of formula (4A'), reference is made to JP-A 2007-145797, JP-A 2008-106045, JP-A 2009-007327, and JP-A 2009-258695.

Examples of the sulfonium salt having an anion of formula (4A) are shown below, but not limited thereto.
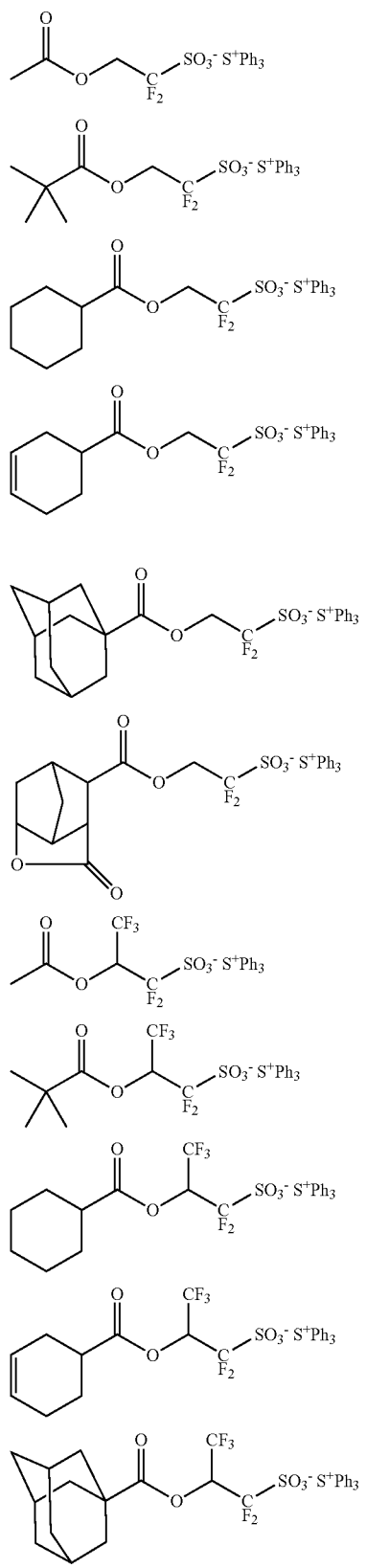
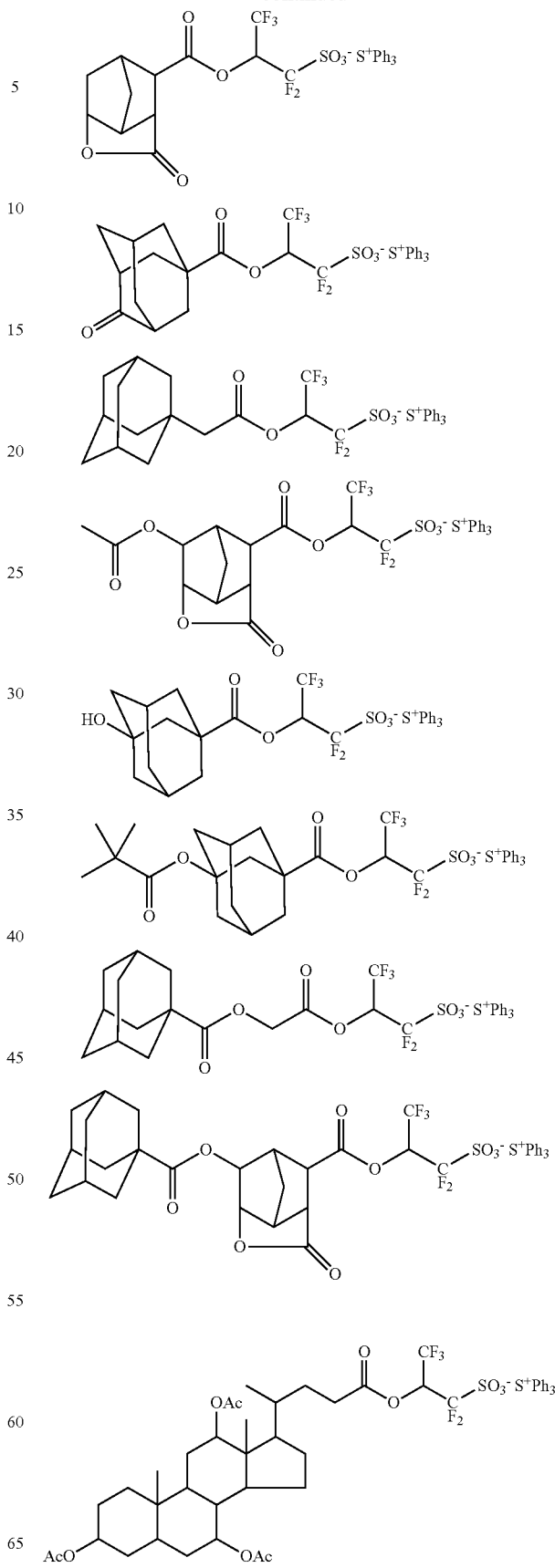

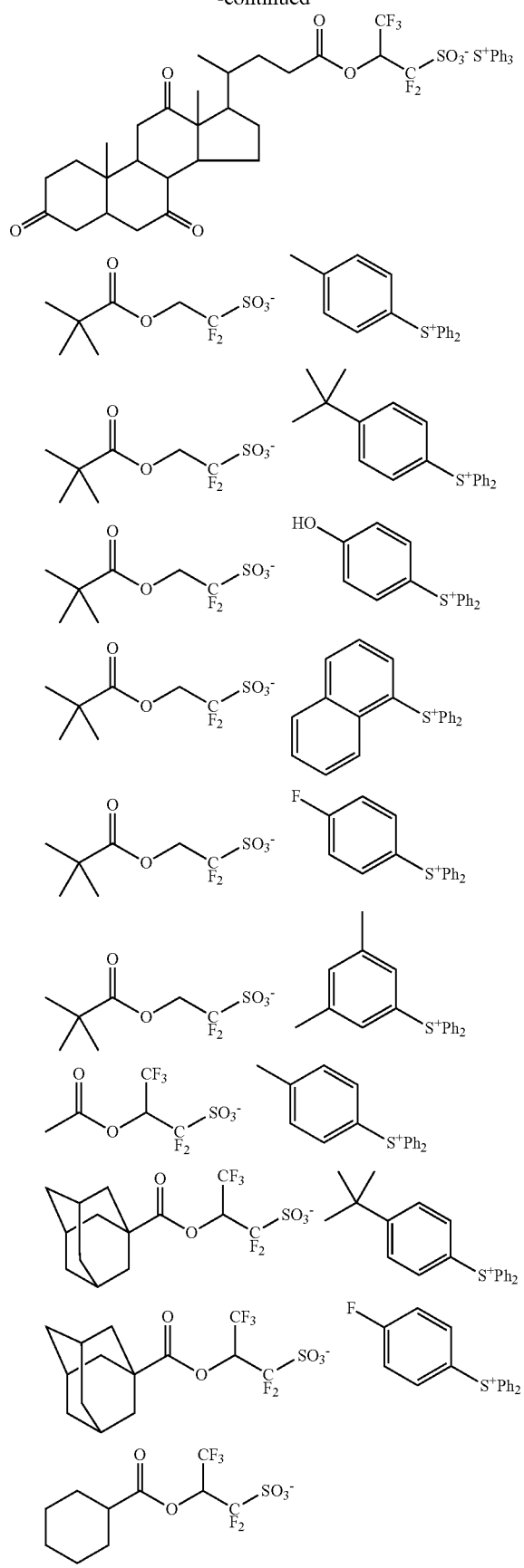
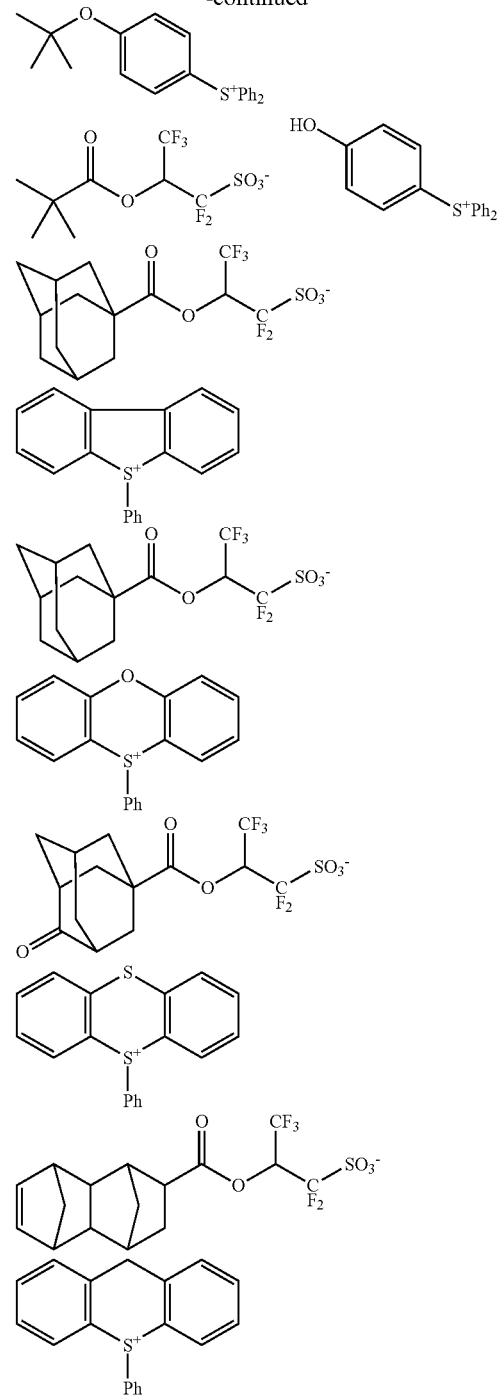

In formula (4B), $R^{fb1}$ and $R^{fb2}$ are each independently fluorine or a straight, branched or cyclic $C_1$-$C_{40}$ monovalent hydrocarbon group which may contain a heteroatom. Suitable monovalent hydrocarbon groups are as exemplified above for $R^{112}$. Preferably $R^{fb1}$ and $R^{fb2}$ each are fluorine or a $C_1$-$C_4$ straight fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and preferably the pair is a fluorinated ethylene or fluorinated propylene group forming a ring structure.

In formula (4C), $R^{fc1}$, $R^{fc2}$ and $R^{fc3}$ are each independently fluorine or a straight, branched or cyclic $C_1$-$C_{40}$ monovalent hydrocarbon group which may contain a heteroatom. Suitable monovalent hydrocarbon groups are as exemplified above for $R^{112}$. Preferably $R^{fc1}$, $R^{fc2}$ and $R^{fc3}$ each are fluorine or a $C_1$-$C_4$ straight fluorinated alkyl group. A pair of $R^{fc1}$ and $R^{fc2}$ may bond together to form a ring with the linkage (—$CF_2$—$SO_2$—$C^-$—$SO_2$—$CF_2$—) to which they are attached, and preferably the pair is a fluorinated ethylene or fluorinated propylene group forming a ring structure.

In formula (4D), $R^{fd}$ is a straight, branched or cyclic $C_1$-$C_{40}$ monovalent hydrocarbon group which may contain a heteroatom. Suitable monovalent hydrocarbon groups are as exemplified above for $R^{112}$.

With respect to the synthesis of the sulfonium salt having an anion of formula (4D), reference is made to JP-A 2010-215608.

Examples of the sulfonium salt having an anion of formula (4D) are shown below, but not limited thereto.

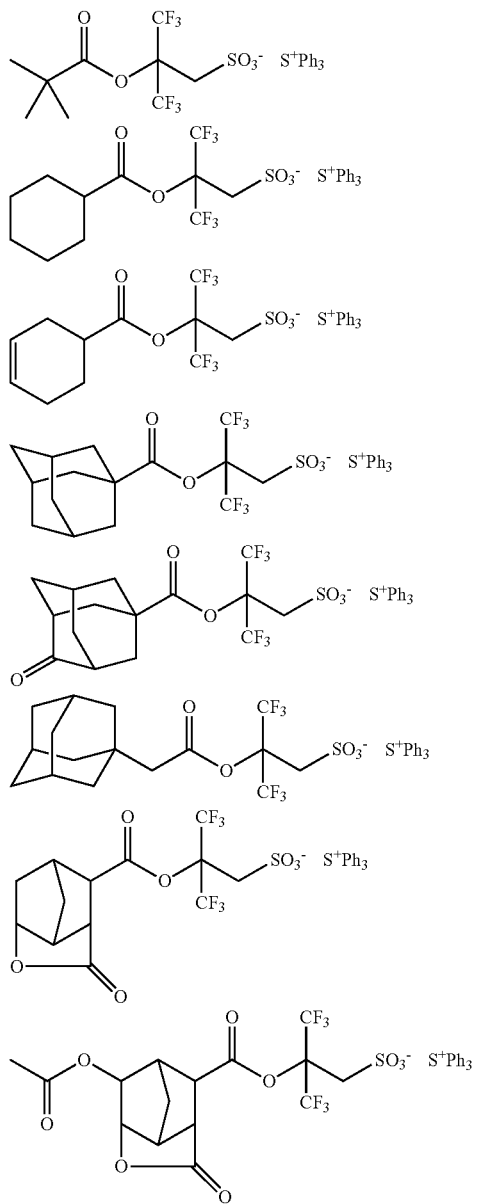
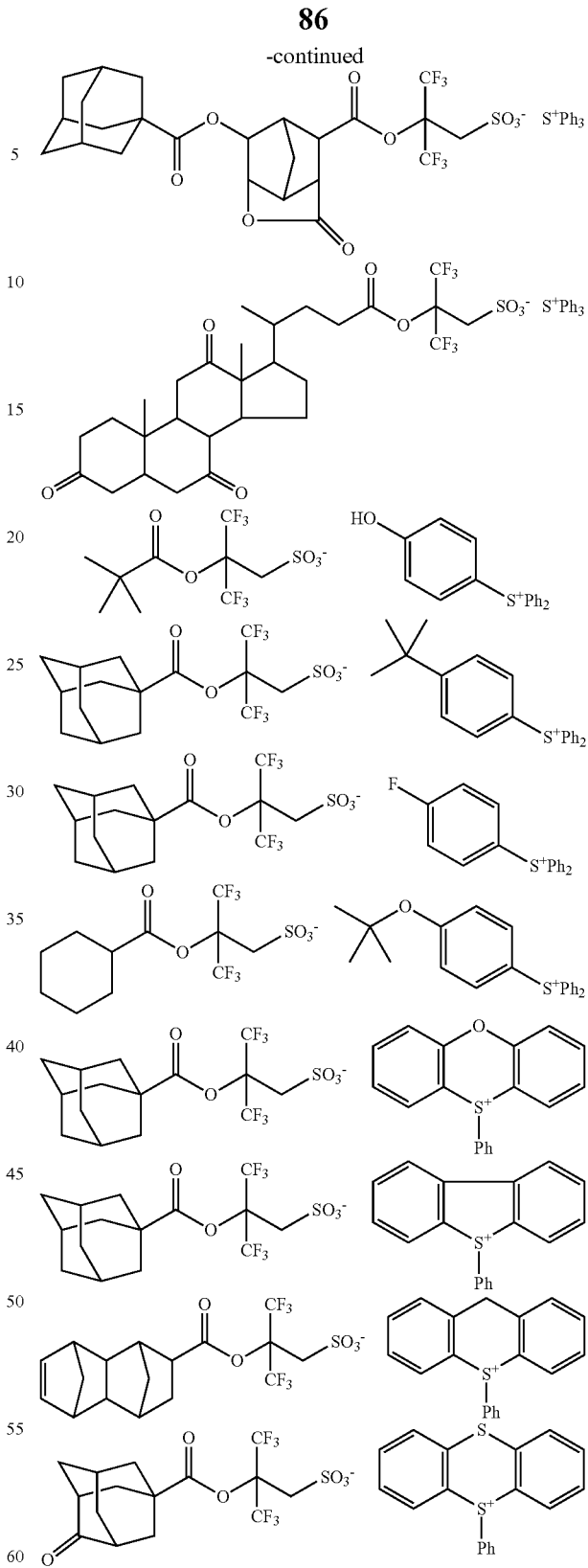

The compound having the anion of formula (4D) has a sufficient acid strength to cleave acid labile groups on the resist polymer because it is free of fluorine at α-position of sulfo group, but has two trifluoromethyl groups at β-position. Thus the compound is a useful PAG.

As the second PAG (D), those having the formula (5) are also preferred.

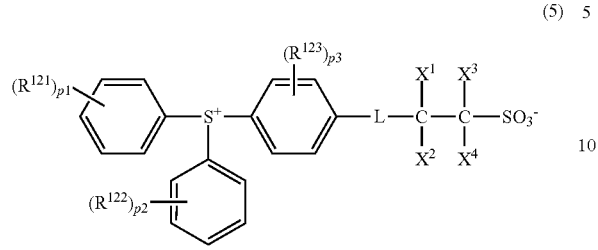

(5)

In formula (5), $R^{121}$, $R^{122}$ and $R^{123}$ are each independently a straight, branched or cyclic $C_1$-$C_{20}$ alkyl group, p1 and p2 are each independently an integer of 0 to 5, p3 is an integer of 0 to 4. L is a single bond, ether bond, or a straight, branched or cyclic $C_1$-$C_{20}$ divalent hydrocarbon group which may contain a heteroatom. $X^1$, $X^2$, $X^3$ and $X^4$ are each independently hydrogen, fluorine or trifluoromethyl, at least one of $X^1$, $X^2$, $X^3$ and $X^4$ being fluorine or trifluoromethyl.

Suitable alkyl groups include methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, and tricyclo[5.2.1.0$^{2,6}$]decanyl. Also included are the foregoing groups in which at least one hydrogen atom is replaced by a moiety containing a heteroatom such as oxygen, sulfur, nitrogen or halogen, or in which at least one carbon atom is replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic acid anhydride or haloalkyl moiety.

Suitable divalent hydrocarbon groups include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic divalent hydrocarbon groups such as cyclopentanediyl, cyclohexanediyl, norbornanediyl, and adamantanediyl; and unsaturated cyclic divalent hydrocarbon groups such as phenylene and naphthylene. Also included are the foregoing groups in which at least one hydrogen atom is replaced by an alkyl moiety such as methyl, ethyl, propyl, n-butyl or t-butyl, or in which at least one hydrogen atom is replaced by a moiety containing a heteroatom such as oxygen, sulfur, nitrogen or halogen, or in which at least one carbon atom is replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic acid anhydride or haloalkyl moiety. Suitable heteroatoms include oxygen, nitrogen, sulfur and halogen, with oxygen being preferred.

Examples of the PAG having formula (5) are shown below, but not limited thereto. Herein G is hydrogen, fluorine or trifluoromethyl.

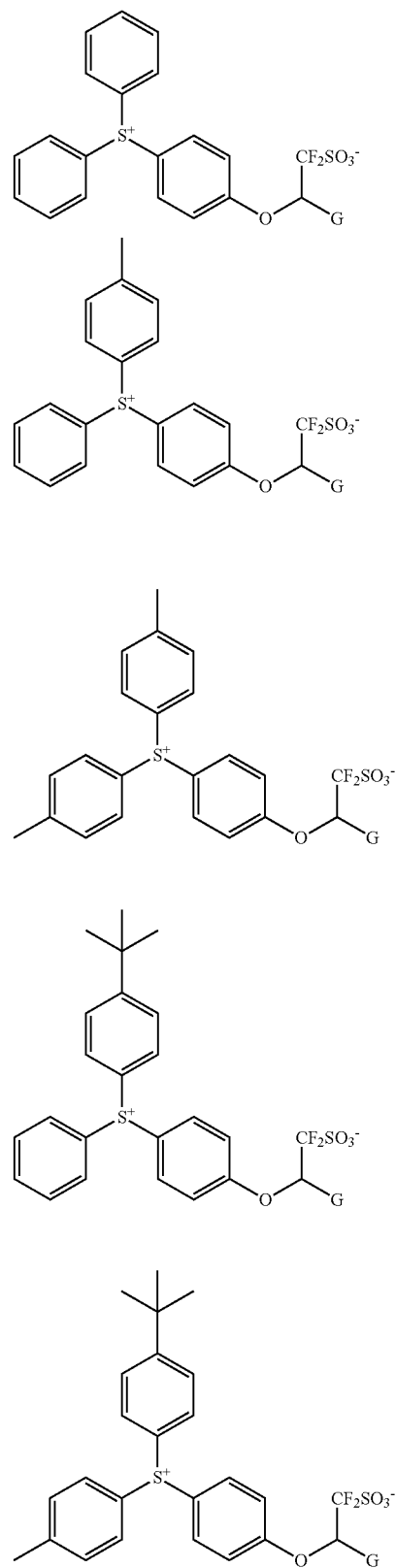

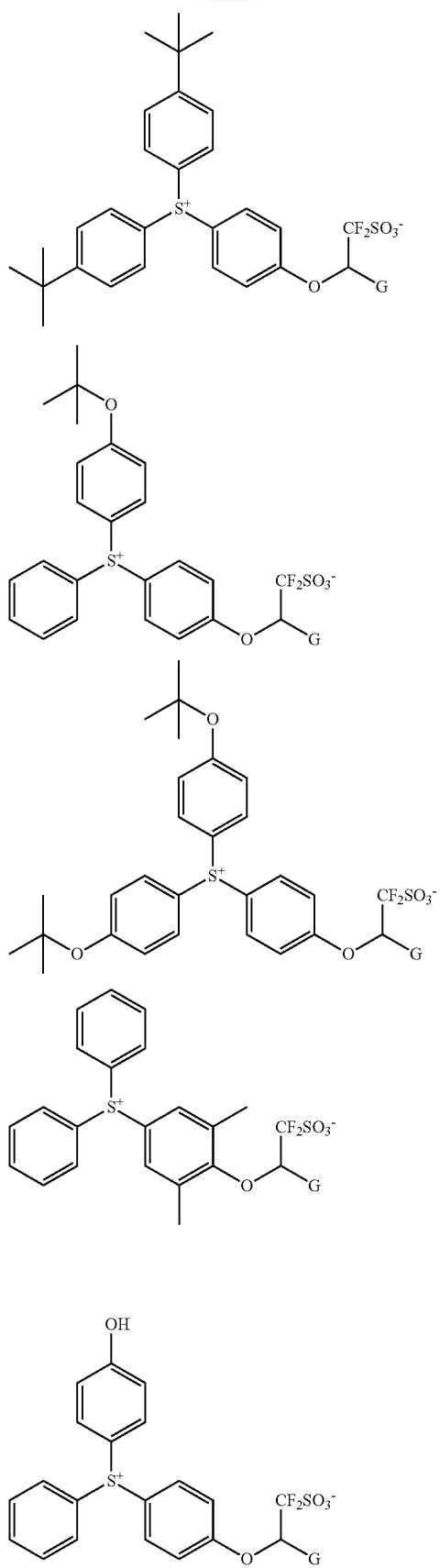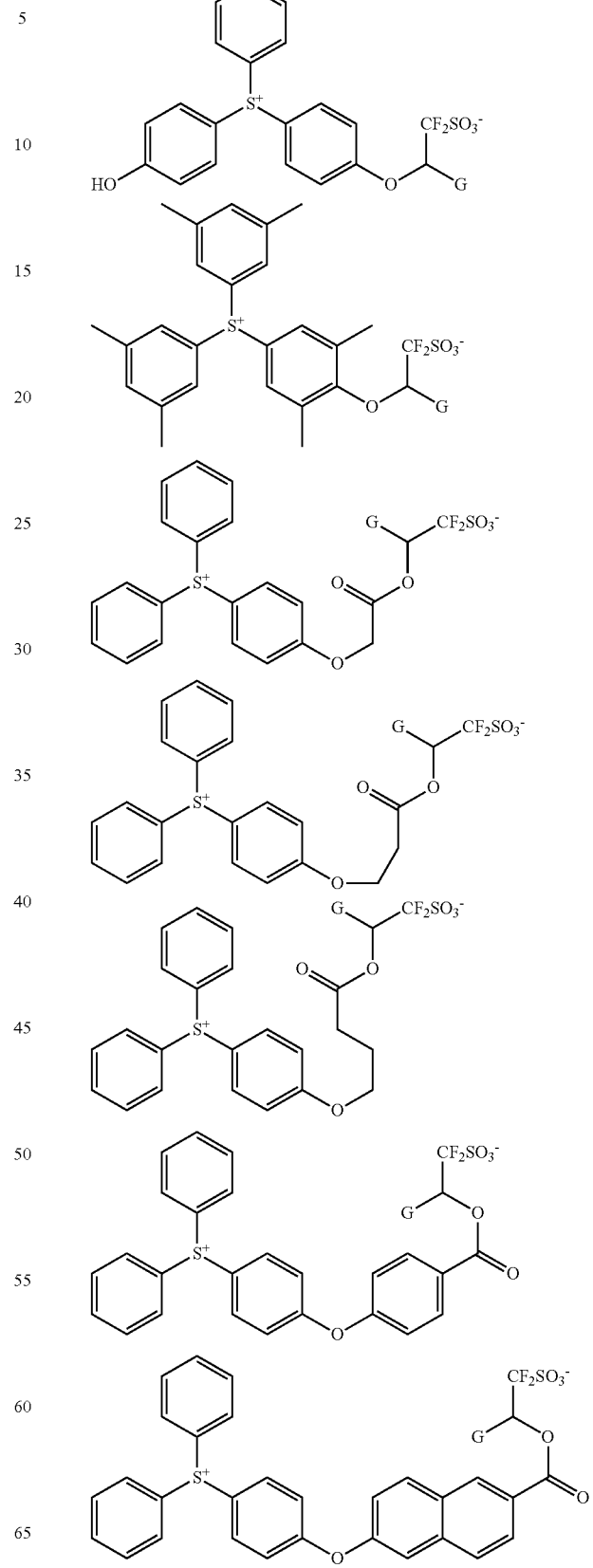

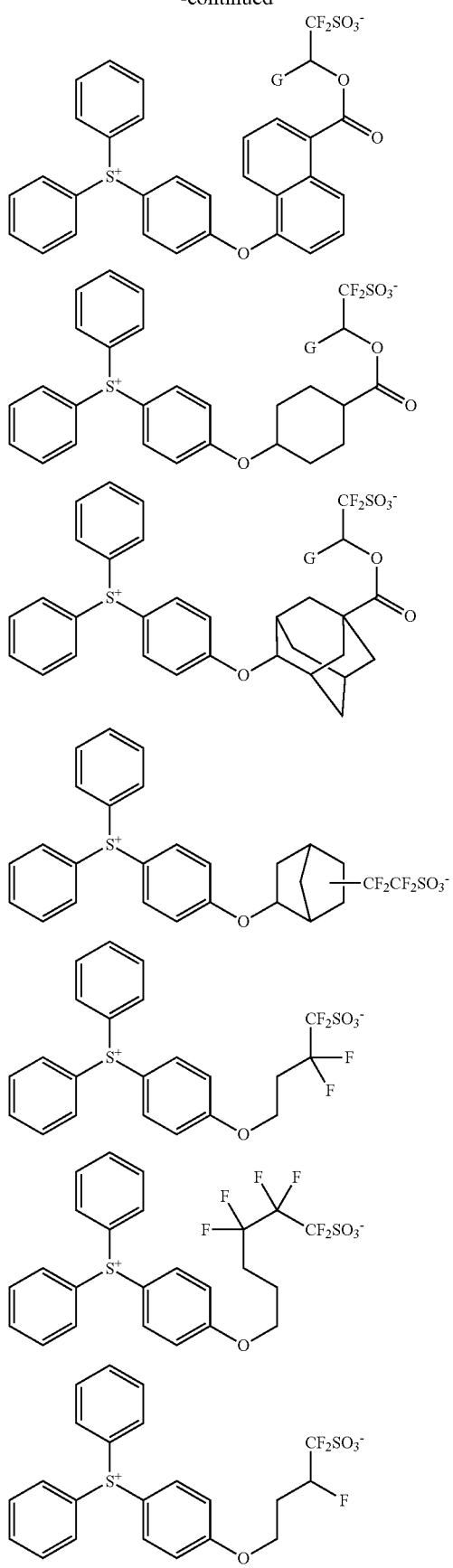

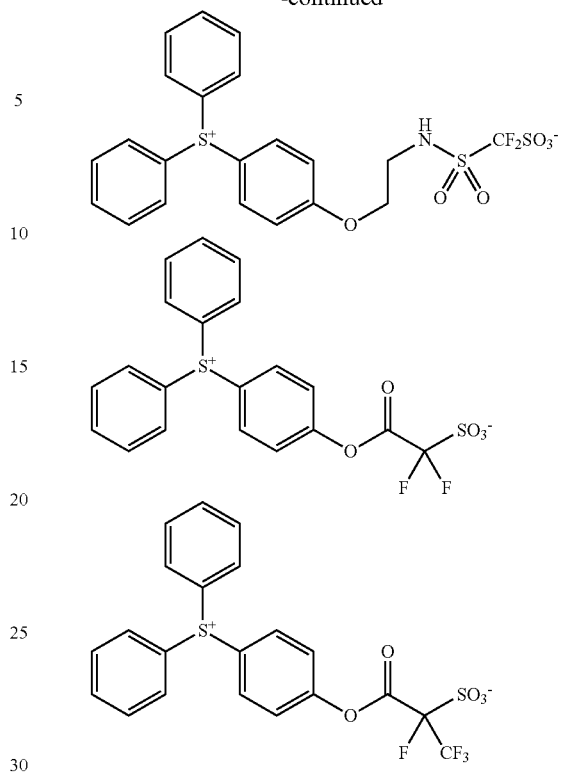

An appropriate amount of the PAG (D) added is 0 to 40 parts, more preferably 0.1 to 40 parts, and even more preferably 0.1 to 20 parts by weight per 100 parts by weight of the base resin (B). An amount in the range ensures good resolution and leaves no foreign particles after resist development or during separation. The second PAGs may be used alone or in admixture.

(E) Quencher

The resist composition may further comprise (E) a quencher. As used herein, the "quencher" refers to a compound capable of trapping the acid generated by the PAG. The quencher is capable of holding down the diffusion rate of acid when the acid generated from PAG diffuses in the resist film.

As the quencher, onium salts having the formulae (6) and (7) are preferred.

$$R^{151}-SO_3^-M^+ \qquad (6)$$

$$R^{152}-CO_2^-M^+ \qquad (7)$$

Herein $R^{151}$ and $R^{152}$ are each independently hydrogen or a straight, branched or cyclic $C_1$-$C_{40}$ monovalent hydrocarbon group which may contain a heteroatom, excluding the hydrocarbon group in which the hydrogen atom bonded to the carbon at α-position relative to the sulfo group is substituted by fluorine or fluoroalkyl, and $M^+$ is an onium cation.

In formula (6), examples of the group $R^{151}$ include hydrogen, methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, adamantyl, phenyl, naphthyl, and anthracenyl. Also included are the foregoing groups in which at least one hydrogen atom is replaced by a moiety containing a heteroatom such as oxygen, sulfur, nitrogen or halogen, or in which at least one carbon atom is replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic acid anhydride or haloalkyl moiety.

In formula (7), examples of the group $R^{152}$ include fluorinated alkyl groups such as trifluoromethyl and trifluoroethyl and fluorinated aryl groups such as pentafluorophenyl and 4-trifluoromethylphenyl as well as those exemplified above for $R^{151}$.

Suitable structures of the anion moiety in formula (6) are shown below, but not limited thereto.

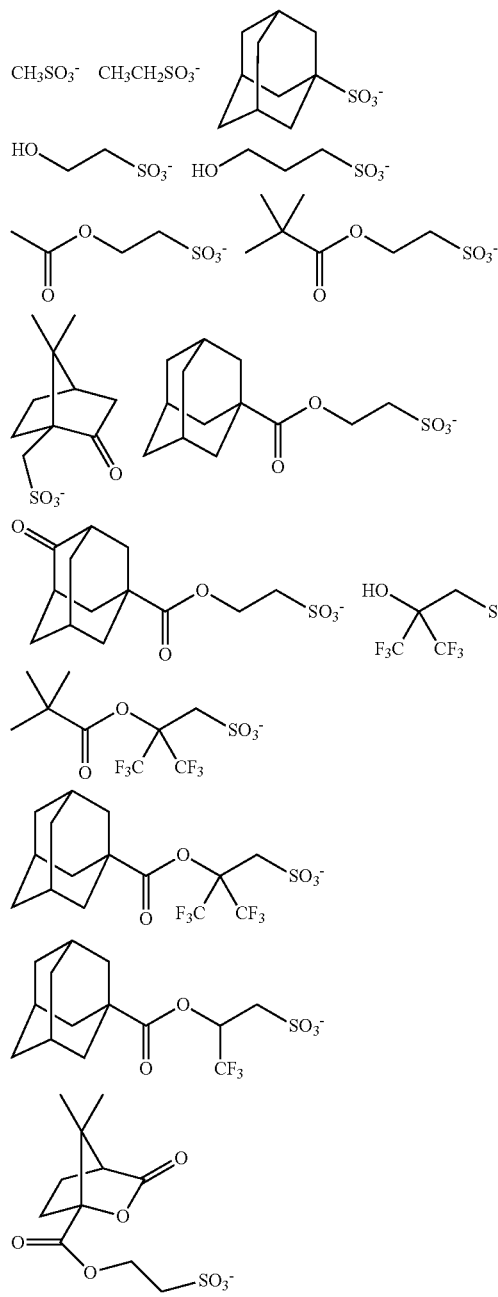

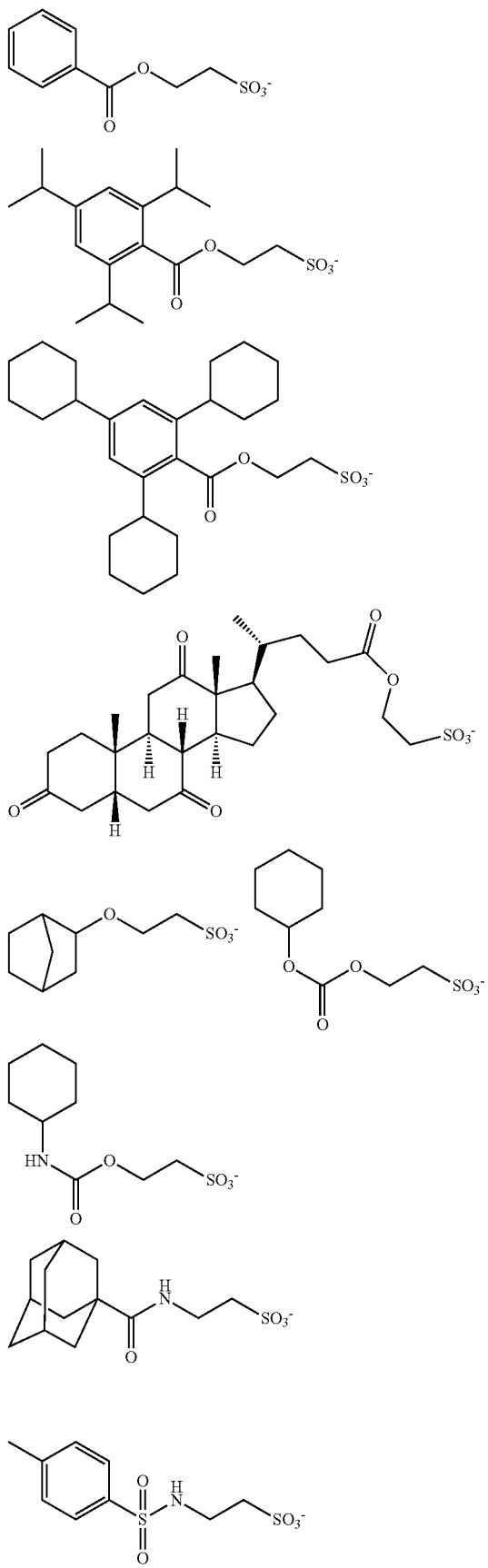

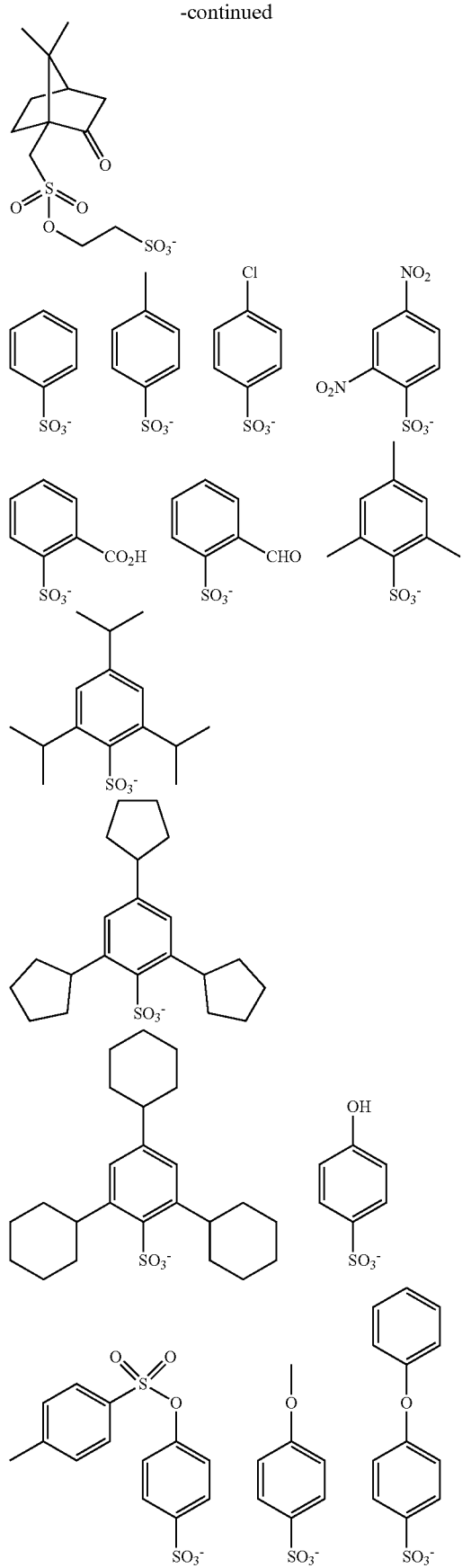
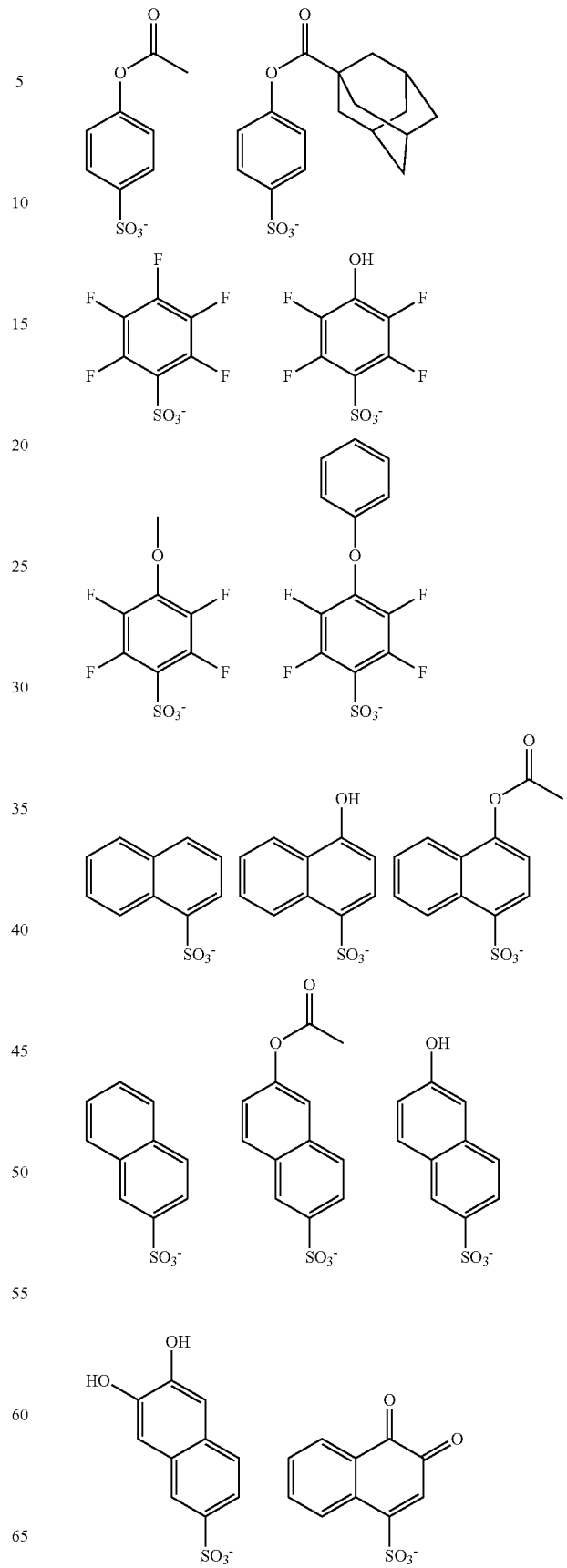

97
-continued
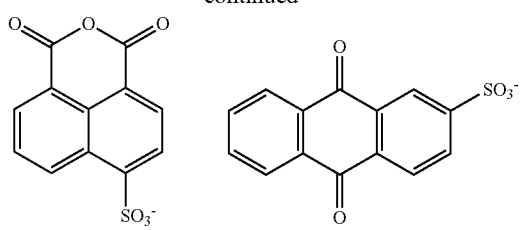
Suitable structures of the anion moiety in formula (7) are shown below, but not limited thereto.
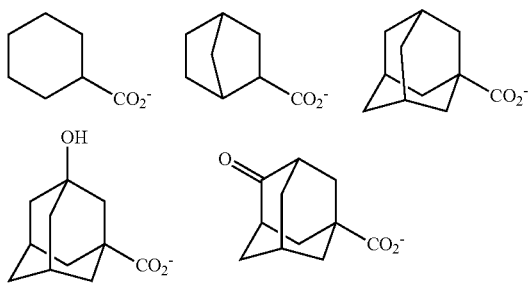
98
-continued
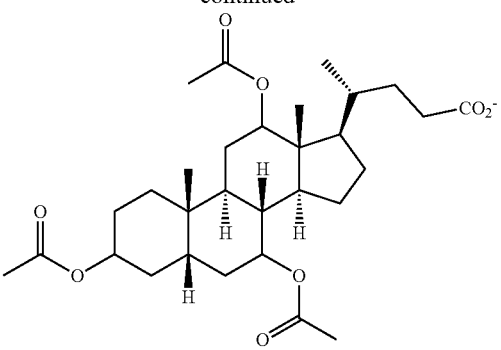
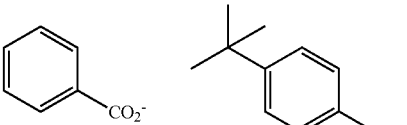
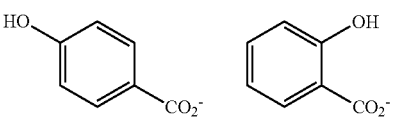
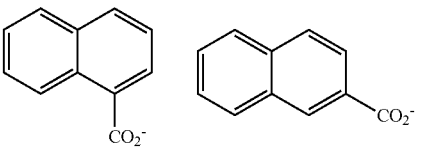
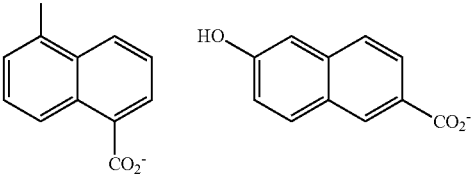
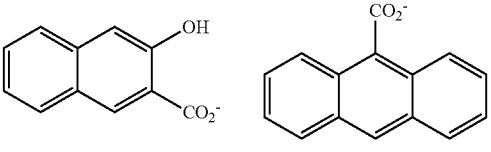
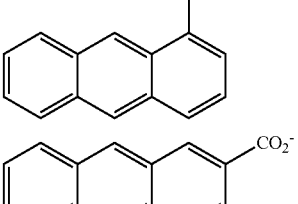
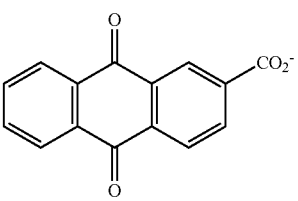
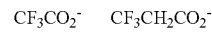
CF$_3$CO$_2^-$   CF$_3$CH$_2$CO$_2^-$
CF$_3$CF$_2$CO$_2^-$   CF$_3$C(CF$_3$)(OH)CO$_2^-$
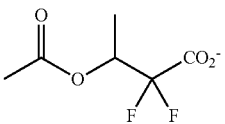

-continued

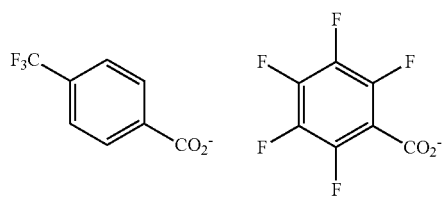

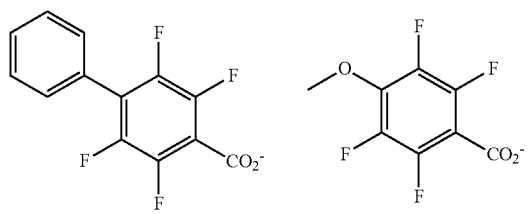

As the onium cation in formulae (6) and (7), those having the following formulae (8), (9) and (10) are preferred.

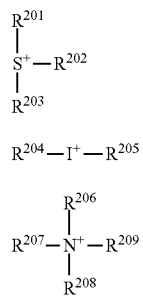

Herein $R^{201}$ to $R^{209}$ are each independently a straight, branched or cyclic $C_1$-$C_{20}$ monovalent hydrocarbon group which may contain a heteroatom. Any two of $R^{201}$ to $R^{203}$ may bond together to form a ring with the sulfur atom to which they are attached. $R^{204}$ and $R^{205}$ may bond together to form a ring with the iodine atom to which they are attached. Any two of $R^{206}$ to $R^{209}$ may bond together to form a ring with the nitrogen atom to which they are attached. Suitable monovalent hydrocarbon groups include alkyl groups such as methyl, ethyl, propyl, isopropyl, n-butyl, s-butyl, t-butyl, t-pentyl, n-pentyl, n-hexyl, n-octyl, cyclopentyl, cyclohexyl, 2-ethylhexyl, cyclopentylmethyl, cyclopentylethyl, cyclohexylmethyl, cyclohexylethyl, norbornyl, oxanorbornyl, tricyclo[5.2.1.0$^{2,6}$]decanyl, and adamantyl, and aryl groups such as phenyl and naphthyl. Also included are the foregoing groups in which at least one hydrogen atom is replaced by a moiety containing a heteroatom such as oxygen, sulfur, nitrogen or halogen, or in which at least one carbon atom is replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic acid anhydride or haloalkyl moiety.

Examples of the onium cation are shown below, but not limited thereto.

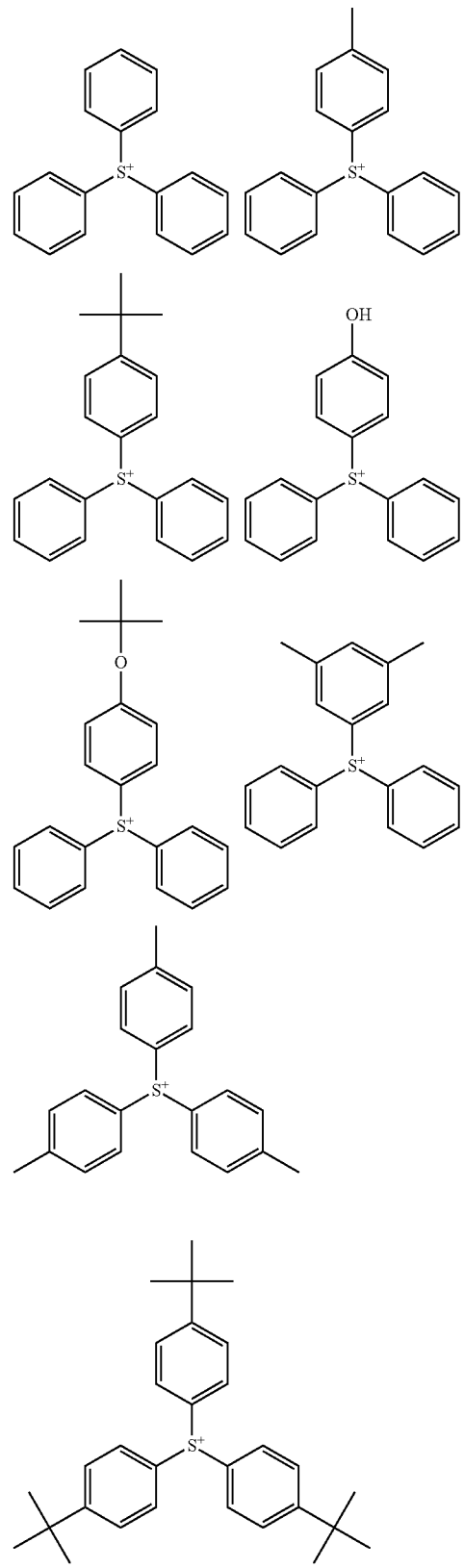

101
-continued
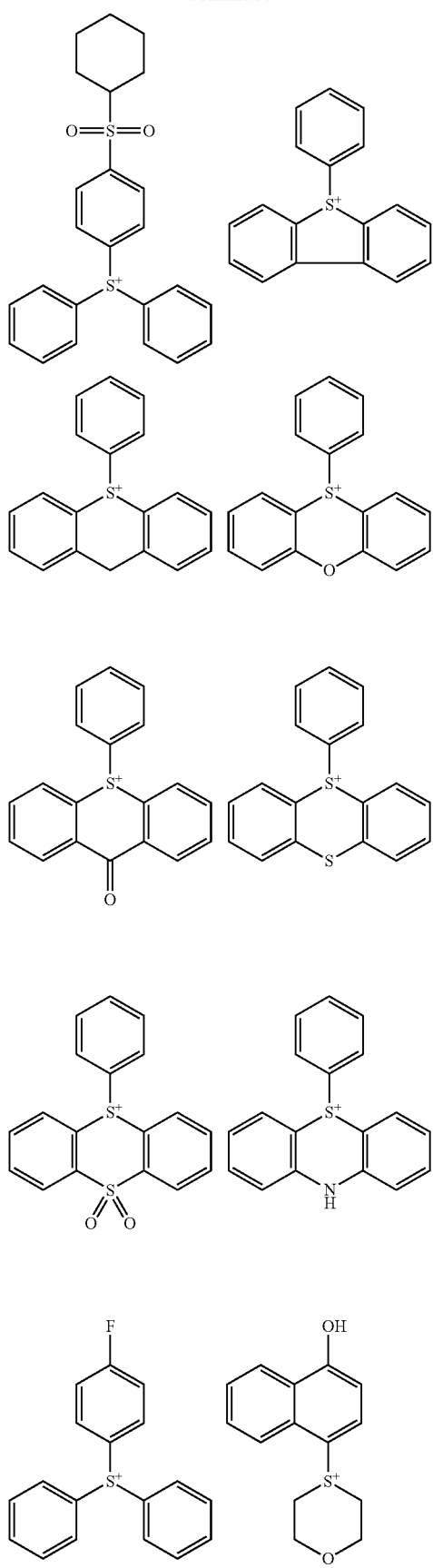
102
-continued
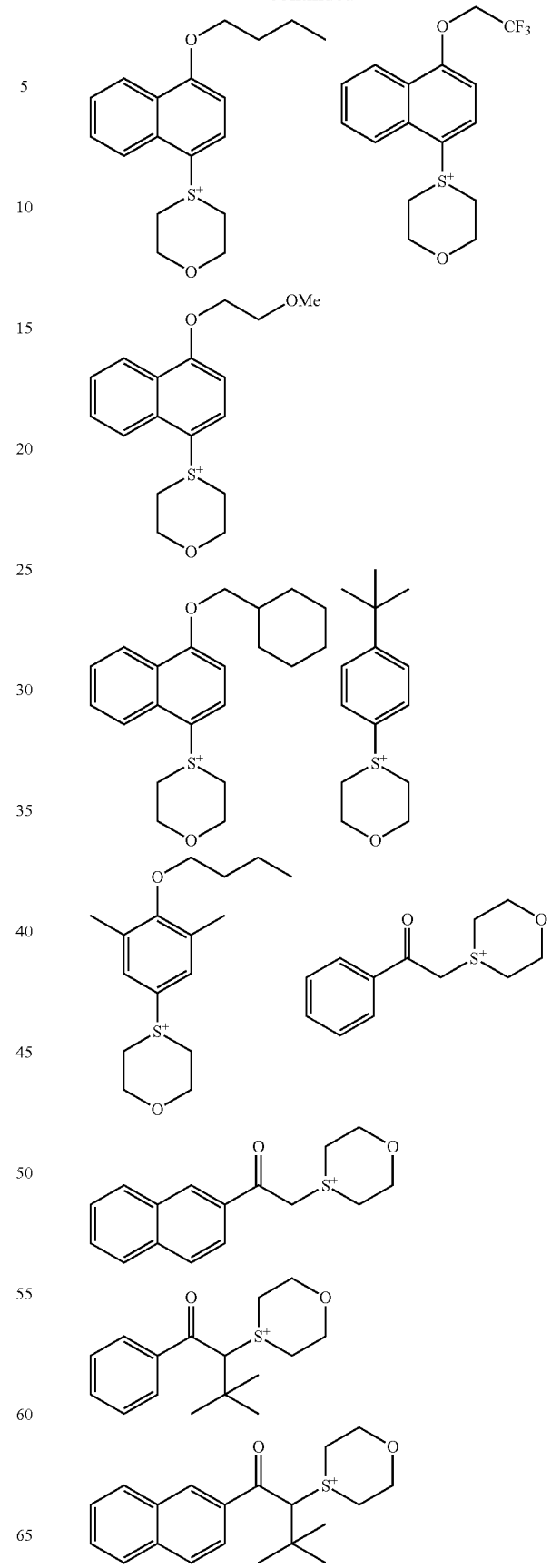

-continued

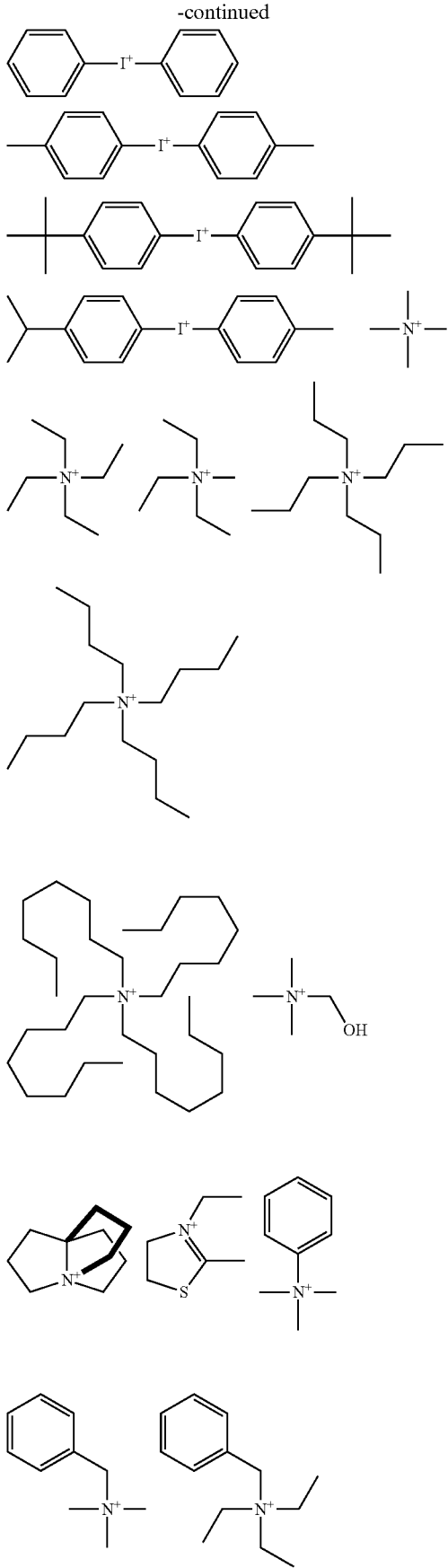

-continued

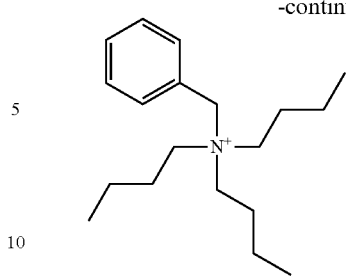

Examples of the onium salt having formula (6) or (7) include any combinations of the foregoing anions and onium cations. Such an onium salt may be readily prepared by ion exchange reaction using any well-known organic chemistry techniques. The ion exchange reaction may be conducted in a standard way, with reference to JP-A 2007-145797, for example.

The onium salt having formula (6) or (7) functions as a quencher since the anion therein is a conjugated base of weak acid. As used herein, the weak acid indicates an acidity insufficient to deprotect an acid labile group from an acid labile group-containing unit in the base resin. The onium salt having formula (6) or (7) functions as a quencher when used in combination with an onium salt type photoacid generator having a conjugated base of a strong acid, typically a sulfonic acid which is fluorinated at α-position as the counter anion. In a system using a mixture of an onium salt capable of generating a strong acid (e.g., α-position fluorinated sulfonic acid) and an onium salt capable of generating a weak acid (e.g., α-position non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion. In this way, the onium salt functions as a quencher.

If a photoacid generator capable of generating a strong acid is an onium salt, an exchange from the strong acid generated upon exposure to high-energy radiation to a weak acid as above can take place, but it rarely happens that the weak acid generated upon exposure to high-energy radiation collides with the unreacted onium salt capable of generating a strong acid to induce a salt exchange. This is because of a likelihood of an onium cation forming an ion pair with a stronger acid anion.

An appropriate amount of the onium salt having formula (6) or (7) is 0 to 40 parts, preferably 0.1 to 40 parts, more preferably 0.1 to 20 parts by weight, per 100 parts by weight of the base resin (B). A larger amount of the onium salt beyond the upper limit may cause degradation of resolution or leave foreign particles after resist development or during stripping. The onium salt having formula (6) or (7) may be used alone or in combination.

As the quencher (E), a photo-degradable onium salt having a nitrogen-containing substituent group may be used in combination with the onium salt having formula (6) or (7), if desired. This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced. With respect to the photo-degradable base, reference may be made to JP-A 2009-109595, 2012-046501, and JP-A 2013-209360, for example.

An appropriate amount of the photo-degradable base is 0 to 40 parts, preferably 0.1 to 40 parts, more preferably 0.1 to 20 parts by weight, per 100 parts by weight of the base resin (B). A larger amount of the photo-degradable base beyond the upper limit may cause degradation of resolution or leave foreign particles after resist development or during stripping. The photo-degradable base may be used alone or in admixture.

An amine compound may be added to the resist composition as the quencher (E). Suitable amine compounds include primary, secondary and tertiary amine compounds, specifically amine compounds having a hydroxyl group, ether bond, ester bond, lactone ring, cyano group or sulfonate bond, as described in JP-A 2008-111103, paragraphs [0146] to [0164] (U.S. Pat. No. 7,537,880), and compounds having primary or secondary amine protected with a carbamate group, as described in JP 3790649.

The amine compound may be used alone or in admixture of two or more. An appropriate amount of the amine compound is 0 to 12 parts, preferably 0.001 to 12 parts, more preferably 0.01 to 8 parts by weight, per 100 parts by weight of the base resin (B). The inclusion of amine compound facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile. The amine compound is also effective for improving adhesion to the substrate.

(F) Surfactant

The resist composition may further comprise (F) a surfactant which is insoluble or substantially insoluble in water and soluble in alkaline developer, and/or a surfactant which is insoluble or substantially insoluble in water and alkaline developer. For the surfactant, reference should be made to those compounds described in JP-A 2010-215608 and JP-A 2011-016746.

While many examples of the surfactant which is insoluble or substantially insoluble in water and alkaline developer are described in the patent documents cited herein, preferred examples are FC-4430, Surflon® S-381, Surfynol® E1004, KH-20 and KH-30, which may be used alone or in admixture. Partially fluorinated oxetane ring-opened polymers having the formula (surf-1) are also useful.

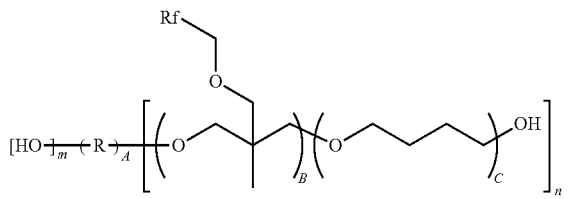

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

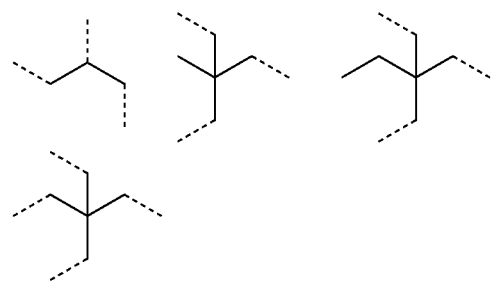

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. "A" is equal to 1, B is an integer of 2 to 25, and C is an integer of 0 to 10. Preferably, B is an integer of 4 to 20, and C is 0 or 1. Note that the formula (surf-1) does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water slippage.

Suitable polymeric surfactants are shown below.

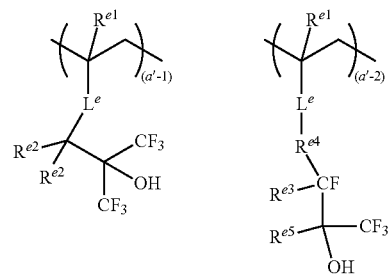

-continued

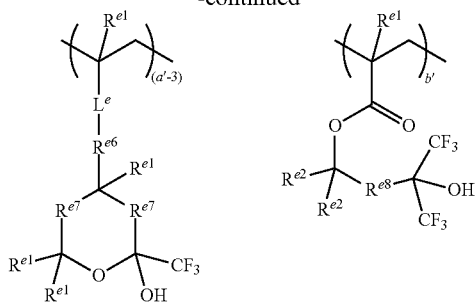

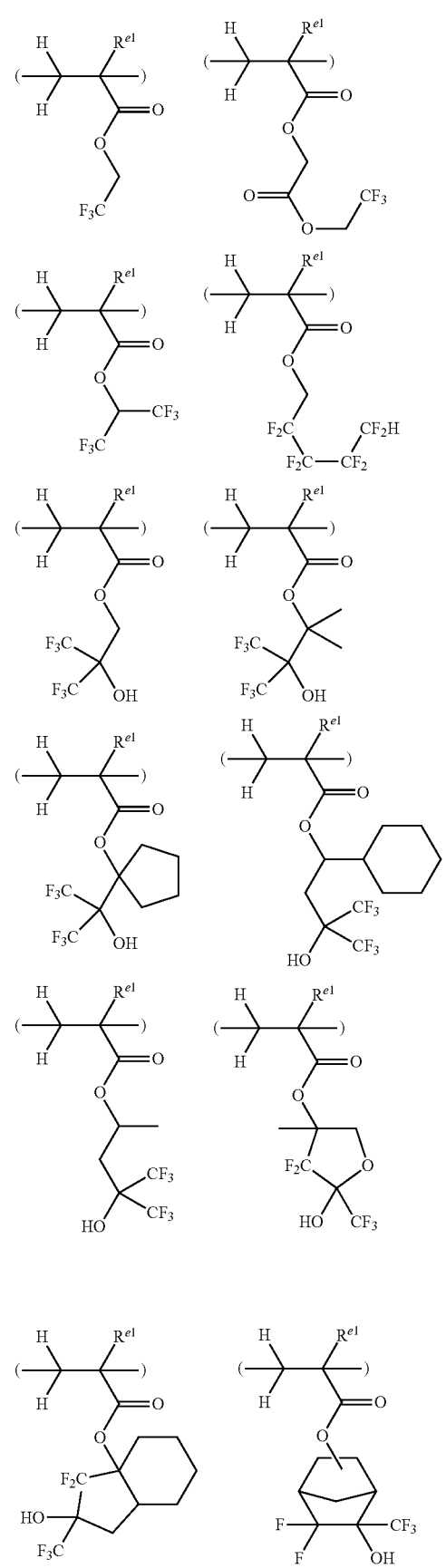

Herein $R^{e1}$ is each independently hydrogen, fluorine, methyl or trifluoromethyl. $R^{e2}$ is each independently hydrogen or a straight, branched or cyclic $C_1$-$C_{20}$ alkyl or fluoroalkyl group, or two $R^{e2}$ in a common unit may bond together to form a ring with the carbon atom to which they are attached, and in this event, they together represent a straight, branched or cyclic $C_2$-$C_{20}$ alkylene or fluoroalkylene group.

$R^{e3}$ is fluorine or hydrogen, or $R^{e3}$ may bond with $R^{e4}$ to form a non-aromatic ring of 3 to 10 carbon atoms in total with the carbon atom to which they are attached. $R^{e4}$ is a straight, branched or cyclic $C_1$-$C_6$ alkylene group in which at least one hydrogen atom may be substituted by a fluorine atom. $R^{e5}$ is a straight or branched $C_1$-$C_{10}$ alkyl group in which at least one hydrogen atom is substituted by a fluorine atom. Alternatively, $R^{e4}$ and $R^{e5}$ may bond together to form a non-aromatic ring with the carbon atoms to which they are attached. In this event, $R^{e4}$, $R^{e5}$ and the carbon atoms to which they are attached together represent a trivalent organic group of 3 to 12 carbon atoms in total. $R^{e6}$ is a single bond or a $C_1$-$C_4$ alkylene.

$R^{e7}$ is each independently a single bond, —O—, or —$CR^{e1}R^{e1}$—. $R^{e8}$ is a straight or branched $C_1$-$C_4$ alkylene group, or may bond with $R^{e2}$ within a common unit to form a $C_3$-$C_6$ non-aromatic ring with the carbon atom to which they are attached.

$R^{e9}$ is methylene, 1,2-ethylene, 1,3-propylene or 1,4-butylene. $R^{e10}$ is a $C_3$-$C_6$ linear perfluoroalkyl group, typically 3H-perfluoropropyl, 4H-perfluorobutyl, 5H-perfluoropentyl or 6H-perfluorohexyl.

$L^e$ is each independently —C(=O)—O—, —O—, or —C(=O)—$R^{e11}$—C(=O)—O— wherein $R^{e11}$ is a straight, branched or cyclic $C_1$-$C_{10}$ alkylene group. The subscripts are in the range: $0 \le (a'\text{-}1) \le 1$, $0 \le (a'\text{-}2) \le 1$, $0 \le (a'\text{-}3) \le 1$, $0 \le b' \le 1$, $0 \le c' \le 1$, and $0 < (a'\text{-}1)+(a'\text{-}2)+(a'\text{-}3)+b'+c' \le 1$.

Examples of these recurring units are shown below, but not limited thereto. Herein $R^{e1}$ is as defined above.

-continued

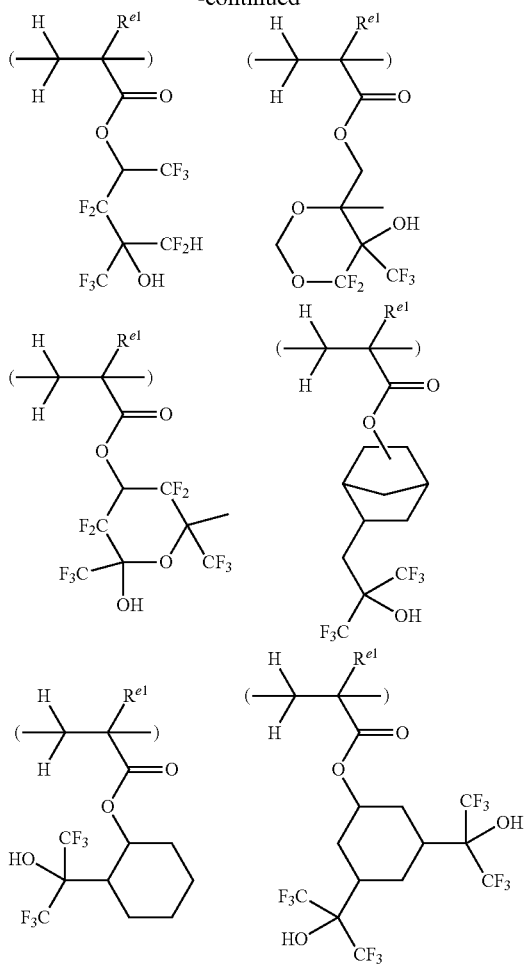

The polymeric surfactant has a Mw of preferably 1,000 to 50,000, more preferably 2,000 to 20,000 as measured by GPC versus polystyrene standards. A surfactant with a Mw within the range may be effective for surface modification and cause no development defects.

For the surfactant which is insoluble or substantially insoluble in water and soluble in alkaline developer, reference may be made to JP-A 2008-122932, 2009-098638, 2009-191151, 2009-192784, 2009-276363, 2010-107695, 2010-134012, 2010-250105, and 2011-042789.

An appropriate amount of component (F) is 0 to 20 parts by weight per 100 parts by weight of the base resin (B). The lower limit is preferably 0.001 part, and more preferably 0.01 part by weight, whereas the upper limit is preferably 15 parts, and more preferably 10 parts by weight.

Process

A further embodiment of the invention is a pattern forming process using the resist composition defined above. A pattern may be formed from the resist composition using any well-known lithography process. The preferred process includes at least the steps of forming a resist film on a substrate, exposing it to high-energy radiation, and developing it in a developer.

Specifically, the resist composition is applied onto a substrate for integrated circuitry fabrication (e.g., Si, $SiO_2$, SiN, SiON, TiN, WSi, BPSG, SOG, organic antireflective film, etc.) or a substrate for mask circuitry fabrication (e.g., Cr, CrO, CrON, $MoSi_2$, $SiO_2$, etc.) by a suitable coating technique such as spin coating. The coating is prebaked on a hotplate at a temperature of 60 to 150° C. for 1 to 10 minutes, preferably 80 to 140° C. for 1 to 5 minutes. The resulting resist film is generally 0.05 to 2 m thick.

Through a mask having a desired pattern disposed over the substrate, the resist film is then exposed to high-energy radiation such as KrF excimer laser, ArF excimer laser or EUV in an exposure dose preferably in the range of 1 to 200 $mJ/cm^2$, more preferably 10 to 100 $mJ/cm^2$. Alternatively, pattern formation may be performed by writing with EB directly in a dose of preferably 1 to 300 $\mu C/cm^2$, more preferably 10 to 200 $\mu C/cm^2$. Light exposure may be done by a conventional lithography process or in some cases, by an immersion lithography process of providing a liquid having a refractive index of at least 1.0 between the projection lens and the resist film. The preferred liquid is water. In the case of immersion lithography, a protective film which is insoluble in water may be formed on the resist film.

The resist film is then baked (PEB) on a hotplate at 60 to 150° C. for 1 to 5 minutes, and preferably at 80 to 140° C. for 1 to 3 minutes. Finally, development is carried out using as the developer an aqueous alkaline solution, such as a 0.1 to 5 wt %, preferably 2 to 3 wt %, aqueous solution of tetramethylammonium hydroxide (TMAH), this being done by a conventional method such as dip, puddle, or spray development for a period of 0.1 to 3 minutes, and preferably 0.5 to 2 minutes. In this way the desired pattern is formed on the substrate.

While the water-insoluble protective film which is used in the immersion lithography serves to prevent any components from being leached out of the resist film and to improve water slippage at the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

Any desired step may be added to the pattern forming process. For example, after a photoresist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

A pattern may also be formed by a double patterning process. The double patterning process includes a trench process of processing an underlay to a 1:3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

In the pattern forming process, an alkaline aqueous solution is often used as the developer. The negative tone development technique using an organic solvent instead is also applicable wherein the unexposed region is developed and dissolved in the organic solvent.

In the organic solvent development, the organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLE

Synthesis Examples, Examples and Comparative Examples are given below by way of illustration and not by way of limitation. The abbreviation "pbw" is parts by weight. For all polymers, Mw and Mn are determined by GPC versus polystyrene standards using THF solvent. THF stands for tetrahydrofuran, MEK for methyl ethyl ketone, MIBK for methyl isobutyl ketone, and DIPE for diisopropyl ether. Analytic instruments are as shown below.

IR: NICOLET 6700 by Thermo Fisher Scientific Inc.
$^1$H-NMR: ECA-500 by JEOL Ltd.
$^{19}$F-NMR: ECA-500 by JEOL Ltd.
MALDI-TOF-MS: S3000 by JEOL Ltd.
GC-MS: GC.6890N MS.5973 by Agilent Technologies

[1] Synthesis of Sulfonium Compounds

Example 1-1

Synthesis of PAG-1

Example 1-1-1

Synthesis of Intermediate A

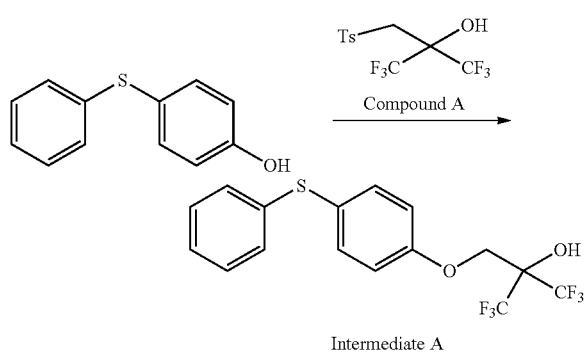

In a mixture of 550 g of THF and 133 g of water was dissolved 220 g of 4-phenylthiophenol. At room temperature, 25 wt % sodium hydroxide aqueous solution was added dropwise to the solution, which was aged for 15 minutes. Thereafter, a solution of 352 g of Compound A in 250 g of THF was added dropwise thereto at room temperature. The solution was aged overnight, after which 5 wt % hydrochloric acid was added thereto for quenching. The reaction solution was diluted with 620 g of hexane and 620 g of toluene, and washed with water. A 1 wt % sodium hydroxide aqueous solution was added to the organic layer, followed by separatory operation. The organic layer was combined with 2.5 wt % hydrochloric acid and washed with water again, followed by separatory operation. The organic layer was concentrated, obtaining 208 g of the end compound, Intermediate A as colorless oily matter (yield 65%).

Figure 2:
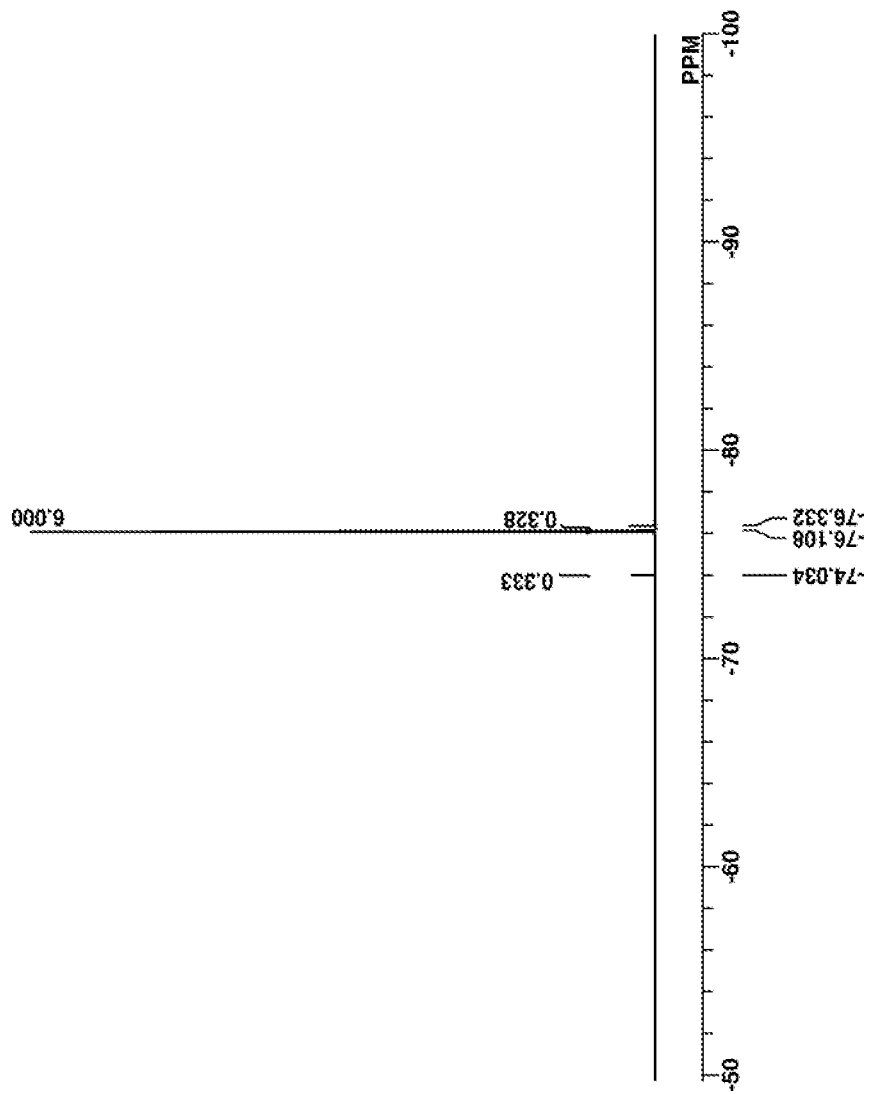
Figure 3:
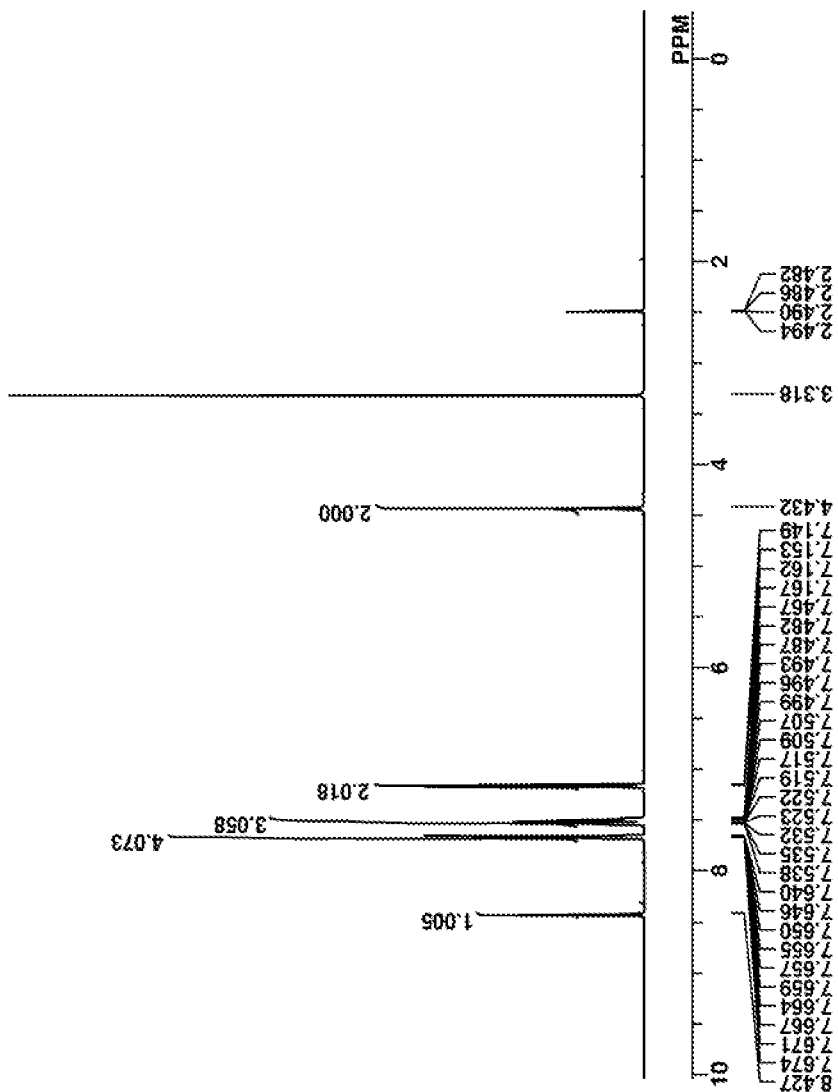
FIGS. 3 and 4 are diagrams showing $^1$H- and $^{19}$F-NMR spectra of Intermediate B in Example 1-1-2, respectively.
Figure 4:
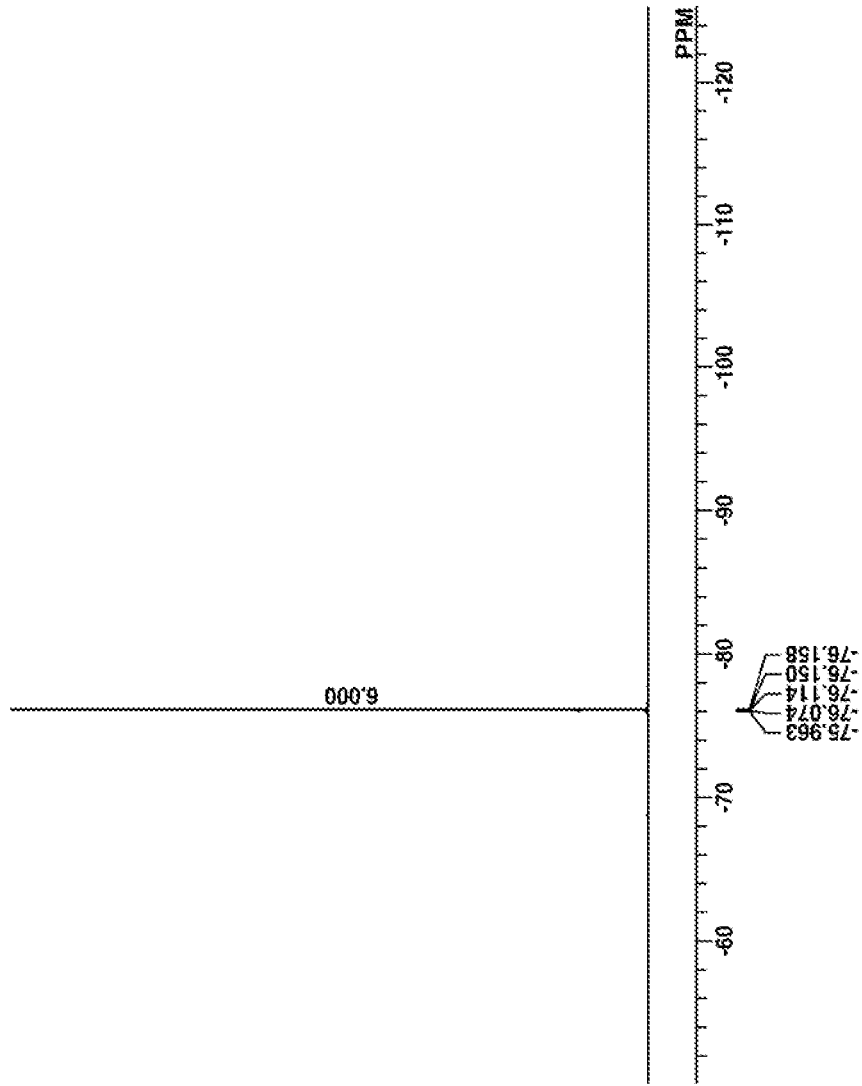

Intermediate A was analyzed by spectroscopy. The NMR spectra, $^1$H- and $^{19}$F-NMR in DMSO-$d_6$ are shown in FIGS. 1 and 2. In $^1$H-NMR analysis, minute amounts of residual solvents (THF, toluene, water) were observed.

IR (D-ATR): 3527, 3072, 1594, 1583, 1494, 1478, 1440, 1408, 1373, 1320, 1222, 1171, 1084, 1062, 1025, 1011, 983, 918, 828, 741, 729, 690 cm$^{-1}$

GC-MS: [M] 382

Example 1-1-2

Synthesis of Intermediate B

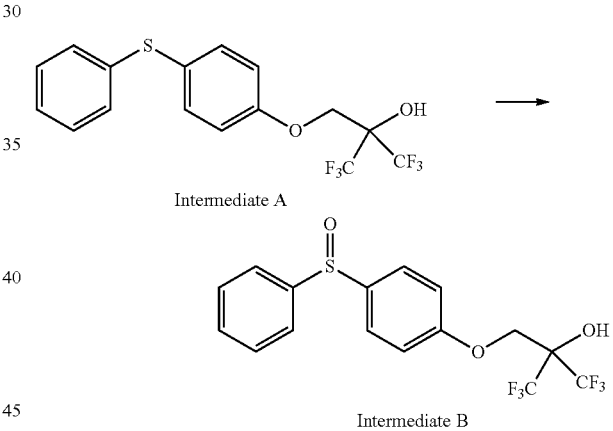

Intermediate A, 183 g, was dissolved in 1,300 g of acetic acid. Under ice cooling, 51 g of 35 wt % hydrogen peroxide water was added to the solution. The solution was aged overnight at room temperature, after which 25 g of sodium thiosulfate in 120 g of water was added dropwise at room temperature. After 1 hour of stirring, the reaction solution was diluted with 2,000 g of ethyl acetate and 1,000 g of toluene and washed with 1,000 g of water. The organic layer was combined with 1 wt % sodium hydroxide aqueous solution, followed by separatory operation. Once the organic layer was washed with water, the organic layer was combined with 2.5 wt % hydrochloric acid. The organic layer was washed with water and concentrated. Ethyl acetate was added to the concentrate to form a 50 wt % ethyl acetate solution. The solution was added dropwise to a 2:1 (in weight ratio) mixture of n-hexane and toluene for crystallization. The resulting white powder was dried in vacuum, obtaining 118 g of the end compound, Intermediate B.

Intermediate B was analyzed by spectroscopy. The NMR spectra, $^1$H- and $^{19}$F-NMR in DMSO-$d_6$ are shown in FIGS.

Example 1-1-3

Synthesis of Intermediate C

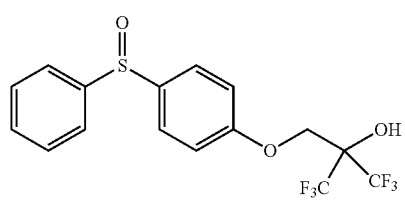

Intermediate B

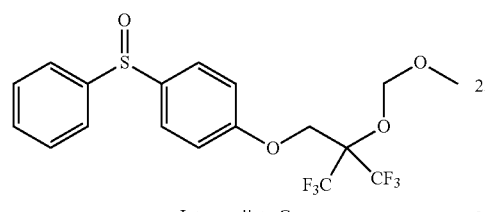

Intermediate C

Intermediate B, 117 g, was dissolved in a mixture of 69 g of diisopropylethylamine and 590 g of acetonitrile. Under ice cooling, 36 g of chloromethyl methyl ether was added dropwise to the solution. The solution was aged overnight at room temperature, after which it was combined with 800 g of water and 800 g of toluene, followed by separatory operation. The organic layer was once washed with water, washed with 1 wt % ammonia water, and washed with water again. The solution was further washed with 1 wt % hydrochloric acid and washed with water. The organic layer was taken out and concentrated under reduced pressure. The concentrate (solid) was dried in vacuum, obtaining 127 g of the end compound, Intermediate C as white crystal (yield 82%).

Figure 5:
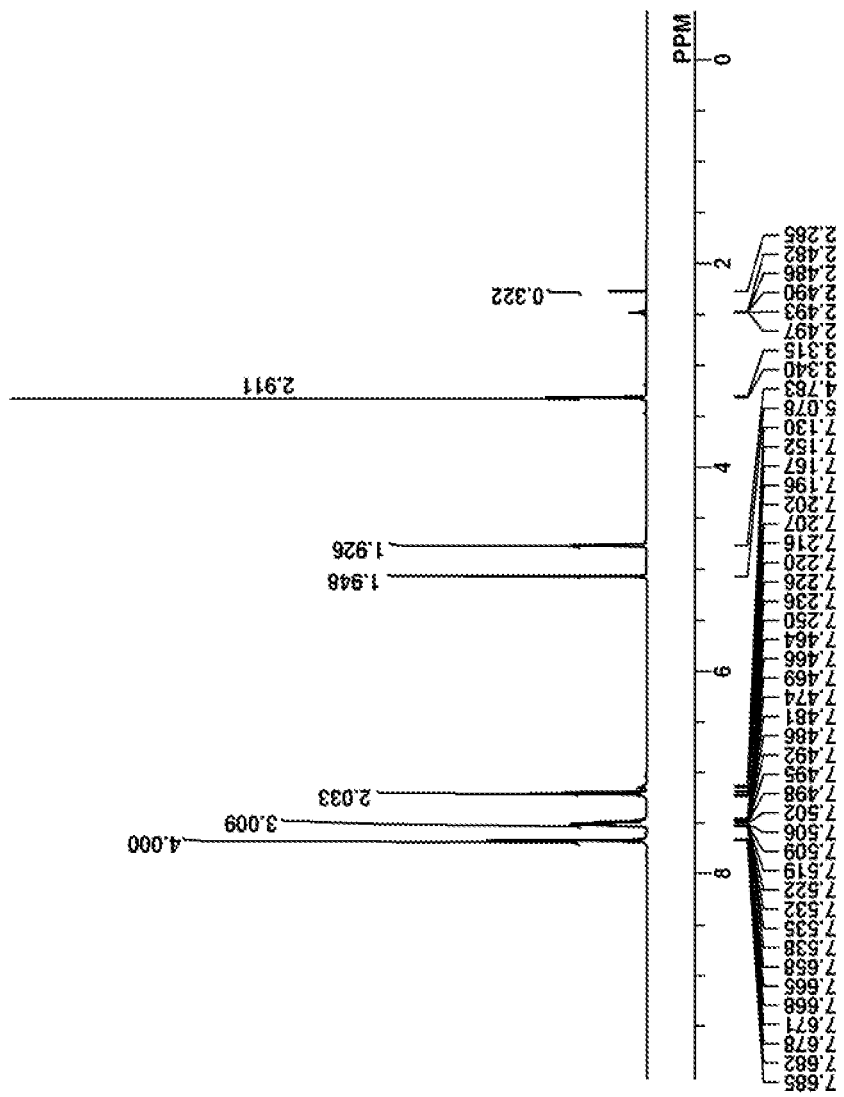
FIGS. 5 and 6 are diagrams showing $^1$H- and $^{19}$F-NMR spectra of Intermediate C in Example 1-1-3, respectively.
Figure 6:
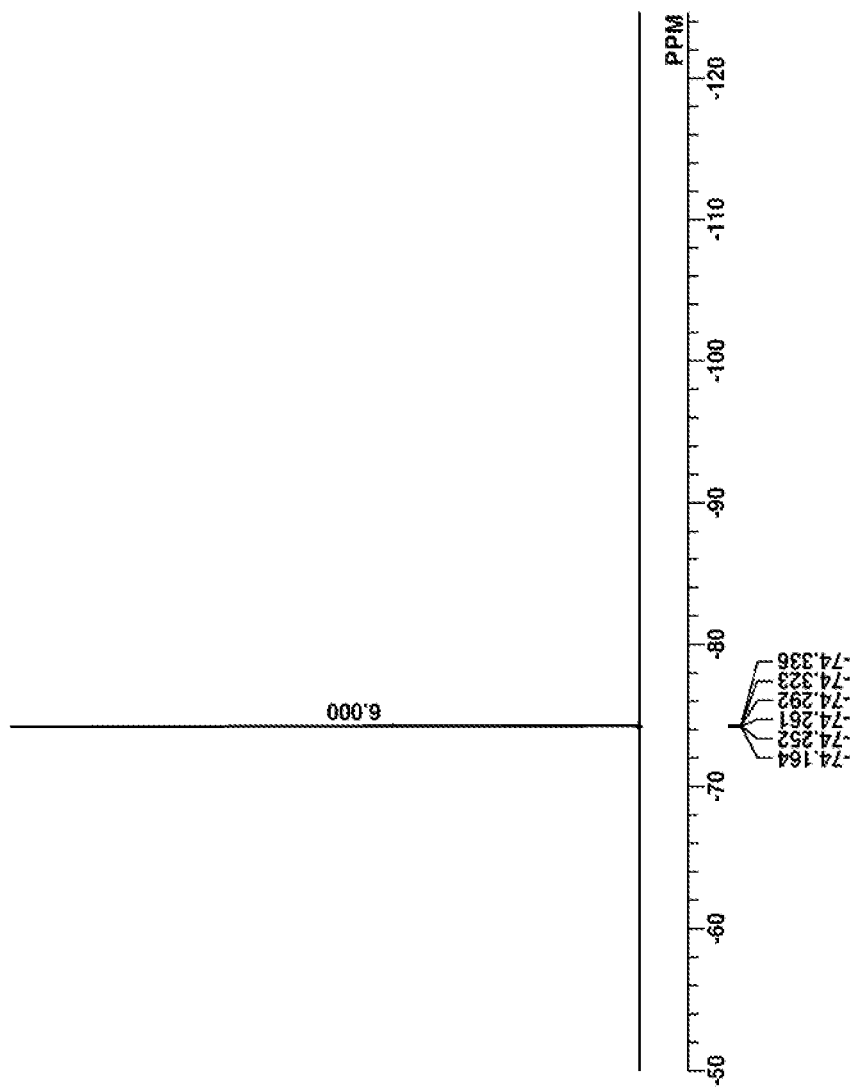

Intermediate C was analyzed by spectroscopy. The NMR spectra, $^1$H- and $^{19}$F-NMR in DMSO-$d_6$ are shown in FIGS. 5 and 6. In $^1$H-NMR analysis, minute amounts of residual solvents (toluene, water) were observed.

IR (D-ATR): 3467, 3065, 2911, 2832, 1593, 1496, 1476, 1444, 1408, 1334, 1284, 1245, 1216, 1152, 1107, 1091, 1079, 1046, 1022, 999, 966, 924, 876, 830, 750, 731, 709, 689, 640, 614, 562 cm$^{-1}$

TOF-MS (MALDI): Positive [M+H]$^+$ 443

Example 1-1-4

Synthesis of Intermediate D

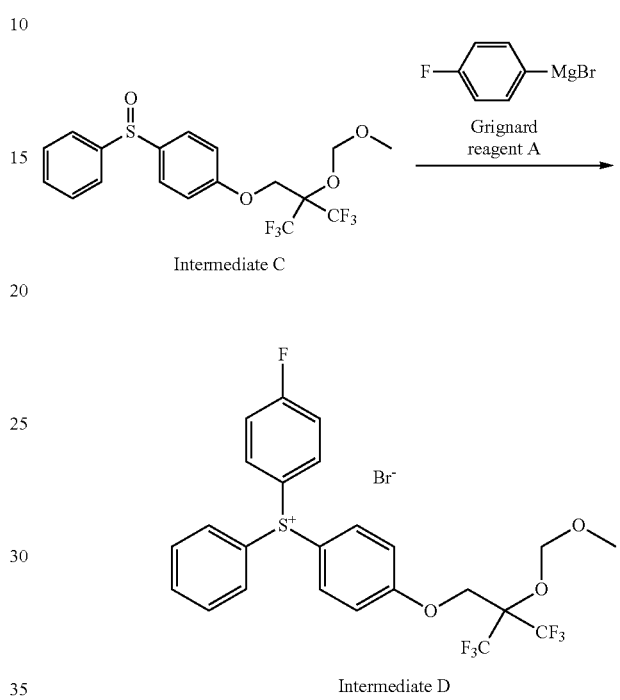

Intermediate C

Intermediate D

Intermediate C, 127 g, was dissolved in 506 g of THF. To the solution under ice cooling, a separately prepared THF solution of Grignard reagent A (corresponding to 3 times the moles of Intermediate C) was added dropwise. Under ice cooling, 93 g of chlorotrimethylsilane was added dropwise to the solution. The solution was aged overnight at room temperature. Under ice cooling, 496 g of 10 wt % ammonium chloride aqueous solution was added to the solution, and 800 g of MIBK and 200 g of water were added thereto. An organic layer containing Intermediate D was taken out and transferred to the subsequent reaction.

Example 1-1-5

Synthesis of Intermediate E

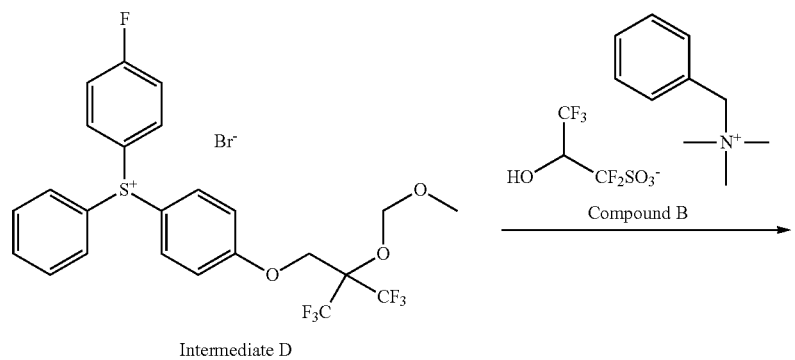

Intermediate D

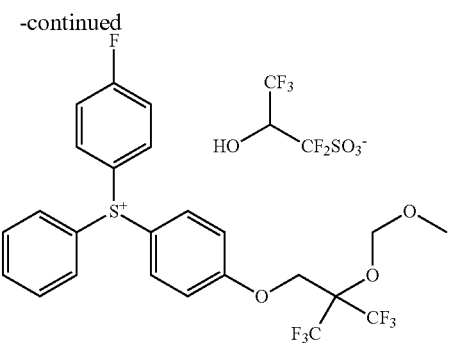

Intermediate E

To the organic layer obtained in Example 1-1-4, 130 g of Compound B and 200 g of water were added, followed by separatory operation. The organic layer was taken out, washed 3 times with 2.5 wt % aqueous solution of Compound B, and washed 5 times with deionized water. The organic layer was concentrated under reduced pressure, obtaining an oily product. DIPE was added to the product for decantation. This was followed by concentration under reduced pressure, obtaining 204 g of the end compound, Intermediate E (yield 68%).

Figure 7:
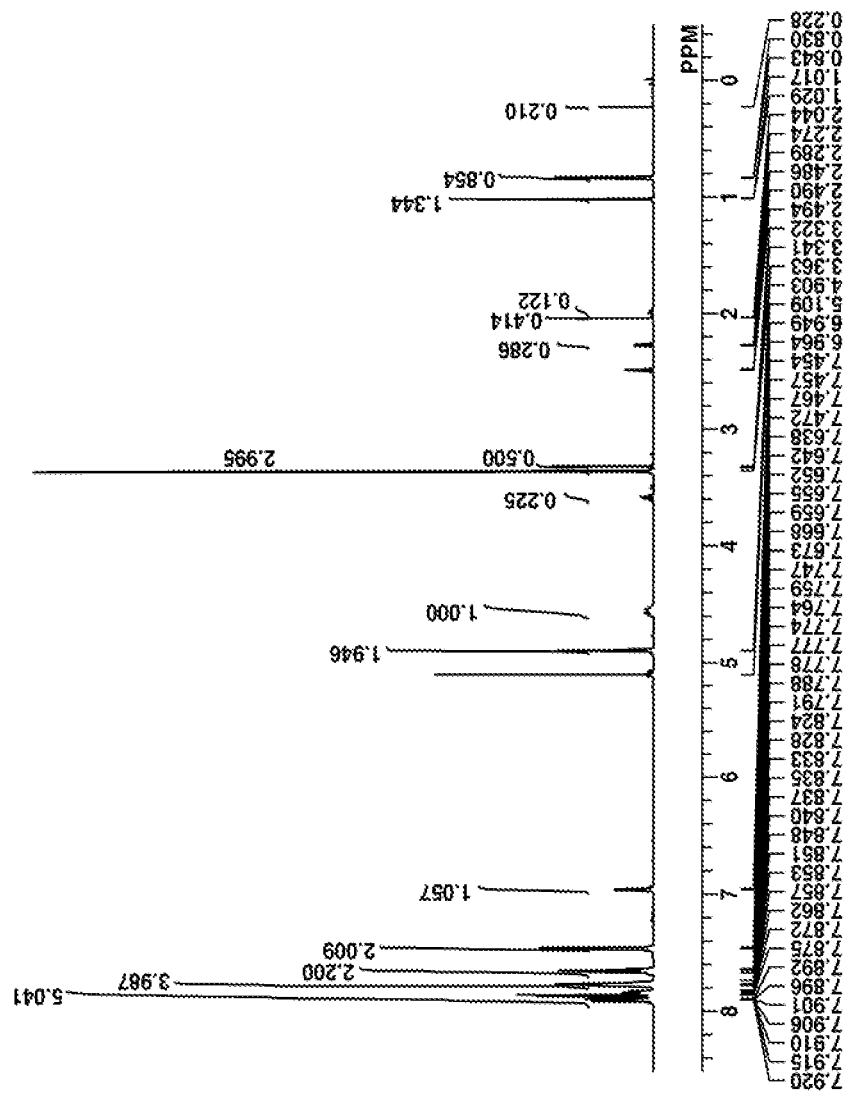
FIGS. 7 and 8 are diagrams showing $^1$H- and $^{19}$F-NMR spectra of Intermediate E in Example 1-1-5, respectively.
Figure 8:
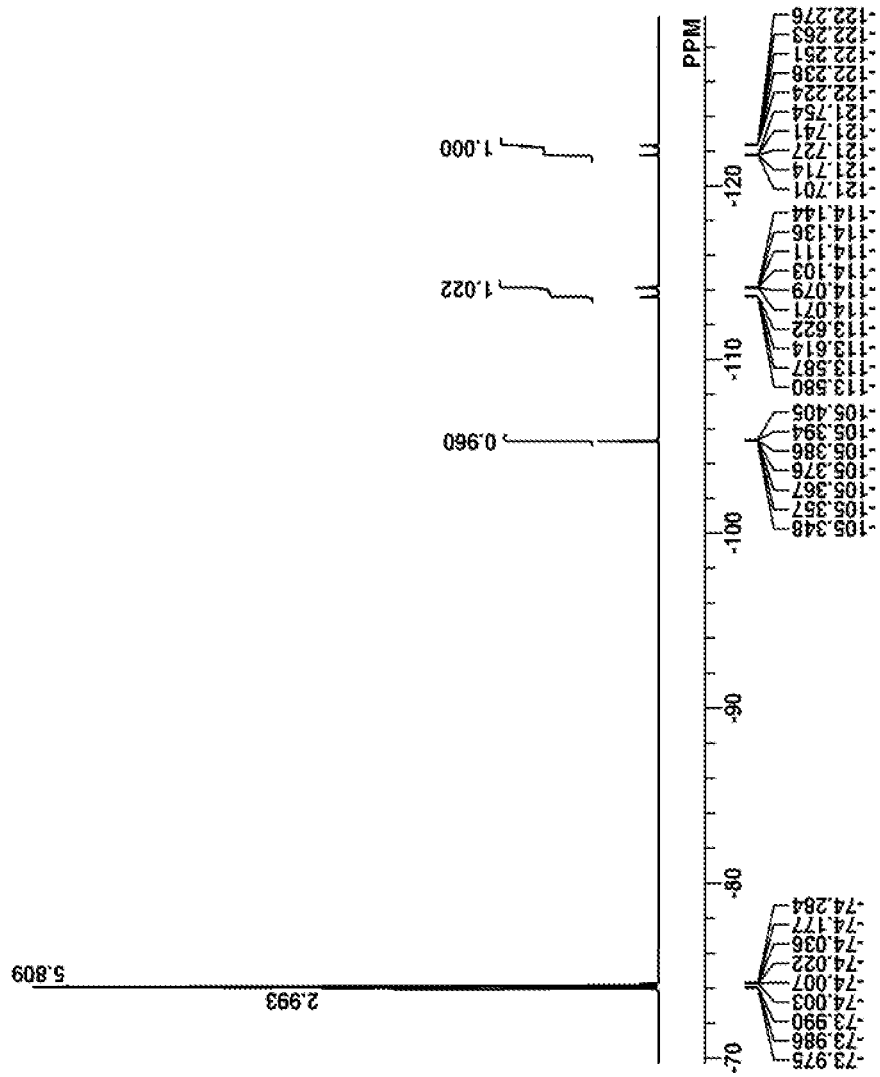

Intermediate E was analyzed by spectroscopy. The NMR spectra, $^1$H- and $^{19}$F-NMR in DMSO-$d_6$ are shown in FIGS. 7 and 8. In $^1$H-NMR analysis, minute amounts of residual solvents (DIPE, MIBK, water) were observed.

IR (D-ATR): 3280, 3103, 2979, 1589, 1494, 1478, 1448, 1407, 1260, 1228, 1156, 1106, 1072, 989, 966, 924, 836, 750, 732, 685, 644, 560 cm$^{-1}$

TOF-MS (MALDI): Positive M$^+$ 521 (corresponding to $(C_6H_5)(C_6H_4F)(C_6H_4OCH_2CH(CF_3)_2OCH_2OCH_3)S^+$)

Negative M$^-$ 229 (corresponding to $CCF_3(OH)CF_2SO_3^-$)

Example 1-1-6

Synthesis of Intermediate F

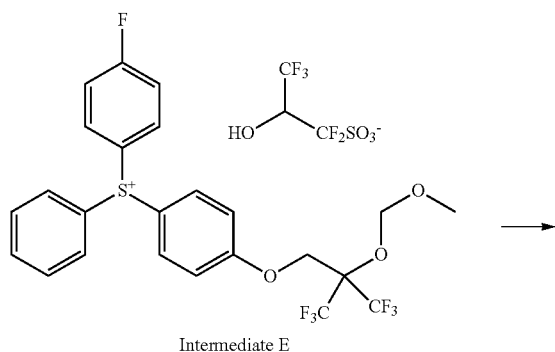

Intermediate E

→

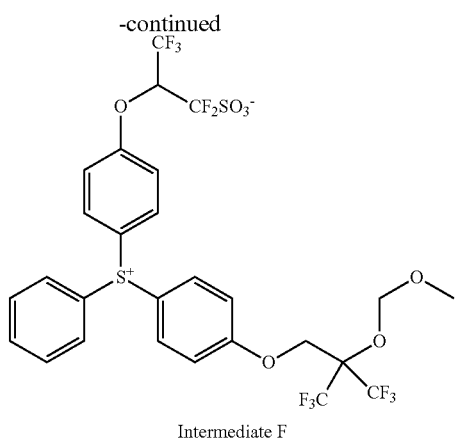

Intermediate F

A solution of 2.5 g of sodium hydride in 125 g of THF was added dropwise to a solution of 45 g of Intermediate E in 121 g of THF below 5° C. The solution was aged overnight at room temperature, after which water was added below 5° C. MIBK, 300 g, was added to the solution, followed by separatory operation. The organic layer was taken out and washed with water, then washed with 1 wt % hydrochloric acid, and washed with water again. The organic layer was taken out and concentrated under reduced pressure, obtaining an oily product. DIPE was added to the oily product for decantation. The solid was collected by filtration and dried in vacuum, obtaining 39 g of Intermediate F as white crystal (yield 58%).

Figure 9:
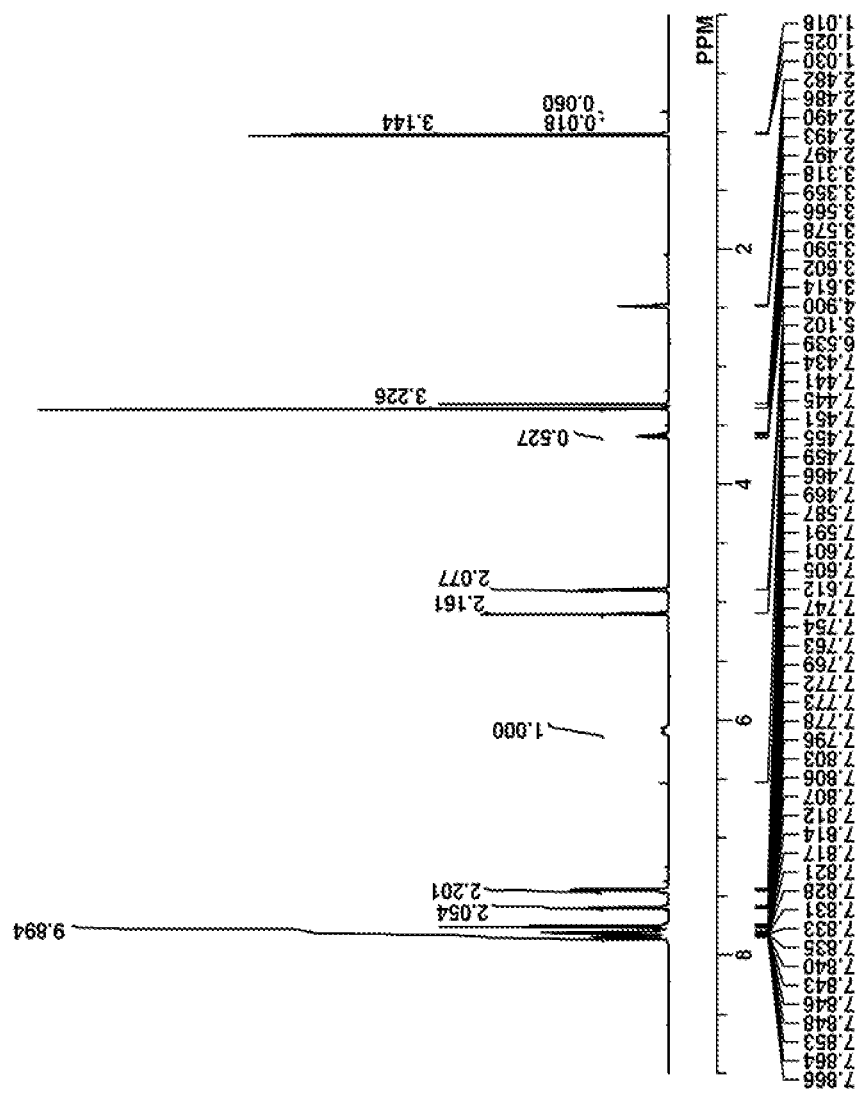
FIGS. 9 and 10 are diagrams showing $^1$H- and $^{19}$F-NMR spectra of Intermediate F in Example 1-1-6, respectively.
Figure 10:
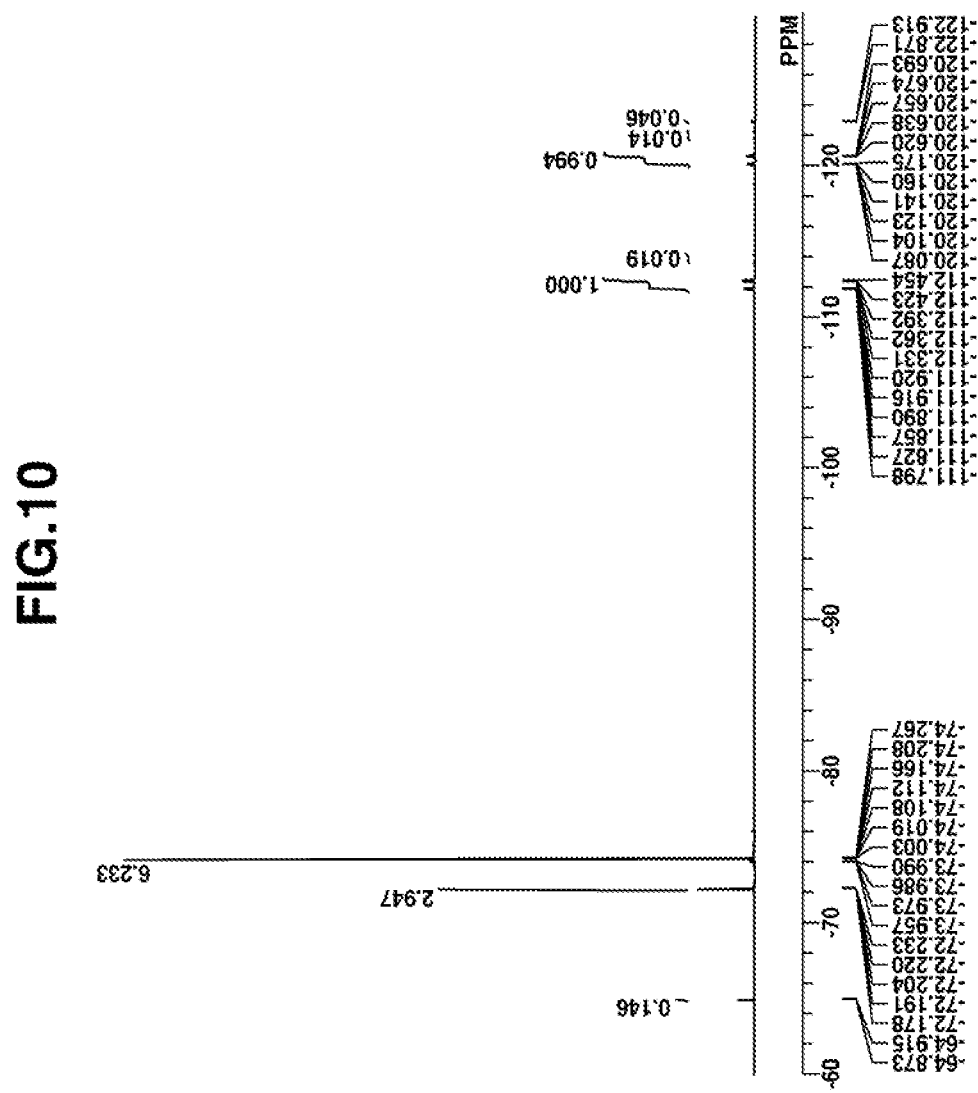

Intermediate F was analyzed by spectroscopy. The NMR spectra, $^1$H- and $^{19}$F-NMR in DMSO-$d_6$ are shown in FIGS. 9 and 10. In $^1$H-NMR analysis, minute amounts of residual solvents (DIPE, water) were observed.

IR (D-ATR): 3511, 3100, 2981, 1588, 1494, 1448, 1417, 1248, 1183, 1154, 1106, 1073, 996, 966, 924, 884, 834, 750, 732, 685, 642, 584 cm$^{-1}$

TOF-MS (MALDI): [M] 731

Example 1-1-7

Synthesis of PAG-1

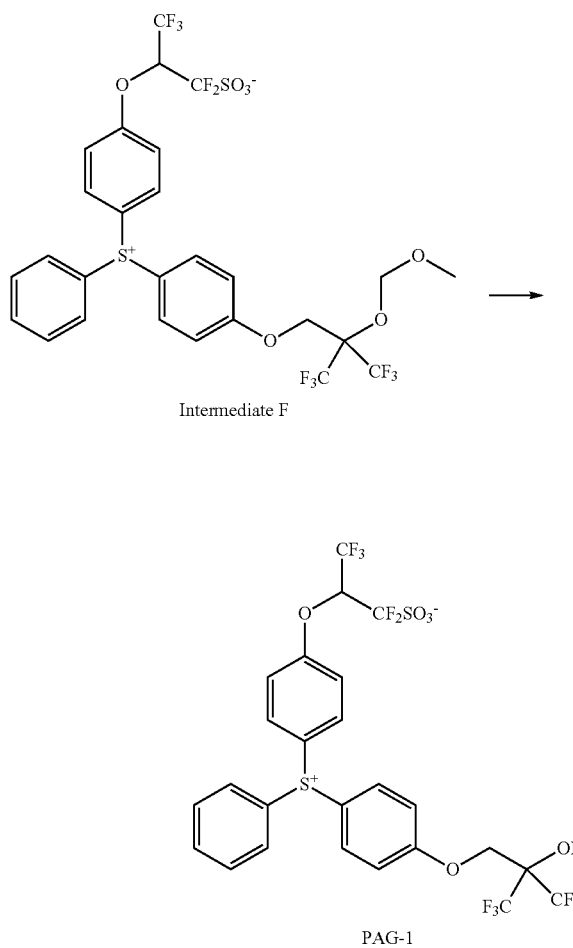

Intermediate F

PAG-1

In a solvent mixture of 80 g of methanol and 20 g of deionized water, 16.5 g of Intermediate F and 1.2 g of 35 wt % hydrochloric acid were dissolved. With stirring, the solution was heated at 50° C. and aged for 20 hours. The completion of reaction was confirmed by $^{19}$F-NMR spectroscopy, whereupon 160 g of MIBK and 160 g of deionized water were added to the solution. After stirring, an organic layer was taken out. The organic layer was washed twice with 240 g of 33 wt % methanol aqueous solution and once with 160 g of deionized water, and concentrated under reduced pressure. The concentrate was diluted with MIBK so as to form a 50 wt % solution, to which 100 g of DIPE was added for crystallization. The precipitate (solid) was collected by filtration and dried in vacuum, obtaining 13.5 g of PAG-1 as white crystal (yield 82%).

Figure 11:
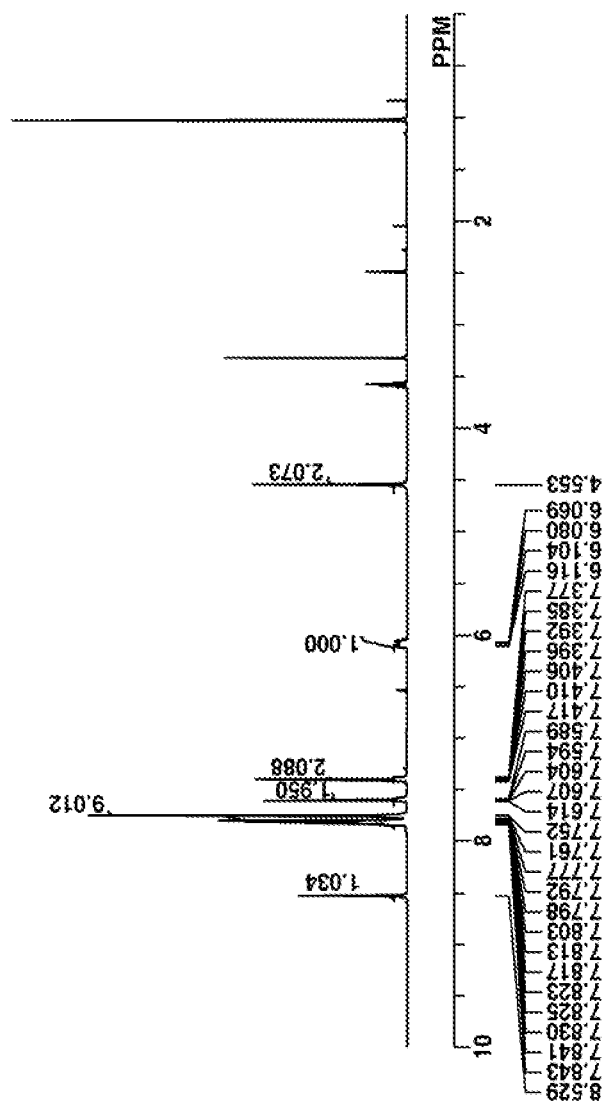
FIGS. 11 and 12 are diagrams showing $^1$H- and $^{19}$F-NMR spectra of PAG-1 in Example 1-1-7, respectively.
Figure 12:
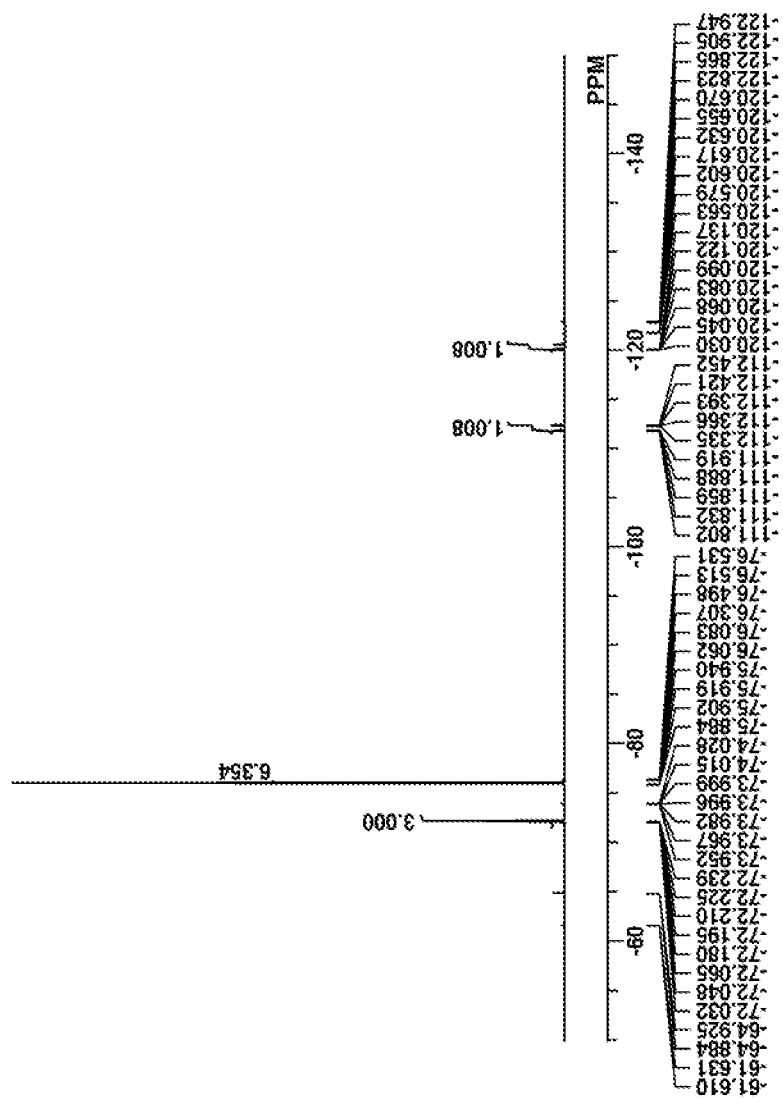

PAG-1 was analyzed by spectroscopy. The NMR spectra, $^1$H- and $^{19}$F-NMR in DMSO-$d_6$ are shown in FIGS. 11 and 12. In $^1$H-NMR analysis, minute amounts of residual solvents (DIPE, MIBK, water) were observed.

IR (D-ATR): 3102, 1589, 1495, 1448, 1417, 1368, 1248, 1180, 1162, 1075, 991, 885, 833, 750, 729, 703, 685, 643, 586, 525 cm$^{-1}$

LCMS: [M+H]$^+$ 687

Example 1-2

Synthesis of PAG-2

Example 1-2-1

Synthesis of Intermediate H

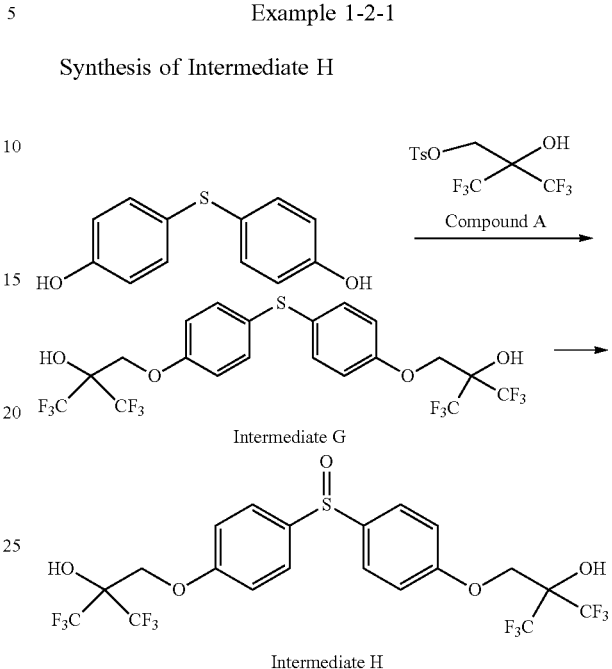

Intermediate G

Intermediate H

In a mixture of 250 g of THF and 60 g of deionized water was dissolved 57.3 g of bis(4-hydroxyphenyl)sulfide. At room temperature, 120 g of 25 wt % sodium hydroxide aqueous solution was added dropwise to the solution, which was aged for 15 minutes. Thereafter, a solution of 176.1 g of Compound A in 250 g of THF was added dropwise thereto at 30° C. The solution was aged overnight at room temperature. Under ice cooling, 365 g of 5 wt % hydrochloric acid was added to the reaction solution for quenching. The reaction solution was extracted with a mixture of 600 g of hexane and 600 g of toluene. The organic layer was washed 3 times with deionized water, 6 times with 0.25 wt % sodium hydroxide aqueous solution, once with 2.5 wt % hydrochloric acid, and 3 times with deionized water. The organic layer was concentrated, obtaining 109.2 g of the end compound, Intermediate G as oily matter. It was used in the subsequent reaction without further purification.

Intermediate G was dissolved in 765.5 g of acetic acid. Under ice cooling, 18.3 g of 35 wt % hydrogen peroxide water was added dropwise to the solution. The solution was aged at room temperature for 14 hours and at 40° C. for a further 5 hours. Then 44 g of 10 wt % sodium thiosulfate aqueous solution was added to the reaction solution, which was stirred for 1 hour to quench the reaction. The reaction solution was concentrated under reduced pressure to remove acetic acid. To the concentrate, 1,000 g of ethyl acetate, 500 g of toluene and 500 g of deionized water were added for dissolution. Further, 25 wt % sodium hydroxide aqueous solution was added, until the water layer reached pH 5, to neutralize the residual acetic acid, after which the organic layer was taken out. The organic layer was washed 3 times with 0.5 wt % sodium hydroxide aqueous solution, once with 2.5 wt % hydrochloric acid, and 3 times with 5 wt % sodium chloride aqueous solution. The organic layer was concentrated under reduced pressure. Hexane was added to the concentrate for precipitation. The precipitate (solid) was collected by filtration and dried in vacuum, obtaining 104.7 g of the end compound, Intermediate H as white solid. (two step yield 70%)

Figure 13:
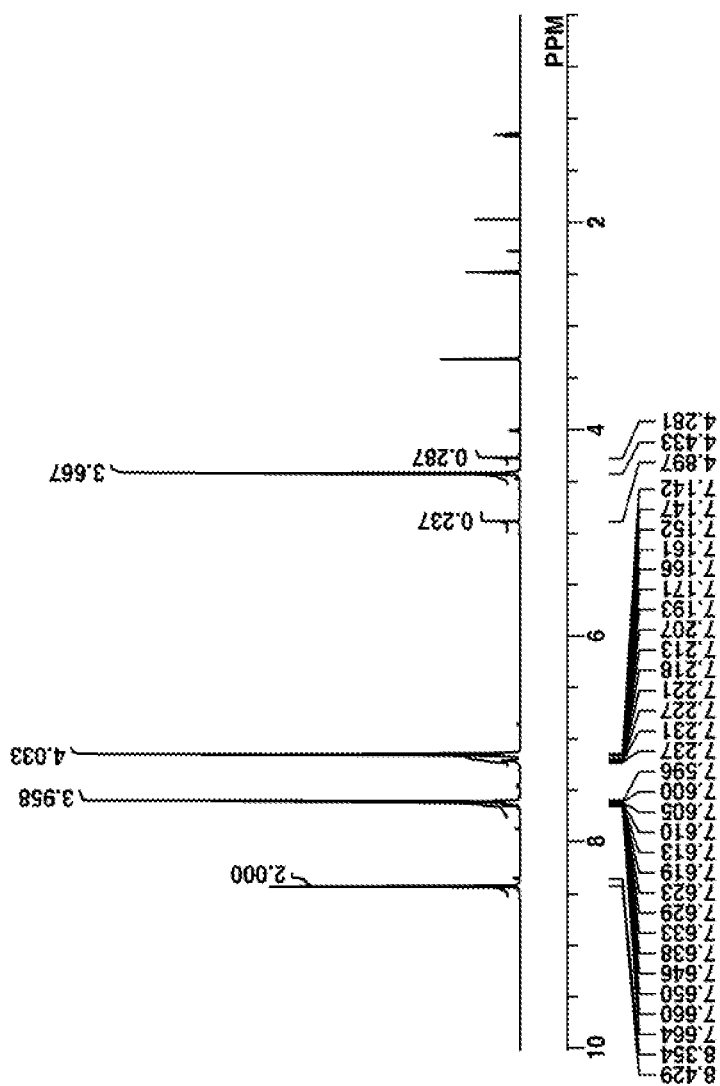
FIGS. 13 and 14 are diagrams showing $^1$H- and $^{19}$F-NMR spectra of Intermediate H in Example 1-2-1, respectively.
Figure 14:
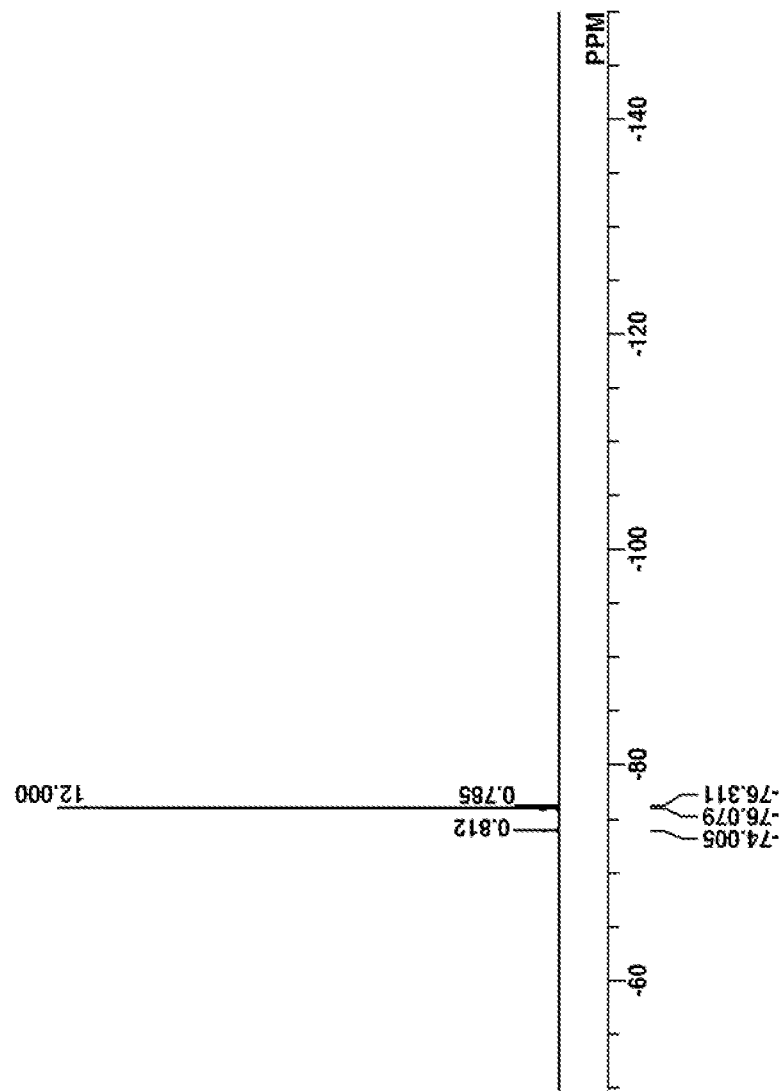

Intermediate H was analyzed by spectroscopy. The NMR spectra, $^1$H- and $^{19}$F-NMR in DMSO-$d_6$ are shown in FIGS. 13 and 14. In $^1$H-NMR analysis, minute amounts of residual solvents (ethyl acetate, toluene, water) were observed.

IR (D-ATR): 3404, 3073, 2885, 2727, 1595, 1498, 1466, 1412, 1373, 1290, 1250, 1218, 1167, 1087, 1065, 1021, 997, 923, 828, 806, 728, 688 cm$^{-1}$

Example 1-2-2

Synthesis of Intermediate I

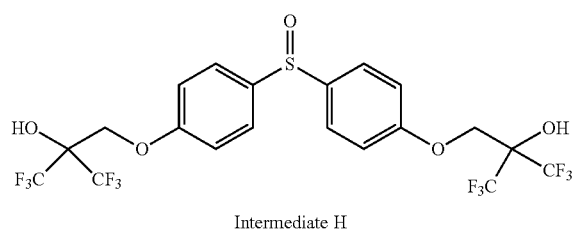

Intermediate H

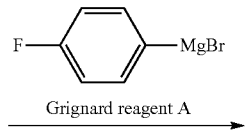

Grignard reagent A tilling off the solvent under reduced pressure. There was obtained 28.9 g of the oily end compound, Intermediate I (yield 93%).

Figure 15:
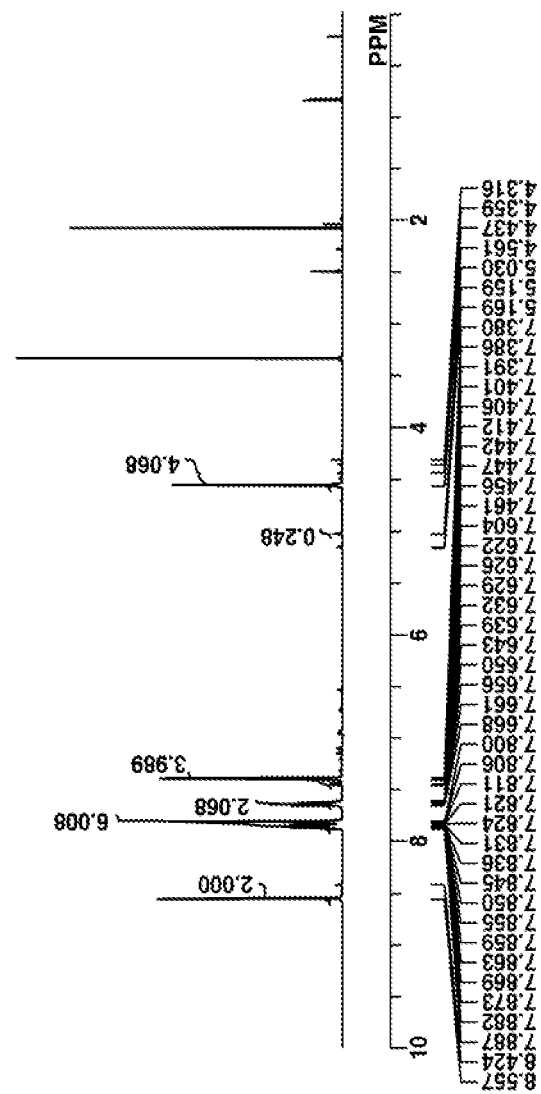
FIGS. 15 and 16 are diagrams showing $^1$H- and $^{19}$F-NMR spectra of Intermediate I in Example 1-2-2, respectively.
Figure 16:
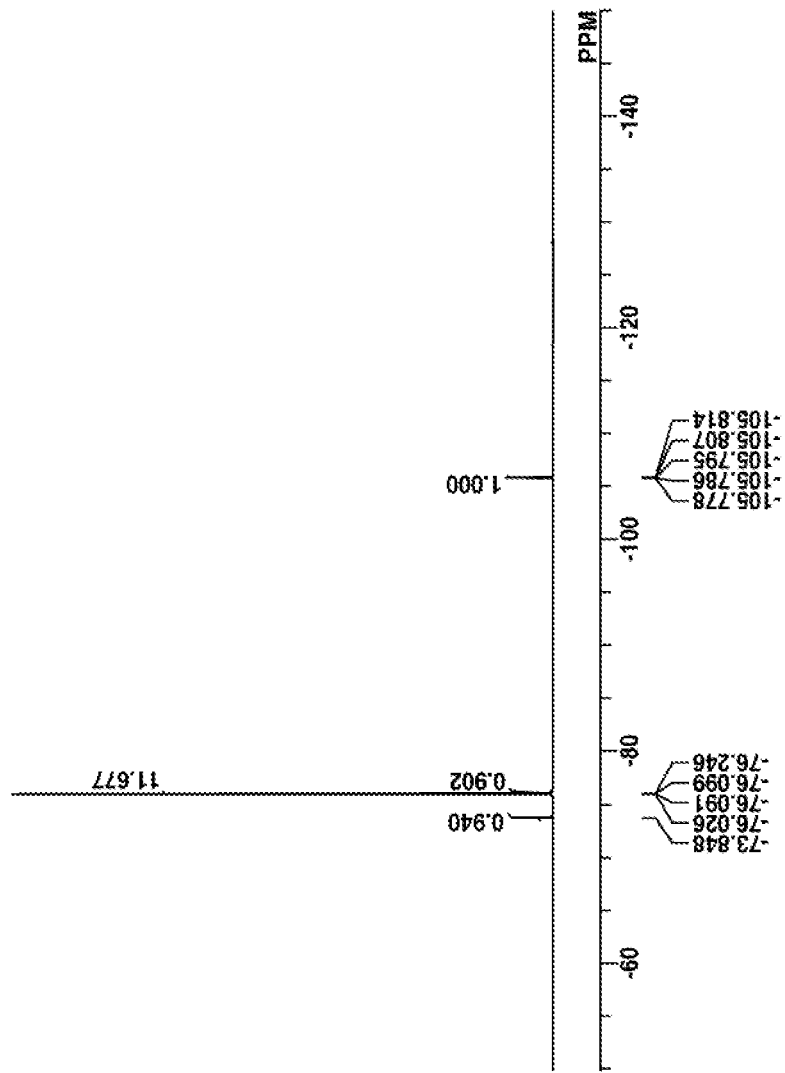

Intermediate I was analyzed by spectroscopy. The NMR spectra, $^1$H- and $^{19}$F-NMR in DMSO-$d_6$ are shown in FIGS. 15 and 16. In $^1$H-NMR analysis, minute amounts of residual solvents (MIBK, acetone, water) were observed.

TOF-MS (MALDI): Positive M$^+$ 673

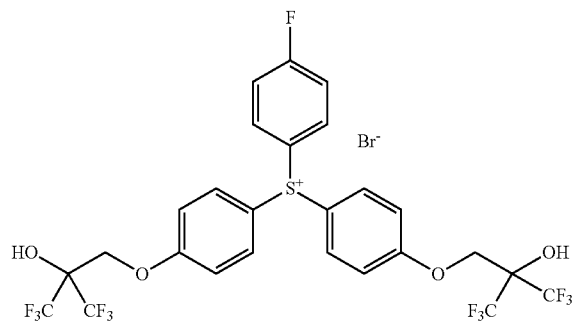

Intermediate I

Intermediate H, 24.3 g, was dissolved in 100 g of THF. To the solution under ice cooling, a separately prepared THF solution of Grignard reagent A (corresponding to 5.5 times the moles of Intermediate H) was added dropwise. Under ice cooling, stirring was continued for 10 minutes. Under ice cooling, 24.4 g of trimethylsilyl chloride was added dropwise to the solution. The solution was warmed at room temperature and stirred overnight. Further, 190 g of 3.5 wt % hydrochloric acid was added to the solution, which was stirred overnight at room temperature. The reaction solution was extracted 3 times with 100 g of methylene chloride. The organic layer was washed 3 times with 5 wt % methanol aqueous solution and concentrated under reduced pressure. MIBK was added to the concentrate, which was concentrated under reduced pressure to remove water. The procedure of adding DIPE to the concentrate, stirring the mixture, and removing the supernatant was repeated 2 times. The residue was dissolved in acetone and concentrated by dis- Example 1-2-3

Synthesis of Intermediate J

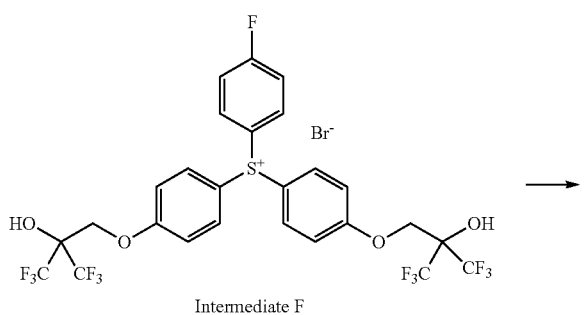

Intermediate F

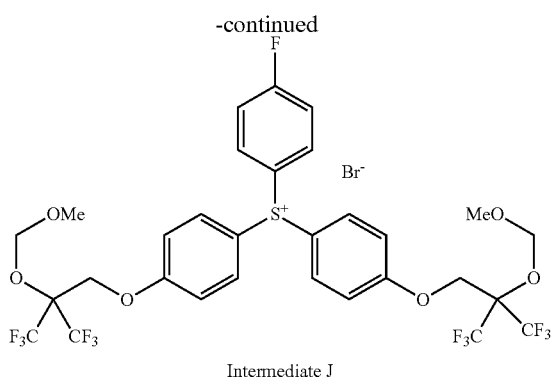

Intermediate J

Intermediate I, 23.9 g, was dissolved in 100 g of acetonitrile. Under ice cooling, 4.91 g of diisopropylethylamine and 2.55 g of chloromethyl methyl ether were added to the solution, which was stirred at room temperature for 1 hour. The procedure of adding 4.91 g of diisopropylethylamine and 2.55 g of chloromethyl methyl ether to the solution under ice cooling, and stirring at room temperature for 1 hour was repeated 4 times. With stirring, the solution was aged overnight at room temperature. Deionized water, 120 g, was added to the solution to quench the reaction. This was followed by addition of 100 g of MIBK and stirring, whereupon an organic layer was taken out. The organic layer was washed 2 times with 10 wt % methanol aqueous solution, 3 times with saturated ammonium chloride aqueous solution, and 3 times with 5 wt % methanol aqueous solution. The organic layer was concentrated under reduced pressure. Methylene chloride was added to the concentrate so as to form a 25 wt % solution, and 300 g of hexane was added for crystallization. The precipitate was collected by filtration, washed twice with hexane, and dried in vacuum, obtaining 21.9 g of the end compound, Intermediate J as solid (yield 82%).

Figure 17:
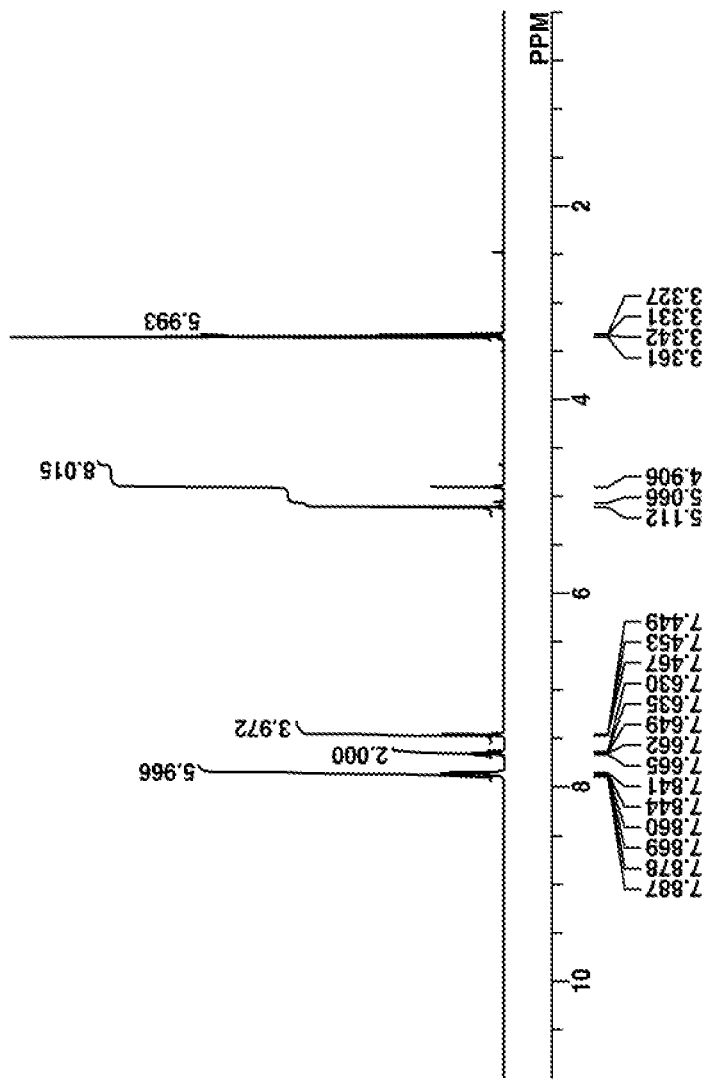
FIGS. 17 and 18 are diagrams showing $^1$H- and $^{19}$F-NMR spectra of Intermediate J in Example 1-2-3, respectively.
Figure 18:
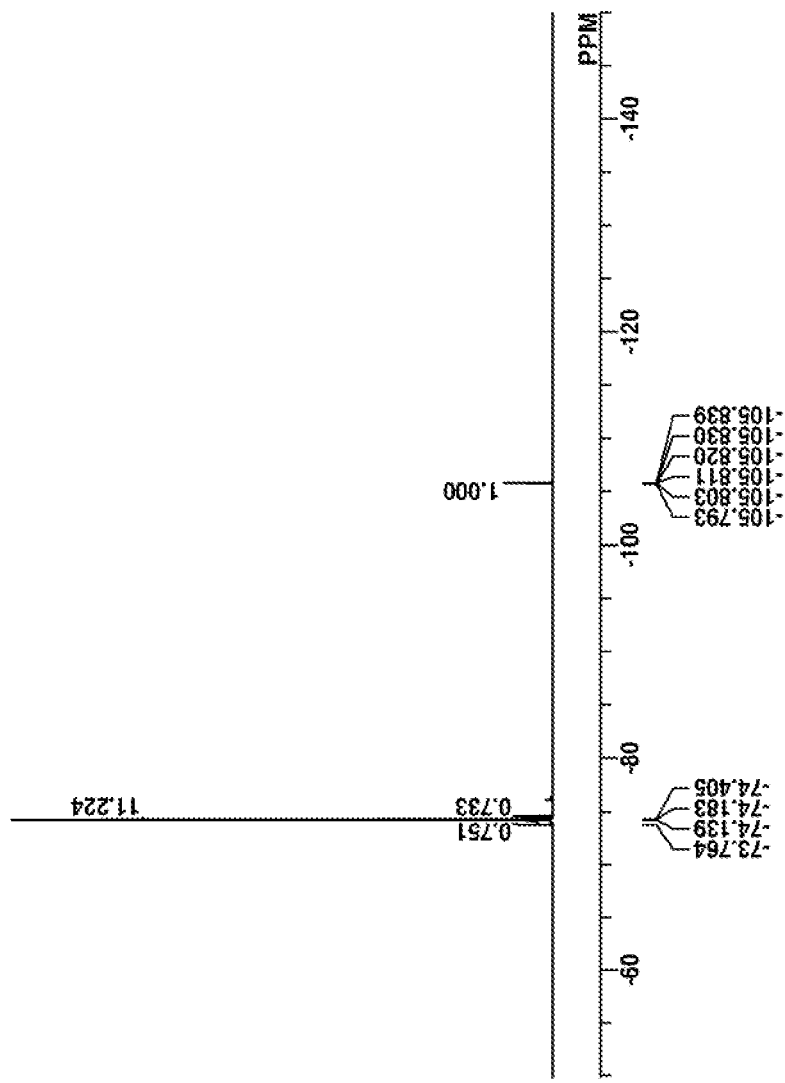

Intermediate J was analyzed by spectroscopy. The NMR spectra, $^1$H- and $^{19}$F-NMR in DMSO-$d_6$ are shown in FIGS. 17 and 18.

IR (D-ATR): 3390, 3045, 3019, 2975, 1589, 1492, 1463, 1417, 1339, 1305, 1258, 1240, 1221, 1185, 1153, 1105, 1080, 1003, 988, 968, 922, 844, 816, 730, 700, 649 cm$^{-1}$

TOF-MS (MALDI): Positive M$^+$ 761

Example 1-2-4

Synthesis of Intermediate K

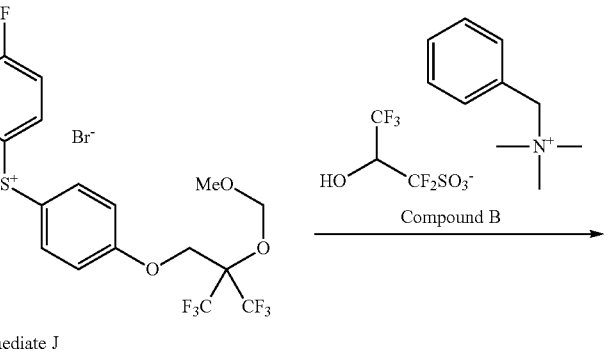

Intermediate J

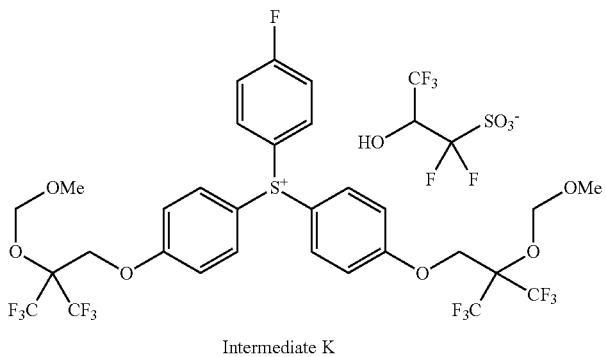

Intermediate K

A mixture of 12 g of Intermediate J, 5.5 g of Compound B, 60 g of MIBK, and 60 g of deionized water was stirred at room temperature, from which an organic layer was taken out. The organic layer was washed twice with 60 g of 1 wt % aqueous solution of Compound B and 3 times with deionized water. The organic layer was concentrated under reduced pressure. The procedure of adding 120 g of hexane to the concentrate, stirring the mixture, and removing the supernatant was repeated 3 times. The remaining oily matter was dissolved in methylene chloride. The solution was concentrated under reduced pressure to remove the solvent, obtaining 14.7 g of the end compound, Intermediate K (yield 99%).

Figure 19:
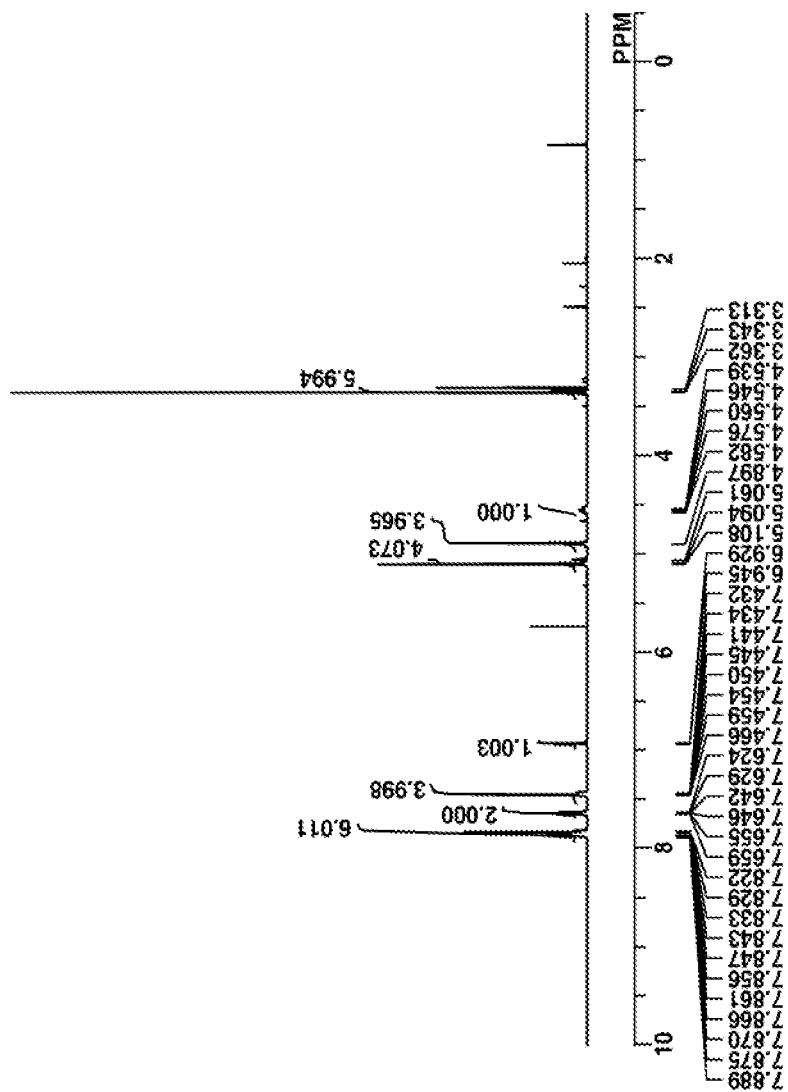
FIGS. 19 and 20 are diagrams showing $^1$H- and $^{19}$F-NMR spectra of Intermediate K in Example 1-2-4, respectively.
Figure 20:
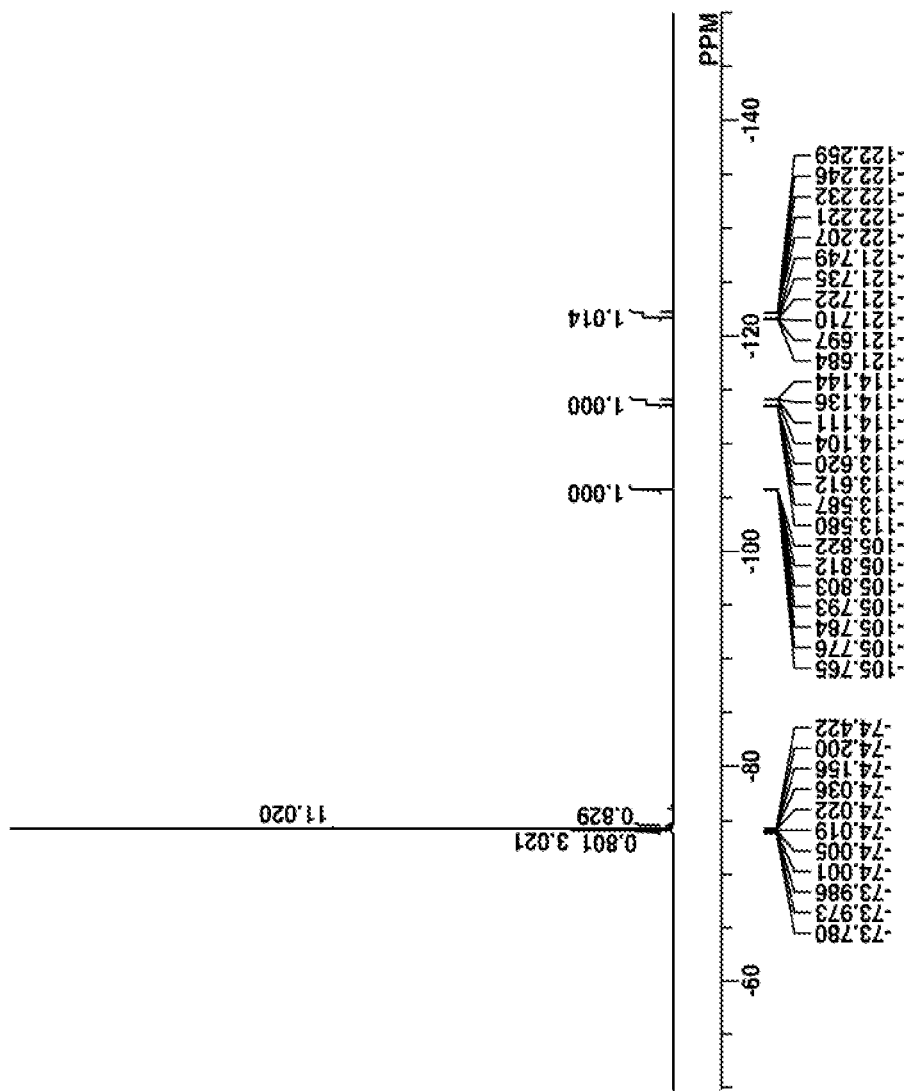

Intermediate K was analyzed by spectroscopy. The NMR spectra, $^1$H- and $^{19}$F-NMR in DMSO-$d_6$ are shown in FIGS. 19 and 20. In $^1$H-NMR analysis, minute amounts of residual solvents (methylene chloride, MIBK, water) were observed.

Example 1-2-5

Synthesis of Intermediate L

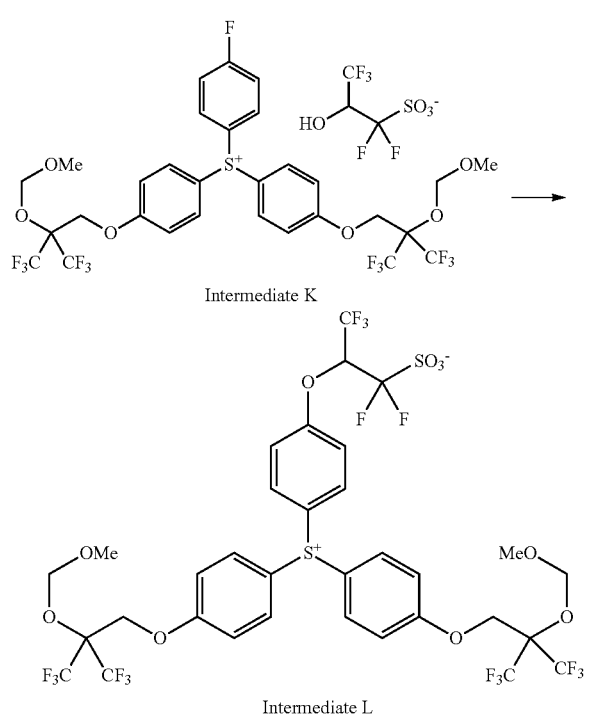

Under ice cooling, a solution of 14.6 g of Intermediate K in 40 g of THF was added dropwise to a mixture of 0.6 g of 55 wt % sodium hydride and 40 g of THF. The solution was stirred at the temperature for 1 hour and further stirred overnight at room temperature. Under ice cooling, 80 g of deionized water was added to the solution to quench the reaction. MIBK, 100 g, was added to the solution, which was stirred. An organic layer was taken out. The organic layer was washed 3 times with deionized water, once with 1 wt % hydrochloric acid, and twice with deionized water. The organic layer was concentrated under reduced pressure, and DIPE was added to the concentrate for crystallization. The precipitate (solid) was collected by filtration and dried in vacuum, obtaining 11.7 g of the end compound, Intermediate L (yield 82%).

Figure 21:
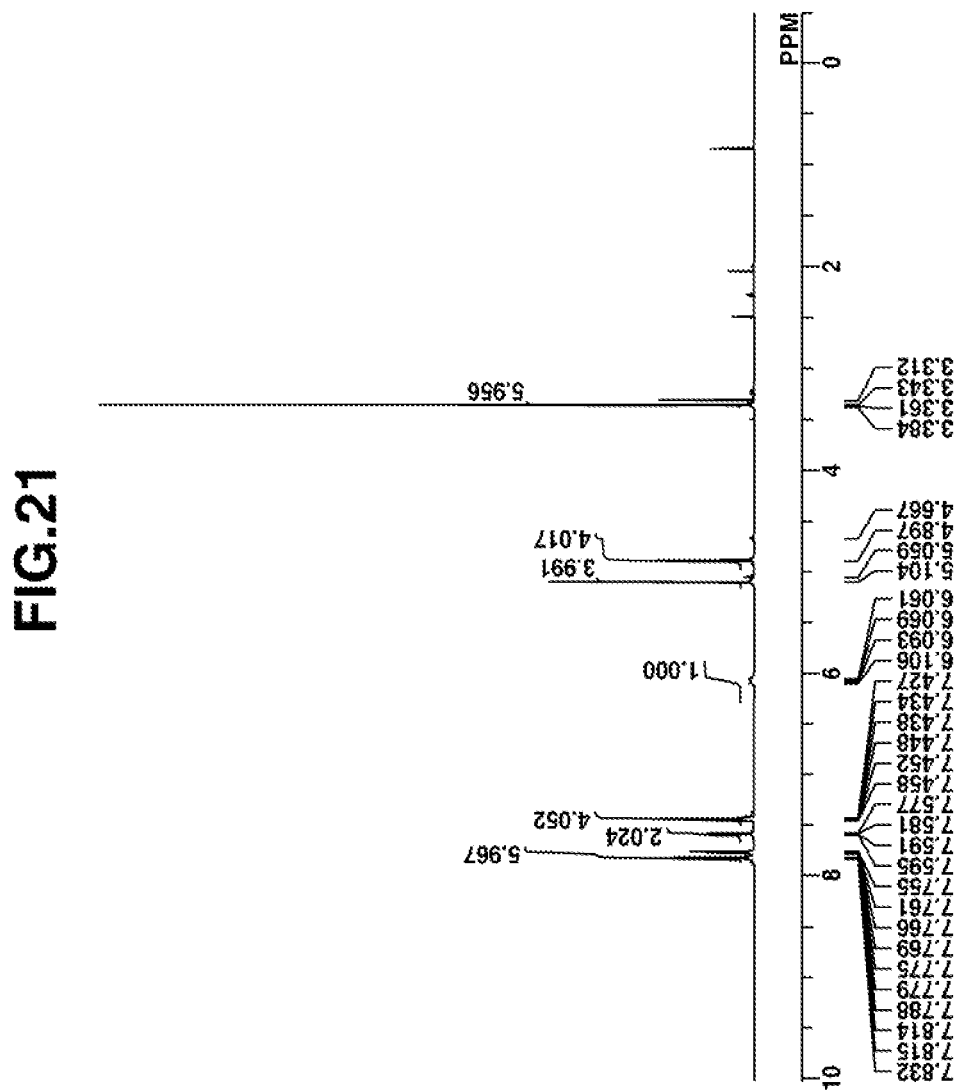
FIGS. 21 and 22 are diagrams showing $^1$H- and $^{19}$F-NMR spectra of Intermediate L in Example 1-2-5, respectively.
Figure 22:

Intermediate L was analyzed by spectroscopy. The NMR spectra, $^1$H- and $^{19}$F-NMR in DMSO-$d_6$ are shown in FIGS. 21 and 22. In $^1$H-NMR analysis, minute amounts of residual solvents (MIBK, water) were observed.

IR (D-ATR): 1589, 1494, 1468, 1336, 1247, 1217, 1182, 1153, 1107, 1079, 993, 966, 924, 881, 833, 732, 644 cm$^{-1}$

TOF-MS (MALDI): [M] 971

Example 1-2-6

Synthesis of PAG-2

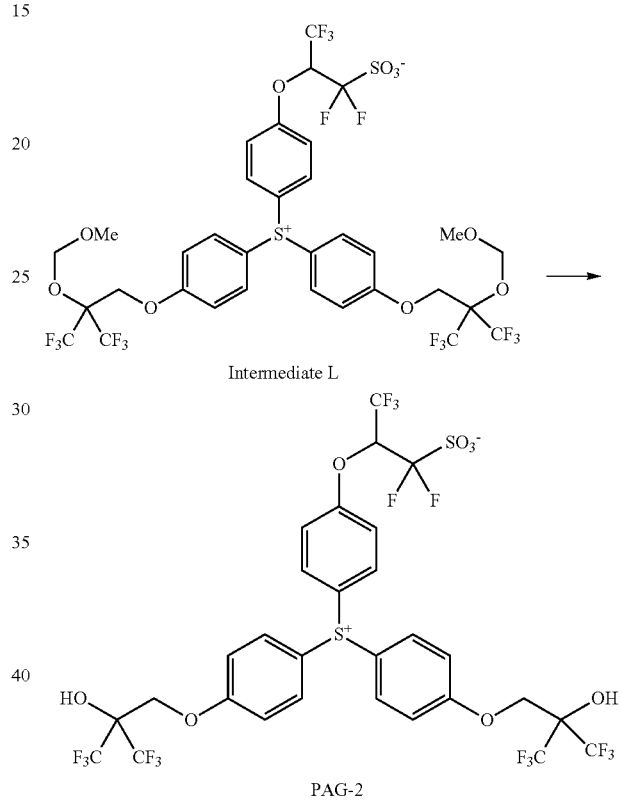

With stirring, 6.5 g of Intermediate L, 6.5 g of 35 wt % hydrochloric acid, 30 g of methanol and 3.5 g of deionized water were mixed and aged at 50° C. for 3 hours. To the solution were added 50 g of MIBK and 50 g of deionized water. After stirring, an organic layer was taken out. The organic layer was washed 3 times with deionized water and concentrated under reduced pressure. Hexane was added to the concentrate for crystallization. The precipitate (solid) was collected by filtration and washed once with DIPE and twice with hexane, and dried in vacuum, obtaining 4.3 g of the target compound, PAG-2 (yield 69%).

Figure 23:
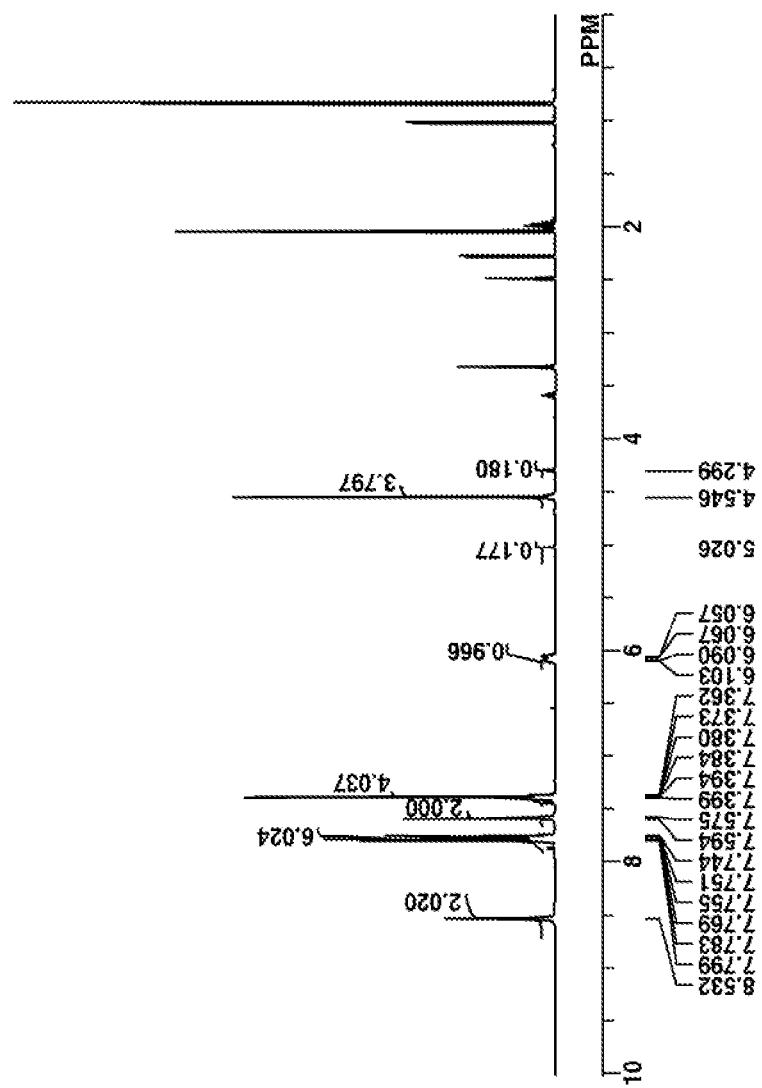
FIGS. 23 and 24 are diagrams showing $^1$H- and $^{19}$F-NMR spectra of PAG-2 in Example 1-2-6, respectively.
Figure 24:
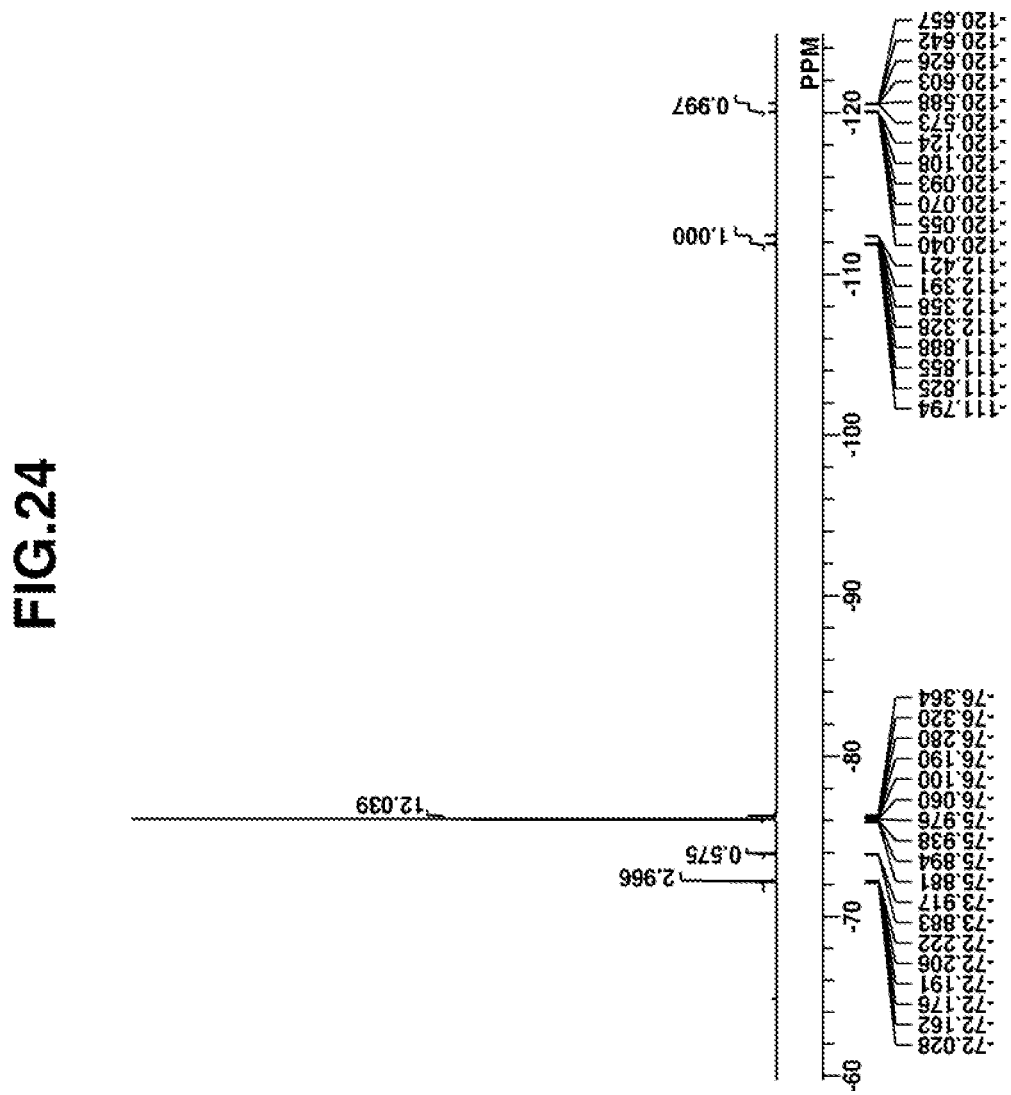

PAG-2 was analyzed by spectroscopy. The NMR spectra, $^1$H- and $^{19}$F-NMR in DMSO-$d_6$ are shown in FIGS. 23 and 24. In $^1$H-NMR analysis, minute amounts of residual solvents (DIPE, MIBK, water) were observed.

IR (D-ATR): 3258, 3107, 2962, 1702, 1589, 1495, 1470, 1417, 1247, 1218, 1176, 1158, 1075, 1059, 987, 884, 830, 729, 643 cm$^{-1}$

TOF-MS (MALDI): [M] 883

Example 1-3

Synthesis of PAG-3

Example 1-3-1

Synthesis of Intermediate N

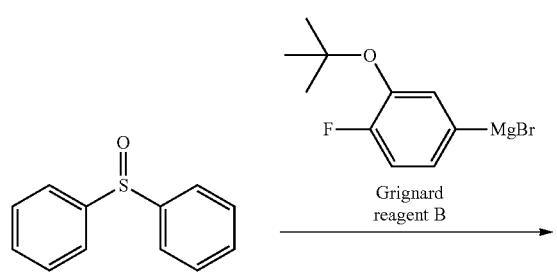

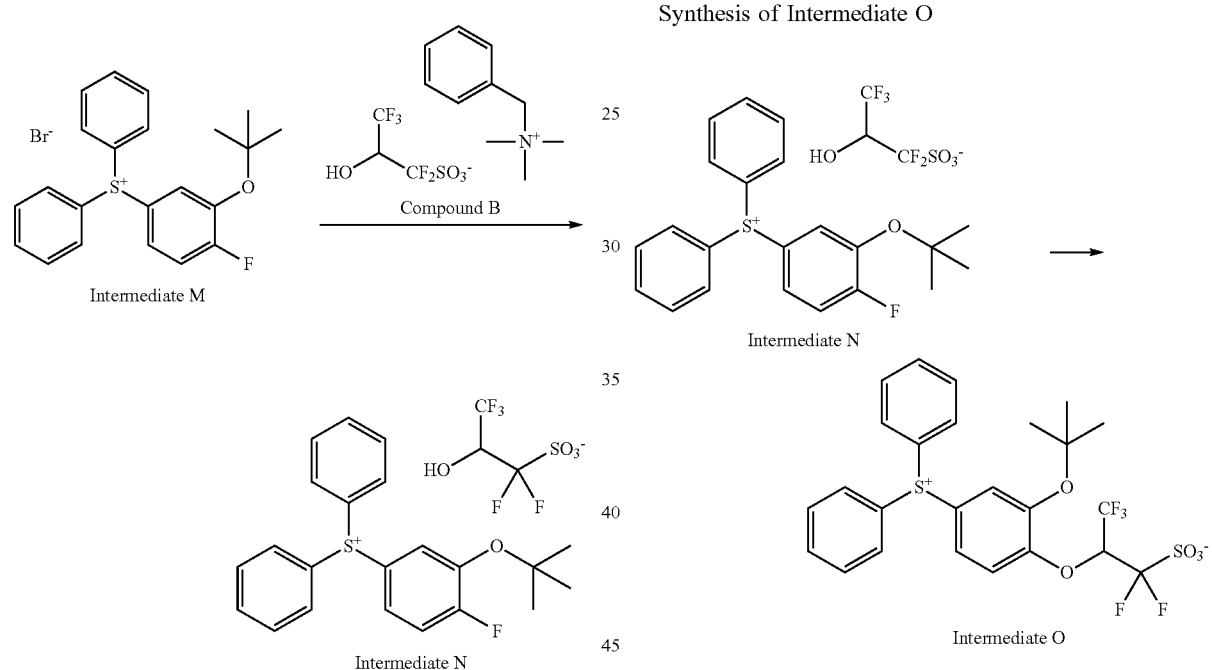

Diphenyl sulfoxide, 20.1 g, was dissolved in 40 g of THF. To the solution under ice cooling, a separately prepared THF solution of Grignard reagent B (corresponding to 3.0 times the moles of diphenyl sulfoxide) was added dropwise. Under ice cooling, 33.5 g of trimethylsilyl chloride was added dropwise to the solution. The solution was stirred and aged for 2.5 hours. Then 85.5 g of 6 wt % ammonium chloride aqueous solution was added to the solution, which was stirred overnight. The solution was combined with 400 g of DIPE and stirred, after which the supernatant was removed. The oily residue was dissolved in a solvent mixture of acetone and methanol, and filtered to remove the inorganic salt. The filtrate was concentrated under reduced pressure and dissolved in deionized water, obtaining an aqueous solution of Intermediate M.

A portion was taken out of the aqueous solution and treated as follows. Namely, 466.4 g (corresponding to 70 mmol) of the aqueous solution of Intermediate M, 37.2 g of Compound B, and 500 g of methylene chloride were mixed and stirred. The insoluble was removed by filtration and an organic layer was taken out. The organic layer was washed 3 times with deionized water. The procedure of concentrating the organic layer under reduced pressure, adding MIBK, concentrating, adding DIPE, stirring and removing the supernatant was repeated twice. This was concentrated again by distilling off the solvent under reduced pressure. There was obtained 34.8 g of the end compound, Intermediate N (two step yield 83%).

Figure 25:
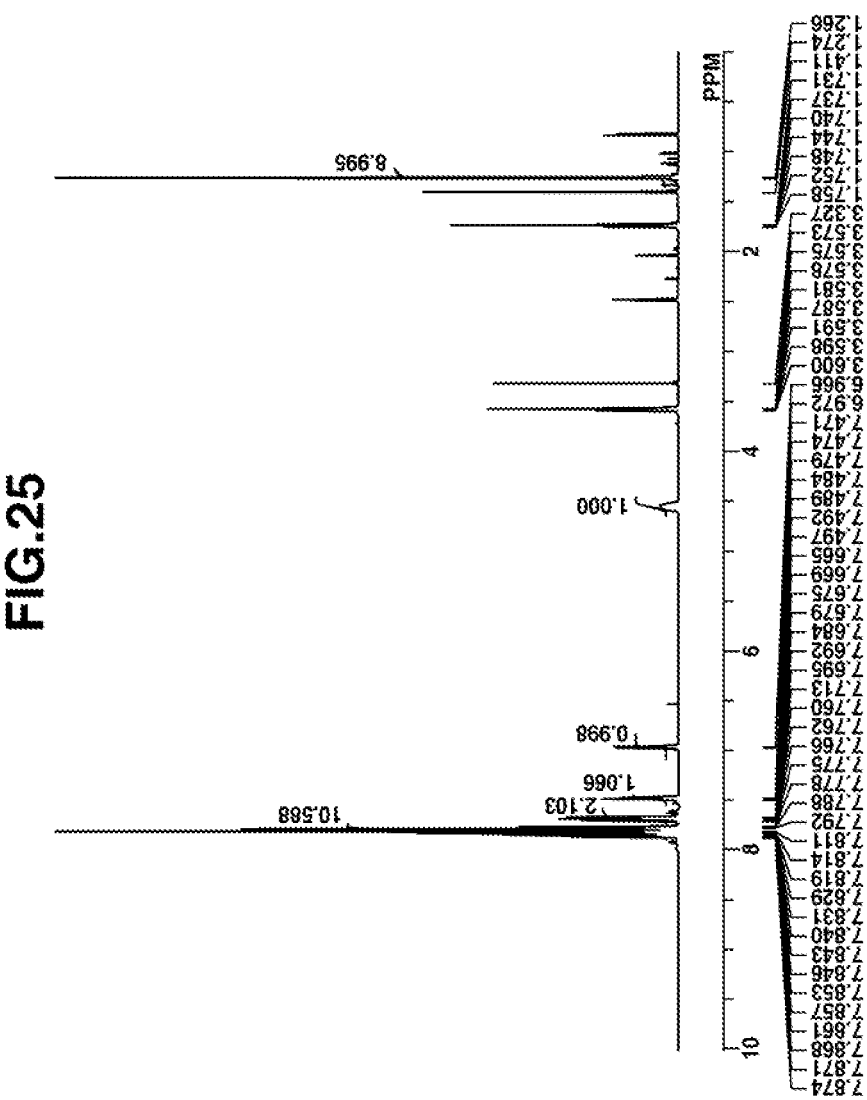
FIGS. 25 and 26 are diagrams showing $^1$H- and $^{19}$F-NMR spectra of Intermediate N in Example 1-3-1, respectively.
Figure 26:
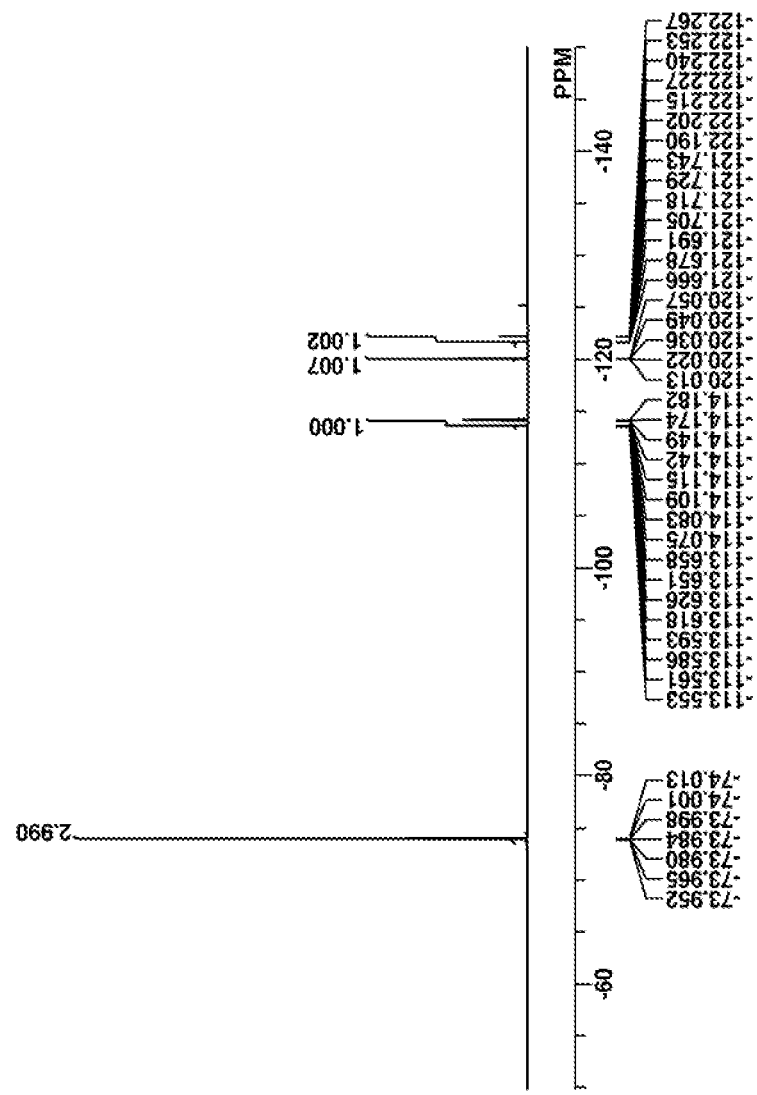

Intermediate N was analyzed by spectroscopy. The NMR spectra, $^1$H- and $^{19}$F-NMR in DMSO-$d_6$ are shown in FIGS. 25 and 26. In $^1$H-NMR analysis, minute amounts of residual solvents (DIPE, THF, MIBK, water) were observed.

Example 1-3-2

Synthesis of Intermediate O

A solution of 34.7 g of Intermediate N in 135 g of THF was added dropwise to a mixture of 2.4 g of 55 wt % sodium hydride and 35 g of THF below 5° C. The solution was aged overnight at room temperature. Below 10° C., 170 g of deionized water was added. To the solution, 270 g of MIBK, 100 g of deionized water and 20 g of methanol were added. An organic layer was taken out by separatory operation. The water layer was extracted with MIBK. The organic layers were combined and washed 3 times with 20 wt % methanol aqueous solution. The organic layer was concentrated under reduced pressure. 50 g of MIBK was added to the concentrate, which was stirred and filtered to collect the precipitate. The precipitate (solid) was washed with 10 g of MIBK and DIPE, and dried in vacuum, obtaining 19.3 g of Intermediate O (yield 60%).

Figure 27:
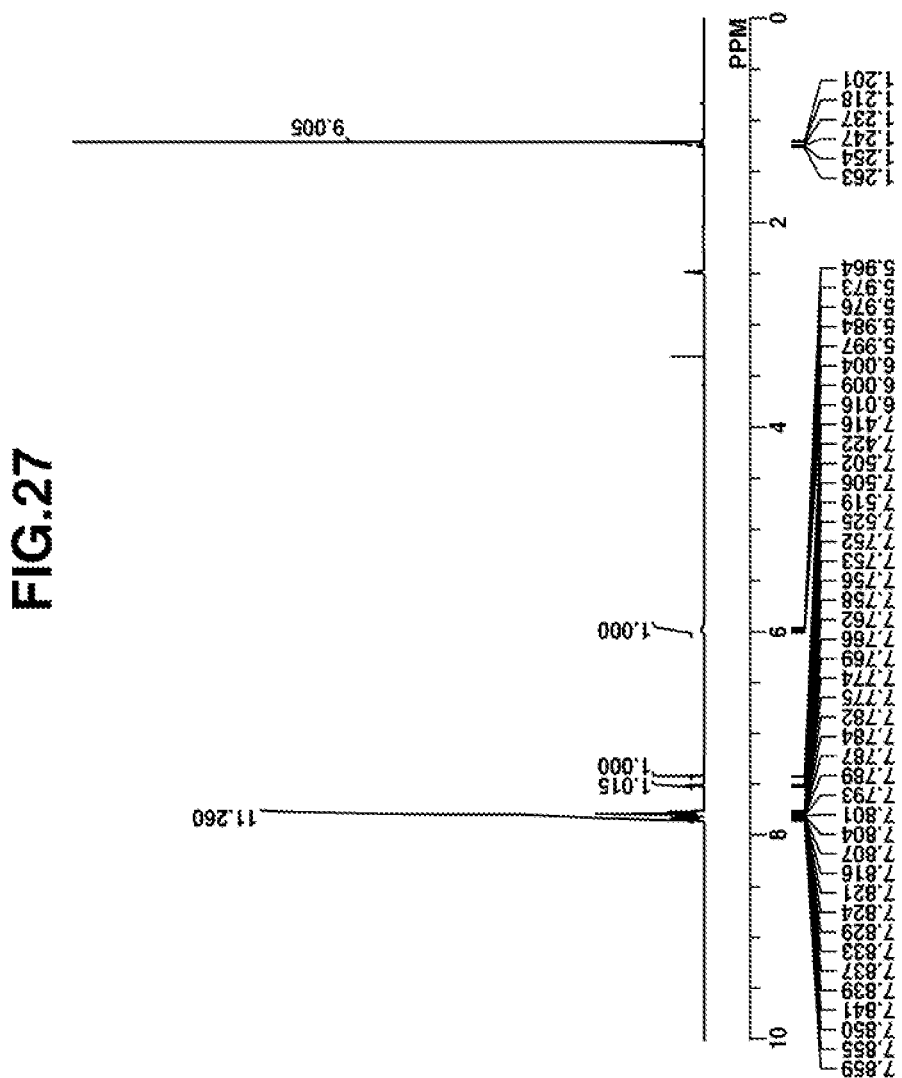
FIGS. 27 and 28 are diagrams showing $^1$H- and $^{19}$F-NMR spectra of Intermediate O in Example 1-3-2, respectively.
Figure 28:
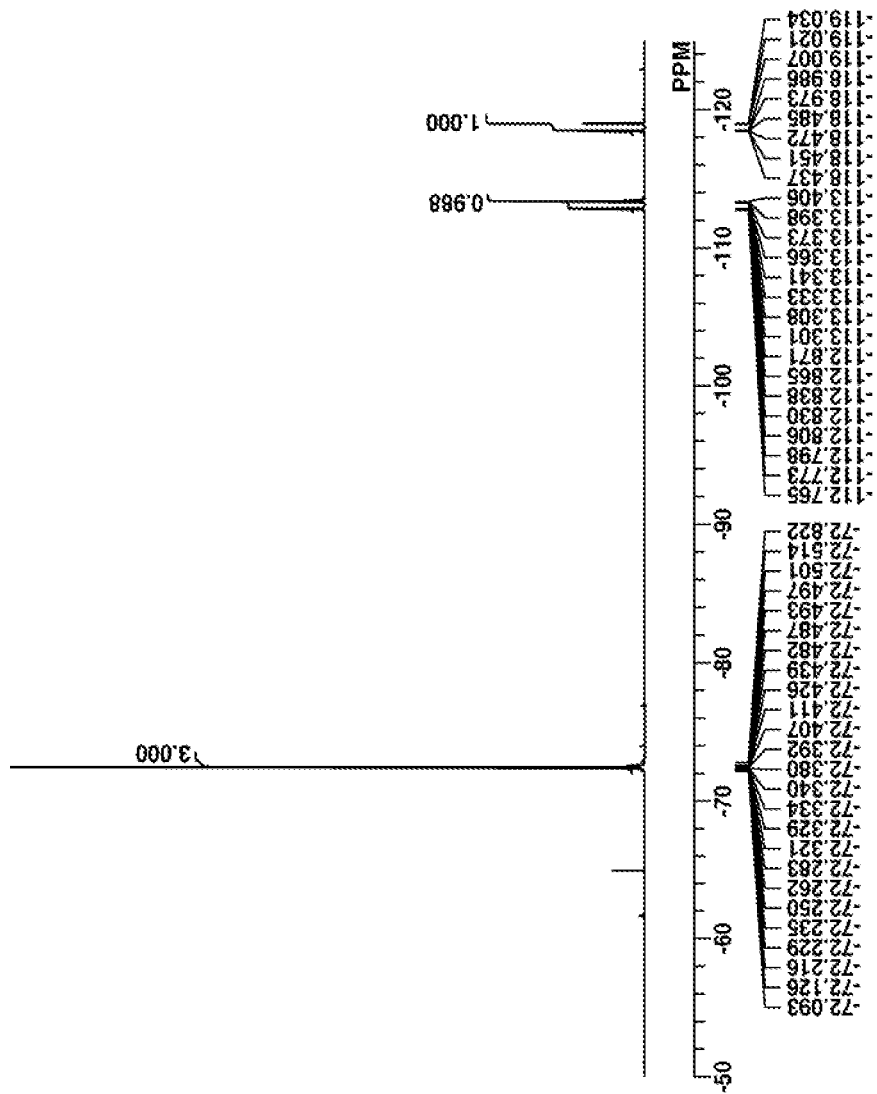

Intermediate O was analyzed by spectroscopy. The NMR spectra, $^1$H- and $^{19}$F-NMR in DMSO-$d_6$ are shown in FIGS. 27 and 28.

Example 1-3-3

Synthesis of Intermediate P

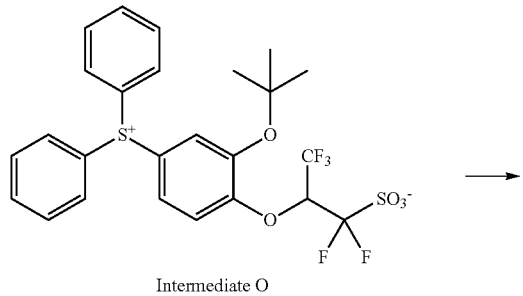

Intermediate O

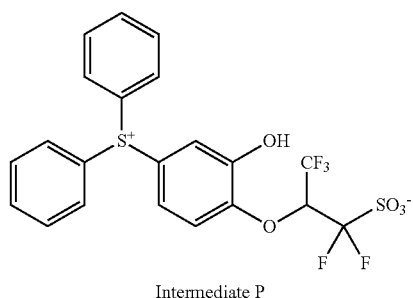

Intermediate P

A mixture of 16.3 g of Intermediate O, 0.3 g of p-toluenesulfonic acid monohydrate, and 163 g of methanol was stirred and aged at room temperature for 65 hours and at 50° C. for 24 hours. The completion of reaction was confirmed by $^{19}$F-NMR spectroscopy, whereupon methyl tert-butyl ether was added to the solution. After stirring, a solid was collected by filtration. The solid was washed with methyl tert-butyl ether and dried in vacuum, obtaining 13.3 g of Intermediate P (yield 91%).

Figure 29:
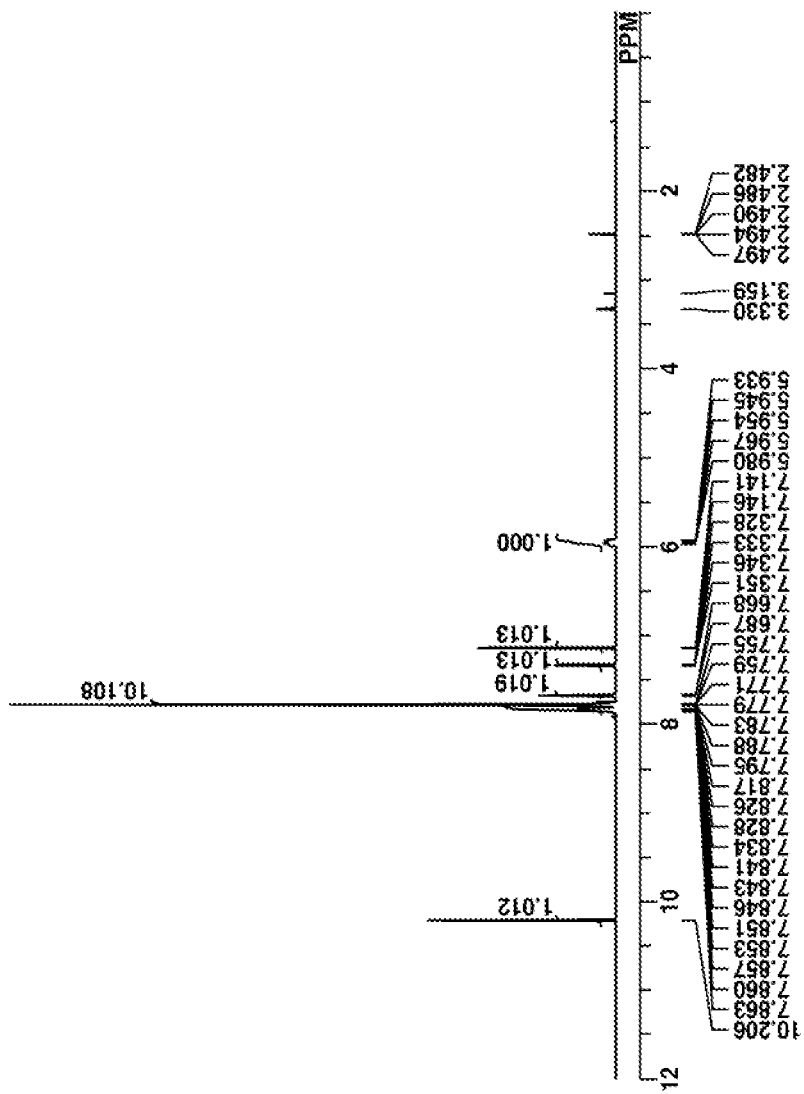
FIGS. 29 and 30 are diagrams showing $^1$H- and $^{19}$F-NMR spectra of Intermediate P in Example 1-3-3, respectively.
Figure 30:
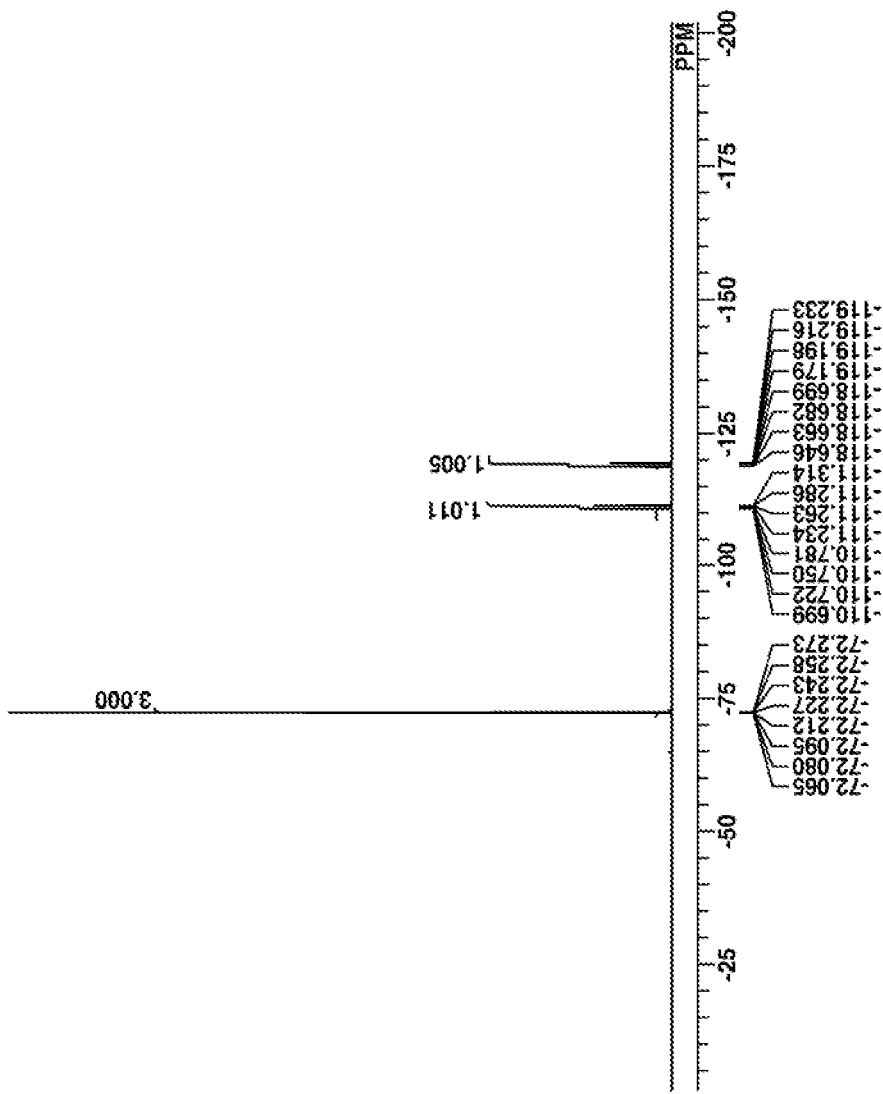

Intermediate P was analyzed by spectroscopy. The NMR spectra, $^{1}$H- and $^{19}$F-NMR in DMSO-$d_6$ are shown in FIGS. 29 and 30. In $^{1}$H-NMR analysis, minute amounts of residual solvents (methanol, water) were observed.

Example 1-3-4

Synthesis of PAG-3

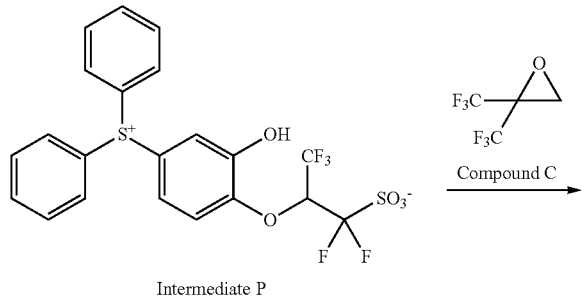

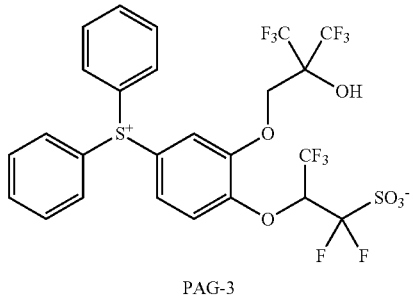

PAG-3

In 50 g of N,N-dimethylformamide were dissolved 9.0 g of Intermediate P and 2.5 g of diisopropylethylamine. Under ice cooling, Compound C was added dropwise to the solution. The solution was stirred overnight at room temperature. Under ice cooling, 70 g of 2 wt % hydrochloric acid was added to the solution to quench the reaction. To the solution, 70 g of MIBK and 10 g of methanol were added, followed by stirring. An organic layer was taken out by separatory operation. The organic layer was washed 3 times with 15 wt % methanol aqueous solution and concentrated under reduced pressure. DIPE was added to the concentrate for crystallization. The precipitate (solid) was filtered, washed with DIPE, and dried in vacuum, obtaining 9.1 g of the target compound, PAG-3 (yield 74%).

Figure 31:
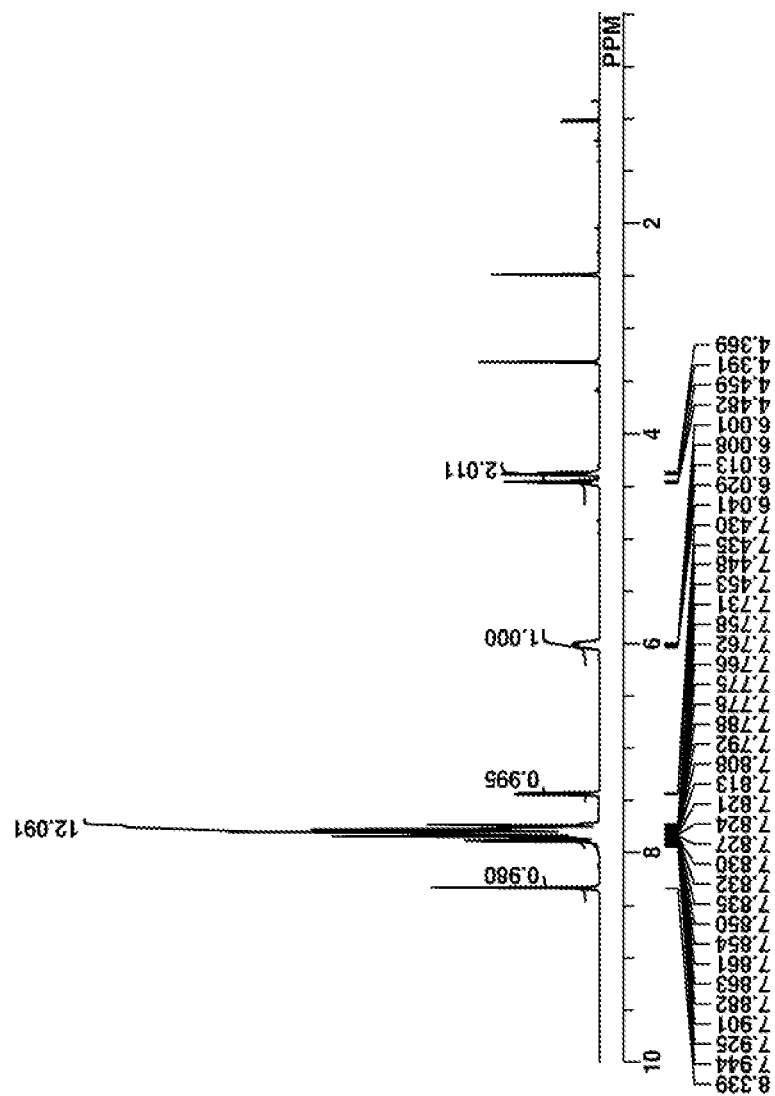
FIGS. 31 and 32 are diagrams showing $^1$H- and $^{19}$F-NMR spectra of PAG-3 in Example 1-3-4, respectively.
Figure 32:
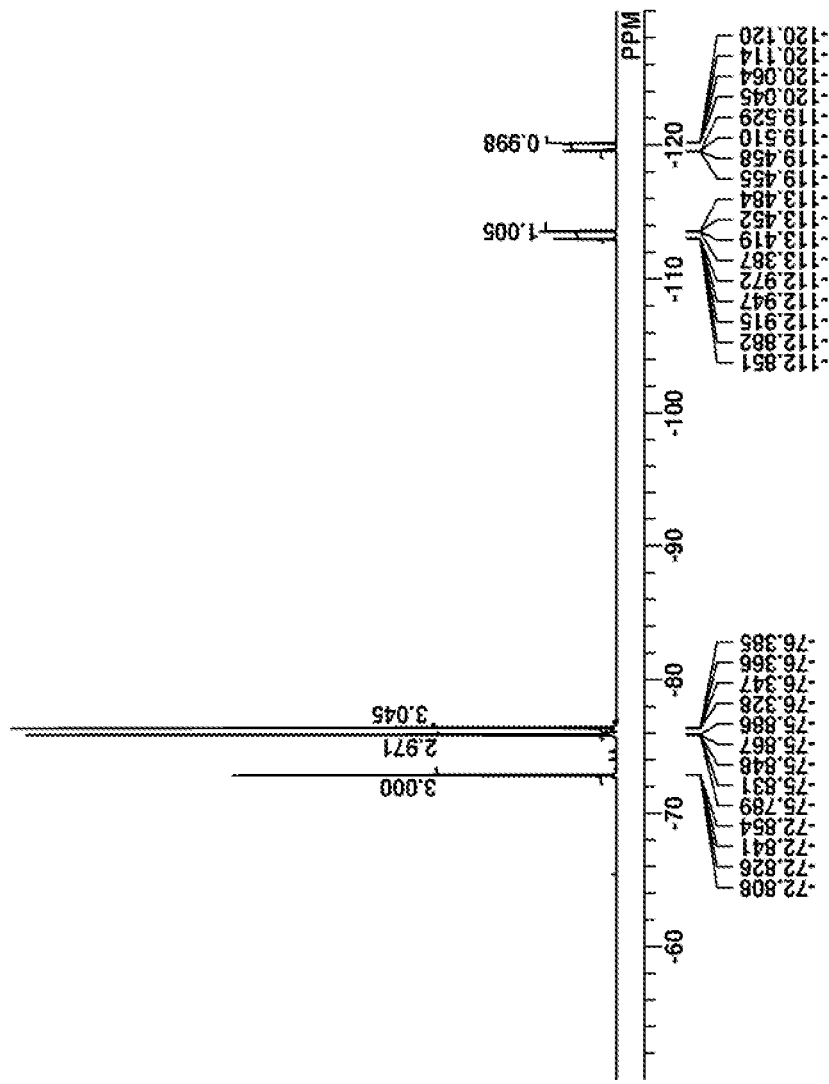

PAG-3 was analyzed by spectroscopy. The NMR spectra, $^{1}$H- and $^{19}$F-NMR in DMSO-$d_6$ are shown in FIGS. 31 and 32. In $^{1}$H-NMR analysis, minute amounts of residual solvents (DIPE, MIBK, water) were observed.

IR (D-ATR): 3304, 3073, 1595, 1510, 1475, 1449, 1412, 1373, 1316, 1261, 1242, 1169, 1089, 1074, 1045, 984, 882, 838, 812, 746, 682, 644, 586 cm$^{-1}$

TOF-MS (MALDI): [M] 687

Examples 1-4 to 1-9

Synthesis of PAG-4 to PAG-9

PAG-4 to PAG-9, identified below, were synthesized in accordance with the procedures of the foregoing Examples.

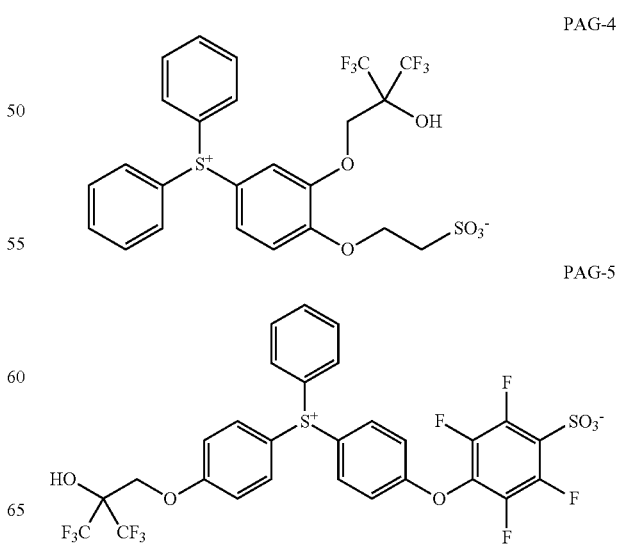

PAG-6

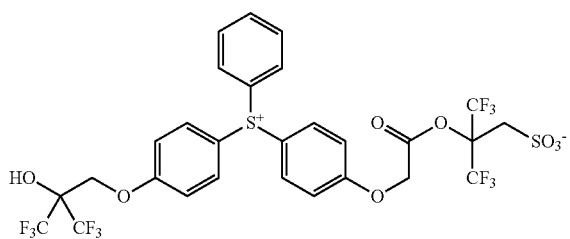

PAG-7

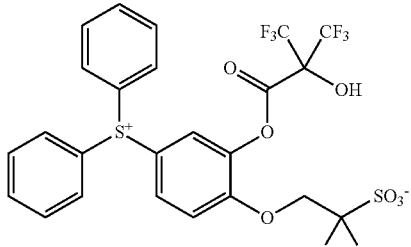

PAG-8

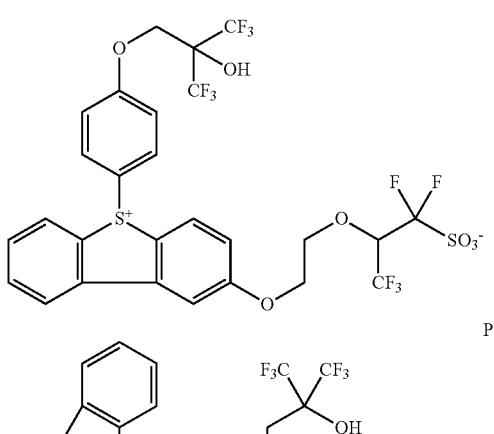

PAG-9

[2] Synthesis of Polymers

Polymers for use in resist compositions were synthesized according to the following formulation.

Synthesis Example 1

Synthesis of Polymer P1

In a flask under nitrogen atmosphere, 22 g of 1-t-butyl-cyclopentyl methacrylate, 17 g of 2-oxotetrahydrofuran-3-yl methacrylate, 0.48 g of dimethyl 2,2'-azobis(2-methylpropionate) (V-601 by Wako Pure Chemical Industries, Ltd.), 0.41 g of 2-mercaptoethanol, and 50 g of MEK were combined to form a monomer/initiator solution. Another flask in nitrogen atmosphere was charged with 23 g of MEK, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The precipitate was collected by filtration, washed twice with 240 g of methanol, and vacuum dried at 50° C. for 20 hours, obtaining 36 g of Polymer P1 in white powder form (yield 90%). On GPC analysis, Polymer P1 had a Mw of 8,800 and a dispersity Mw/Mn of 1.94.

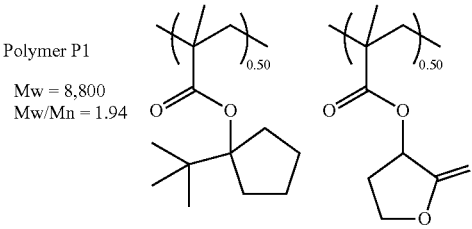

Polymer P1

Mw = 8,800
Mw/Mn = 1.94

Synthesis Examples 2 to 5

Synthesis of Polymers P2 to P5

Polymers P2 to P5 were synthesized by the same procedure as in Synthesis Example 1 aside from changing the type and amount of monomers.

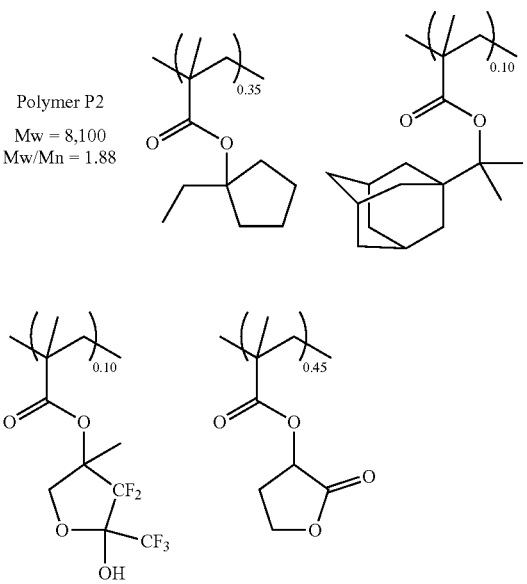

Polymer P2

Mw = 8,100
Mw/Mn = 1.88

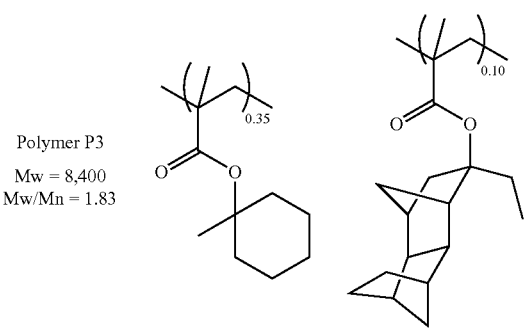

Polymer P3

Mw = 8,400
Mw/Mn = 1.83

-continued

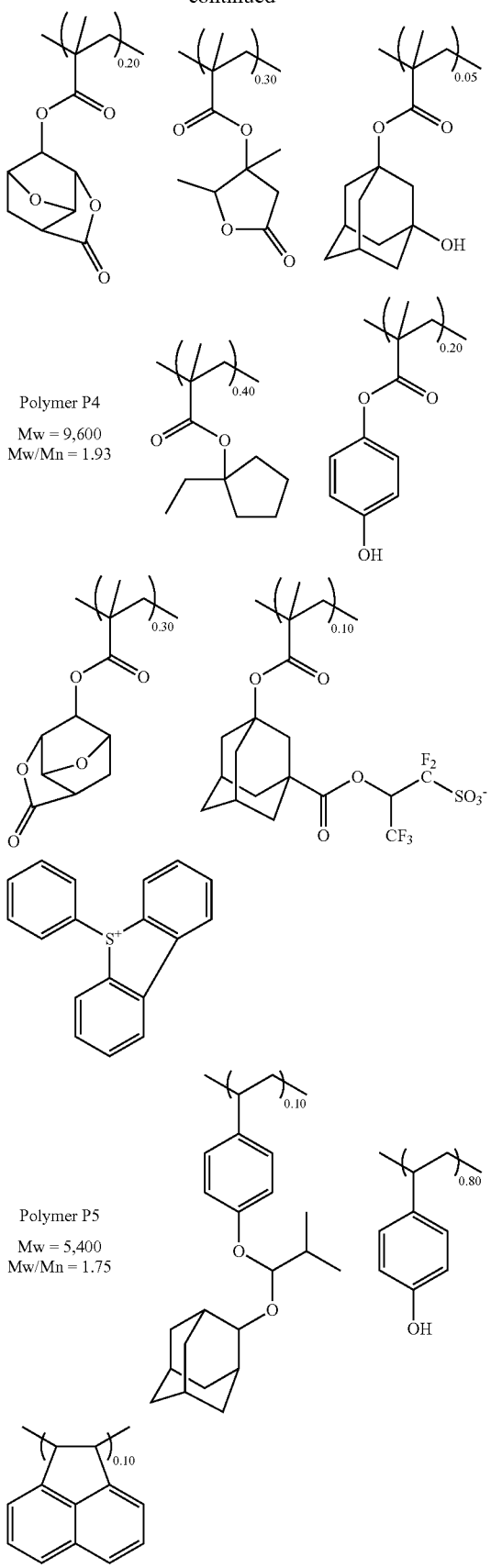

Polymer P4
Mw = 9,600
Mw/Mn = 1.93

Polymer P5
Mw = 5,400
Mw/Mn = 1.75

[3] Preparation of Resist Composition

Examples 2-1 to 2-17 and Comparative Examples 1-1 to 1-13

Resist compositions in solution form were prepared by dissolving selected components in an organic solvent containing 100 ppm of surfactant FC-4430 (3M) in accordance with the formulation shown in Tables 1 and 2, and filtering through a Teflon® filter with a pore size of 0.2 μm.

The solvent, second PAG, quencher, and alkali-soluble surfactant (SF-1) used herein are identified below.

Solvent:
  PGMEA=propylene glycol monomethyl ether acetate
  GBL=γ-butyrolactone
  CyH=cyclohexanone
  EL=ethyl lactate
  DAA=diacetone alcohol Second PAG:
  PAG-X: the compound described in JP-A 2010-215608

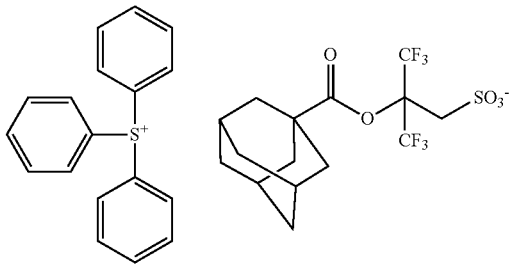
PAG-X

PAG-A: the compound described in JP-A 2007-145797

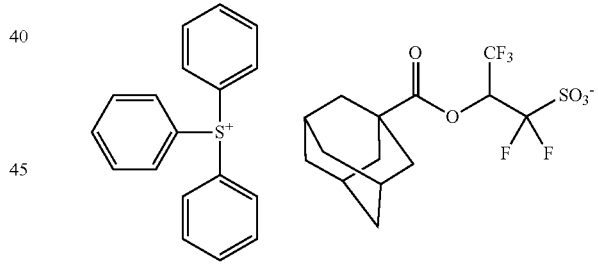
PAG-A

PAG-B: the compound described in JP 4621806

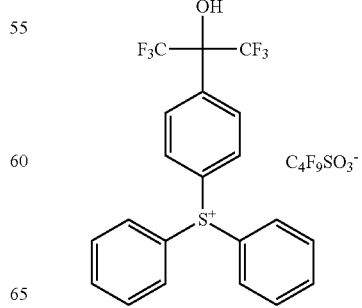
PAG-B

PAG-C: the compound described in JP-A 2013-167826
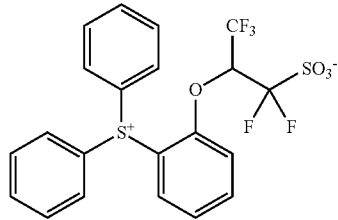
PAG-D: the compound described in JP-A 2013-167826
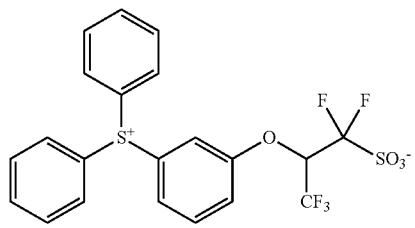
PAG-E: the compound described in JP-A 2013-167826
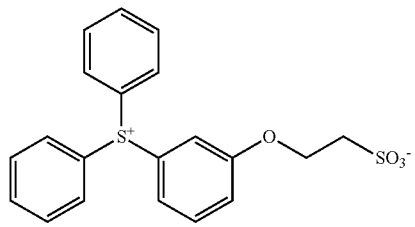
PAG-F: the compound described in JP-A 2013-167826
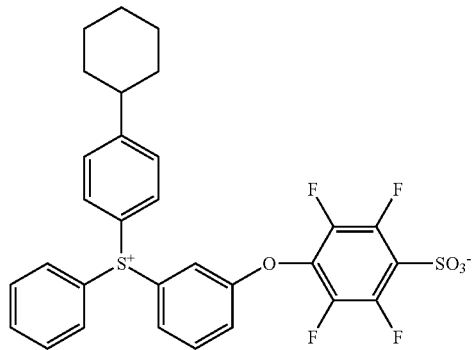
PAG-G: the compound described in JP-A 2013-167826
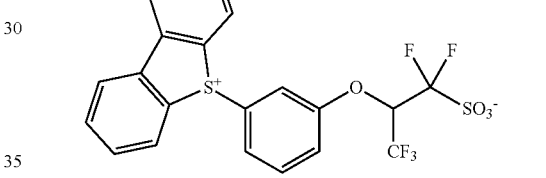
PAG-H: the compound described in JP-A 2013-167826
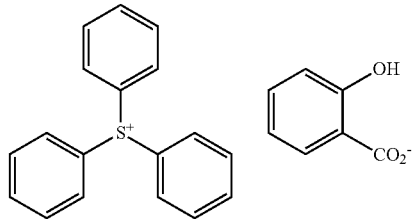
Quencher:
Q-1: 1-(tert-butoxycarbonyl)-4-hydroxypiperidine
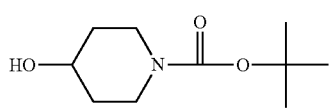
Q-2: triphenylsulfonium salicylate Alkali-soluble surfactant (SF-1): polymer of the following formula

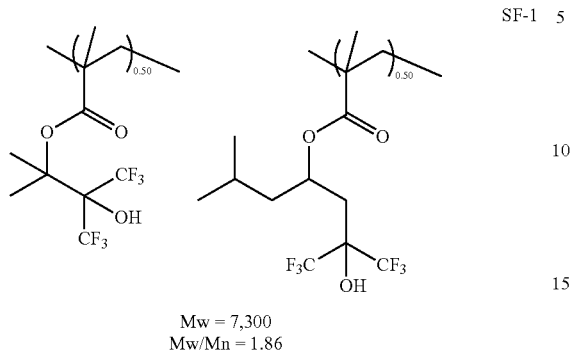

SF-1

Mw = 7,300
Mw/Mn = 1.86

TABLE 1

|  |  | Resist composition | Polymer (pbw) | PAG (pbw) | Quencher (pbw) | Surfactant (pbw) | Solvent (weight ratio) (pbw) |
| --- | --- | --- | --- | --- | --- | --- | --- |
| Example | 2-1 | R1 | P1 (80) | PAG-1 (8.0) | Q-1 (1.1) | SF-1 (3.0) | PGMEA/GBL (9/1) (1,920) |
|  | 2-2 | R2 | P1 (80) | PAG-2 (9.0) | Q-1 (1.1) | SF-1 (3.0) | PGMEA/GBL (9/1) (1,920) |
|  | 2-3 | R3 | P1 (80) | PAG-3 (8.0) | Q-1 (1.1) | SF-1 (3.0) | PGMEA/GBL (9/1) (1,920) |
|  | 2-4 | R4 | P1 (80) | PAG-A (5.0) PAG-4 (3.0) | — | SF-1 (3.0) | PGMEA/GBL (9/1) (1,920) |
|  | 2-5 | R5 | P1 (80) | PAG-5 (5.0) PAG-X (3.0) | Q-1 (1.1) | SF-1 (3.0) | PGMEA/GBL (9/1) (1,920) |
|  | 2-6 | R6 | P1 (80) | PAG-6 (10.5) | Q-2 (1.5) | SF-1 (3.0) | PGMEA/GBL (9/1) (1,920) |
|  | 2-7 | R7 | P1 (80) | PAG-7 (8.5) | Q-1 (1.1) | SF-1 (3.0) | PGMEA/GBL (9/1) (1,920) |
|  | 2-8 | R8 | P1 (80) | PAG-8 (6.5) PAG-X (2.0) | Q-1 (1.1) | SF-1 (3.0) | PGMEA/GBL (9/1) (1,920) |
|  | 2-9 | R9 | P1 (80) | PAG-9 (6.5) PAG-X (2.0) | Q-1 (1.1) | SF-1 (3.0) | PGMEA/GBL (9/1) (1,920) |
|  | 2-10 | R10 | P2 (80) | PAG-1 (9.0) | Q-2 (1.0) | SF-1 (3.0) | PGMEA/GBL (9/1) (1,920) |
|  | 2-11 | R11 | P2 (80) | PAG-3 (9.0) | Q-2 (1.0) | SF-1 (3.0) | PGMEA/GBL (9/1) (1,920) |
|  | 2-12 | R12 | P3 (80) | PAG-1 (8.0) PAG-X (2.0) | Q-2 (0.5) | SF-1 (3.0) | PGMEA/GBL (9/1) (1,920) |
|  | 2-13 | R13 | P4 (80) | PAG-1 (10.0) | Q-2 (4.0) | SF-1 (3.0) | PGMEA/CyH/DAA (4/20/1) (1,920) |
|  | 2-14 | R14 | P4 (80) | PAG-5 (10.0) | Q-2 (4.0) | SF-1 (3.0) | PGMEA/CyH/DAA (4/20/1) (1,920) |
|  | 2-15 | R15 | P4 (80) | PAG-9 (10.0) | Q-2 (4.0) | SF-1 (3.0) | PGMEA/CyH/DAA (4/20/1) (1,920) |
|  | 2-16 | R16 | P5 (80) | PAG-4 (8.0) | Q-2 (4.0) | SF-1 (3.0) | PGMEA/EL (3/7) (3,860) |
|  | 2-17 | R17 | P5 (80) | PAG-6 (5.0) | Q-2 (3.0) | SF-1 (3.0) | PGMEA/EL (3/7) (3,860) |

TABLE 2

|  |  | Resist composition | Polymer (pbw) | PAG (pbw) | Quencher (pbw) | Surfactant (pbw) | Solvent (weight ratio) (pbw) |
| --- | --- | --- | --- | --- | --- | --- | --- |
| Comparative Example | 1-1 | R18 | P1 (80) | PAG-A (8.0) | Q-1 (1.1) | SF-1 (3.0) | PGMEA/GBL (9/1) (1,920) |
|  | 1-2 | R19 | P1 (80) | PAG-B (8.0) | Q-1 (1.1) | SF-1 (3.0) | PGMEA/GBL (9/1) (1,920) |
|  | 1-3 | R20 | P1 (80) | PAG-C (8.0) | Q-1 (1.1) | SF-1 (3.0) | PGMEA/GBL (9/1) (1,920) |
|  | 1-4 | R21 | P1 (80) | PAG-D (8.0) | Q-1 (1.1) | SF-1 (3.0) | PGMEA/GBL (9/1) (1,920) |

TABLE 2-continued

| Resist composition | Polymer (pbw) | PAG (pbw) | Quencher (pbw) | Surfactant (pbw) | Solvent (weight ratio) (pbw) |
|---|---|---|---|---|---|
| 1-5 | R22 | P1 (80) | PAG-A (5.0) PAG-E (3.0) | — | SF-1 (3.0) | PGMEA/GBL (9/1) (1,920) |
| 1-6 | R23 | P1 (80) | PAG-F (5.0) PAG-X (3.0) | Q-1 (1.1) | SF-1 (3.0) | PGMEA/GBL (9/1) (1,920) |
| 1-7 | R24 | P1 (80) | PAG-G (8.0) | Q-1 (1.1) | SF-1 (3.0) | PGMEA/GBL (9/1) (1,920) |
| 1-8 | R25 | P1 (80) | PAG-H (6.5) PAG-X (2.0) | Q-1 (1.1) | SF-1 (3.0) | PGMEA/GBL (9/1) (1,920) |
| 1-9 | R26 | P4 (80) | PAG-D (10.0) | Q-2 (4.0) | SF-1 (3.0) | PGMEA/CyH/DAA (4/20/1) (1,920) |
| 1-10 | R27 | P4 (80) | PAG-F (10.0) | Q-2 (4.0) | SF-1 (3.0) | PGMEA/CyH/DAA (4/20/1) (1,920) |
| 1-11 | R28 | P4 (80) | PAG-H (10.0) | Q-2 (4.0) | SF-1 (3.0) | PGMEA/CyH/DAA (4/20/1) (1,920) |
| 1-12 | R29 | P5 (80) | PAG-E (8.0) | Q-2 (4.0) | SF-1 (3.0) | PGMEA/EL (3/7) (3,860) |
| 1-13 | R30 | P5 (80) | PAG-F (8.0) | Q-2 (3.0) | SF-1 (3.0) | PGMEA/EL (3/7) (3,860) |

[4] ArF Immersion Lithography Test

Examples 3-1 to 3-12 and Comparative Examples 2-1 to 2-8

On a substrate (silicon wafer), a spin-on carbon film ODL-102 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, each of the resist compositions (R1 to R12, R18 to R25) was spin coated, then baked on a hotplate at 100° C. for 60 seconds to form a resist film of 80 nm thick. Using an ArF excimer laser immersion lithography scanner NSR-610C (Nikon Corp., NA 1.30, σ 0.98/0.78, 35° cross-pole illumination, azimuthally polarized illumination), the resist film was exposed imagewise through a 6% halftone phase shift mask bearing a line pattern with a line width of 50 nm and a pitch of 100 nm (on-wafer size). Water was used as the immersion liquid. The resist film was baked (PEB) at 100° C. for 60 seconds and developed in n-butyl acetate for 30 seconds to form a negative tone line-and-space (L/S) pattern with a space width of 50 nm and a pitch of 100 nm.

The pattern was observed under CD-SEM CG4000 (Hitachi High-Technologies Corp.).

Evaluation of Sensitivity

The optimum dose (Eop, mJ/cm$^2$) which provided a 1:1 L/S pattern was determined and reported as an index of sensitivity.

Evaluation of LWR

The L/S pattern formed by exposure in the optimum dose (determined in the sensitivity evaluation) was observed under TD-SEM S-9380 (Hitachi High-Technologies Corp.). The space width was measured at longitudinally spaced apart 10 points, from which a 3-fold value (3σ) of standard deviation (σ) was determined and reported as LWR. A smaller value indicates a pattern having a less roughness and more uniform space width.

Evaluation of MEF

A L/S pattern was formed by exposure in the optimum dose (determined in the sensitivity evaluation) through a mask with the pitch fixed and the line width varied. Mask error factor (MEF) was calculated from variations of the mask line width and the pattern space width according to the following equation:

MEF=(pattern space width)/(mask line width)−b wherein b is a constant. A value closer to unity (1) indicates better performance.

Evaluation of Defect Density

Further, defects in the pattern as developed were inspected by a flaw detector KLA2800 (KLA-Tencor). A defect density (count/cm$^2$) was computed by dividing the total number of detected defects by a detection area. The pattern formed was an iterated 50-nm 1:1 L/S pattern. The defect inspection conditions included light source UV, inspected pixel size 0.28 μm, and cell-to-cell mode. In this test, the sample was rated good for a defect density of less than 0.05 defect/cm$^2$ and NG for a density of equal to or more than 0.05 defect/cm$^2$.

The results are shown in Table 3.

TABLE 3

|  |  | Resist composition | Sensitivity (mJ/cm$^2$) | LWR (nm) | MEF | Defect density |
|---|---|---|---|---|---|---|
| Example | 3-1 | R1 | 25 | 2.9 | 3.1 | Good |
|  | 3-2 | R2 | 30 | 3.2 | 3.3 | Good |
|  | 3-3 | R3 | 25 | 3.0 | 3.0 | Good |
|  | 3-4 | R4 | 27 | 3.3 | 3.6 | Good |
|  | 3-5 | R5 | 26 | 3.1 | 3.4 | Good |
|  | 3-6 | R6 | 25 | 3.0 | 3.5 | Good |
|  | 3-7 | R7 | 26 | 3.3 | 2.9 | Good |
|  | 3-8 | R8 | 30 | 3.4 | 3.7 | Good |
|  | 3-9 | R9 | 31 | 3.5 | 3.5 | Good |
|  | 3-10 | R10 | 24 | 3.1 | 3.3 | Good |
|  | 3-11 | R11 | 26 | 3.3 | 3.3 | Good |
|  | 3-12 | R12 | 27 | 2.8 | 2.9 | Good |
| Comparative Example | 2-1 | R18 | 24 | 4.5 | 4.8 | NG |
|  | 2-2 | R19 | 29 | 5.2 | 5.0 | Good |
|  | 2-3 | R20 | 38 | 4.4 | 4.2 | NG |
|  | 2-4 | R21 | 36 | 4.3 | 4.2 | NG |
|  | 2-5 | R22 | 33 | 4.5 | 4.0 | NG |
|  | 2-6 | R23 | 36 | 4.0 | 4.2 | NG |
|  | 2-7 | R24 | 33 | 3.9 | 4.7 | Good |
|  | 2-8 | R25 | 37 | 4.2 | 4.8 | NG |

As seen from the results of Table 3, the resist compositions comprising sulfonium compounds within the scope of the invention offer advantages including a high sensitivity, a good balance of LWR and MEF, and minimal defects. These data demonstrate that the inventive resist compositions are useful in the ArF immersion lithography.

[5] EUV Lithography Test

Examples 4-1 to 4-3 and Comparative Examples 3-1 to 3-3

Each resist composition (R13 to R15 or R26 to R28) was spin coated on a silicon substrate having a 20-nm coating of silicon-containing spin-on hard mask SHB-A940 (silicon content 43 wt %, Shin-Etsu Chemical Co., Ltd.) and pre-baked on a hot plate at 105° C. for 60 seconds to form a resist film of 60 nm thick. Using an EUV scanner NXE3300 (ASML, NA 0.33, σ 0.9/0.6, quadrupole illumination), the resist film was exposed to EUV through a mask bearing a hole pattern having a pitch 46 nm+20% bias (on-wafer size). The resist film was baked (PEB) on a hotplate at 100° C. for 60 seconds and developed in a 2.38 wt % TMAH aqueous solution for 30 seconds to form a hole pattern having a size of 23 nm.

The resist pattern was observed under CD-SEM (CG-5000, Hitachi High-Technologies Corp.). The exposure dose that provides a hole pattern having a size of 23 nm is reported as sensitivity. The size of 50 holes was measured, from which a size variation (3σ) was computed and reported as CDU.

The resist composition is shown in Table 4 together with the sensitivity and CDU of EUV lithography.

TABLE 4

| | | Resist composition | Sensitivity (mJ/cm$^2$) | CDU (nm) |
|---|---|---|---|---|
| Example | 4-1 | R13 | 20 | 2.5 |
| | 4-2 | R14 | 19 | 2.7 |
| | 4-3 | R15 | 21 | 2.9 |
| Comparative Example | 3-1 | R26 | 25 | 3.8 |
| | 3-2 | R27 | 26 | 4.0 |
| | 3-3 | R28 | 26 | 4.1 |

It is demonstrated in Table 4 that resist compositions comprising sulfonium compounds within the scope of the invention offer a high sensitivity and improved CDU. The inventive resist compositions are also useful in the EUV lithography.

[6] EB Writing Test

Examples 5-1 to 5-2 and Comparative Examples 4-1 to 4-2

Using a coater/developer system ACT-M (Tokyo Electron Ltd.), each of the resist compositions R16, R17, R29 and R30 was spin coated onto a mask blank of 152 mm squares having the outermost surface of silicon oxide (vapor primed with hexamethyldisilazane) and prebaked on a hotplate at 110° C. for 600 seconds to form a resist film of 80 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blank was exposed to EB using an EB writer system EBM-5000Plus (NuFlare Technology Inc., accelerating voltage 50 kV), then baked (PEB) at 110° C. for 600 seconds, and developed in a 2.38 wt % TMAH aqueous solution, thereby yielding a negative resist pattern.

The patterned mask blank was observed under a top-down scanning electron microscope (TD-SEM). The optimum exposure (Eop) was defined as the exposure dose (μC/cm$^2$) which provided a 1:1 resolution of a 200-nm 1:1 line-and-space pattern. The maximum resolution of the resist was defined as the minimum line width of a L/S pattern that could be resolved at the optimum exposure. The LER of a 200-nm L/S pattern was measured under SEM. The resist pattern was visually observed and judged whether or not the pattern profile was rectangular.

Evaluation of Development Residue Defects

A resist film was formed under the same conditions as above. The resist film was directly (i.e., imagewise exposure omitted) baked at 110° C. for 600 seconds and developed in a 2.38 wt % TMAH aqueous solution. Using a mask defect monitor M2351 (Lasertec Corp.), development residues were counted. The total count of defects after development was determined. The sample was rated good when the total count of defects is less than 300, or poor when the total count of defects is equal to or more than 300.

The test results are shown in Table 5.

TABLE 5

| | | Resist composition | Eop (μC/cm$^2$) | Maximum resolution (nm) | LER (nm) | Pattern profile | Defects |
|---|---|---|---|---|---|---|---|
| Example | 5-1 | R16 | 49 | 39 | 4.5 | rectangular | good |
| | 5-2 | R17 | 47 | 43 | 4.4 | rectangular | good |
| Comparative | 4-1 | R29 | 50 | 58 | 5.6 | inversely tapered | poor |
| Example | 4-2 | R30 | 49 | 60 | 5.8 | inversely tapered | poor |

As seen from the data in Table 5, the resist compositions containing sulfonium compounds within the scope of the invention as PAG exhibit advantages including high maximum resolution, improved LER, satisfactory pattern profile, and minimal defects. The inventive resist compositions are also useful in the EB lithography.

It is evident from the data in Tables 3 to 5 that the resist compositions containing sulfonium compounds within the scope of the invention as PAG exhibit a good balance of sensitivity, LWR, LER, and CDU. Satisfactory results are also obtained with respect to defects. The inventive PAG has the advantages of suppressed acid diffusion owing to its betaine structure and improved compatibility and hence more uniform dispersion owing to its hexafluoroalcohol unit, which lead to improvements in LWR, LER and CDU. Further the improved compatibility leads to a reduction of defects.

Japanese Patent Application No. 2017-161031 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium compound having the formula (1):

wherein L$^1$ is a straight, branched or cyclic C$_1$-C$_{20}$ divalent hydrocarbon group which may contain a heteroatom-containing moiety, X is an ether bond, and Z is a group of sulfonium cation structure having the formula (1A), (1B) or (1C):

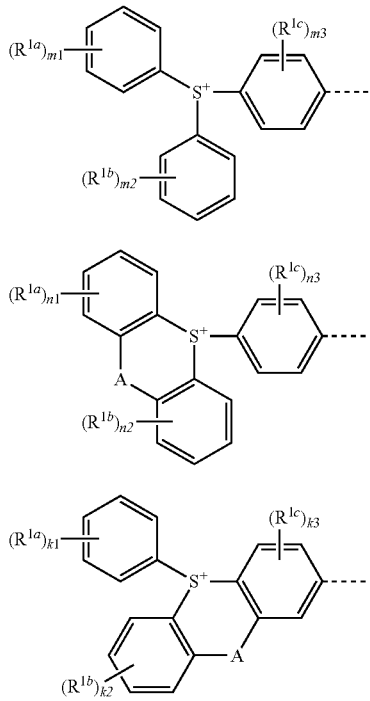

wherein the broken line denotes a valence bond to X,
A is a single bond, methylene, carbonyl, sulfinyl, sulfonyl, amino, ether bond, thioether bond, ester bond, carbonate bond, carbamate bond or sulfonic acid ester bond,
$R^{1a}$ to $R^{1c}$ are each independently a straight, branched or cyclic $C_1$-$C_{20}$ monovalent hydrocarbon group which may contain a heteroatom-containing moiety, at least one of $R^{1a}$ to $R^{1c}$ being a group of the formula (1-1) shown below, with the proviso that where at least two $R^{1a}$ are included, two of them may bond together to form a ring with carbon atoms on the benzene ring to which they are attached, where at least two $R^{1b}$ are included, two of them may bond together to form a ring with carbon atoms on the benzene ring to which they are attached, and where at least two $R^{1c}$ are included, two of them may bond together to form a ring with carbon atoms on the benzene ring to which they are attached,
m1, m2 and m3 are integers in the range: $0 \leq m1 \leq 5$, $0 \leq m2 \leq 5$, $0 \leq m3 \leq 4$, and $m1+m2+m3 \geq 1$,
n1, n2 and n3 are integers in the range: $0 \leq n1 \leq 4$, $0 \leq n2 \leq 4$, $0 \leq n3 \leq 4$, and $n1+n2+n3 \geq 1$,
k1, k2 and k3 are integers in the range: $0 \leq k1 \leq 5$, $0 \leq k2 \leq 4$, $0 \leq k3 \leq 3$, and $k1+k2+k3 \geq 1$,

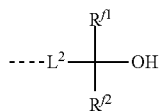

(1-1)

wherein $L^2$ is a straight, branched or cyclic $C_1$-$C_{20}$ divalent hydrocarbon group which may contain a heteroatom-containing moiety, $R^{f1}$ and $R^{f2}$ are each independently hydrogen, a straight, branched or cyclic $C_1$-$C_{20}$ alkyl, fluorine, or straight, branched or cyclic $C_1$-$C_{20}$ fluoroalkyl having at least one fluorine atom, at least one of $R^{f1}$ and $R^{f2}$ being fluorine or fluoroalkyl, the broken line denotes a valence bond.

2. The sulfonium compound of claim 1 wherein $R^{f1}$ and $R^{f2}$ are trifluoromethyl.

3. The sulfonium compound of claim 1 which has the formula (2):

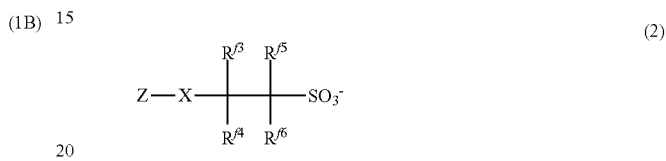

wherein X and Z are as defined above, $R^{f3}$, $R^{f4}$, $R^{f5}$ and $R^{f6}$ are each independently hydrogen, fluorine or trifluoromethyl.

4. The sulfonium compound of claim 3 wherein both $R^{f5}$ and $R^{f6}$ are fluorine.

5. A photoacid generator comprising the sulfonium compound of claim 1.

6. A resist composition comprising the photoacid generator of claim 5.

7. The resist composition of claim 6, further comprising a base resin containing a polymer comprising recurring units having the formula (a) and recurring units having the formula (b):

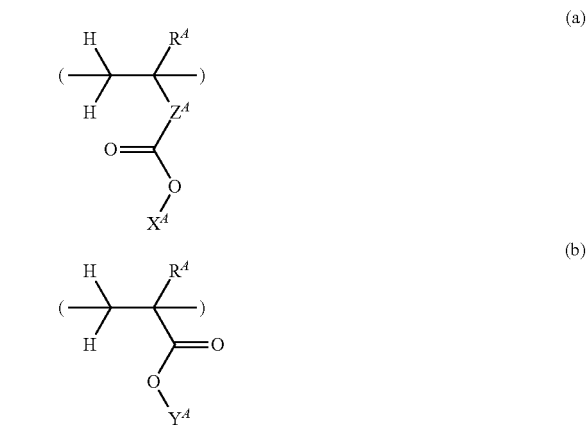

wherein $R^A$ is hydrogen, fluorine, methyl or trifluoromethyl, $Z^A$ is a single bond, phenylene group, naphthylene group or (backbone)-C(=O)—O—Z'—, Z' is a straight, branched or cyclic $C_1$-$C_{10}$ alkylene group which may contain a hydroxyl moiety, ether bond, ester bond or lactone ring, or phenylene group or naphthylene group, $X^A$ is an acid labile group, and $Y^A$ is hydrogen or a polar group having at least one structure selected from the group consisting of hydroxyl, cyano, carbonyl, carboxyl, ether bond, ester bond, sulfonic acid ester bond, carbonate bond, lactone ring, sultone ring and carboxylic anhydride.

8. The resist composition of claim 6, further comprising an organic solvent.

9. The resist composition of claim 6, further comprising a photoacid generator other than the photoacid generator comprising the sulfonium compound of formula (I).

10. The resist composition of claim 9 wherein the other photoacid generator has the formula (4) or (5):

(4)

wherein $R^{101}$, $R^{102}$, and $R^{103}$ are each independently straight, branched or cyclic $C_1$-$C_{20}$ monovalent hydrocarbon group which may contain a heteroatom, any two of $R^{101}$, $R^{102}$ and $R^{103}$ may bond together to form a ring with the sulfur atom to which they are attached, and $X^-$ is an anion selected from the formulae (4A) to (4D):

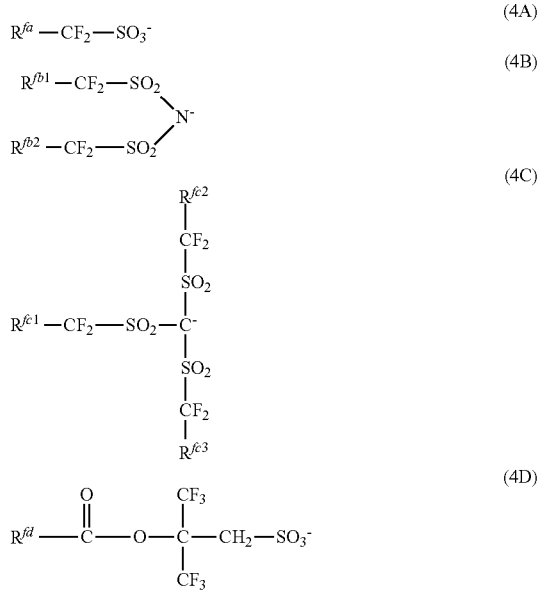

wherein $R^{fa}$, $R^{fb1}$, $R^{fb2}$, $R^{fc1}$, $R^{fc2}$ and $R^{fc3}$ are each independently fluorine or a straight, branched or cyclic $C_1$-$C_{40}$ monovalent hydrocarbon group which may contain a heteroatom, or a pair of $R^{fb1}$ and $R^{fb2}$, or $R^{fc1}$ and $R^{fc2}$ may bond together to form a ring with the carbon atom to which they are attached and any intervening atoms, $R^{fd}$ is a straight, branched or cyclic $C_1$-$C_{40}$ monovalent hydrocarbon group which may contain a heteroatom,

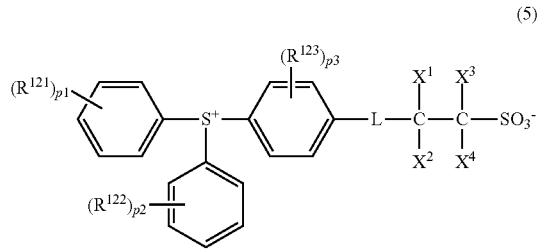

(5)

wherein $R^{121}$, $R^{122}$ and $R^{123}$ are each independently a straight, branched or cyclic $C_1$-$C_{20}$ alkyl group, L is a single bond, ether bond, or a straight, branched or cyclic $C_1$-$C_{20}$ divalent hydrocarbon group which may contain a heteroatom, $X^1$, $X^2$, $X^3$ and $X^4$ are each independently hydrogen, fluorine or trifluoromethyl, at least one of $X^1$, $X^2$, $X^3$ and $X^4$ is fluorine or trifluoromethyl, p1 and p2 are each independently an integer of 0 to 5, and p3 is an integer of 0 to 4.

11. The resist composition of claim 6, further comprising an onium salt having the formula (6) or (7):

$$R^{151}-SO_3^-M^+ \quad (6)$$

$$R^{152}-CO_2^-M^+ \quad (7)$$

wherein $R^{151}$ and $R^{152}$ are each independently hydrogen or a straight, branched or cyclic $C_1$-$C_{40}$ monovalent hydrocarbon group which may contain a heteroatom, exclusive of hydrocarbon groups in which the hydrogen atom in bond with the carbon atom at α-position relative to the sulfo group is replaced by a fluorine atom or fluoroalkyl moiety, and $M^+$ is an onium cation.

12. The resist composition of claim 6, further comprising an amine compound.

13. The resist composition of claim 6, further comprising a surfactant which is insoluble or substantially insoluble in water and soluble in alkaline developer, and/or a surfactant which is insoluble or substantially insoluble in water and alkaline developer.

14. A pattern forming process comprising the steps of applying the resist composition of claim 6 onto a substrate, prebaking to form a resist film, exposing a selected region of the resist film to KrF excimer laser, ArF excimer laser, EB or EUV, baking, and developing the exposed resist film in a developer.

15. The pattern forming process of claim 14 wherein the developing step uses an alkaline aqueous solution as the developer, thereby forming a positive pattern in which an exposed region of the resist film is dissolved away and an unexposed region of the resist film is not dissolved.

16. The pattern forming process of claim 14 wherein the developing step uses an organic solvent as the developer, thereby forming a negative pattern in which an unexposed region of the resist film is dissolved away and an exposed region of the resist film is not dissolved.

17. The pattern forming process of claim 16 wherein the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

18. The process of claim 14 wherein the exposure step is carried out by immersion lithography while a liquid having a refractive index of at least 1.0 is held between the resist film and a projection lens.

19. The process of claim 18, further comprising the step of coating a protective film on the resist film prior to the exposure step, wherein immersion lithography is carried out while the liquid is held between the protective film and the projection lens.

\* \* \* \* \*